US010669320B2

(12) United States Patent
Joglekar et al.

(10) Patent No.: US 10,669,320 B2
(45) Date of Patent: Jun. 2, 2020

(54) MPS1 AND KNL1 PHOSPHORYLATION SYSTEM

(71) Applicant: The Regents of the University of Michigan, Ann Arbor, MI (US)

(72) Inventors: Ajit P. Joglekar, Ann Arbor, MI (US); Pavithra Aravamudhan, Nashville, TN (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/355,824

(22) Filed: Nov. 18, 2016

(65) Prior Publication Data

US 2017/0137478 A1  May 18, 2017

Related U.S. Application Data

(60) Provisional application No. 62/256,971, filed on Nov. 18, 2015.

(51) Int. Cl.
*C07K 14/47* (2006.01)
*C12N 9/12* (2006.01)
*A61K 38/45* (2006.01)

(52) U.S. Cl.
CPC .............. *C07K 14/47* (2013.01); *A61K 38/45* (2013.01); *C12N 9/12* (2013.01); *C12Y 207/12002* (2013.01); *C07K 2319/70* (2013.01)

(58) Field of Classification Search
CPC .............................. C12N 9/12; C07K 2319/30
USPC ................................................ 435/194, 69.7
See application file for complete search history.

(56) References Cited

U.S. PATENT DOCUMENTS

| | | | |
|---|---|---|---|
| 5,139,941 A | 8/1992 | Muzyczka et al. |
| 5,173,414 A | 12/1992 | Lebkowski et al. |
| 5,676,954 A | 10/1997 | Brigham |
| 5,843,742 A | 12/1998 | Natsoulis et al. |
| 5,908,777 A | 6/1999 | Lee et al. |
| 5,994,132 A | 11/1999 | Chamberlain et al. |
| 6,057,158 A | 5/2000 | Chamberlain et al. |
| 6,063,622 A | 5/2000 | Chamberlain et al. |
| 6,083,750 A | 7/2000 | Chamberlain et al. |
| 6,451,596 B1 | 9/2002 | Chamberlain et al. |
| 6,916,846 B2 | 7/2005 | Farrar et al. |

FOREIGN PATENT DOCUMENTS

| | | |
|---|---|---|
| WO | WO 1992001070 | 1/1992 |
| WO | WO 1993003769 | 3/1993 |
| WO | WO 2009146929 | 12/2009 |
| WO | WO 2013176772 | 11/2013 |
| WO | WO 2014093661 | 6/2014 |

OTHER PUBLICATIONS

Aravamudhan et al, The kinetochore encodes a mechanical switch to disrupt spindle assembly checkpoint signalling. Nature Cell Biology vol. 17 | No. 7 | Jul. 2015 p. 868-879.*
Espert et al, PP2A-B56 opposes Mps1 phosphorylation of Knl1 and thereby promotes spindle assembly checkpoint silencing. J Cell Biol. Sep. 29, 2014; 206(7): 833-842.*
Rajakulendran et al, A dimerization-dependent mechanism drives RAF catalytic activation. Nature, Sep. 24, 2009;461(7263):p. 542-5. doi: 10.1038/nature08314. Epub Sep. 2, 2009.*
Aravamudhan et al., Assembling the protein architecture of the budding yeast kinetochore-microtubule attachment using FRET. Curr Biol. Jul. 7, 2014;24(13):1437-46.
Aravamudhan et al., The budding yeast point centromere associates with two Cse4 molecules during mitosis. Curr Biol. May 6, 2013;23(9):770-4.
Aravamudhan et al., The kinetochore encodes a mechanical switch to disrupt spindle assembly checkpoint signalling. Nat Cell Biol. Jul. 2015;17(7):868-79.
Ballister et al., Recruitment of Mad1 to metaphase kinetochores is sufficient to reactivate the mitotic checkpoint. J Cell Biol. Mar. 17, 2014;204(6):901-8.
Biggins et al., The conserved protein kinase Ipl1 regulates microtubule binding to kinetochores in budding yeast. Genes Dev. Mar. 1, 1999;13(5):532-44.
Carter, Adeno-associated virus vectors. Curr Opin Biotechnol. Oct. 1992;3(5):533-9.
Cheeseman et al., Mitotic spindle integrity and kinetochore function linked by the Duo1p/Dam1p complex. J Cell Biol. Jan. 8, 2001;152(1):197-212.
Ciferri et al., Implications for kinetochore-microtubule attachment from the structure of an engineered Ndc80 complex. Cell. May 2, 2008;133(3):427-39.
Daum et al., Ska3 is required for spindle checkpoint silencing and the maintenance of chromosome cohesion in mitosis. Curr Biol. Sep. 15, 2009;19(17):1467-72.
Deluca et al., Nuf2 and Hec1 are required for retention of the checkpoint proteins Mad1 and Mad2 to kinetochores. Curr Biol. Dec. 2, 2003;13(23):2103-9.
Espeut et al., Microtubule binding by KNL1 contributes to spindle checkpoint silencing at the kinetochore. J Cell Biol. Feb. 20, 2012;196(4):469-82.
Felgner et al., Cationic liposome-mediated transfection. Nature. Jan. 26, 1989;337(6205):387-8.
Felgner et al., Lipofection: a highly efficient, lipid-mediated DNA-transfection procedure. Proc Natl Acad Sci U S A. Nov. 1987;84(21):7413-7.
Ferrari et al., New developments in the generation of Ad-free, high-titer rAAV gene therapy vectors. Nat Med. Nov. 1997;3(11):1295-7.

(Continued)

*Primary Examiner* — Sheridan Swope
(74) *Attorney, Agent, or Firm* — Casimir Jones SC; David W. Staple

(57) ABSTRACT

Provided herein are compositions and methods for the treatment of cancer by activating the spindle assembly checkpoint (SAC) in cells. In particular, dimerized Mps1 and Spc105/KNL1 constructs are provided as tunable activators of SAC, allowing for control of chromosome segregation accuracy and prevention of aneuploidies that are common in cancer.

4 Claims, 64 Drawing Sheets

Specification includes a Sequence Listing.

(56) References Cited

OTHER PUBLICATIONS

Foley et al., Microtubule attachment and spindle assembly checkpoint signalling at the kinetochore. Nat Rev Mol Cell Biol. Jan. 2013;14(1):25-37.
Fraschini et al., Role of the kinetochore protein Ndc10 in mitotic checkpoint activation in *Saccharomyces cerevisiae*. Mol Genet Genomics. Sep. 2001;266(1):115-25.
Funabiki et al., Making an effective switch at the kinetochore by phosphorylation and dephosphorylation. Chromosoma. Jun. 2013;122(3):135-58.
Ghaemmaghami et al., Global analysis of protein expression in yeast. Nature. Oct. 16, 2003;425(6959):737-41.
Gillett et al., Spindle checkpoint proteins and chromosome-microtubule attachment in budding yeast. J Cell Biol. Feb. 16, 2004;164(4):535-46.
Goh et al., NDC10: a gene involved in chromosome segregation in *Saccharomyces cerevisiae*. J Cell Biol. May 1993;121(3):503-12.
Golub et al., Oligomerization of the ABL tyrosine kinase by the Ets protein TEL in human leukemia. Mol Cell Biol. Aug. 1996;16(8):4107-16.
Graham et al., Manipulation of adenovirus vectors. Methods Mol Biol. 1991;7:109-28.
Gregorevic et al., Systemic delivery of genes to striated muscles using adeno-associated viral vectors. Nat Med. Aug. 2004;10(8):828-34.
Guimaraes et al., Kinetochore-microtubule attachment relies on the disordered N-terminal tail domain of Hec1. Curr Biol. Nov. 25, 2008;18(22):1778-84.
Harbury et al., A switch between two-, three-, and four-stranded coiled coils in GCN4 leucine zipper mutants. Science. Nov. 26, 1993;262(5138):1401-7.
Hardwick et al., Activation of the budding yeast spindle assembly checkpoint without mitotic spindle disruption. Science. Aug. 16, 1996;273(5277):953-6.
Haruki et al., The anchor-away technique: rapid, conditional establishment of yeast mutant phenotypes. Mol Cell. Sep. 26, 2008;31(6):925-32.
Heinrich et al., Mph1 kinetochore localization is crucial and upstream in the hierarchy of spindle assembly checkpoint protein recruitment to kinetochores. J Cell Sci. Oct. 15, 2012;125(Pt 20):4720-7.
Hewitt et al., Sustained Mps1 activity is required in mitosis to recruit O-Mad2 to the Mad1-C-Mad2 core complex. J Cell Biol. Jul. 12, 2010;190(1):25-34.
Howell et al., Cytoplasmic dynein/dynactin drives kinetochore protein transport to the spindle poles and has a role in mitotic spindle checkpoint inactivation. J. Cell Biol. 155, 1159-1172 (2001).
Howell et al., Spindle checkpoint protein dynamics at kinetochores in living cells. Curr Biol. Jun. 8, 2004;14(11):953-64.
Hsu et al., Ndc80 internal loop interacts with Dis1/TOG to ensure proper kinetochore-spindle attachment in fission yeast. Curr Biol. Feb. 8, 2011;21(3):214-20.
Hug et al., Liposomes for the transformation of eukaryotic cells. Biochim Biophys Acta. Jul. 26, 1991;1097(1):1-17.
Ito et al., Centromere-tethered Mps1 pombe homolog (Mph1) kinase is a sufficient marker for recruitment of the spindle checkpoint protein Bub1, but not Mad1. Proc Natl Acad Sci U S A. Jan. 3, 2012;109(1):209-14.
Jelluma et al., Release of Mps1 from kinetochores is crucial for timely anaphase onset. J Cell Biol. Oct. 18, 2010;191(2):281-90.
Joglekar et al., A sensitized emission based calibration of FRET efficiency for probing the architecture of macromolecular machines. Cell Mol Bioeng. 2013;6(4):369-382.
Joglekar et al., In vivo protein architecture of the eukaryotic kinetochore with nanometer scale accuracy. Curr Biol. Apr. 28, 2009;19(8):694-9.
Joglekar et al., Molecular architecture of a kinetochore-microtubule attachment site. Nat Cell Biol. Jun. 2006;8(6):581-5.
Jones et al., Chemical genetics reveals a role for Mps1 kinase in kinetochore attachment during mitosis.Curr Biol. Jan. 26, 2005;15(2):160-5.
Kemmler et al., Mimicking Ndc80 phosphorylation triggers spindle assembly checkpoint signalling. EMBO J. Apr. 22, 2009;28(8):1099-110.
Kim et al., Phosphorylation of the spindle checkpoint protein Mad2 regulates its conformational transition. Proc Natl Acad Sci U S A. Nov. 16, 2010;107(46):19772-7.
Kotin, Prospects for the use of adeno-associated virus as a vector for human gene therapy. Hum Gene Ther. Jul. 1994;5(7):793-801.
Kuijt et al., Conditional targeting of MAD1 to kinetochores is sufficient to reactivate the spindle assembly checkpoint in metaphase. Chromosoma. Oct. 2014;123(5):471-80.
Lebkowski et al., Adeno-associated virus: a vector system for efficient introduction and integration of DNA into a variety of mammalian cell types. Mol Cell Biol. Oct. 1988;8(10):3988-96.
Li et al., The mitotic spindle is required for loading of the DASH complex onto the kinetochore. Genes Dev. Jan. 15, 2002;16(2):183-97.
Liu et al., The MPS1 family of protein kinases. Annu Rev Biochem. 2012;81:561-85.
London et al., Mad1 kinetochore recruitment by Mps1-mediated phosphorylation of Bub1 signals the spindle checkpoint. Genes Dev. Jan. 15, 2014;28(2):140-52.
London et al., Phosphoregulation of Spc105 by Mps1 and PP1 regulates Bub1 localization to kinetochores. Curr Biol. May 22, 2012;22(10):900-6.
Maldonado et al., Constitutive Mad1 targeting to kinetochores uncouples checkpoint signalling from chromosome biorientation. Nat Cell Biol. Apr. 2011;13(4):475-82.
Marco et al., *S. cerevisiae* chromosomes biorient via gradual resolution of syntely between S phase and anaphase. Cell. Aug. 29, 2013;154(5):1127-39.
Maresca et al., Intrakinetochore stretch is associated with changes in kinetochore phosphorylation and spindle assembly checkpoint activity. J Cell Biol. Feb. 9, 2009;184(3):373-81.
Martinez-Bueno et al., BacTregulators: a database of transcriptional regulators in bacteria and archaea. Bioinformatics. Nov. 1, 2004;20(16):2787-91.
McClelland et al., The highly conserved Ndc80 complex is required for kinetochore assembly, chromosome congression, and spindle checkpoint activity. Genes Dev. Jan. 1, 2003;17(1):101-14.
McEwen et al., Kinetochore fiber maturation in PtK1 cells and its implications for the mechanisms of chromosome congression and anaphase onset. J Cell Biol. Jun. 30, 1997;137(7):1567-80.
McIntosh, Structural and mechanical control of mitotic progression. Cold Spring Harb Symp Quant Biol. 1991;56:613-9.
Monaco et al., The RGF oligomerization domain mediates kinase activation and re-localization of the RET/PTC3 oncoprotein to the plasma membrane. Oncogene. Feb. 1, 2001;20(5):599-608.
Muzyczka, Use of adeno-associated virus as a general transduction vector for mammalian cells. Curr Top Microbiol Immunol. 1992;158:97-129.
Nakajima et al., Ipl1/Aurora-dependent phosphorylation of Sli15/INCENP regulates CPC-spindle interaction to ensure proper microtubule dynamics. J Cell Biol. Jul. 11, 2011;194(1):137-53.
Nijenhuis et al., A TPR domain-containing N-terminal module of MPS1 is required for its kinetochore localization by Aurora B. J Cell Biol. Apr. 15, 2013;201(2):217-31.
Norden et al., The NoCut pathway links completion of cytokinesis to spindle midzone function to prevent chromosome breakage. Cell. Apr. 7, 2006;125(1):85-98.
Pagliuca et al., Roles for the conserved Spc105p/Kre28p complex in kinetochoremicrotubule binding and the spindle assembly checkpoint. PLoS One. Oct. 28, 2009;4(10):e7640.
Palframan et al., Anaphase inactivation of the spindle checkpoint. Science. Aug. 4, 2006;313(5787):680-4.
Petrovic et al., Modular assembly of RWD domains on the Mis12 complex underlies outer kinetochore organization. Mol Cell. Feb. 20, 2014;53(4):591-605.

(56) References Cited

OTHER PUBLICATIONS

Pinsky et al., Protein phosphatase 1 regulates exit from the spindle checkpoint in budding yeast. Curr Biol. Jul. 28, 2009;19(14):1182-7.
Pinsky et al., The Ipl1-Aurora protein kinase activates the spindle checkpoint by creating unattached kinetochores. Nat Cell Biol. Jan. 2006;8(1):78-83.
Primorac et al., Bub3 reads phosphorylated MELT repeats to promote spindle assembly checkpoint signaling. Elife. Sep. 24, 2013;2:e01030.
Ramey et al., Subunit organization in the Dam1 kinetochore complex and its ring around microtubules. Mol Biol Cell. Nov. 2011;22(22):4335-42.
Ramos et al., The TetR family of transcriptional repressors. Microbiol Mol Biol Rev. Jun. 2005;69(2):326-56.
Rosenberg et al., KNL1/Spc105 recruits PP1 to silence the spindle assembly checkpoint. Curr Biol. Jun. 7, 2011;21(11):942-7.
Sacristan et al., Joined at the hip: kinetochores, microtubules, and spindle assembly checkpoint signaling. Trends Cell Biol. Jan. 2015;25(1):21-8.
Santaguida et al., The life and miracles of kinetochores. Embo J. Sep. 2, 2009;28(17):2511-31.
Scott et al., Interactions between Mad1p and the nuclear transport machinery in the yeast *Saccharomyces cerevisiae*. Mol Biol Cell. Sep. 2005;16(9):4362-74.
Shelling et al., Targeted integration of transfected and infected adeno-associated virus vectors containing the neomycin resistance gene. Gene Ther. May 1994;1(3):165-9.
Shimogawa et al., Mps1 phosphorylation of Dam1 couples kinetochores to microtubule plus ends at metaphase. Curr Biol. Aug. 8, 2006;16(15):1489-501.
Sprague et al., Mechanisms of microtubule-based kinetochore positioning in the yeast metaphase spindle. Biophys J. Jun. 2003;84(6):3529-46.
Straubinger et al., Liposomes as carriers for intracellular delivery of nucleic acids. Methods Enzymol. 1983;101:512-27.
Tien et al., Kinetochore biorientation in *Saccharomyces cerevisiae* requires a tightly folded conformation of the Ndc80 complex. Genetics. Dec. 2014;198(4):1483-93.
Tipton et al., Monopolar spindle 1 (MPS1) kinase promotes production of closed MAD2 (C-MAD2) conformer and assembly of the mitotic checkpoint complex. J Biol Chem. Dec. 6, 2013;288(49):35149-58.
Uchida et al., Kinetochore stretching inactivates the spindle assembly checkpoint. J Cell Biol. Feb. 9, 2009;184(3):383-90.
Ung et al., Heterologous dimerization domains functionally substitute for the double-stranded RNA binding domains of the kinase PKR. EMBO J. Jul. 16, 2001;20(14):3728-37.
Varma et al., Recruitment of the human Cdt1 replication licensing protein by the loop domain of Hec1 is required for stable kinetochore-microtubule attachment. Nat Cell Biol. May 13, 2012;14(6):593-603.
Wan et al., Protein architecture of the human kinetochore microtubule attachment site. Cell. May 15, 2009;137(4):672-84.
Wang et al., Architecture and flexibility of the yeast Ndc80 kinetochore complex. J Mol Biol. Nov. 21, 2008;383(4):894-903.
Wei et al., Molecular organization of the Ndc80 complex, an essential kinetochore component. Proc Natl Acad Sci U S A. Apr. 12, 2005;102(15):5363-7.
Wei et al., Structure of a central component of the yeast kinetochore: the Spc24p/Spc25p globular domain. Structure. Jun. 2006;14(6):1003-9.
Yeong et al., Exit from mitosis in budding yeast: biphasic inactivation of the Cdc28-Clb2 mitotic kinase and the role of Cdc20. Mol Cell. Mar. 2000;5(3):501-11.
Zhang et al., The Ndc80 internal loop is required for recruitment of the Ska complex to establish end-on microtubule attachment to kinetochores. J Cell Sci. Jul. 1, 2012;125(Pt 13):3243-5.
Zhou et al., Adeno-associated virus 2-mediated high efficiency gene transfer into immature and mature subsets of hematopoietic progenitor cells in human umbilical cord blood. J Exp Med. Jun. 1, 1994;179(6):1867-75.
Zhou, Polymer models of protein stability, folding, and interactions. Biochemistry. Mar. 2, 2004;43(8):2141-54.

\* cited by examiner

FIG. 3A
FIG. 3B
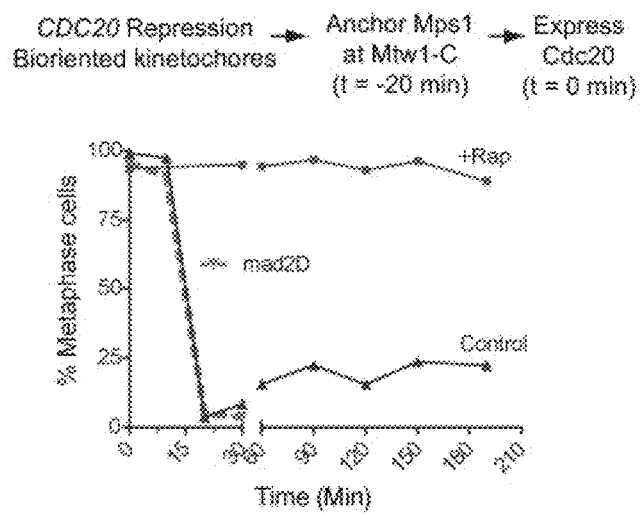
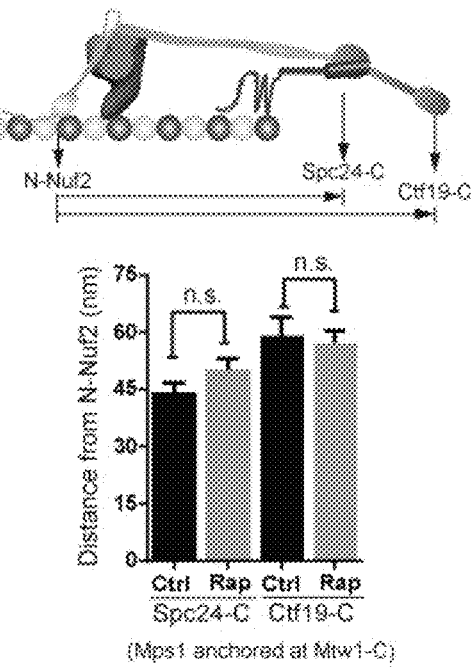
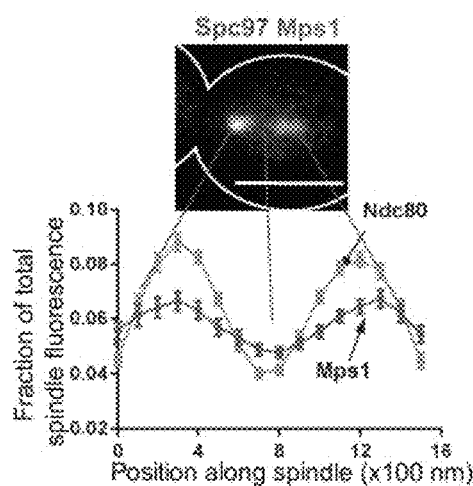
FIG. 3C

FIG. 13B
FIG. 13A
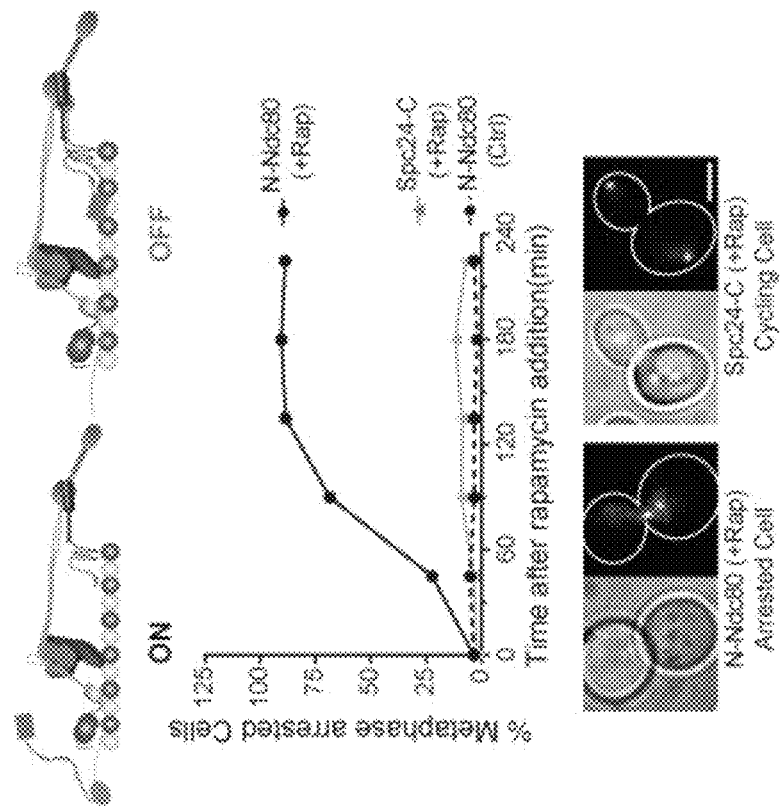
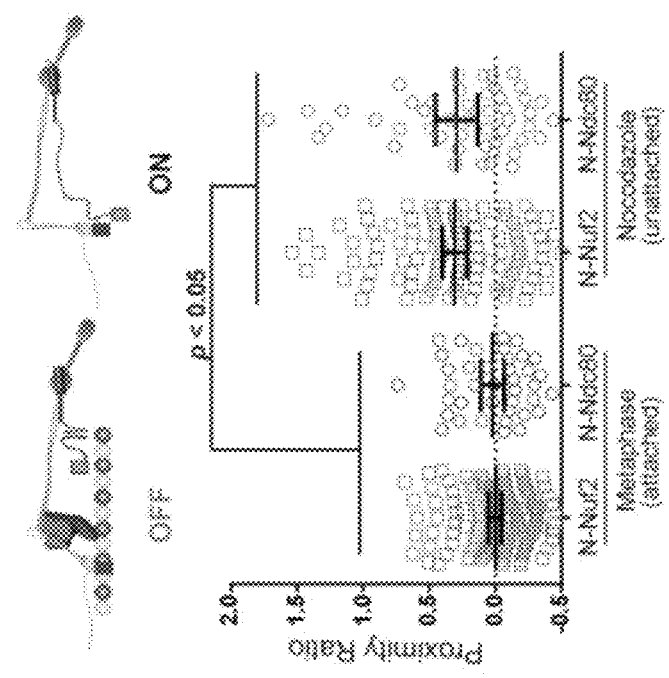

| Protein | % Coverage | | |
|---|---|---|---|
| | Nocodazole | Rapamycin | Rapa. + cross-linking |
| GFP | 77 | 29 | 34 |
| mCherry | 0 | 75 | 45.5 |
| FK506 1A | 72 | 56 | 54 |
| FKBP12 | 2.5 | 7 | 2 |
| FKBP10 | 0 | 24 | 0 |
| KNL1 | 5 | 4 | 4 |
| Mps1 | 0 | 19 | 19 |
| Bub1 | 0 | 15 | 11 |
| Bub3 | 0 | 20 | 29 |
| BubR1 | 0 | 0 | 7 |

FIG. 20A
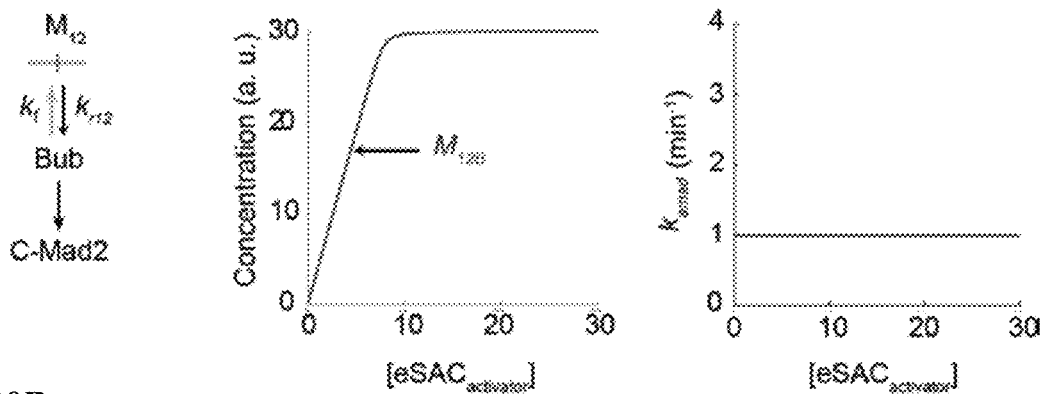
FIG. 20B
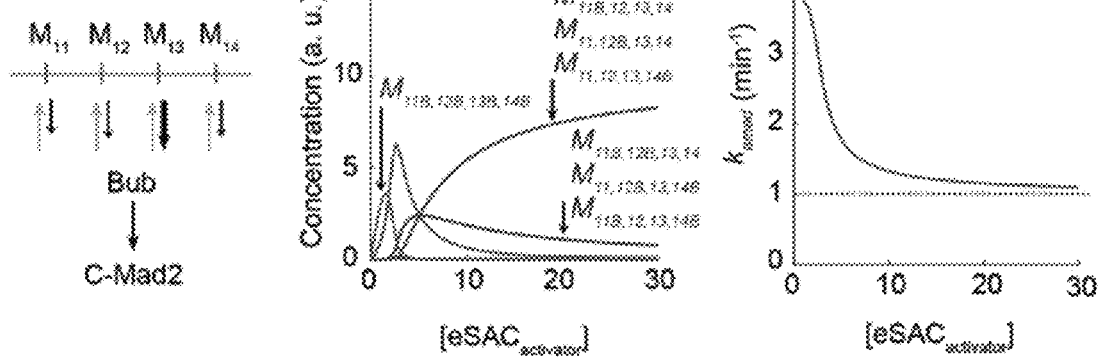
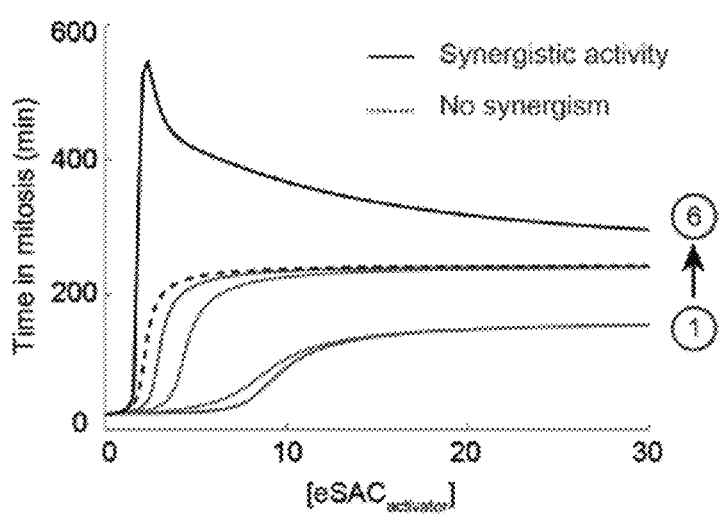
FIG. 20C

FIG. 30A
FIG. 30B
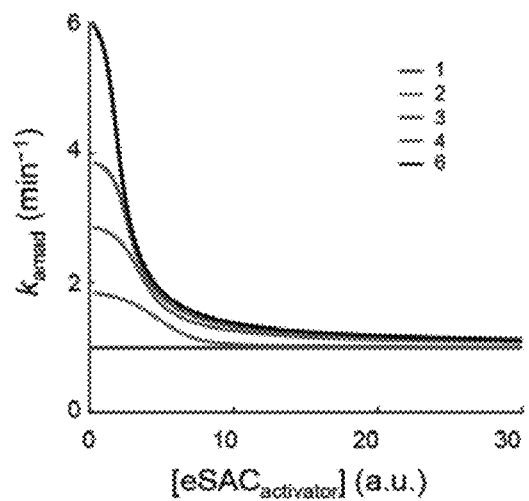
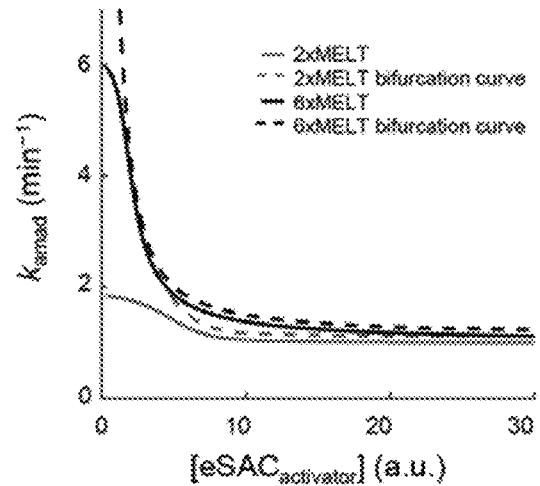
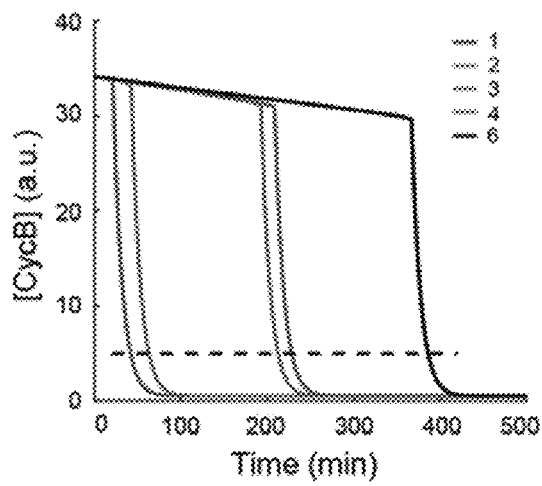
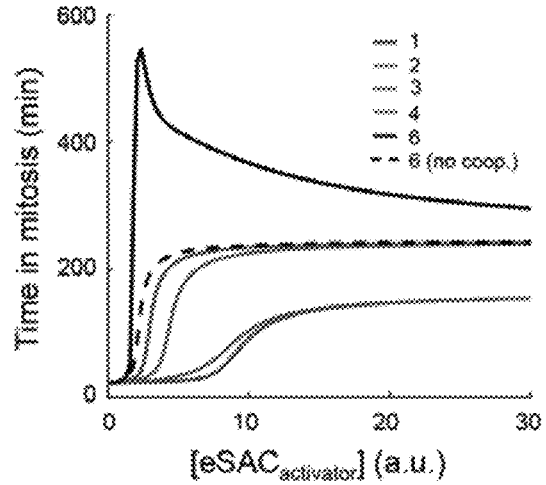
FIG. 30C
FIG. 30D

FIG. 31

| Parameter | Value | Parameter | Value | Parameter | Value |
|---|---|---|---|---|---|
| $k_4$ | 1.02 | $k_{2\_2}$ | $2*k_2$ | $k_{34\_34}$ | $2*k_{34}$ |
| $k_3$ | 1 | $k_{234}$ | $k_2+k_3+k_4$ | $k_{34\_24}$ | $k_{34}+k_{24}$ |
| $k_2$ | 1 | $k_{4\_34}$ | $k_4+k_{34}$ | $k_{34\_23}$ | $k_{34}+k_{23}$ |
| $k_1$ | 1.01 | $k_{4\_24}$ | $k_4+k_{24}$ | $k_{2\_234}$ | $k_2+k_{234}$ |
| $k_{34}$ | $k_3+k_4$ | $k_{4\_23}$ | $k_4+k_{23}$ | $k_{24\_34}$ | $k_{24}+k_{34}$ |
| $k_{24}$ | $k_2+k_4$ | $k_{3\_34}$ | $k_3+k_{34}$ | $k_{24\_24}$ | $2*k_{24}*1.08$ |
| $k_{23}$ | $k_2+k_3$ | $k_{3\_24}$ | $k_3+k_{24}$ | $k_{24\_23}$ | $k_{24}+k_{23}$ |
| $k_{14}$ | $k_1+k_4$ | $k_{3\_23}$ | $k_3+k_{23}$ | $k_{23\_34}$ | $k_{23}+k_{34}$ |
| $k_{13}$ | $k_1+k_3$ | $k_{34\_4}$ | $k_{34}+k_4$ | $k_{23\_24}$ | $k_{23}+k_{24}$ |
| $k_{12}$ | $k_1+k_2$ | $k_{34\_3}$ | $k_{34}+k_3$ | $k_{23\_23}$ | $2*k_{23}$ |
| $k_{123}$ | $k_1+k_2+k_3$ | $k_{34\_2}$ | $k_{34}+k_2$ | $k_{234\_4}$ | $k_{234}+k_4$ |
| $k_{124}$ | $k_1+k_2+k_4$ | $k_{2\_34}$ | $k_2+k_{34}$ | $k_{234\_3}$ | $k_{234}+k_3$ |
| $k_{134}$ | $k_1+k_3+k_4$ | $k_{2\_24}$ | $k_2+k_{24}$ | $k_{234\_2}$ | $k_{234}+k_2$ |
| $k_{1234}$ | $k_1+k_2+k_3+k_4$ | $k_{2\_23}$ | $k_2+k_{23}$ | $k_{34\_234}$ | $k_{34}+k_{234}$ |
| $k_{4\_4}$ | $2*k_4*1.2$ | $k_{24\_4}$ | $k_{24}+k_4$ | $k_{24\_234}$ | $(k_{24}+k_{234})*1.05$ |
| $k_{4\_3}$ | $k_4+k_3$ | $k_{24\_3}$ | $k_{24}+k_3$ | $k_{23\_234}$ | $k_{23}+k_{234}$ |
| $k_{4\_2}$ | $k_4+k_2$ | $k_{24\_2}$ | $k_{24}+k_2$ | $k_{234\_34}$ | $k_{234}+k_{34}$ |
| $k_{3\_4}$ | $k_3+k_4$ | $k_{23\_4}$ | $k_{23}+k_4$ | $k_{234\_24}$ | $(k_{234}+k_{24})*1.05$ |
| $k_{3\_3}$ | $2*k_3$ | $k_{23\_3}$ | $k_{23}+k_3$ | $k_{234\_23}$ | $k_{234}+k_{23}$ |
| $k_{3\_2}$ | $k_3+k_2$ | $k_{23\_2}$ | $k_{23}+k_2$ | $k_{234\_234}$ | $2*k_{234}*1.05$ |
| $k_{2\_4}$ | $k_2+k_4$ | $k_{4\_234}$ | $k_4+k_{234}$ | | |
| $k_{2\_3}$ | $k_2+k_3$ | $k_{3\_234}$ | $k_3+k_{234}$ | | |

SEQUENCE LISTING

```
<160> NUMBER OF SEQ ID NOS: 24

<210> SEQ ID NO 1
<211> LENGTH: 857
<212> TYPE: PRT
<213> ORGANISM: Homo sapiens

<400> SEQUENCE: 1

Met Glu Ser Glu Asp Leu Ser Gly Arg Glu Leu Thr Ile Asp Ser Ile
1               5                   10                  15

Met Asn Lys Val Arg Asp Ile Lys Asn Lys Phe Lys Asn Glu Asp Leu
            20                  25                  30
```

```
Thr Asp Glu Leu Ser Leu Asn Lys Ile Ser Ala Asp Thr Asp Asn
         35                  40                  45

Ser Gly Thr Val Asn Gln Ile Met Met Met Ala Asn Asn Pro Glu Asp
 50                      55                  60

Trp Leu Ser Leu Leu Leu Lys Leu Glu Lys Asn Ser Val Pro Leu Ser
 65                  70                  75                  80

Asp Ala Leu Leu Asn Lys Leu Ile Gly Arg Tyr Ser Gln Ala Ile Glu
                 85                  90                  95

Ala Leu Pro Pro Asp Lys Tyr Gly Gln Asn Glu Ser Phe Ala Arg Ile
             100                 105                 110

Gln Val Arg Phe Ala Glu Leu Lys Ala Ile Gln Glu Pro Asp Asp Ala
         115                 120                 125

Arg Asp Tyr Phe Gln Met Ala Arg Ala Asn Cys Lys Lys Phe Ala Phe
 130                 135                 140

Val His Ile Ser Phe Ala Gln Phe Glu Leu Ser Gln Gly Asn Val Lys
 145                 150                 155                 160

Lys Ser Lys Gln Leu Leu Gln Lys Ala Val Glu Arg Gly Ala Val Pro
                 165                 170                 175

Leu Glu Met Leu Glu Ile Ala Leu Arg Asn Leu Asn Leu Gln Lys Lys
             180                 185                 190

Gln Leu Leu Ser Glu Glu Lys Lys Asn Leu Ser Ala Ser Thr Val
         195                 200                 205

Leu Thr Ala Gln Glu Ser Phe Ser Gly Ser Leu Gly His Leu Gln Asn
 210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                 245                 250                 255

Asn Ser Leu Arg Gln Thr Asn Lys Thr Lys Gln Ser Cys Pro Phe Gly
             260                 265                 270

Arg Val Pro Val Asn Leu Leu Asn Ser Pro Asp Cys Asp Val Lys Thr
         275                 280                 285

Asp Asp Ser Val Val Pro Cys Phe Met Lys Arg Gln Thr Ser Arg Ser
 290                 295                 300

Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
                 325                 330                 335

Glu Pro Leu Val Ser Asp Glu Lys Ser Ser Glu Leu Ile Ile Thr Asp
             340                 345                 350

Ser Ile Thr Leu Lys Asn Lys Thr Glu Ser Ser Leu Leu Ala Lys Leu
         355                 360                 365

Glu Glu Thr Lys Glu Tyr Gln Glu Pro Glu Val Pro Glu Ser Asn Gln
 370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                 405                 410                 415

Asn Thr Glu Gln Lys His Thr Thr Phe Glu Gln Pro Val Phe Ser Val
             420                 425                 430

Ser Lys Gln Ser Pro Pro Ile Ser Thr Ser Lys Trp Phe Asp Pro Lys
         435                 440                 445

Ser Ile Cys Lys Thr Pro Ser Ser Asn Thr Leu Asp Asp Tyr Met Ser
```

```
              450                 455                 460
Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
                500                 505                 510

Ser Ala Asn Glu Cys Ile Ser Val Lys Gly Arg Ile Tyr Ser Ile Leu
                515                 520                 525

Lys Gln Ile Gly Ser Gly Gly Ser Ser Lys Val Phe Gln Val Leu Asn
530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
                580                 585                 590

Ile Thr Asp Gln Tyr Ile Tyr Met Val Met Glu Cys Gly Asn Ile Asp
            595                 600                 605

Leu Asn Ser Trp Leu Lys Lys Lys Ser Ile Asp Pro Trp Glu Arg
            610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
                660                 665                 670

Pro Asp Thr Thr Ser Val Val Lys Asp Ser Gln Val Gly Thr Val Asn
            675                 680                 685

Tyr Met Pro Pro Glu Ala Ile Lys Asp Met Ser Ser Ser Arg Glu Asn
        690                 695                 700

Gly Lys Ser Lys Ser Lys Ile Ser Pro Lys Ser Asp Val Trp Ser Leu
705                 710                 715                 720

Gly Cys Ile Leu Tyr Tyr Met Thr Tyr Gly Lys Thr Pro Phe Gln Gln
                725                 730                 735

Ile Ile Asn Gln Ile Ser Lys Leu His Ala Ile Ile Pro Asn His
            740                 745                 750

Glu Ile Glu Phe Pro Asp Ile Pro Glu Lys Asp Leu Gln Asp Val Leu
            755                 760                 765

Lys Cys Cys Leu Lys Arg Asp Pro Lys Gln Arg Ile Ser Ile Pro Glu
            770                 775                 780

Leu Leu Ala His Pro Tyr Val Gln Ile Gln Thr His Pro Val Asn Gln
785                 790                 795                 800

Met Ala Lys Gly Thr Thr Glu Glu Met Lys Tyr Val Leu Gly Gln Leu
                805                 810                 815

Val Gly Leu Asn Ser Pro Asn Ser Ile Leu Lys Ala Ala Lys Thr Leu
                820                 825                 830

Tyr Glu His Tyr Ser Gly Gly Glu Ser His Asn Ser Ser Ser Ser Lys
                835                 840                 845

Thr Phe Glu Lys Lys Arg Gly Lys Lys
    850                 855
```

<210> SEQ ID NO 2

```
<211> LENGTH: 358
<212> TYPE: PRT
<213> ORGANISM: Homo sapiens

<400> SEQUENCE: 2

Ala Thr Pro Leu Gln Asn Leu Gln Val Leu Ala Ser Ser Ala Asn
1               5                   10                  15

Glu Cys Ile Ser Val Lys Gly Arg Ile Tyr Ser Ile Leu Lys Gln Ile
                20                  25                  30

Gly Ser Gly Gly Ser Ser Lys Val Phe Gln Val Leu Asn Glu Lys Lys
            35                  40                  45

Gln Ile Tyr Ala Ile Lys Tyr Val Asn Leu Glu Glu Ala Asp Asn Gln
50                  55                  60

Thr Leu Asp Ser Tyr Arg Asn Glu Ile Ala Tyr Leu Asn Lys Leu Gln
65                  70                  75                  80

Gln His Ser Asp Lys Ile Ile Arg Leu Tyr Asp Tyr Glu Ile Thr Asp
                85                  90                  95

Gln Tyr Ile Tyr Met Val Met Glu Cys Gly Asn Ile Asp Leu Asn Ser
            100                 105                 110

Trp Leu Lys Lys Lys Ser Ile Asp Pro Trp Glu Arg Lys Ser Tyr
            115                 120                 125

Trp Lys Asn Met Leu Glu Ala Val His Thr Ile His Gln His Gly Ile
        130                 135                 140

Val His Ser Asp Leu Lys Pro Ala Asn Phe Leu Ile Val Asp Gly Met
145                 150                 155                 160

Leu Lys Leu Ile Asp Phe Gly Ile Ala Asn Gln Met Gln Pro Asp Thr
                165                 170                 175

Thr Ser Val Val Lys Asp Ser Gln Val Gly Thr Val Asn Tyr Met Pro
            180                 185                 190

Pro Glu Ala Ile Lys Asp Met Ser Ser Ser Arg Glu Asn Gly Lys Ser
        195                 200                 205

Lys Ser Lys Ile Ser Pro Lys Ser Asp Val Trp Ser Leu Gly Cys Ile
210                 215                 220

Leu Tyr Tyr Met Thr Tyr Gly Lys Thr Pro Phe Gln Gln Ile Ile Asn
225                 230                 235                 240

Gln Ile Ser Lys Leu His Ala Ile Ile Asp Pro Asn His Glu Ile Glu
                245                 250                 255

Phe Pro Asp Ile Pro Glu Lys Asp Leu Gln Asp Val Leu Lys Cys Cys
            260                 265                 270

Leu Lys Arg Asp Pro Lys Gln Arg Ile Ser Ile Pro Glu Leu Leu Ala
        275                 280                 285

His Pro Tyr Val Gln Ile Gln Thr His Pro Val Asn Gln Met Ala Lys
290                 295                 300

Gly Thr Thr Glu Glu Met Lys Tyr Val Leu Gly Gln Leu Val Gly Leu
305                 310                 315                 320

Asn Ser Pro Asn Ser Ile Leu Lys Ala Ala Lys Thr Leu Tyr Glu His
                325                 330                 335

Tyr Ser Gly Gly Glu Ser His Asn Ser Ser Ser Lys Thr Phe Glu
            340                 345                 350

Lys Lys Arg Gly Lys Lys
        355

<210> SEQ ID NO 3
<211> LENGTH: 358
<212> TYPE: PRT
```

<213> ORGANISM: Artificial sequence
<220> FEATURE:
<223> OTHER INFORMATION: Synthetic peptide

<400> SEQUENCE: 3

```
Ala Thr Pro Leu Gln Asn Leu Gln Val Leu Ala Ser Ser Ala Asn
1               5                   10                  15

Glu Cys Ile Ser Val Lys Gly Arg Ile Tyr Ser Ile Leu Lys Gln Ile
                20                  25                  30

Gly Ser Gly Gly Ser Ser Lys Val Phe Gln Val Leu Asn Glu Lys Lys
            35                  40                  45

Gln Ile Tyr Ala Ile Lys Tyr Val Asn Leu Glu Glu Ala Asp Asn Gln
50                  55                  60

Thr Leu Asp Ser Tyr Arg Asn Glu Ile Ala Tyr Leu Asn Lys Leu Gln
65                  70                  75                  80

Gln His Ser Asp Lys Ile Ile Arg Leu Tyr Asp Tyr Glu Ile Thr Asp
                85                  90                  95

Gln Tyr Ile Tyr Met Val Ala Glu Cys Gly Asn Ile Asp Leu Asn Ser
            100                 105                 110

Trp Leu Lys Lys Lys Ser Ile Asp Pro Trp Glu Arg Lys Ser Tyr
        115                 120                 125

Trp Lys Asn Met Leu Glu Ala Val His Thr Ile His Gln His Gly Ile
    130                 135                 140

Val His Ser Asp Leu Lys Pro Ala Asn Phe Leu Ile Val Asp Gly Met
145                 150                 155                 160

Leu Lys Leu Ile Asp Phe Gly Ile Ala Asn Gln Met Gln Pro Asp Thr
                165                 170                 175

Thr Ser Val Val Lys Asp Ser Gln Val Gly Thr Val Asn Tyr Met Pro
            180                 185                 190

Pro Glu Ala Ile Lys Asp Met Ser Ser Ser Arg Glu Asn Gly Lys Ser
        195                 200                 205

Lys Ser Lys Ile Ser Pro Lys Ser Asp Val Trp Ser Leu Gly Cys Ile
    210                 215                 220

Leu Tyr Tyr Met Thr Tyr Gly Lys Thr Pro Phe Gln Gln Ile Ile Asn
225                 230                 235                 240

Gln Ile Ser Lys Leu His Ala Ile Ile Asp Pro Asn His Glu Ile Glu
                245                 250                 255

Phe Pro Asp Ile Pro Glu Lys Asp Leu Gln Asp Val Leu Lys Cys Cys
            260                 265                 270

Leu Lys Arg Asp Pro Lys Gln Arg Ile Ser Ile Pro Glu Leu Leu Ala
        275                 280                 285

His Pro Tyr Val Gln Ile Gln Thr His Pro Val Asn Gln Met Ala Lys
    290                 295                 300

Gly Thr Thr Glu Glu Met Lys Tyr Val Leu Gly Gln Leu Val Gly Leu
305                 310                 315                 320

Asn Ser Pro Asn Ser Ile Leu Lys Ala Ala Lys Thr Leu Tyr Glu His
                325                 330                 335

Tyr Ser Gly Gly Glu Ser His Asn Ser Ser Ser Lys Thr Phe Glu
            340                 345                 350

Lys Lys Arg Gly Lys Lys
        355
```

<210> SEQ ID NO 4
<211> LENGTH: 2342
<212> TYPE: PRT

<213> ORGANISM: Homo sapiens

<400> SEQUENCE: 4

```
Met Asp Gly Val Ser Ser Glu Ala Asn Glu Asn Asp Asn Ile Glu
1               5                   10                  15

Arg Pro Val Arg Arg Arg His Ser Ser Ile Leu Lys Pro Pro Arg Ser
            20                  25                  30

Pro Leu Gln Asp Leu Arg Gly Gly Asn Glu Arg Val Gln Glu Ser Asn
        35                  40                  45

Ala Leu Arg Asn Lys Lys Asn Ser Arg Arg Val Ser Phe Ala Asp Thr
    50                  55                  60

Ile Lys Val Phe Gln Thr Glu Ser His Met Lys Ile Val Arg Lys Ser
65                  70                  75                  80

Glu Met Glu Gly Cys Ser Ala Met Val Pro Ser Gln Leu Gln Leu Leu
                85                  90                  95

Pro Pro Gly Phe Lys Arg Phe Ser Cys Leu Ser Leu Pro Glu Thr Glu
            100                 105                 110

Thr Gly Glu Asn Leu Leu Leu Ile Gln Asn Lys Lys Leu Glu Asp Asn
        115                 120                 125

Tyr Cys Glu Ile Thr Gly Met Asn Thr Leu Leu Ser Ala Pro Ile His
    130                 135                 140

Thr Gln Met Gln Gln Lys Glu Phe Ser Ile Ile Glu His Thr Arg Glu
145                 150                 155                 160

Arg Lys His Ala Asn Asp Gln Thr Val Ile Phe Ser Asp Glu Asn Gln
                165                 170                 175

Met Asp Leu Thr Ser Ser His Thr Val Met Ile Thr Lys Gly Leu Leu
            180                 185                 190

Asp Asn Pro Ile Ser Glu Lys Ser Thr Lys Ile Asp Thr Thr Ser Phe
        195                 200                 205

Leu Ala Asn Leu Lys Leu His Thr Glu Asp Ser Arg Met Lys Lys Glu
    210                 215                 220

Val Asn Phe Ser Val Asp Gln Asn Thr Ser Ser Glu Asn Lys Ile Asp
225                 230                 235                 240

Phe Asn Asp Phe Ile Lys Arg Leu Lys Thr Gly Lys Cys Ser Ala Phe
                245                 250                 255

Pro Asp Val Pro Asp Lys Glu Asn Phe Glu Ile Pro Ile Tyr Ser Lys
            260                 265                 270

Glu Pro Asn Ser Ala Ser Ser Thr His Gln Met His Val Ser Leu Lys
        275                 280                 285

Glu Asp Glu Asn Asn Ser Asn Ile Thr Arg Leu Phe Arg Glu Lys Asp
    290                 295                 300

Asp Gly Met Asn Phe Thr Gln Cys His Thr Ala Asn Ile Gln Thr Leu
305                 310                 315                 320

Ile Pro Thr Ser Ser Glu Thr Asn Ser Arg Glu Ser Lys Gly Asn Asp
                325                 330                 335

Ile Thr Ile Tyr Gly Asn Asp Phe Met Asp Leu Thr Phe Asn His Thr
            340                 345                 350

Leu Gln Ile Leu Pro Ala Thr Gly Asn Phe Ser Glu Ile Glu Asn Gln
        355                 360                 365

Thr Gln Asn Ala Met Asp Val Thr Thr Gly Tyr Gly Thr Lys Ala Ser
    370                 375                 380

Gly Asn Lys Thr Val Phe Lys Ser Lys Gln Asn Thr Ala Phe Gln Asp
385                 390                 395                 400
```

```
Leu Ser Ile Asn Ser Ala Asp Lys Ile His Ile Thr Arg Ser His Ile
                405                 410                 415

Met Gly Ala Glu Thr His Ile Val Ser Gln Thr Cys Asn Gln Asp Ala
            420                 425                 430

Arg Ile Leu Ala Met Thr Pro Glu Ser Ile Tyr Ser Asn Pro Ser Ile
        435                 440                 445

Gln Gly Cys Lys Thr Val Phe Tyr Ser Ser Cys Asn Asp Ala Met Glu
    450                 455                 460

Met Thr Lys Cys Leu Ser Asn Met Arg Glu Lys Asn Leu Leu Lys
465                 470                 475                 480

His Asp Ser Asn Tyr Ala Lys Met Tyr Cys Asn Pro Asp Ala Met Ser
                485                 490                 495

Ser Leu Thr Glu Lys Thr Ile Tyr Ser Gly Glu Asn Met Asp Ile
            500                 505                 510

Thr Lys Ser His Thr Val Ala Ile Asp Asn Gln Ile Phe Lys Gln Asp
        515                 520                 525

Gln Ser Asn Val Gln Ile Ala Ala Pro Thr Pro Glu Lys Glu Met
    530                 535                 540

Met Leu Gln Asn Leu Met Thr Thr Ser Glu Asp Gly Lys Met Asn Val
545                 550                 555                 560

Asn Cys Asn Ser Val Pro His Val Ser Lys Glu Arg Ile Gln Gln Ser
                565                 570                 575

Leu Ser Asn Pro Leu Ser Ile Ser Leu Thr Asp Arg Lys Thr Glu Leu
            580                 585                 590

Leu Ser Gly Glu Asn Met Asp Leu Thr Glu Ser His Thr Ser Asn Leu
        595                 600                 605

Gly Ser Gln Val Pro Leu Ala Ala Tyr Asn Leu Ala Pro Glu Ser Thr
    610                 615                 620

Ser Glu Ser His Ser Gln Ser Lys Ser Ser Asp Glu Cys Glu Glu
625                 630                 635                 640

Ile Thr Lys Ser Arg Asn Glu Pro Phe Gln Arg Ser Asp Ile Ile Ala
                645                 650                 655

Lys Asn Ser Leu Thr Asp Thr Trp Asn Lys Asp Lys Asp Trp Val Leu
            660                 665                 670

Lys Ile Leu Pro Tyr Leu Asp Lys Asp Ser Pro Gln Ser Ala Asp Cys
        675                 680                 685

Asn Gln Glu Ile Ala Thr Ser His Asn Ile Val Tyr Cys Gly Gly Val
    690                 695                 700

Leu Asp Lys Gln Ile Thr Asn Arg Asn Thr Val Ser Trp Glu Gln Ser
705                 710                 715                 720

Leu Phe Ser Thr Thr Lys Pro Leu Phe Ser Ser Gly Gln Phe Ser Met
                725                 730                 735

Lys Asn His Asp Thr Ala Ile Ser Ser His Thr Val Lys Ser Val Leu
            740                 745                 750

Gly Gln Asn Ser Lys Leu Ala Glu Pro Leu Arg Lys Ser Leu Ser Asn
        755                 760                 765

Pro Thr Pro Asp Tyr Cys His Asp Lys Met Ile Ile Cys Ser Glu Glu
    770                 775                 780

Glu Gln Asn Met Asp Leu Thr Lys Ser His Thr Val Val Ile Gly Phe
785                 790                 795                 800

Gly Pro Ser Glu Leu Gln Glu Leu Gly Lys Thr Asn Leu Glu His Thr
                805                 810                 815

Thr Gly Gln Leu Thr Thr Met Asn Arg Gln Ile Ala Val Lys Val Glu
```

```
                820                 825                 830
Lys Cys Gly Lys Ser Pro Ile Glu Lys Ser Gly Val Leu Lys Ser Asn
            835                 840                 845
Cys Ile Met Asp Val Leu Glu Asp Glu Ser Val Gln Lys Pro Lys Phe
850                 855                 860
Pro Lys Glu Lys Gln Asn Val Lys Ile Trp Gly Arg Lys Ser Val Gly
865                 870                 875                 880
Gly Pro Lys Ile Asp Lys Thr Ile Val Phe Ser Glu Asp Lys Asn
                885                 890                 895
Asp Met Asp Ile Thr Lys Ser Tyr Thr Ile Glu Ile Asn His Arg Pro
            900                 905                 910
Leu Leu Glu Lys Arg Asp Cys His Leu Val Pro Leu Ala Gly Thr Ser
            915                 920                 925
Glu Thr Ile Leu Tyr Thr Cys Arg Gln Asp Asp Met Glu Ile Thr Arg
            930                 935                 940
Ser His Thr Thr Ala Leu Glu Cys Lys Thr Val Ser Pro Asp Glu Ile
945                 950                 955                 960
Thr Thr Arg Pro Met Asp Lys Thr Val Val Phe Val Asp Asn His Val
                965                 970                 975
Glu Leu Glu Met Thr Glu Ser His Thr Val Phe Ile Asp Tyr Gln Glu
            980                 985                 990
Lys Glu Arg Thr Asp Arg Pro Asn Phe Glu Leu Ser Gln Arg Lys Ser
            995                 1000                1005
Leu Gly Thr Pro Thr Val Ile Cys Thr Pro Thr Glu Glu Ser Val
    1010                1015                1020
Phe Phe Pro Gly Asn Gly Glu Ser Asp Arg Leu Val Ala Asn Asp
    1025                1030                1035
Ser Gln Leu Thr Pro Leu Glu Glu Trp Ser Asn Asn Arg Gly Pro
    1040                1045                1050
Val Glu Val Ala Asp Asn Met Glu Leu Ser Lys Ser Ala Thr Cys
    1055                1060                1065
Lys Asn Ile Lys Asp Val Gln Ser Pro Gly Phe Leu Asn Glu Pro
    1070                1075                1080
Leu Ser Ser Lys Ser Gln Arg Arg Lys Ser Leu Lys Leu Lys Asn
    1085                1090                1095
Asp Lys Thr Ile Val Phe Ser Glu Asn His Lys Asn Asp Met Asp
    1100                1105                1110
Ile Thr Gln Ser Cys Met Val Glu Ile Asp Asn Glu Ser Ala Leu
    1115                1120                1125
Glu Asp Lys Glu Asp Phe His Leu Ala Gly Ala Ser Lys Thr Ile
    1130                1135                1140
Leu Tyr Ser Cys Gly Gln Asp Asp Met Glu Ile Thr Arg Ser His
    1145                1150                1155
Thr Thr Ala Leu Glu Cys Lys Thr Leu Leu Pro Asn Glu Ile Ala
    1160                1165                1170
Ile Arg Pro Met Asp Lys Thr Val Leu Phe Thr Asp Asn Tyr Ser
    1175                1180                1185
Asp Leu Glu Val Thr Asp Ser His Thr Val Phe Ile Asp Cys Gln
    1190                1195                1200
Ala Thr Glu Lys Ile Leu Glu Glu Asn Pro Lys Phe Gly Ile Gly
    1205                1210                1215
Lys Gly Lys Asn Leu Gly Val Ser Phe Pro Lys Asp Asn Ser Cys
    1220                1225                1230
```

-continued

```
Val Gln Glu Ile Ala Glu Lys Gln Ala Leu Ala Val Gly Asn Lys
    1235                1240                1245

Ile Val Leu His Thr Glu Gln Lys Gln Leu Phe Ala Ala Thr
    1250                1255                1260

Asn Arg Thr Thr Asn Glu Ile Ile Lys Phe His Ser Ala Ala Met
    1265                1270                1275

Asp Glu Lys Val Ile Gly Lys Val Val Asp Gln Ala Cys Thr Leu
    1280                1285                1290

Glu Lys Ala Gln Val Glu Ser Cys Gln Leu Asn Asn Arg Asp Arg
    1295                1300                1305

Arg Asn Val Asp Phe Thr Ser Ser His Ala Thr Ala Val Cys Gly
    1310                1315                1320

Ser Ser Asp Asn Tyr Ser Cys Leu Pro Asn Val Ile Ser Cys Thr
    1325                1330                1335

Asp Asn Leu Glu Gly Ser Ala Met Leu Leu Cys Asp Lys Asp Glu
    1340                1345                1350

Glu Lys Ala Asn Tyr Cys Pro Val Gln Asn Asp Leu Ala Tyr Ala
    1355                1360                1365

Asn Asp Phe Ala Ser Glu Tyr Tyr Leu Glu Ser Glu Gly Gln Pro
    1370                1375                1380

Leu Ser Ala Pro Cys Pro Leu Leu Glu Lys Glu Glu Val Ile Gln
    1385                1390                1395

Thr Ser Thr Lys Gly Gln Leu Asp Cys Val Ile Thr Leu His Lys
    1400                1405                1410

Asp Gln Asp Leu Ile Lys Asp Pro Arg Asn Leu Leu Ala Asn Gln
    1415                1420                1425

Thr Leu Val Tyr Ser Gln Asp Leu Gly Glu Met Thr Lys Leu Asn
    1430                1435                1440

Ser Lys Arg Val Ser Phe Lys Leu Pro Lys Asp Gln Met Lys Val
    1445                1450                1455

Tyr Val Asp Asp Ile Tyr Val Ile Pro Gln Pro His Phe Ser Thr
    1460                1465                1470

Asp Gln Pro Pro Leu Pro Lys Lys Gly Gln Ser Ser Ile Asn Lys
    1475                1480                1485

Glu Glu Val Ile Leu Ser Lys Ala Gly Asn Lys Ser Leu Asn Ile
    1490                1495                1500

Ile Glu Asn Ser Ser Ala Pro Ile Cys Glu Asn Lys Pro Lys Ile
    1505                1510                1515

Leu Asn Ser Glu Glu Trp Phe Ala Ala Ala Cys Lys Lys Glu Leu
    1520                1525                1530

Lys Glu Asn Ile Gln Thr Thr Asn Tyr Asn Thr Ala Leu Asp Phe
    1535                1540                1545

His Ser Asn Ser Asp Val Thr Lys Gln Val Ile Gln Thr His Val
    1550                1555                1560

Asn Ala Gly Glu Ala Pro Asp Pro Val Ile Thr Ser Asn Val Pro
    1565                1570                1575

Cys Phe His Ser Ile Lys Pro Asn Leu Asn Asn Leu Asn Gly Lys
    1580                1585                1590

Thr Gly Glu Phe Leu Ala Phe Gln Thr Val His Leu Pro Pro Leu
    1595                1600                1605

Pro Glu Gln Leu Leu Glu Leu Gly Asn Lys Ala His Asn Asp Met
    1610                1615                1620
```

-continued

His Ile Val Gln Ala Thr Glu Ile His Asn Ile Asn Ile Ile Ser
1625                1630                1635

Ser Asn Ala Lys Asp Ser Arg Asp Glu Glu Asn Lys Lys Ser His
1640                1645                1650

Asn Gly Ala Glu Thr Thr Ser Leu Pro Pro Lys Thr Val Phe Lys
1655                1660                1665

Asp Lys Val Arg Arg Cys Ser Leu Gly Ile Phe Leu Pro Arg Leu
1670                1675                1680

Pro Asn Lys Arg Asn Cys Ser Val Thr Gly Ile Asp Asp Leu Glu
1685                1690                1695

Gln Ile Pro Ala Asp Thr Thr Asp Ile Asn His Leu Glu Thr Gln
1700                1705                1710

Pro Val Ser Ser Lys Asp Ser Gly Ile Gly Ser Val Ala Gly Lys
1715                1720                1725

Leu Asn Leu Ser Pro Ser Gln Tyr Ile Asn Glu Glu Asn Leu Pro
1730                1735                1740

Val Tyr Pro Asp Glu Ile Asn Ser Ser Asp Ser Ile Asn Ile Glu
1745                1750                1755

Thr Glu Glu Lys Ala Leu Ile Glu Thr Tyr Gln Lys Glu Ile Ser
1760                1765                1770

Pro Tyr Glu Asn Lys Met Gly Lys Thr Cys Asn Ser Gln Lys Arg
1775                1780                1785

Thr Trp Val Gln Glu Glu Glu Asp Ile His Lys Glu Lys Lys Ile
1790                1795                1800

Arg Lys Asn Glu Ile Lys Phe Ser Asp Thr Thr Gln Asp Arg Glu
1805                1810                1815

Ile Phe Asp His His Thr Glu Glu Asp Ile Asp Lys Ser Ala Asn
1820                1825                1830

Ser Val Leu Ile Lys Asn Leu Ser Arg Thr Pro Ser Ser Cys Ser
1835                1840                1845

Ser Ser Leu Asp Ser Ile Lys Ala Asp Gly Thr Ser Leu Asp Phe
1850                1855                1860

Ser Thr Tyr Arg Ser Ser Gln Met Glu Ser Gln Phe Leu Arg Asp
1865                1870                1875

Thr Ile Cys Glu Glu Ser Leu Arg Glu Lys Leu Gln Asp Gly Arg
1880                1885                1890

Ile Thr Ile Arg Glu Phe Phe Ile Leu Leu Gln Val His Ile Leu
1895                1900                1905

Ile Gln Lys Pro Arg Gln Ser Asn Leu Pro Gly Asn Phe Thr Val
1910                1915                1920

Asn Thr Pro Pro Thr Pro Glu Asp Leu Met Leu Ser Gln Tyr Val
1925                1930                1935

Tyr Arg Pro Lys Ile Gln Ile Tyr Arg Glu Asp Cys Glu Ala Arg
1940                1945                1950

Arg Gln Lys Ile Glu Glu Leu Lys Leu Ser Ala Ser Asn Gln Asp
1955                1960                1965

Lys Leu Leu Val Asp Ile Asn Lys Asn Leu Trp Glu Lys Met Arg
1970                1975                1980

His Cys Ser Asp Lys Glu Leu Lys Ala Phe Gly Ile Tyr Leu Asn
1985                1990                1995

Lys Ile Lys Ser Cys Phe Thr Lys Met Thr Lys Val Phe Thr His
2000                2005                2010

Gln Gly Lys Val Ala Leu Tyr Gly Lys Leu Val Gln Ser Ala Gln

Asn Glu Arg Glu Lys Leu Gln Ile Lys Ile Asp Glu Met Asp Lys
            2030                2035                2040

Ile Leu Lys Lys Ile Asp Asn Cys Leu Thr Glu Met Glu Thr Glu
        2045                2050                2055

Thr Lys Asn Leu Glu Asp Glu Glu Lys Asn Asn Pro Val Glu Glu
    2060                2065                2070

Trp Asp Ser Glu Met Arg Ala Ala Glu Lys Glu Leu Glu Gln Leu
2075                2080                2085

Lys Thr Glu Glu Glu Glu Leu Gln Arg Asn Leu Leu Glu Leu Glu
        2090                2095                2100

Val Gln Lys Glu Gln Thr Leu Ala Gln Ile Asp Phe Met Gln Lys
    2105                2110                2115

Gln Arg Asn Arg Thr Glu Glu Leu Leu Asp Gln Leu Ser Leu Ser
2120                2125                2130

Glu Trp Asp Val Val Glu Trp Ser Asp Asp Gln Ala Val Phe Thr
        2135                2140                2145

Phe Val Tyr Asp Thr Ile Gln Leu Thr Ile Thr Phe Glu Glu Ser
    2150                2155                2160

Val Val Gly Phe Pro Phe Leu Asp Lys Arg Tyr Arg Lys Ile Val
2165                2170                2175

Asp Val Asn Phe Gln Ser Leu Leu Asp Glu Asp Gln Ala Pro Pro
        2180                2185                2190

Ser Ser Leu Leu Val His Lys Leu Ile Phe Gln Tyr Val Glu Glu
    2195                2200                2205

Lys Glu Ser Trp Lys Lys Thr Cys Thr Thr Gln His Gln Leu Pro
2210                2215                2220

Lys Met Leu Glu Glu Phe Ser Leu Val Val His His Cys Arg Leu
        2225                2230                2235

Leu Gly Glu Glu Ile Glu Tyr Leu Lys Arg Trp Gly Pro Asn Tyr
    2240                2245                2250

Asn Leu Met Asn Ile Asp Ile Asn Asn Asn Glu Leu Arg Leu Leu
2255                2260                2265

Phe Ser Ser Ala Ala Phe Ala Lys Phe Glu Ile Thr Leu Phe
        2270                2275                2280

Leu Ser Ala Tyr Tyr Pro Ser Val Pro Leu Pro Ser Thr Ile Gln
    2285                2290                2295

Asn His Val Gly Asn Thr Ser Gln Asp Asp Ile Ala Thr Ile Leu
2300                2305                2310

Ser Lys Val Pro Leu Glu Asn Asn Tyr Leu Lys Asn Val Val Lys
        2315                2320                2325

Gln Ile Tyr Gln Asp Leu Phe Gln Asp Cys His Phe Tyr His
    2330                2335                2340

<210> SEQ ID NO 5
<211> LENGTH: 521
<212> TYPE: PRT
<213> ORGANISM: Homo sapiens

<400> SEQUENCE: 5

Met Asp Gly Val Ser Ser Glu Ala Asn Glu Glu Asn Asp Asn Ile Glu
1               5                   10                  15

Arg Pro Val Arg Arg His Ser Ser Ile Leu Lys Pro Pro Arg Ser
            20                  25                  30

```
Pro Leu Gln Asp Leu Arg Gly Gly Asn Glu Arg Val Gln Glu Ser Asn
             35                  40                  45
Ala Leu Arg Asn Lys Lys Asn Ser Arg Arg Val Ser Phe Ala Asp Thr
 50                  55                  60
Ile Lys Val Phe Gln Thr Glu Ser His Met Lys Ile Val Arg Lys Ser
 65                  70                  75                  80
Glu Met Glu Gly Cys Ser Leu Asp Met Gly Pro Ser Glu Leu Gln Glu
                 85                  90                  95
Leu Gly Lys Thr Asn Leu Glu His Thr Thr Gly Gln Leu Thr Thr Met
                100                 105                 110
Asn Arg Gln Ile Ala Val Lys Val Glu Lys Cys Gly Lys Ser Pro Ile
            115                 120                 125
Glu Lys Ser Gly Val Leu Lys Ser Asn Cys Ile Met Asp Val Leu Glu
        130                 135                 140
Asp Glu Ser Val Gln Lys Pro Lys Phe Pro Lys Glu Lys Gln Asn Val
145                 150                 155                 160
Lys Ile Trp Gly Arg Lys Ser Val Gly Gly Pro Lys Ile Asp Lys Thr
                165                 170                 175
Ile Val Phe Ser Glu Asp Asp Lys Asn Asp Met Asp Ile Thr Lys Ser
            180                 185                 190
Tyr Thr Ile Glu Ile Asn His Arg Pro Leu Leu Glu Lys Arg Asp Cys
        195                 200                 205
His Leu Val Pro Leu Ala Gly Thr Ser Glu Thr Ile Leu Tyr Thr Cys
210                 215                 220
Gly Gln Asp Asp Met Glu Ile Thr Arg Ser His Thr Thr Ala Leu Glu
225                 230                 235                 240
Cys Lys Thr Val Ser Pro Asp Glu Ile Thr Thr Arg Pro Met Asp Lys
                245                 250                 255
Thr Val Val Phe Val Asp Asn His Val Glu Leu Glu Met Thr Glu Ser
            260                 265                 270
His Thr Val Phe Ile Asp Tyr Gln Glu Lys Glu Arg Thr Asp Arg Pro
        275                 280                 285
Asn Phe Glu Leu Ser Gln Arg Lys Ser Leu Gly Thr Pro Thr Val Leu
290                 295                 300
Asp Gly Pro Ser Glu Leu Gln Glu Leu Gly Lys Thr Asn Leu Glu His
305                 310                 315                 320
Thr Thr Gly Gln Leu Thr Thr Met Asn Arg Gln Ile Ala Val Lys Val
                325                 330                 335
Glu Lys Cys Gly Lys Ser Pro Ile Glu Lys Ser Gly Val Leu Lys Ser
            340                 345                 350
Asn Cys Ile Met Asp Val Leu Glu Asp Glu Ser Val Gln Lys Pro Lys
        355                 360                 365
Phe Pro Lys Glu Lys Gln Asn Val Lys Ile Trp Gly Arg Lys Ser Val
370                 375                 380
Gly Gly Pro Lys Ile Asp Lys Thr Ile Val Phe Ser Glu Asp Asp Lys
385                 390                 395                 400
Asn Asp Met Asp Ile Thr Lys Ser Tyr Thr Ile Glu Ile Asn His Arg
                405                 410                 415
Pro Leu Leu Glu Lys Arg Asp Cys His Leu Val Pro Leu Ala Gly Thr
            420                 425                 430
Ser Glu Thr Ile Leu Tyr Thr Cys Gly Gln Asp Asp Met Glu Ile Thr
        435                 440                 445
Arg Ser His Thr Thr Ala Leu Glu Cys Lys Thr Val Ser Pro Asp Glu
```

```
                    450                 455                 460
Ile Thr Thr Arg Pro Met Asp Lys Thr Val Val Phe Val Asp Asn His
465                 470                 475                 480

Val Glu Leu Glu Met Thr Glu Ser His Thr Val Phe Ile Asp Tyr Gln
                485                 490                 495

Glu Lys Glu Arg Thr Asp Arg Pro Asn Phe Glu Leu Ser Gln Arg Lys
                500                 505                 510

Ser Leu Gly Thr Pro Thr Val Leu Glu
            515                 520

<210> SEQ ID NO 6

<400> SEQUENCE: 6

000

<210> SEQ ID NO 7
<211> LENGTH: 917
<212> TYPE: PRT
<213> ORGANISM: Saccharomyces cerevisiae

<400> SEQUENCE: 7

Met Asn Val Asp Glu Arg Ser Arg Ile Gly Gly Arg Glu Lys Asp Ala
1               5                   10                  15

Gly Pro Gly Lys Gly Ile Leu Lys Gln Asn Gln Ser Ser Gln Met Thr
            20                  25                  30

Ser Ser Phe Leu Glu Asn Pro Gly Val Arg Ile Pro Thr Arg Ile Ile
        35                  40                  45

Thr Lys Lys Glu Val Leu Asp Gly Ser Asn Thr Thr Ser Arg Ile Asn
    50                  55                  60

Thr Ser Asn Leu Gln Ser Met Val Lys Arg Arg Val Ser Phe Ala Pro
65                  70                  75                  80

Asp Val Thr Leu His Ser Phe Thr Phe Val Pro Glu Gln Asn Asn Glu
                85                  90                  95

Ile Lys Glu Pro Arg Arg Arg Lys Thr Ser Thr Asn Ser Pro Thr Lys
            100                 105                 110

Ile Ser Ser Gln Glu Glu Pro Leu Val Thr Ser Thr Gln Ile Asp Asp
        115                 120                 125

Ala Arg Thr Glu Glu Lys Thr Ala Ala Glu Asp Pro Asp Thr Ser
    130                 135                 140

Gly Met Glu Leu Thr Glu Pro Ile Val Ala Thr Ser Asp Ser Asn Lys
145                 150                 155                 160

Ala Ser Gln His Asp Pro Thr Ser Met Glu Met Thr Glu Val Phe Pro
                165                 170                 175

Arg Ser Ile Arg Gln Lys Asn Pro Asp Val Glu Gly Glu Ser Ile Glu
            180                 185                 190

Ser Ser Gln Gln Ile Asp Asp Val Glu Ala Val Arg Glu Glu Thr Met
        195                 200                 205

Glu Leu Thr Ala Ile His Asn Val His Asp Tyr Asp Ser Ile Ser Glu
    210                 215                 220

Asp Thr Val Glu Gly Glu Pro Ile Asp Leu Thr Glu Tyr Glu Ser Lys
225                 230                 235                 240

Pro Tyr Val Pro Asn Ser Val Ser Arg Ser Thr Gly Lys Ser Ser Asp
                245                 250                 255

Tyr Ser Val Glu Arg Ser Asn Asp Lys Ser Asp Leu Ser Lys Ser Glu
            260                 265                 270
```

```
Asn Lys Thr Asn Ser Ser Gln Pro Met Glu Ile Thr Asp Ile Phe His
        275                 280                 285

Ala Asp Pro Gln Asn Pro Met Gly Leu His Ser Asp Asn Asn Ile Asn
    290                 295                 300

Asp Asp Gly Asn Glu Met Glu Leu Thr Gln Ile Gln Thr Asn Phe Asp
305                 310                 315                 320

Arg Asp Asn His His Ile Asp Glu Ser Ser Glu Lys His Ala Phe
                325                 330                 335

Ser Ser Asn Lys Arg Arg Lys Leu Asp Thr Val Ser Asp Tyr Ala Ala
        340                 345                 350

Ser Val Thr Thr Pro Val Lys Glu Ala Lys Asp Thr Ser Gly Glu Asp
        355                 360                 365

Asn Asp Gly Asp Leu Glu Met Met Glu Lys Met Ser Pro Ile Thr Phe
    370                 375                 380

Ser Asp Val Asp Asn Lys Ile Gly Thr Arg Ser Asn Asp Val Phe Thr
385                 390                 395                 400

Ile Glu Pro Gly Thr Glu Asp Thr Gly Met Gln Thr Ala Thr Asp Asp
                405                 410                 415

Glu Glu Asp Gly Glu Asn Val Asp Asp Asn Gly Asn Lys Ile Val Glu
            420                 425                 430

Lys Thr Arg Leu Pro Glu Ile Asp Lys Glu Gly Gln Ser Gly Ile Ala
        435                 440                 445

Leu Pro Thr Gln Asp Tyr Thr Leu Arg Glu Phe Ile Asn Glu Val Gly
    450                 455                 460

Val Gly Phe Leu Asp Thr Lys Leu Ile Asp Asp Leu Asp Lys Lys Val
465                 470                 475                 480

Asn Phe Pro Leu Asn Ser Phe Asn Phe Val Glu Asn Gln Arg Ile Asp
                485                 490                 495

Asn Val Phe Ser Ala Phe Tyr Met Asp Ile Pro Ile Leu Glu Val Glu
            500                 505                 510

Ala Phe Arg Cys Lys Glu Leu Trp Arg Ser Ile Asn Glu Ser Lys Asp
        515                 520                 525

Lys Phe Lys Asp Phe Glu Ala Gln Ile Asp Lys Ser His Pro Pro Leu
    530                 535                 540

Leu Leu Gln Glu Tyr Phe Ser Ser Asp Glu Lys Met Lys Gln Leu Met
545                 550                 555                 560

Arg Asp Gln Leu Gln Leu Val Lys Gly Tyr Ser Lys Leu Glu Ala Ala
                565                 570                 575

Met Glu Trp Tyr Glu Trp Arg Lys Lys Gln Leu Asn Gly Leu Glu Leu
            580                 585                 590

Ile Leu Ala Glu Asn Leu Asn Thr Leu Lys Arg Glu Tyr Glu Lys Leu
        595                 600                 605

Asn Glu Glu Val Glu Lys Val Asn Ser Ile Arg Gly Lys Ile Arg Lys
    610                 615                 620

Leu Asn Glu Ala Ile Lys Glu Glu Ile Arg Ser Leu Lys Asn Leu Pro
625                 630                 635                 640

Ser Asp Ser Tyr Lys Pro Thr Leu Met Asn Arg Ile Lys Ile Glu Ala
                645                 650                 655

Phe Lys Gln Glu Leu Met Glu His Ser Ile Ser Leu Ser Ser Ser Asn
            660                 665                 670

Asp Phe Thr Gln Glu Met Arg Ser Leu Lys Leu Ala Ile Ala Lys Lys
        675                 680                 685
```

```
Ser Asn Asp Leu Leu Thr Leu Arg Ser Glu Val Ala Ser Ile Asp Lys
    690                 695                 700

Lys Ile Glu Lys Arg Lys Leu Phe Thr Arg Phe Asp Leu Pro Lys Leu
705                 710                 715                 720

Arg Asp Thr Leu Lys Ile Leu Glu Ser Leu Thr Gly Val Arg Phe Leu
                    725                 730                 735

Lys Phe Ser Lys Ala Thr Leu Ser Ile Ala Phe Leu Gln Leu Asp Asp
            740                 745                 750

Leu Arg Val Asp Ile Asn Leu Ala Asn Phe Lys Asn Asn Pro Leu Ser
                755                 760                 765

Ser Met Lys Val Met Asn Asp Ser Asn Asn Asp Met Ser Tyr His
    770                 775                 780

Leu Phe Thr Met Leu Leu Lys Asn Val Glu Ala Glu His Gln Asp Ser
785                 790                 795                 800

Met Leu Ser Asn Leu Phe Phe Ala Met Lys Lys Trp Arg Pro Leu Leu
                805                 810                 815

Lys Tyr Ile Lys Leu Leu Lys Leu Leu Phe Pro Val Lys Ile Thr Gln
            820                 825                 830

Thr Glu Glu Glu Ala Leu Leu Gln Phe Lys Asp Tyr Asp Arg Arg
                835                 840                 845

Asn Lys Thr Ala Phe Phe Tyr Val Ile Ser Leu Val Ser Phe Ala Gln
850                 855                 860

Gly Val Phe Ser Glu Asn Gly Gln Ile Pro Met Lys Val His Ile Ser
865                 870                 875                 880

Thr Gln Gln Asp Tyr Ser Pro Ser Arg Glu Val Leu Ser Asp Arg Ile
                885                 890                 895

Thr His Lys Ile Ser Gly Val Leu Pro Ser Phe Thr Lys Ser Arg Ile
            900                 905                 910

His Leu Glu Phe Thr
            915

<210> SEQ ID NO 8
<211> LENGTH: 210
<212> TYPE: PRT
<213> ORGANISM: Saccharomyces cerevisiae

<400> SEQUENCE: 8

Thr Val Thr Ser Thr Gln Ile Asp Asp Ala Arg Thr Glu Glu Lys Thr
1               5                   10                  15

Ala Ala Glu Glu Asp Pro Asp Thr Ser Gly Met Glu Leu Thr Glu Pro
                20                  25                  30

Ile Val Ala Thr Ser Asp Ser Asn Lys Ala Ser Gln His Asp Pro Thr
            35                  40                  45

Ser Met Glu Met Thr Glu Val Phe Pro Arg Ser Ile Arg Gln Lys Asn
    50                  55                  60

Pro Asp Val Glu Gly Glu Ser Ile Glu Ser Ser Gln Gln Ile Asp Asp
65                  70                  75                  80

Val Glu Ala Val Arg Glu Glu Thr Met Glu Leu Thr Ala Ile His Asn
                85                  90                  95

Val His Asp Tyr Asp Ser Ile Ser Glu Asp Thr Val Glu Gly Glu Pro
            100                 105                 110

Ile Asp Leu Thr Glu Tyr Glu Ser Lys Pro Tyr Val Pro Asn Ser Val
        115                 120                 125

Ser Arg Ser Thr Gly Lys Ser Ser Asp Tyr Ser Val Glu Arg Ser Asn
    130                 135                 140
```

```
Asp Lys Ser Asp Leu Ser Lys Ser Glu Asn Lys Thr Asn Ser Ser Gln
145                 150                 155                 160

Pro Met Glu Ile Thr Asp Ile Phe His Ala Asp Pro Gln Asn Pro Met
                165                 170                 175

Gly Leu His Ser Asp Asn Asn Ile Asn Asp Asp Gly Asn Glu Met Glu
            180                 185                 190

Leu Thr Gln Ile Gln Thr Asn Phe Asp Arg Asp Asn His His Ile Asp
        195                 200                 205

Glu Ser
    210

<210> SEQ ID NO 9

<400> SEQUENCE: 9

000

<210> SEQ ID NO 10
<211> LENGTH: 24
<212> TYPE: PRT
<213> ORGANISM: Artificial sequence
<220> FEATURE:
<223> OTHER INFORMATION: Synthetic peptide

<400> SEQUENCE: 10

Arg Ile Pro Gly Leu Ile Asn Ser Gly Gly Gly Gly Ser Gly Gly
1               5                   10                  15

Gly Ser Gly Gly Gly Gly Ala Ser
            20

<210> SEQ ID NO 11
<211> LENGTH: 7
<212> TYPE: PRT
<213> ORGANISM: Artificial sequence
<220> FEATURE:
<223> OTHER INFORMATION: Synthetic peptide

<400> SEQUENCE: 11

Ser Gly Gly Gly Gly Ala Ser
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic peptide

<400> SEQUENCE: 12

Arg Ile Pro Gly Leu Ile Lys
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Gly Ala Ala Ala Ala Gly
1               5
```

-continued

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Arg Ile Pro Gly Leu Ile Asn
1               5

<210> SEQ ID NO 15
<211> LENGTH: 909
<212> TYPE: PRT
<213> ORGANISM: Artificial sequence
<220> FEATURE:
<223> OTHER INFORMATION: Synthetic peptide

<400> SEQUENCE: 15

Met Glu Gly Cys Ser Leu Asp Met Gly Pro Ser Glu Leu Gln Glu Leu
1               5                   10                  15

Gly Lys Thr Asn Leu Glu His Thr Thr Gly Gln Leu Thr Thr Met Asn
            20                  25                  30

Arg Gln Ile Ala Val Lys Val Glu Lys Cys Gly Lys Ser Pro Ile Glu
        35                  40                  45

Lys Ser Gly Val Leu Lys Ser Asn Cys Ile Met Asp Val Leu Glu Asp
    50                  55                  60

Glu Ser Val Gln Lys Pro Lys Phe Pro Lys Glu Lys Gln Asn Val Lys
65                  70                  75                  80

Ile Trp Gly Arg Lys Ser Val Gly Pro Lys Ile Asp Lys Thr Ile
                85                  90                  95

Val Phe Ser Glu Asp Asp Lys Asn Asp Met Asp Ile Thr Lys Ser Tyr
            100                 105                 110

Thr Ile Glu Ile Asn His Arg Pro Leu Leu Glu Lys Arg Asp Cys His
        115                 120                 125

Leu Val Pro Leu Ala Gly Thr Ser Glu Thr Ile Leu Tyr Thr Cys Gly
    130                 135                 140

Gln Asp Asp Met Glu Ile Thr Arg Ser His Thr Thr Ala Leu Glu Cys
145                 150                 155                 160

Lys Thr Val Ser Pro Asp Glu Ile Thr Thr Arg Pro Met Asp Lys Thr
                165                 170                 175

Val Val Phe Val Asp Asn His Val Glu Leu Glu Met Thr Glu Ser His
            180                 185                 190

Thr Val Phe Ile Asp Tyr Gln Glu Lys Glu Arg Thr Asp Arg Pro Asn
        195                 200                 205

Phe Glu Leu Ser Gln Arg Lys Ser Leu Gly Thr Pro Thr Val Leu Asp
    210                 215                 220

Gly Pro Ser Glu Leu Gln Glu Leu Gly Lys Thr Asn Leu Glu His Thr
225                 230                 235                 240

Thr Gly Gln Leu Thr Thr Met Asn Arg Gln Ile Ala Val Lys Val Glu
                245                 250                 255

Lys Cys Gly Lys Ser Pro Ile Glu Lys Ser Gly Val Leu Lys Ser Asn
            260                 265                 270

Cys Ile Met Asp Val Leu Glu Asp Glu Ser Val Gln Lys Pro Lys Phe
        275                 280                 285

Pro Lys Glu Lys Gln Asn Val Lys Ile Trp Gly Arg Lys Ser Val Gly
    290                 295                 300

-continued

```
Gly Pro Lys Ile Asp Lys Thr Ile Val Phe Ser Glu Asp Asp Lys Asn
305                 310                 315                 320

Asp Met Asp Ile Thr Lys Ser Tyr Thr Ile Glu Ile Asn His Arg Pro
                325                 330                 335

Leu Leu Glu Lys Arg Asp Cys His Leu Val Pro Leu Ala Gly Thr Ser
            340                 345                 350

Glu Thr Ile Leu Tyr Thr Cys Gly Gln Asp Asp Met Glu Ile Thr Arg
        355                 360                 365

Ser His Thr Thr Ala Leu Glu Cys Lys Thr Val Ser Pro Asp Glu Ile
    370                 375                 380

Thr Thr Arg Pro Met Asp Lys Thr Val Val Phe Val Asp Asn His Val
385                 390                 395                 400

Glu Leu Glu Met Thr Glu Ser His Thr Val Phe Ile Asp Tyr Gln Glu
                405                 410                 415

Lys Glu Arg Thr Asp Arg Pro Asn Phe Glu Leu Ser Gln Arg Lys Ser
            420                 425                 430

Leu Gly Thr Pro Thr Val Leu Glu Gly Ala Gly Gly Leu Ile Lys
        435                 440                 445

Met Val Ser Lys Gly Glu Glu Asp Asn Met Ala Ser Leu Pro Ala Thr
450                 455                 460

His Glu Leu His Ile Phe Gly Ser Ile Asn Gly Val Asp Phe Asp Met
465                 470                 475                 480

Val Gly Gln Gly Thr Gly Asn Pro Asn Asp Gly Tyr Glu Glu Leu Asn
                485                 490                 495

Leu Lys Ser Thr Lys Gly Asp Leu Gln Phe Ser Pro Trp Ile Leu Val
            500                 505                 510

Pro His Ile Gly Tyr Gly Phe His Gln Tyr Leu Pro Tyr Pro Asp Gly
        515                 520                 525

Met Ser Pro Phe Gln Ala Ala Met Val Asp Gly Ser Gly Tyr Gln Val
    530                 535                 540

His Arg Thr Met Gln Phe Glu Asp Gly Ala Ser Leu Thr Val Asn Tyr
545                 550                 555                 560

Arg Tyr Thr Tyr Glu Gly Ser His Ile Lys Gly Glu Ala Gln Val Lys
                565                 570                 575

Gly Thr Gly Phe Pro Ala Asp Gly Pro Val Met Thr Asn Ser Leu Thr
            580                 585                 590

Ala Ala Asp Trp Cys Arg Ser Lys Lys Thr Tyr Pro Asn Asp Lys Thr
        595                 600                 605

Ile Ile Ser Thr Phe Lys Trp Ser Tyr Thr Thr Gly Asn Gly Lys Arg
    610                 615                 620

Tyr Arg Ser Thr Ala Arg Thr Thr Tyr Thr Phe Ala Lys Pro Met Ala
625                 630                 635                 640

Ala Asn Tyr Leu Lys Asn Gln Pro Met Tyr Val Phe Arg Lys Thr Glu
                645                 650                 655

Leu Lys His Ser Lys Thr Glu Leu Asn Phe Lys Glu Trp Gln Lys Ala
            660                 665                 670

Phe Thr Asp Val Met Gly Met Asp Glu Leu Tyr Lys Phe Glu Ser Gly
        675                 680                 685

Gly Ser Glu Ser Arg Gly Val Gln Val Glu Thr Ile Ser Pro Gly Asp
    690                 695                 700

Gly Arg Thr Phe Pro Lys Arg Gly Gln Thr Cys Val Val His Tyr Thr
705                 710                 715                 720

Gly Met Leu Glu Asp Gly Lys Lys Phe Asp Ser Ser Arg Asp Arg Asn
```

```
            725                 730                 735
Lys Pro Phe Lys Phe Met Leu Gly Lys Gln Glu Val Ile Arg Gly Trp
            740                 745                 750

Glu Glu Gly Val Ala Gln Met Ser Val Gly Gln Arg Ala Lys Leu Thr
            755                 760                 765

Ile Ser Pro Asp Tyr Ala Tyr Gly Ala Thr Gly His Pro Gly Ile Ile
            770                 775                 780

Pro Pro His Ala Thr Leu Val Phe Asp Val Glu Leu Leu Lys Leu Glu
785                 790                 795                 800

Thr Arg Gly Val Gln Val Glu Thr Ile Ser Pro Gly Asp Gly Arg Thr
                    805                 810                 815

Phe Pro Lys Arg Gly Gln Thr Cys Val Val His Tyr Thr Gly Met Leu
                    820                 825                 830

Glu Asp Gly Lys Lys Phe Asp Ser Ser Arg Asp Arg Asn Lys Pro Phe
                    835                 840                 845

Lys Phe Met Leu Gly Lys Gln Glu Val Ile Arg Gly Trp Glu Glu Gly
            850                 855                 860

Val Ala Gln Met Ser Val Gly Gln Arg Ala Lys Leu Thr Ile Ser Pro
865                 870                 875                 880

Asp Tyr Ala Tyr Gly Ala Thr Gly His Pro Gly Ile Ile Pro Pro His
                    885                 890                 895

Ala Thr Leu Val Phe Asp Val Glu Leu Leu Lys Leu Glu
            900                 905

<210> SEQ ID NO 16
<211> LENGTH: 701
<212> TYPE: PRT
<213> ORGANISM: Artificial sequence
<220> FEATURE:
<223> OTHER INFORMATION: Synthetic peptide

<400> SEQUENCE: 16

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
                85                  90                  95

Lys Thr Ser Pro Val Ala Thr Met Val Ser Lys Gly Glu Glu Asp Asn
            100                 105                 110

Met Ala Ile Ile Lys Glu Phe Met Arg Phe Lys Val His Met Glu Gly
        115                 120                 125

Ser Val Asn Gly His Glu Phe Glu Ile Glu Gly Glu Gly Glu Gly Arg
    130                 135                 140

Pro Tyr Glu Gly Thr Gln Thr Ala Lys Leu Lys Val Thr Lys Gly Gly
145                 150                 155                 160

Pro Leu Pro Phe Ala Trp Asp Ile Leu Ser Pro Gln Phe Met Tyr Gly
                165                 170                 175

Ser Lys Ala Tyr Val Lys His Pro Ala Asp Ile Pro Asp Tyr Leu Lys
```

-continued

```
            180                 185                 190
Leu Ser Phe Pro Glu Gly Phe Lys Trp Glu Arg Val Met Asn Phe Glu
            195                 200                 205
Asp Gly Gly Val Val Thr Val Thr Gln Asp Ser Ser Leu Gln Asp Gly
            210                 215                 220
Glu Phe Ile Tyr Lys Val Lys Leu Arg Gly Thr Asn Phe Pro Ser Asp
225                 230                 235                 240
Gly Pro Val Met Gln Lys Lys Thr Met Gly Trp Glu Ala Ser Ser Glu
            245                 250                 255
Arg Met Tyr Pro Glu Asp Gly Ala Leu Lys Gly Glu Ile Lys Gln Arg
            260                 265                 270
Leu Lys Leu Lys Asp Gly Gly His Tyr Asp Ala Glu Val Lys Thr Thr
            275                 280                 285
Tyr Lys Ala Lys Lys Pro Val Gln Leu Pro Gly Ala Tyr Asn Val Asn
            290                 295                 300
Ile Lys Leu Asp Ile Thr Ser His Asn Glu Asp Tyr Thr Ile Val Glu
305                 310                 315                 320
Gln Tyr Glu Arg Ala Glu Gly Arg His Ser Thr Gly Gly Met Asp Glu
            325                 330                 335
Leu Tyr Lys Ala Gly Leu Met Ala Thr Pro Leu Gln Asn Leu Gln Val
            340                 345                 350
Leu Ala Ser Ser Ala Asn Glu Cys Ile Ser Val Lys Gly Arg Ile
            355                 360                 365
Tyr Ser Ile Leu Lys Gln Ile Gly Ser Gly Gly Ser Ser Lys Val Phe
            370                 375                 380
Gln Val Leu Asn Glu Lys Lys Gln Ile Tyr Ala Ile Lys Tyr Val Asn
385                 390                 395                 400
Leu Glu Glu Ala Asp Asn Gln Thr Leu Asp Ser Tyr Arg Asn Glu Ile
            405                 410                 415
Ala Tyr Leu Asn Lys Leu Gln Gln His Ser Asp Lys Ile Ile Arg Leu
            420                 425                 430
Tyr Asp Tyr Glu Ile Thr Asp Gln Tyr Ile Tyr Met Val Met Glu Cys
            435                 440                 445
Gly Asn Ile Asp Leu Asn Ser Trp Leu Lys Lys Lys Ser Ile Asp
            450                 455                 460
Pro Trp Glu Arg Lys Ser Tyr Trp Lys Asn Met Leu Glu Ala Val His
465                 470                 475                 480
Thr Ile His Gln His Gly Ile Val His Ser Asp Leu Lys Pro Ala Asn
            485                 490                 495
Phe Leu Ile Val Asp Gly Met Leu Lys Leu Ile Asp Phe Gly Ile Ala
            500                 505                 510
Asn Gln Met Gln Pro Asp Thr Thr Ser Val Val Lys Asp Ser Gln Val
            515                 520                 525
Gly Thr Val Asn Tyr Met Pro Pro Glu Ala Ile Lys Asp Met Ser Ser
            530                 535                 540
Ser Arg Glu Asn Gly Lys Ser Lys Ser Lys Ile Ser Pro Lys Ser Asp
545                 550                 555                 560
Val Trp Ser Leu Gly Cys Ile Leu Tyr Tyr Met Thr Tyr Gly Lys Thr
            565                 570                 575
Pro Phe Gln Gln Ile Ile Asn Gln Ile Ser Lys Leu His Ala Ile Ile
            580                 585                 590
Asp Pro Asn His Glu Ile Glu Phe Pro Asp Ile Pro Glu Lys Asp Leu
            595                 600                 605
```

```
Gln Asp Val Leu Lys Cys Cys Leu Lys Arg Asp Pro Lys Gln Arg Ile
        610                 615                 620
Ser Ile Pro Glu Leu Leu Ala His Pro Tyr Val Gln Ile Gln Thr His
625                 630                 635                 640
Pro Val Asn Gln Met Ala Lys Gly Thr Thr Glu Glu Met Lys Tyr Val
                645                 650                 655
Leu Gly Gln Leu Val Gly Leu Asn Ser Pro Asn Ser Ile Leu Lys Ala
            660                 665                 670
Ala Lys Thr Leu Tyr Glu His Tyr Ser Gly Gly Glu Ser His Asn Ser
        675                 680                 685
Ser Ser Ser Lys Thr Phe Glu Lys Lys Arg Gly Lys Lys
        690                 695                 700
```

<210> SEQ ID NO 17
<211> LENGTH: 19
<212> TYPE: PRT
<213> ORGANISM: Artificial sequence
<220> FEATURE:
<223> OTHER INFORMATION: Synthetic peptide

<400> SEQUENCE: 17

```
Thr Ile Val Phe Ser Glu Asp Asp Lys Asn Asp Met Asp Ile Thr Lys
1               5                   10                  15
Ser Tyr Thr
```

<210> SEQ ID NO 18
<211> LENGTH: 18
<212> TYPE: PRT
<213> ORGANISM: Artificial sequence
<220> FEATURE:
<223> OTHER INFORMATION: Synthetic peptide

<400> SEQUENCE: 18

```
Thr Ile Leu Tyr Thr Cys Arg Gln Asp Asp Met Glu Ile Thr Arg Ser
1               5                   10                  15
His Thr
```

<210> SEQ ID NO 19
<211> LENGTH: 18
<212> TYPE: PRT
<213> ORGANISM: Artificial sequence
<220> FEATURE:
<223> OTHER INFORMATION: Synthetic peptide

<400> SEQUENCE: 19

```
Thr Val Val Phe Val Asp Asn His Val Glu Leu Glu Met Thr Glu Ser
1               5                   10                  15
His Thr
```

<210> SEQ ID NO 20
<211> LENGTH: 25
<212> TYPE: RNA
<213> ORGANISM: Artificial sequence
<220> FEATURE:
<223> OTHER INFORMATION: Synthetic siRNA

<400> SEQUENCE: 20
gaguucuucu cauucggcau caaca                                         25

<210> SEQ ID NO 21
<211> LENGTH: 19

```
<212> TYPE: RNA
<213> ORGANISM: Artificial sequence
<220> FEATURE:
<223> OTHER INFORMATION: Synthetic siRNA

<400> SEQUENCE: 21
gauggugaau uguggaaua                                                    19

<210> SEQ ID NO 22
<211> LENGTH: 19
<212> TYPE: PRT
<213> ORGANISM: Homo sapiens

<400> SEQUENCE: 22

Thr Ile Val Phe Ser Glu Asp Asp Lys Asn Asp Met Asp Ile Thr Lys
1               5                   10                  15

Ser Tyr Thr

<210> SEQ ID NO 23
<211> LENGTH: 18
<212> TYPE: PRT
<213> ORGANISM: Homo sapiens

<400> SEQUENCE: 23

Thr Ile Leu Tyr Thr Cys Arg Gln Asp Asp Met Glu Ile Thr Arg Ser
1               5                   10                  15

His Thr

<210> SEQ ID NO 24
<211> LENGTH: 18
<212> TYPE: PRT
<213> ORGANISM: Homo sapiens

<400> SEQUENCE: 24

Thr Val Val Phe Val Asp Asn His Val Glu Leu Glu Met Thr Glu Ser
1               5                   10                  15

His Thr
```

…

MPS1 AND KNL1 PHOSPHORYLATION SYSTEM

CROSS REFERENCE TO RELATED APPLICATIONS

The present invention claims the priority benefit of U.S. Provisional Patent Application 62/256,971, filed Nov. 18, 2015, which is incorporated by reference in its entirety.

STATEMENT REGARDING FEDERAL FUNDING

This invention was made with government support under grants GM105948 and GM112992 awarded by the National Institutes of Health. The government has certain rights in the invention.

FIELD

Provided herein are compositions and methods for the treatment of cancer by activating the spindle assembly checkpoint (SAC) in cells. In particular, dimerized Mps1 and Spc105/KNL1 constructs are provided as tunable activators of SAC, allowing for control of chromosome segregation accuracy and prevention of aneuploidies that are common in cancer.

BACKGROUND

Genetic instability, which includes both numerical and structural chromosomal abnormalities, is a hallmark of cancer. The spindle assembly checkpoint (SAC) is a mechanism by which cells ensure proper chromosome segregation and thereby maintain the euploid status of cells. Breakdown of the SAC contributes to cellular aneuploidy, which can lead to tumorigenesis and cancer. Compositions that prevent aneuploidy-related cancers are needed.

SUMMARY

Provided herein are compositions and methods for the treatment of cancer by activating the spindle assembly checkpoint (SAC) in cells. In particular, dimerized Mps1 and Spc105/KNL1 constructs are provided as tunable activators of SAC, allowing for control of chromosome segregation accuracy and prevention of aneuploidies that are common in cancer.

In some embodiments, provided herein are systems comprising: (a) an Mps1 polypeptide linked to a first dimerization element; and (b) a Spc105/KNL1 polypeptide linked to a second dimerization element, wherein dimerization of the first dimerization element and second dimerization element facilitates phosphorylation of the Spc105/KNL1 polypeptide by the Mps1 polypeptide. In some embodiments, the Mps1 polypeptide comprises a kinase domain having at least 70% sequence similarity (e.g., 70%, 75%, 80%, 85%, 90%, 95%, 98%, 99%, 100%, or ranges therebetween) with all or a portion of a kinase domain of a wild-type Mps1 protein (SEQ ID NO:2), and retains all or a portion of the kinase activity of the wild-type Mps1 protein. In some embodiments, the Mps1 polypeptide comprises a kinase domain having at least 70% sequence identity (e.g., 70%, 75%, 80%, 85%, 90%, 95%, 98%, 99%, 100%, or ranges therebetween) with all or a portion of a kinase domain of a wild-type Mps1 protein (SEQ ID NO:2), and retains all or a portion of the kinase activity of the wild-type Mps1 protein. In some embodiments, the Mps1 polypeptide comprises at least 70% sequence identity (e.g., 70%, 75%, 80%, 85%, 90%, 95%, 98%, 99%, 100%, or ranges therebetween) with a portion a wild-type Mps1 protein (e.g., comprising a kinase domain) of at least 50 amino acids (e.g. >50 amino acids, >100 amino acids, >150 amino acids, >200 amino acids, >250 amino acids, >300 amino acids, >350 amino acids). In some embodiments, the Mps1 polypeptide comprises at least 70% sequence identity (e.g., 70%, 75%, 80%, 85%, 90%, 95%, 98%, 99%, 100%, or ranges therebetween) with a portion a wild-type Mps1 protein of not more than 500 amino acids (e.g. <500 amino acids, <450 amino acids, <400 amino acids, <350 amino acids, <300 amino acids, <250 amino acids, <200 amino acids, <150 amino acids, <100 amino acids). In some embodiments, the Spc105/KNL1 polypeptide comprises a phosphodomain having at least 70% sequence similarity (e.g., 70%, 75%, 80%, 85%, 90%, 95%, 98%, 99%, 100%, or ranges therebetween) with all or a portion of a phosphodomain of a wild-type Spc105 (SEQ ID NO:8) or KNL1 (SEQ ID NO:5) protein, and retains all or a portion of the capacity of the wild-type Spc105 or KNL1 protein to be phosphorylated by Mps. In some embodiments, the Spc105/KNL1 polypeptide comprises a phosphodomain having at least 70% sequence identity (e.g., 70%, 75%, 80%, 85%, 90%, 95%, 98%, 99%, 100%, or ranges therebetween) with all or a portion of a phosphodomain of a wild-type Spc105 (SEQ ID NO:8) or KNL1 (SEQ ID NO:5) protein, and retains all or a portion of the capacity of the wild-type Spc105 or KNL1 protein to be phosphorylated by Mps. In some embodiments, the Spc105/KNL1 polypeptide comprises at least 70% sequence identity (e.g., 70%, 75%, 80%, 85%, 90%, 95%, 98%, 99%, 100%, or ranges therebetween) with a portion of a wild-type Spc105 (SEQ ID NO:8) or KNL1 (SEQ ID NO:5) protein of at least 50 amino acids (e.g. >50 amino acids, >100 amino acids, >150 amino acids, >200 amino acids, >250 amino acids, >300 amino acids, >350 amino acids, >400 amino acids, >450 amino acids, >500 amino acids). In some embodiments, the Spc105/KNL1 polypeptide comprises at least 70% sequence identity (e.g., 70%, 75%, 80%, 85%, 90%, 95%, 98%, 99%, 100%, or ranges therebetween) with a portion of a wild-type Spc105 (SEQ ID NO:8) or KNL1 (SEQ ID NO:5) protein of not more than 500 amino acids (e.g. <500 amino acids, <450 amino acids, <400 amino acids, <350 amino acids, <300 amino acids, <250 amino acids, <200 amino acids, <150 amino acids, <100 amino acids). In some embodiments, the phosphorylation of the Spc105/KNL1 polypeptide by the Mps1 polypeptide is sufficient to activate a spindle assembly checkpoint (SAC) is a cell within which the phosphorylation occurs. In some embodiments, the first or second dimerization element is Frb and the other dimerization element is Fkbp12. In some embodiments, systems further comprise a dimerization inducer, wherein the dimerization inducer tunably alters the degree of dimerization in a concentration dependent manner.

In some embodiments, provided herein are compositions comprising an Mps1 polypeptide linked to a dimerization element. In some embodiments, the Mps1 polypeptide comprises a kinase domain having at least 70% sequence similarity (e.g., 70%, 75%, 80%, 85%, 90%, 95%, 98%, 99%, 100%, or ranges therebetween) with all or a portion of a kinase domain of a wild-type Mps1 protein (SEQ ID NO:2), and retains all or a portion of the kinase activity of the wild-type Mps1 protein. In some embodiments, the Mps1 polypeptide comprises a kinase domain having at least 70% sequence identity (e.g., 70%, 75%, 80%, 85%, 90%, 95%, 98%, 99%, 100%, or ranges therebetween) with all or a portion of a kinase domain of a wild-type Mps1 protein (SEQ ID NO:2), and retains all or a portion of the kinase activity of the wild-type Mps1 protein. In some embodiments, the dimerization element is Frb or Fkbp12.

In some embodiments, polypeptides and constrcuts are modified or provided in delivery systems to reduce immunogenicity.

In some embodiments, provided herein are compositions comprising a Spc105/KNL1 polypeptide linked to a dimerization element. In some embodiments, the Spc105/KNL1 polypeptide comprises a phosphodomain having at least 70% sequence similarity (e.g., 70%, 75%, 80%, 85%, 90%, 95%, 98%, 99%, 100%, or ranges therebetween) with all or a portion of a phosphodomain of a wild-type Spc105 (SEQ ID NO:8) or KNL1 (SEQ ID NO:5) protein, and retains all or a portion of the capacity of the wild-type Spc105 or KNL1 protein to be phosphorylated by Mps. In some embodiments, the Spc105/KNL1 polypeptide comprises a phosphodomain having at least 70% sequence identity (e.g., 70%, 75%, 80%, 85%, 90%, 95%, 98%, 99%, 100%, or ranges therebetween) with all or a portion of a phosphodomain of a wild-type Spc105 or KNL1 protein, and retains all or a portion of the capacity of the wild-type Spc105 (SEQ ID NO:8) or KNL1 (SEQ ID NO:5) protein to be phosphorylated by Mps. In some embodiments, the dimerization element is Frb or Fkbp12.

In some embodiments, provided herein are methods of activating a spindle assembly checkpoint (SAC) in a cell comprising administering to the cell a system or composition comprising: a Spc105/KNL1 polypeptide linked to a dimerization element and/or a Mps1 polypeptide linked to a dimerization element. In some embodiments, activating the SAC prevents aneuploidies in the cell. In some embodiments, the cell is within a tissue, organ, or subject, and the SAC is activated in all or a group of cells within the tissue, organ, or subject. In some embodiments, activating the SAC treats or prevents cancer in the cells, tissue, organ, or subject.

BRIEF DESCRIPTION OF THE DRAWINGS

FIG. 3A-C. Testing the sensitivity of SAC signaling steps to the attachment status of the kinetochore. (a) Cell-cycle progression of three different strains following release from metaphase. Solid lines indicate cell-cycle progress of a strain expressing Mtw1-2xFkbp12 and Mps1-Frb released into media with or without rapamycin. The dotted line indicates cell-cycle progression of a mad2Δ strain similarly released from metaphase arrest. Plotted points represent the average values calculated from independent experiments. (b) Separation between the centroids of fluorescently labelled kinetochore proteins along the spindle axis obtained by high-resolution co-localization in unperturbed metaphase cells (Ctrl) and rapamycin-treated cells (Rap—rapamycin added to anchor Mps1 at Mtw1-C. (c) Left: Fractional intensity distributions of Mps1-Frb-GFP (which autonomously localizes along the spindle in the absence of rapamycin) and Ndc80-GFP along the spindle in cells arrested in metaphase using CDC20 repression (spindle pole bodies visualized using Spc97-mCherry). Right: Bub3 and Mad1 do not localize to kinetochores under the same conditions. Mad1 puncta correspond to its known localization to the nuclear envelope. Scale bar, ~3 μm.

FIG. 13A-B. The proximity between the CH domains of Ndc80 and the phosphodomain of Spc105 within the kinetochore controls SAC signaling. (a) Scatter plot: Proximity ratio measurements for FRET between mCherry-Nuf2 or mCherry-Ndc80 and GFP-Spc105 in attached (metaphase) and unattached (nocodazole-treated) kinetochores. (b) Cell-cycle kinetics after anchoring Spc105$^{120:329}$ at the indicated positions in strains expressing spc105$^{-6A}$.

(c) Dam1 complex (visualized with Ask1-mCherry) is retained at the SAC-inactive cluster, whereas it is significantly reduced at the SAC-active clusters in nocodazole. Quantification of Ask1-mCherry fluorescence measured relative to Spc24-mCherry fluorescence is displayed on the right. (d) Measurement of FRET between GFP-Spc105 and either mCherry-Nuf2 or mCherry-Ndc80 in SAC-active and SAC-inactive kinetochore clusters. FRET between mCherry-Nuf2 (or mCherry-Ndc80) and GFP-Spc105 in the SAC-inactive kinetochore cluster is higher than metaphase FRET value, and significantly lower than the FRET observed in the SAC-active cluster.

Figure 15:
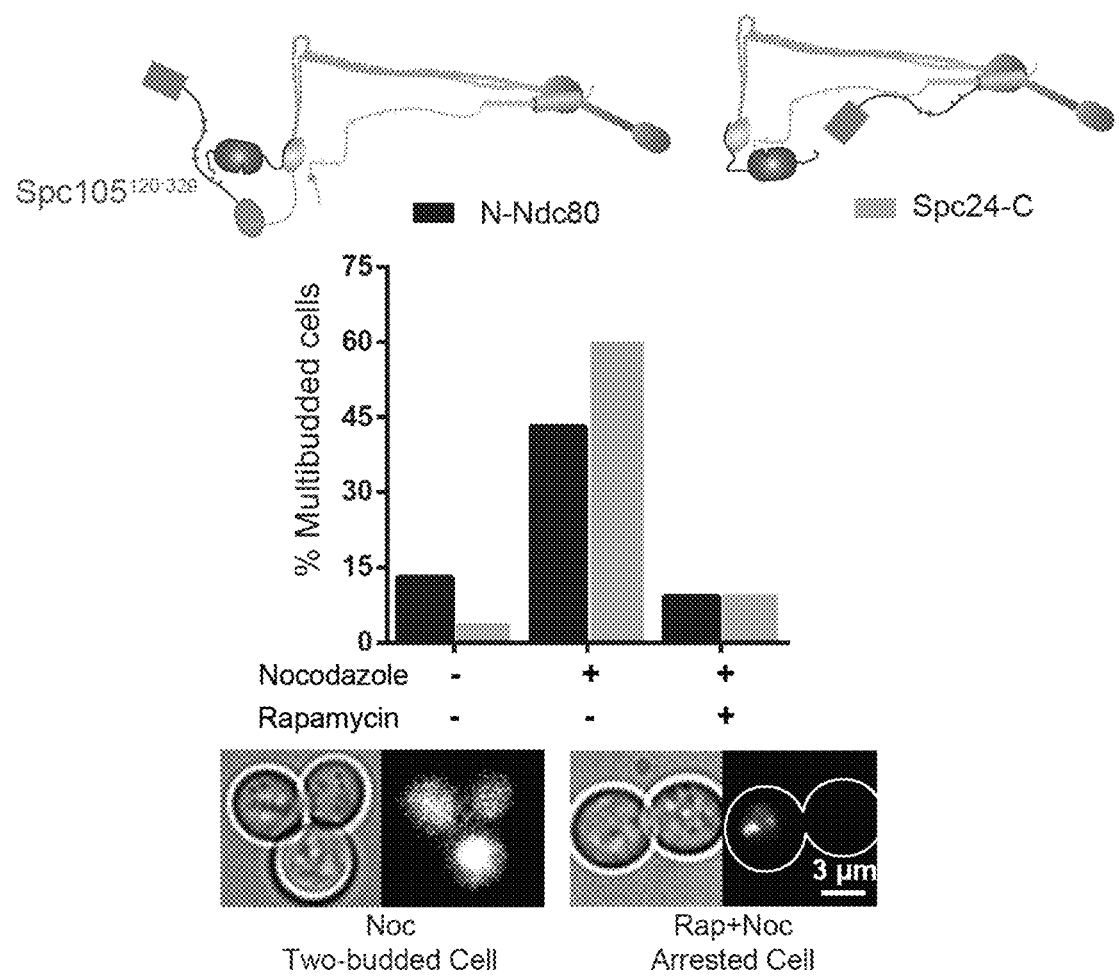

FIG. 15. Spc105$^{120:329:6A}$ restores the SAC when it is anchored to unattached kinetochores in SAC-null strains. Top: Experimental scheme. Bar graph: Fraction of nocodazole-treated cells with two buds in the presence and absence of rapamycin in cells expressing spc105-6A (see micrographs on the left). When Spc105$^{120:329:6A}$ was anchored either at N-Ndc80 or at Spc24-C, it restored the SAC. The cells arrested with large buds (transmitted light micrograph on the right). In this condition, Spc105$^{120:329:6A}$ is visible as multiple puncta corresponding to kinetochore clusters that form when budding yeast cells are treated with nocodazole.

Figure 16:
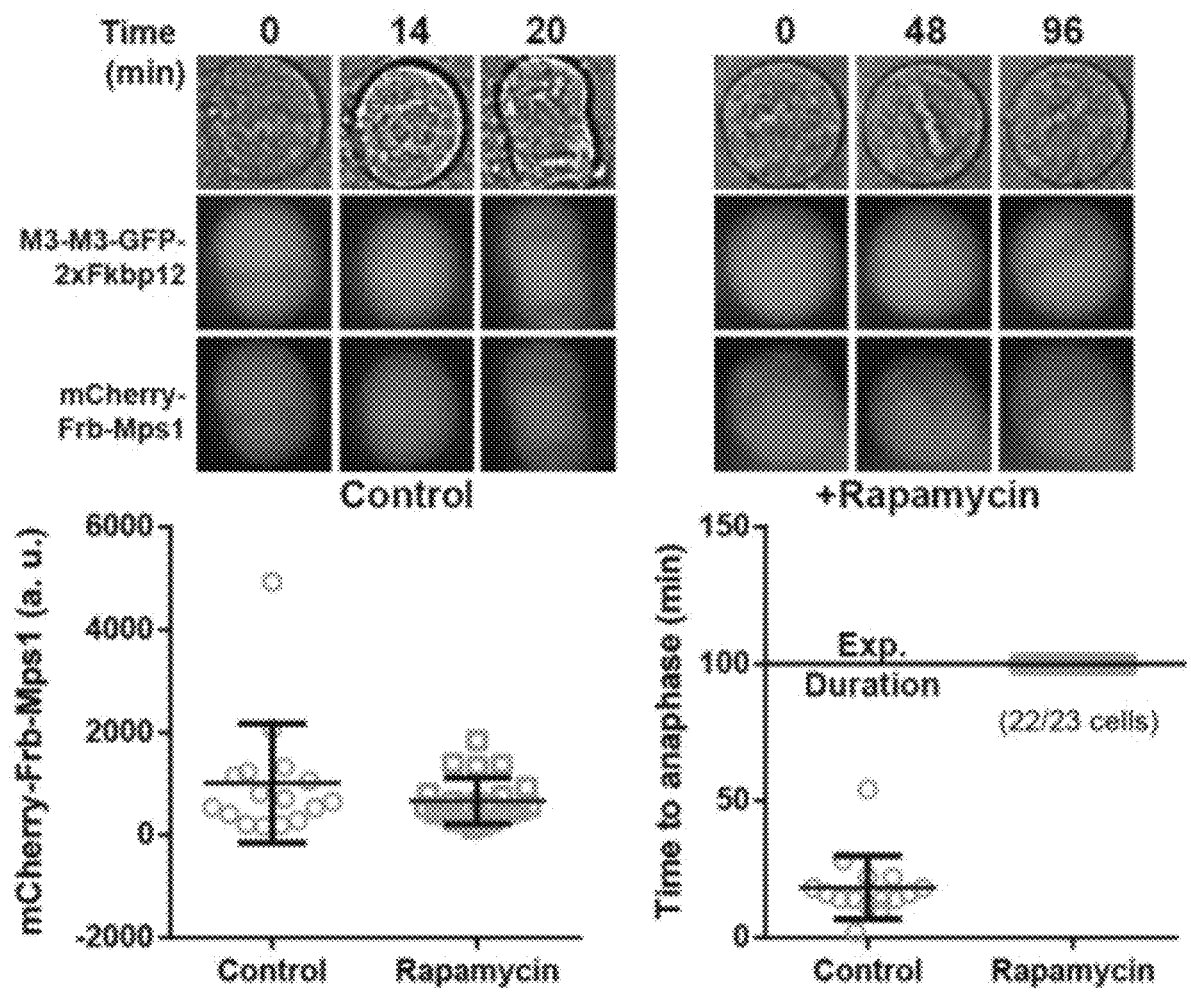

FIG. 16. Induced dimerization of KNL-1 phosphodomain (M3-M3) & Mps1 induces a prolonged metaphase arrest. Top: representative micrographs. Bottom left: Mps1 is expressed at equivalent levels in the analyzed cells. Bottom right: Time spent in metaphase (0 min: begin observation).

FIG. 17A-E. Cytosolic dimerization of the Mps1 kinase domain and a minimal KNL1 phosphodomain is sufficient to induce metaphase arrest. (A) Diagram of the SAC signaling cascade. Black arrows imply protein recruitment to the kinetochore, gray arrows mark cytoplasmic reactions. (B) Exemplary scheme for conditional dimerization Mps1 with the minimal KNL1 phosphodomain. (C) Top, Bright-field and fluorescence images of HeLa cells from time lapse imaging display the indicated proteins. Elapsed time (minutes) indicated in the top left corner. Scale bar ~2.4 microns. Bottom, Duration of mitosis in a 2-hour time-lapse experiment (n=55 and 98 for DMSO and Rapamycin respectively). (D) Time until anaphase entry after treatment with either DMSO (n=30) or Reversine (n=27, ≥2 independent trials) of cells in rapamycin-induced arrest. (E) Top, eSAC schematic. Left, Duration of mitosis for untreated and rapamycin-treated cells (n=629 and 2705 respectively). Top right, Psuedocolored fluorescence image of a cell in rapamycin-induced metaphase arrest stained as indicated, Bottom right: absence of kinetochore localization of the phosphodomain visualized by neon fluorescence (scale bar ~1.2 µm). Horizontal lines indicate mean±s.e.m. intervals in all scatterplots.

FIG. 18A-F. eSAC induces metaphase arrest in a kinetochore-independent manner. (A) Phosphoregulation of the eSAC phosphodomain and KNL1 analyzed by immunoblotting for the indicated proteins. (B) Left, Reversine treatment inactivates the SAC and significantly accelerates cell division (n=432 and 199 for untreated and Reversine-treated cells respectively, Mann-Whitney test). Right, Effect of Reversine on eSAC activity based on the partially Reversine-resistant Mps1S611R kinase domain (n=621 and 1193 for Rapamycin and Rapamycin+Reversine respectively; 2 trials). (C) Effect of the Aurora B inhibitor ZM447439 on the eSAC-induced mitotic arrest (n=931 and 205 for Rapamycin and Rapamycin+ZM447439 respectively; 2 trials). (D) Activity of the membrane-targeted eSAC (n=697 and 1056 for untreated and Rapamycin-treated cells respectively, 2 trials). Right, Confocal images display protein localizations as indicated. Scale bar ~5 µm. (E) Mass spectrometry analysis of immunoprecipitated eSAC phosphodomain under the indicated conditions. (F) Effect of RNAi-mediated depletion of either BubR1 or Mad2 on eSAC activity (n=78, 390, 300,191, 72 and 140 respectively, 2 trials). Bar height=mean, error bars display s.e.m. Horizontal lines in scatter plots display mean+/−s.e.m.

FIG. 19A-I. Dose-response characteristics of the eSAC reveal mechanisms that achieve ultra-high sensitivity and automatic gain modulation. (A) Hypothetical relationships between the number of signaling kinetochores and SAC signal. (B) Schematics of the eSAC phosphodomains. c, Montages of bright-field images and fluorescence heat-maps of representative cells (Δt=20 minutes for 1-MELT and 30 minutes for 6-MELT phosphodomain montage). (D-F) Dose (Mps1 kinase domain fluorescence at the beginning of mitosis) vs. response (duration of mitosis) relationship for the indicated eSAC phosphodomains (n=2572, 2791, and 2705 respectively from ≥2 trials). Duration of mitosis at 0 eSAC abundance was obtained from the mean duration of mitosis for the respective cell line in the absence of rapamycin. Each gray circle represents one cell. Open squares represent the means of binned data; error bars represent s.e.m. Curves in d and e: 4-parameter sigmoid fits. Curve in D: Lowess filtered data. (G) Dose-response curves for all five phosphodomains. (H) Activation thresholds and (I) maximal mitotic duration calculated from either the sigmoidal fits or graphically by interpolation for F.

FIG. 20A-C. Mathematical model of the eSAC and simulation of the dose-response curves. (A-B) Model of eSAC phosphodomains containing 1 and 4 MELT repeats respectively. It represents the binding of all SAC proteins by the single "Bub" unit. The amino acid sequence of each MELT repeat (labeled by its repeat number in KNL1) determines its binding affinity for Bub. Graphs display the steady-state abundance of different Bub-bound phosphodomain species (left) and the rate of closed/active Mad2 formation stimulated by these phosphodomains (right) as a function of eSAC activator concentration. Each species is designated by the MELT repeat numbers that it contains, the specific MELT bound by Bub. (C) Simulated dose-response curves obtained by relaying the signaling activity of the eSAC model to a previously described model for a bistable switch that governs mitotic exit. The dashed and solid black curves display the dose-response characteristics for the phosphodomain with 6 MELT repeats without and with synergistic activity respectively.

Figures 21A, 21B:
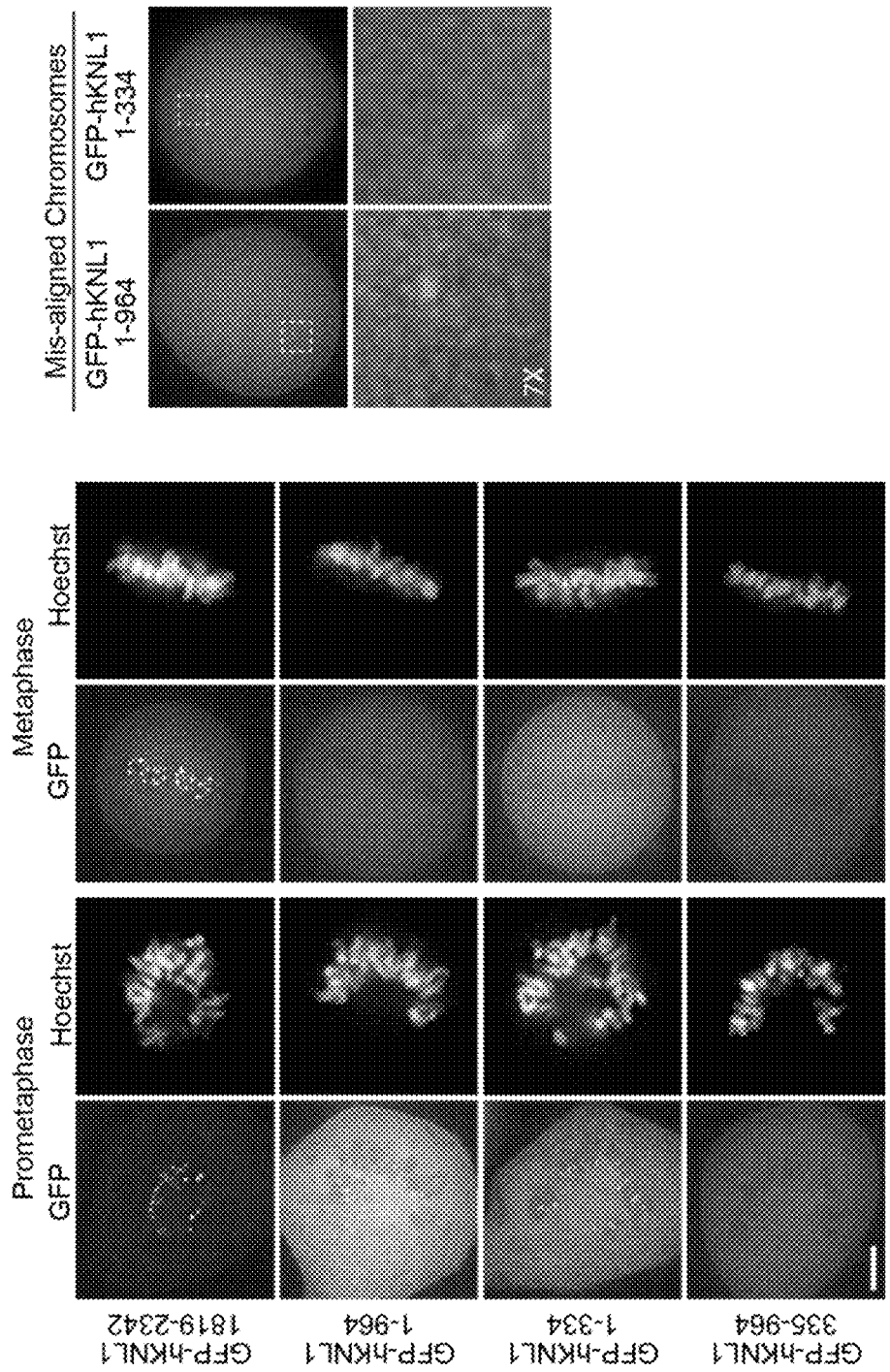

FIG. 21A-B. Assessment of kinetochore-localization domains within KNL1. (A) Fluorescent images showing the localization of the indicated KNL1 regions as GFP fusions in live HeLa cells (numbers alongside each micrograph denote the residues in each construct). The kinetochore-binding domain at the C-terminus of KNL1 strongly localized to kinetochores. Residues proximal to the N-terminus also transiently localized to kinetochores only in prometaphase (Scale bar=5 μm). (B) Images at the top display metaphase cells with misaligned chromosomes. KNL1 fragments containing the N-terminus also localized to kinetochores on these chromosomes. Dashed boxes highlight the magnified areas shown in the bottom right panel.

Figure 22A:
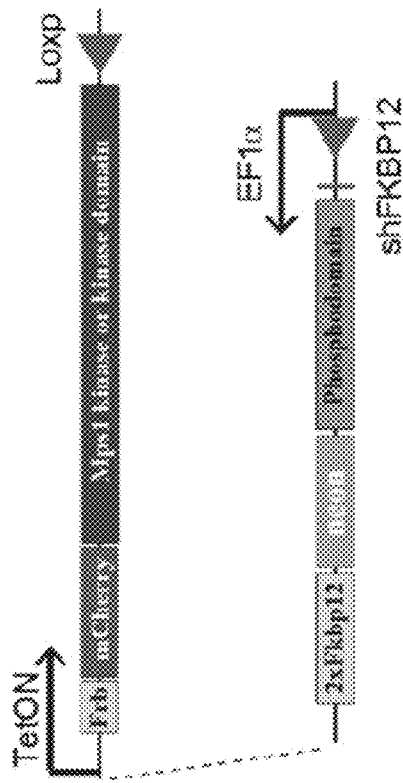
Figure 22B:
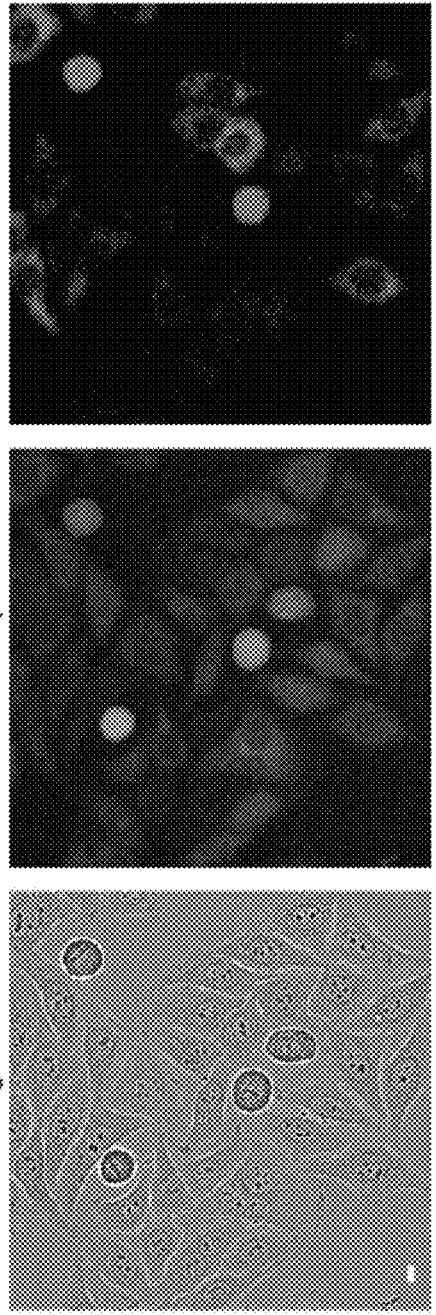

FIG. 22A-B. Schematic of eSAC cell-line construction. (A) Each eSAC cell line was created by integrating a bi-cistronic cassette in the HeLa genome at a unique Loxp site via Cre-mediated recombination. (B) The Phosphodomain-neonGFP-2xFkbp12, wherein the phosphodomain cassette can contain a specified numbers of MELT repeats, is constitutively expressed by the EF1α promoter. The 5' UTR of this gene also contains a sequence encoding shRNA against the endogenous FKBP protein. Frb-mCherry-Mps1, wherein Mps1 can be either the full length gene or just the sequence encoding its kinase domain is expressed conditionally from a TetON promoter.

Figure 23A:
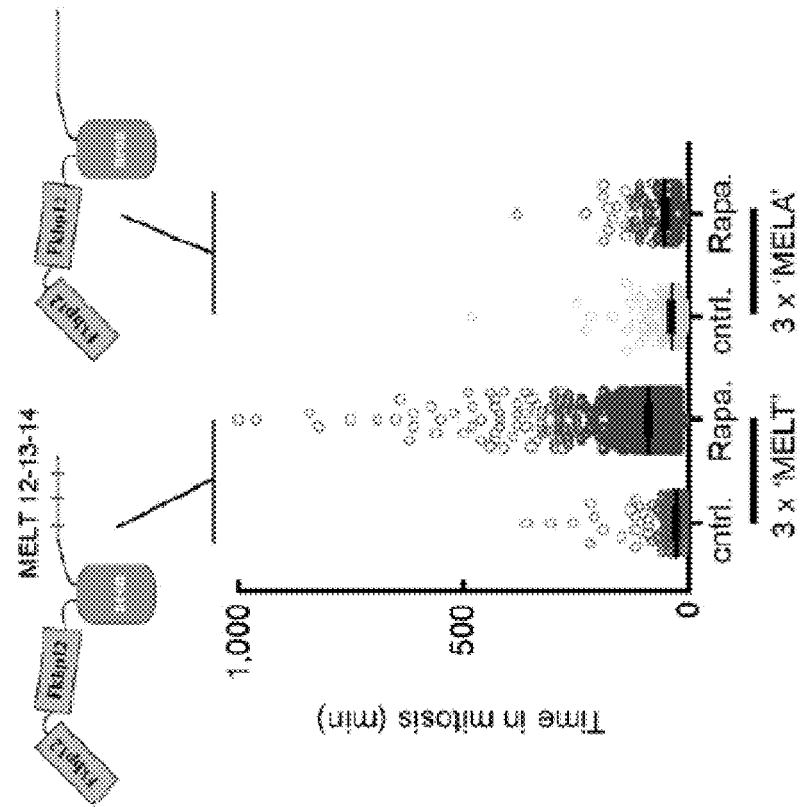
Figure 23B:
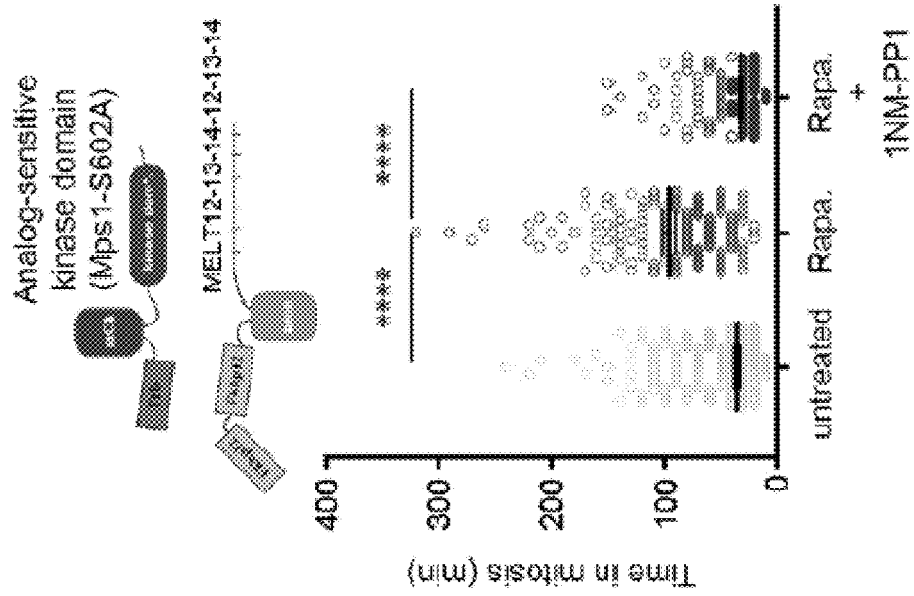

FIG. 23A-B. Phosphorylation of the MELT repeats in the minimal KNL1 phosphodomain by the Mps1 kinase domain is necessary for eSAC activity. (A) Kinase activity of the Mps1 kinase domain is necessary for the rapamycin-induced mitotic arrest. Rapamycin-induced dimerization of the analog-sensitive allele of the Mps1 kinase domain, Mps1S602A, with the minimal phosphodomain (displayed in the cartoon at the top) produced a weak mitotic arrest. The weak eSAC-induced arrest likely indicates a significantly reduced activity of the mutant kinase domain. Combined treatment with Rapamycin and the ATP analog 1NM-PP1 (10 μM) abrogated the eSAC-induced arrest. Cells expressing >5 a. u. of Frb-mCherry-Mps1S602A were used for this analysis (n=177, 206, and 332 respectively; p<0.0001, Mann-Whitney test). (B) Phosphorylatable MELT repeats are necessary for rapamycin-induced mitotic arrest. The minimal phosphodomain used in the experiment is displayed at the top. n=853, 2238, 252, and 313 respectively. In both A and B, black horizontal lines display mean±s.e.m.

Figure 24A:
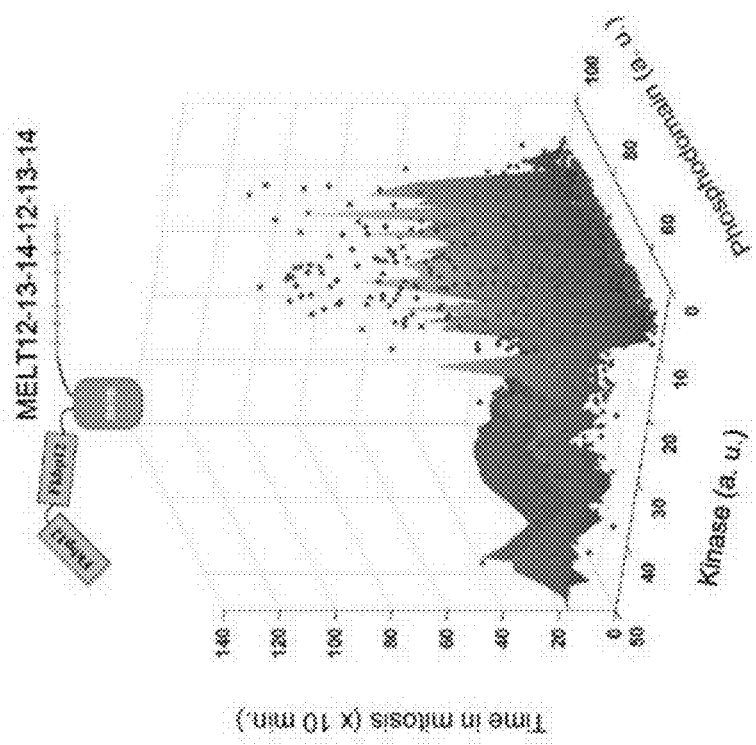
Figure 24B:
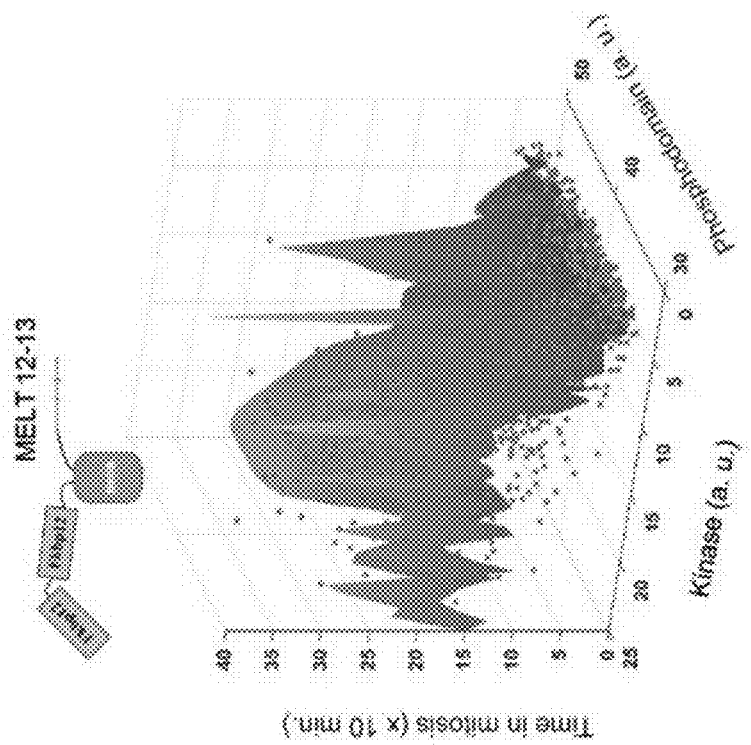

FIG. 24A-B. Duration of the eSAC-induced metaphase arrest correlates strongly with the cellular abundance of the kinase domain, but not with the abundance of the phosphodomain. (A-B) Dependence of eSAC-induced mitotic duration on the abundance of the phosphodomain (neonGreen fluorescence) and Mps1 kinase domain (mCherry fluorescence) shown for minimal KNL1 phosphodomains containing 2 and 6 MELT repeats respectively (n=1376 for a and n=1877 for b). The surface was calculated using the 'grid-data' function with cubic interpolation in MatLab.

Figure 25B:
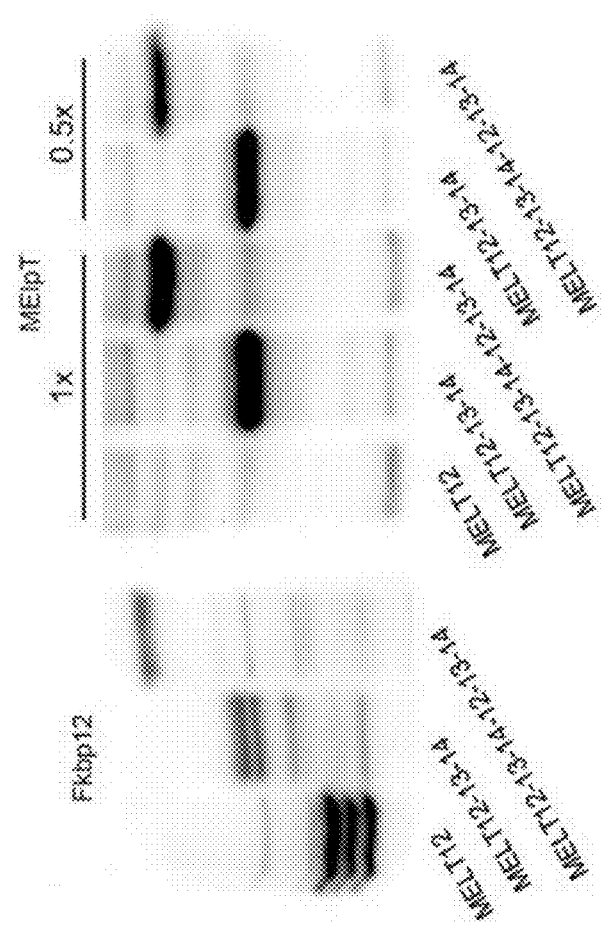
Figure 25A:
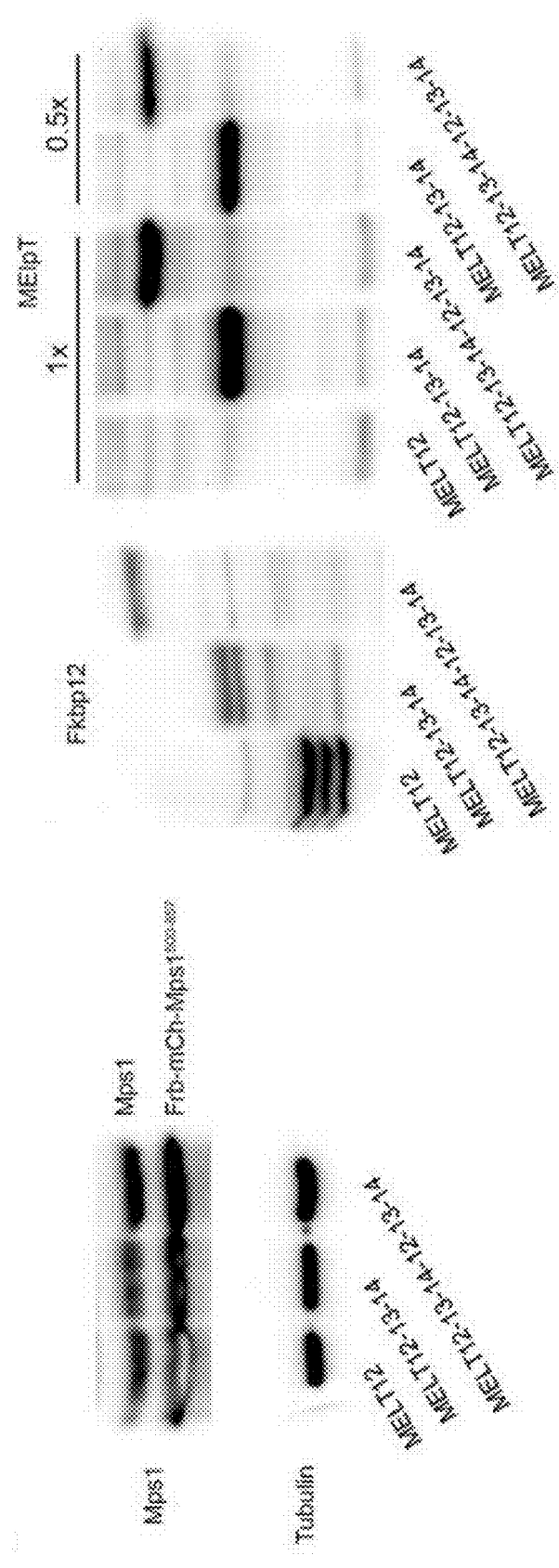
Figure 26A:
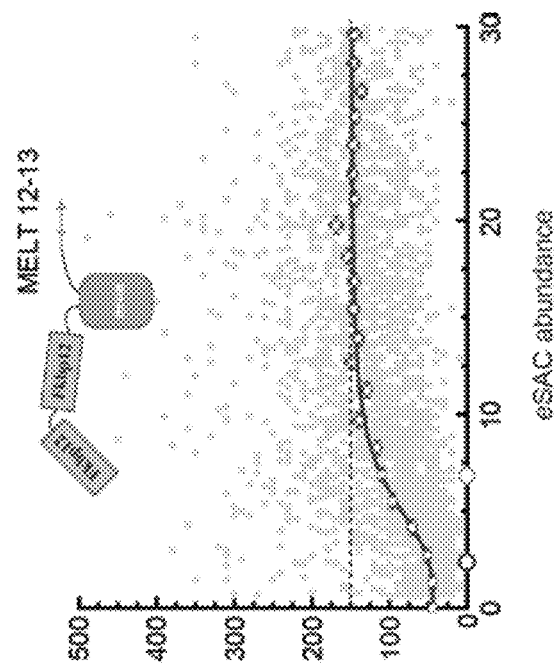
Figure 26B:
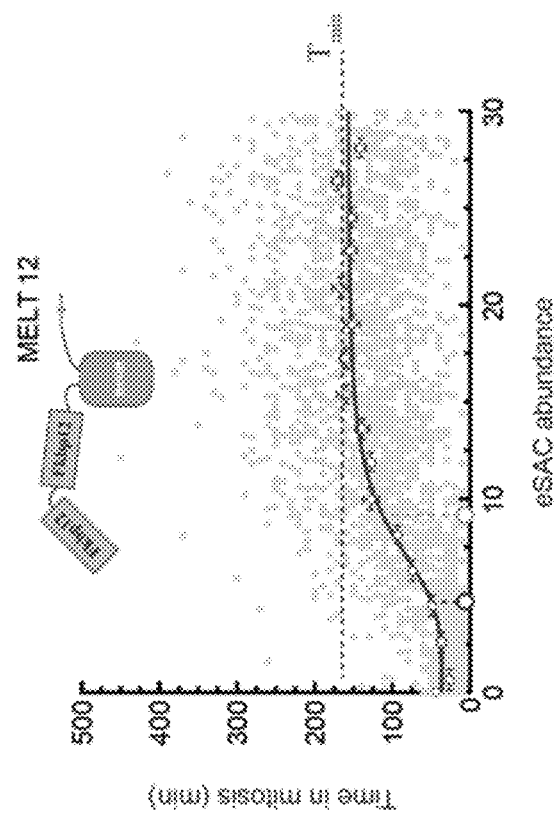
Figure 26D:
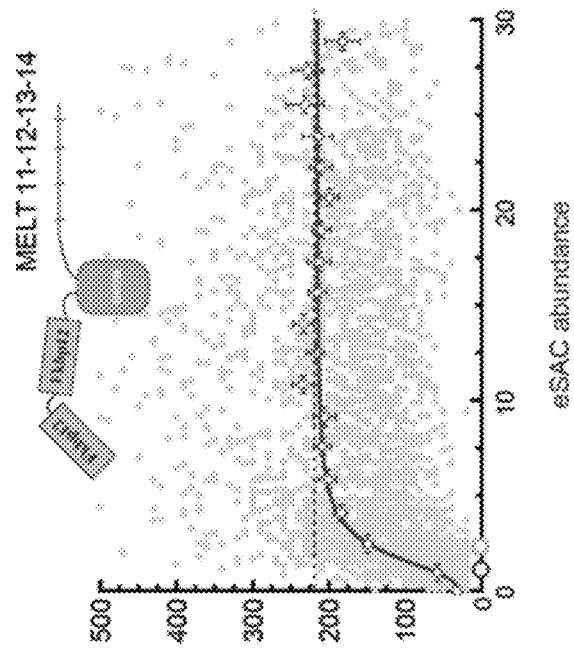
Figure 26C:
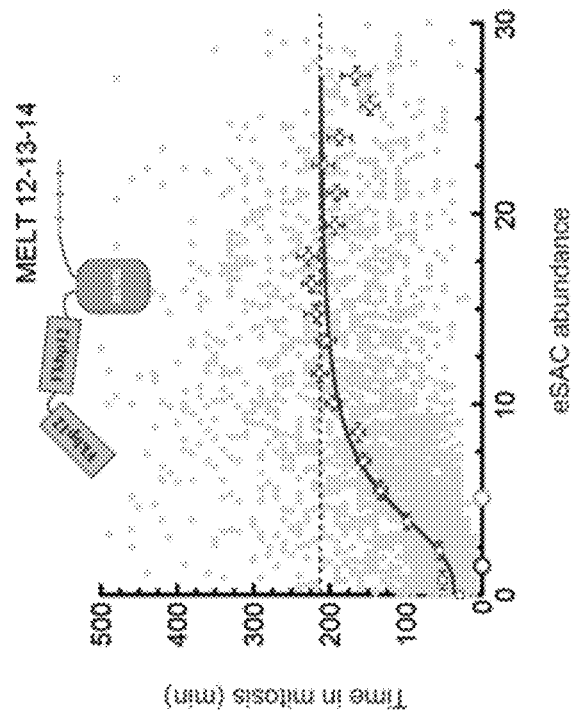
Figure 26E:
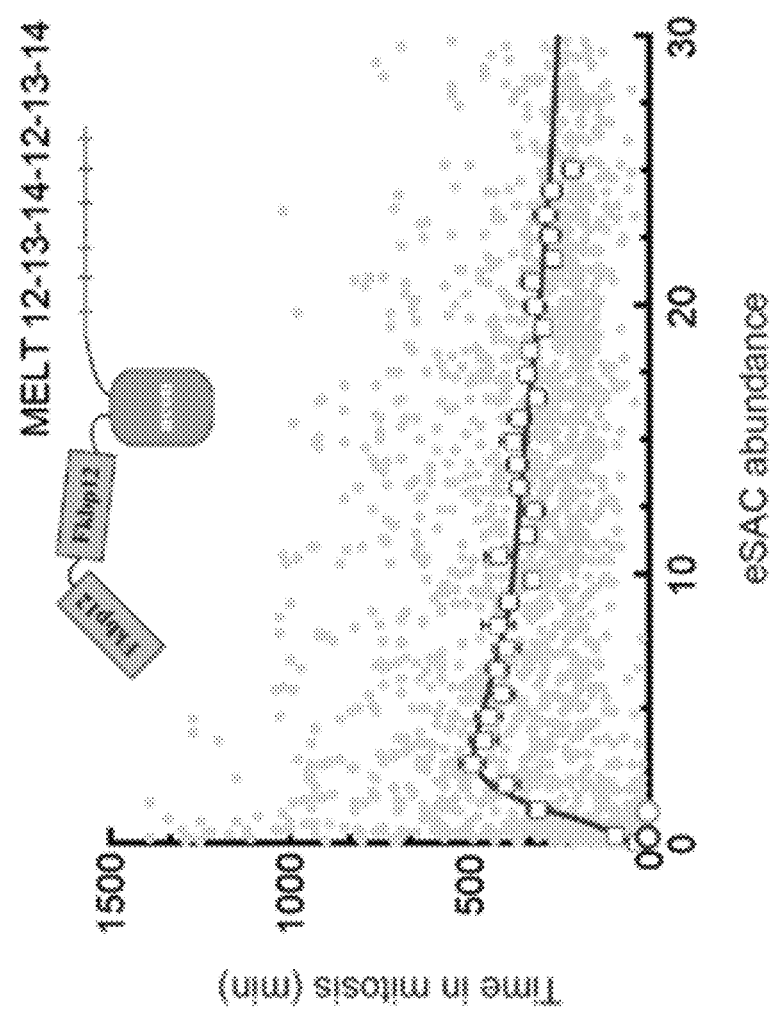

FIG. 25A-B. The abundance of the eSAC kinase domain is comparable with that of the endogenous Mps1 kinase. (A) Comparison of the expression level of the endogenous Mps1 and the eSAC Mps1 kinase domain (Frb-mCherry-Mps1$^{500-857}$) for three different cell lines expressing the indicated phosphodomains. Total cell lysates probed with an antibody against the C-terminus of Mps1, which is present in the kinase domain used for the eSAC. (B) Assessment of the expression levels of the eSAC phosphodomains (antibody against the Fkbp12 protein) and their phosphorylation after rapamycin-induced dimerization with Mps1 (phosphospecific antibody against MELT$^{13}$ does not recognize the phosphodomain containing MELT$^{12}$ alone).

FIG. 26A-E. Dose-response characteristics for the indicated phosphodomains (n=2572, 2969, 3043, 2791, and 2705 respectively from N≥2 independent trials). Open squares represent mean values of binned data, error bars represent s.e.m.

Figure 27A:
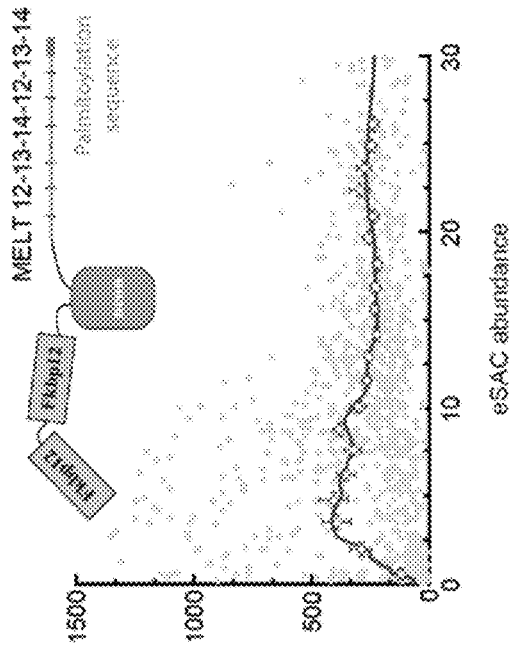
Figure 27B:
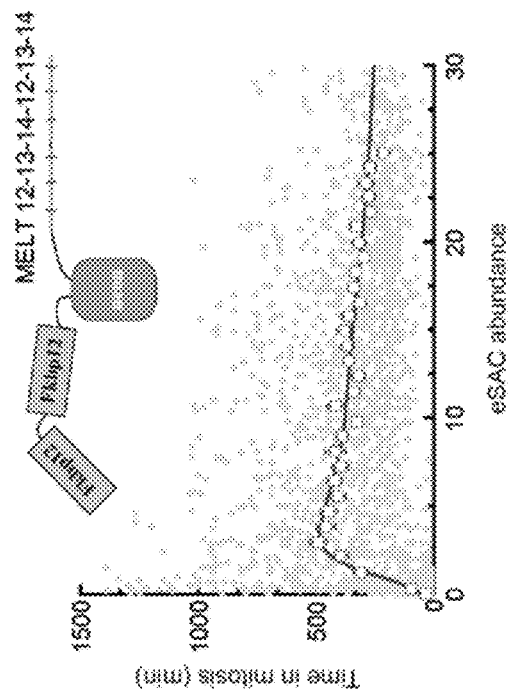
Figure 27C:
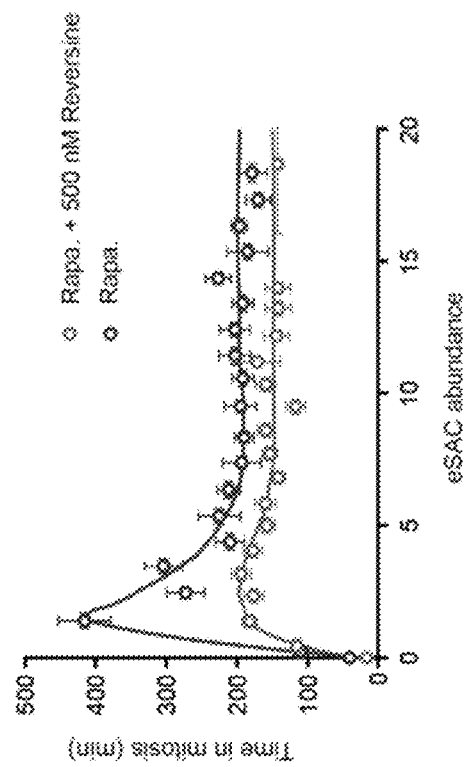
Figure 28B:
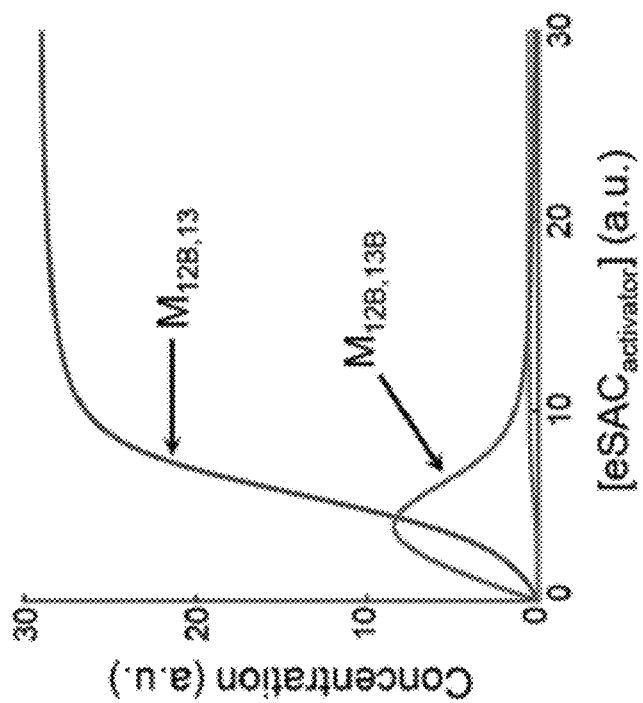
Figure 28A:
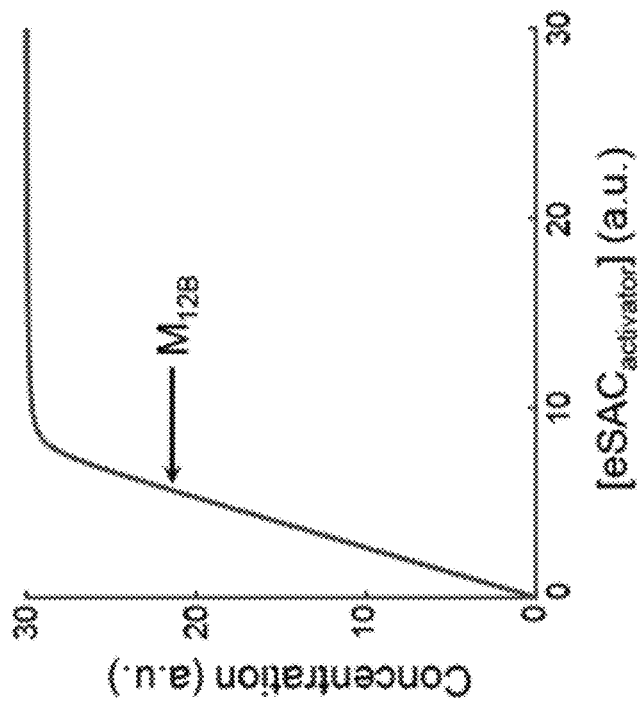
Figure 28D:
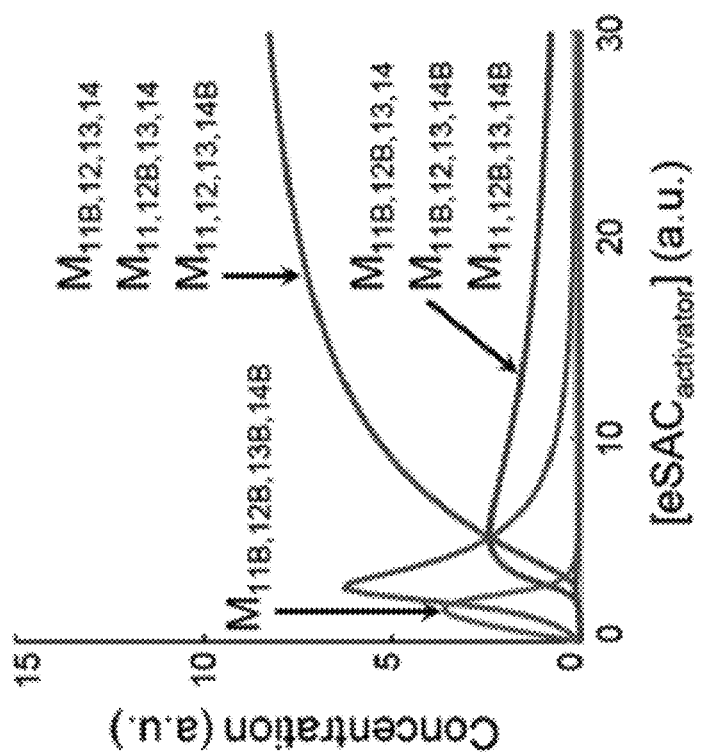
Figure 28C:
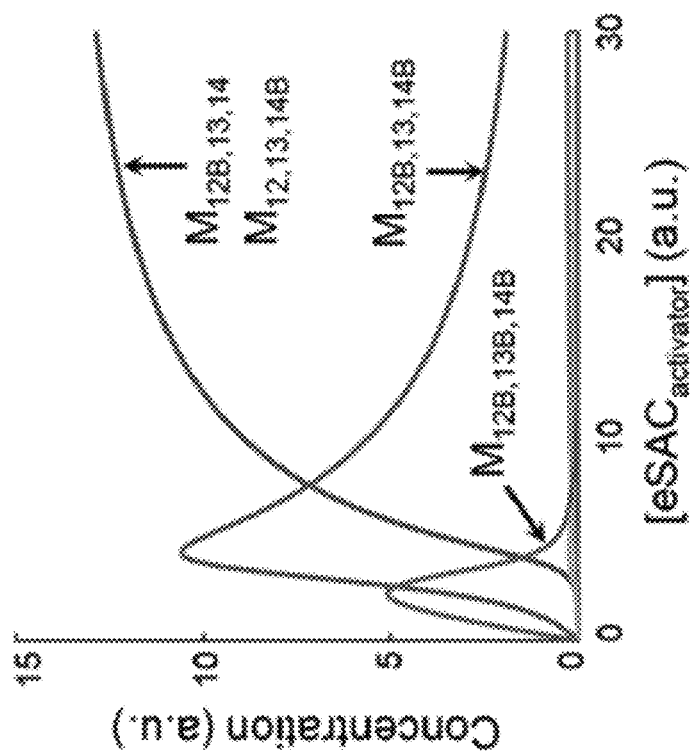
Figure 28E:
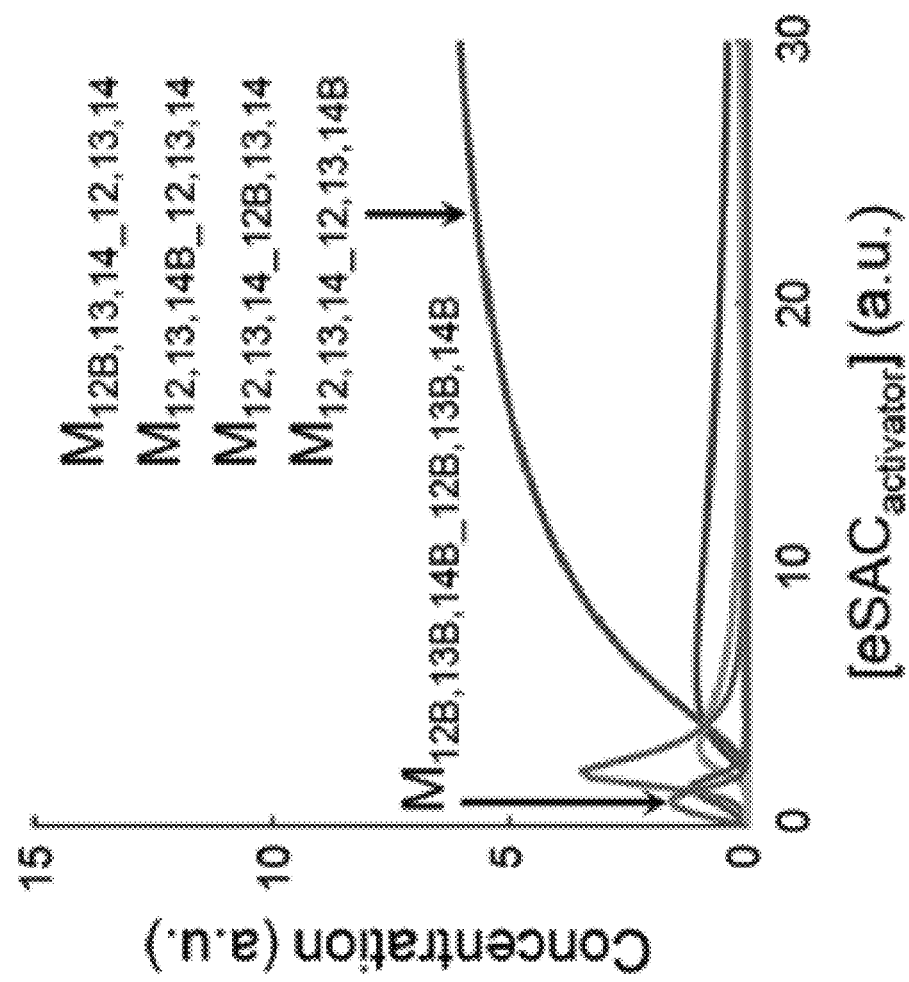

FIG. 27A-C. The eSAC dose-response relationship is maintained even when it is localized to the plasma membrane, and when the endogenous Mps1 kinase is inhibited. (A-B) Dose-response characteristics of a phosphodomain containing 6 MELT repeats when it is cytosolic (a, n=2705 re-plotted from FIG. 19F) and when it is targeted to the plasma membrane (b, n=1056). (C) The complex nature of the dose-response characteristics is retained even when the endogenous SAC activation switch is inactivated by inhibiting the kinase activity of the endogenous Mps1. Open squares and circles represent averages of binned data, error bars represent s.e.m.

FIG. 28A-E. Abundance of different Bub-bound species for the five eSAC phosphodomains at different concentrations of the eSAC activator complexes. (A-E) The abbreviations for different Bub-bound phosphodomain species are as follows. The subscripted number following the M denotes the rank of the MELT repeat in the KNL1 phosphodomain (see FIG. 4A). For example, $M_{12}$ symbolizes the eSAC phosphodomain with one MELT motif, and $M_{12,13,14\_12,13,14}$ symbolizes the phosphodomain with six MELT repeats. The subscript 'B' in front of the number signifies that the MELT motif denoted by the number is bound by Bub. The concentration of Bub is assumed to be 30 a.u.

Figure 29:
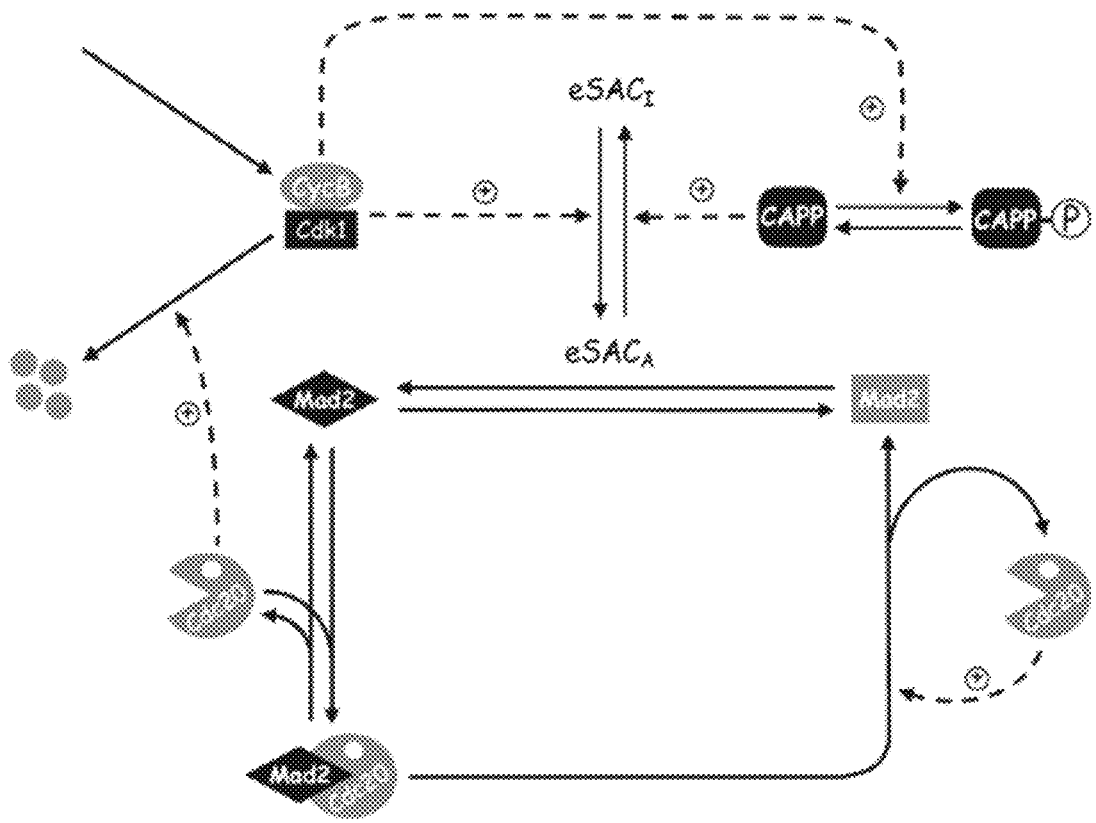

FIG. 29. Schematic of the model used to simulate anaphase onset. An active eSAC produces the Closed form of Mad2, which sequesters Cdc20 as part of the MCC. This eSAC activity is promoted by high CyclinB-CDK1, and inhibited by an unspecified phosphatase (CAPP). High CyclinB-CDK1 activity also inhibits the activity of the phosphatase. eSAC catalyzes the formation of the closed/active Mad2 at a rate $k_{amad}$ determined by: (a) the amino acid sequences of the MELT repeats in the eSAC phosphodomain, (b) potentially synergistic activity of the MELT repeats, and (c) abundance of the eSAC activator. Closed/active Mad2 sequesters Cdc20, and thus inhibits the APC. Free Cdc20 acts with APC to degrade Cyclin B and to promote the dissociation of the Mad2-Cdc20 complex. Thus, $k_{amad}$ also determines the rate of degradation of Cyclin B by the APC. When Cyclin B levels fall below the minimum threshold value, the two feedback loops work concurrently to rapidly drive the cell out of mitosis.

FIG. 30A-D. (A) Dependence of the weighted average rate of generation of Closed/active Mad2, $k_{amad}$, by different eSAC phosphodomain plotted on the eSAC abundance. (B) $k_{amad}$ curves for eSAC phosphodomains containing 2 and 6 MELT repeats, along with their corresponding bifurcation curves ($k_{amad}$ values above/below which the switch is ON/OFF). (C) Time dependence of [CycB] for different phosphodomains. It is assumed that the cell exits mitosis when the Cyclin B concentration falls below 5 a.u. (dashed line). (D) Dependence of time in mitosis on [eSAC] for different phosphodomains. The dashed curve corresponds to dose response curve for the phosphodomain containing 6 MELT repeats calculated by assuming that cooperativity is absent.

DEFINITIONS

As used herein "CASCS" and "KNL1" refer to the same human protein (Pubmed AccessionNo.Q8NG31) that is involved in spindle-assembly checkpoint signaling, correct chromosome alignment during mitosis, and attachment of the kinetochores to the spindle microtubules. "Spc105" refers to analogous protein in yeast (Pubmed Accession No. P53148). "Spc105/KNL1" is used herein to refer collectively to these proteins and other variants thereof.

As used herein, the term "aneuploidy" refers to an abnormal number of chromosomes within a cell. Aneuploidy includes an imbalance of genetic material caused by loss or gain of part of any chromosome (segmental aneuploidy). Accordingly, in some embodiments, aneuploid cells may have three copies of part of one chromosome and only one copy of part of the other chromosome. In other embodiments, aneuploid cells may contain an addition or deletion of one or more entire (whole) chromosomes. In other embodiments, aneuploid cells may contain an addition or deletion of one or more chromosomal arms or portions thereof. Accordingly, in some embodiments, aneuploid cells may be monosomic, trisomic, tetrasomic, etc., for one or more chromosomes or chromosomal regions. In some embodiments, aneuploid cells may have a loss of one or both copies of one or more chromosomes or chromosomal regions. In some embodiments, a region of about 0.01%, about 0.1%, about 1%, about 10%, about 25%, about 50%, or a higher, lower, or intermediate percentage of each of one or more chromosomes may be lost (e.g., one copy or both copies absent from a cell) or duplicated (e.g., three, four, or more copies in a cell). It should be appreciated that aneuploidy also may be associated with one or more additional chromosomal rearrangements including translocations, inversions, etc., of one or more chromosomal regions.

As used herein, the terms "Mps1 element", "Mps1 component", and "Mps1 polypeptide" refer to a polypeptide that is capable of performing the Spc105/KNL1-phosphorylating function of Mps-1 and activating the SAC. In some embodiments, an Mps1 element or polypeptide comprises significant sequence identity (e.g., >70%) with wild-type Mps1 (SEQ ID NO:1) or a fragment thereof (e.g., all or a portion of the Mps-1 kinase domain (SEQ ID NO:2)). In some embodiments, phosphorylation of Spc105/KNL1 or a Spc105/KNL1 polypeptide by an Mps-1 polypeptide is sufficient for activating the SAC.

As used herein, the terms "Spc105/KNL1 element", "Spc105/KNL1 component", and "Mps1 element polypeptide", refer to polypeptide that is capable of being phosphorylated by Mps1 (or an Mps1 polypeptide) and activating the SAC. In some embodiments, an Spc105/KNL1 polypeptide comprises significant sequence identity (e.g., >70%) with wild-type Spc105 (SEQ ID NO:7) or KNL1 (SEQ ID NO:4) or a fragment thereof (e.g., all or a portion of the phosphodomain of Spc105 (SEQ ID NO: 8) or KNL1 (SEQ ID NO: 5)). In some embodiments, phosphorylation of an Spc105/KNL1 polypeptide by Mps1 or an Mps1 polypeptide is sufficient for activating the SAC.

As used herein, the term "tunable" refers to the adjustability of an activity within a system. A particular activity may be adjustable by controlling the level or concentration of one or more components responsible for the activity, or by the inclusion of an enhancer or inhibitor of the activity or an interaction responsible for the activity. For example, the activity of a complex (e.g., dimer) may be "tuned" by altering (e.g., increasing or decreasing) the concentration of one or more components (e.g., Spc105/KNL1 and Mps1 fragments) of the complex, and/or by the altering the concentration (or the presence or absence) of one or more effectors (e.g., enhancer, inhibitor, etc.) of complex (e.g., dimer) formation.

As used herein, the term "dimer" refers to a noncovalent complex of two protein, polypeptide, and/or peptide components. In some embodiments, a first protein, polypeptide, and/or peptide component comprises a dimerization domain (e.g., a peptide or polypeptide segment) to facilitate dimerization of a functional domain with a second protein, polypeptide, and/or peptide component. In some embodiments, a first protein, polypeptide, and/or peptide component is linked to a non-peptide/non-polypeptide element to facilitate dimerization with a second protein, polypeptide, and/or peptide component.

As used herein, unless otherwise specified, the terms "peptide" and "polypeptide" refer to polymer compounds of two or more amino acids joined through the main chain by peptide amide bonds (—C(O)NH—). The term "peptide" typically refers to short amino acid polymers (e.g., chains having fewer than 25 amino acids), whereas the term "polypeptide" typically refers to longer amino acid polymers (e.g., chains having more than 25 amino acids).

As used herein, the term "phosphodomain" refers to a portion of a protein, polypeptide, or peptide that is the substrate for a kinase and is phosphorylated thereby under appropriate conditions. A phosphodomain is sufficient to support phosphorylation outside of the context of a greater protein sequence. The term "phosphorylation site" refers to a position or group of several amino acids within a phosphodomain where phosphorylation occurs. The phosphorylation site may not be capable of supporting phosphorylation outside of the context of a phosphodomain. A phosphodomain may comprise multiple phosphorylation sites. A protein or polypeptide may comprise one or more phosphodomains.

As used herein, the term "wild-type," refers to a gene or gene product (e.g., protein) that has the characteristics (e.g., sequence) of that gene or gene product isolated from a naturally occurring source, and is most frequently observed in a population. In contrast, the term "mutant" refers to a gene or gene product that displays modifications in sequence when compared to the wild-type gene or gene product. It is noted that "naturally-occurring mutants" are genes or gene products that occur in nature, but have altered sequences when compared to the wild-type gene or gene product; they are not the most commonly occurring sequence. "Synthetic mutants" are genes or gene products that have altered sequences when compared to the wild-type gene or gene product and do not occur in nature. Mutant genes or gene products may be naturally occurring sequences that are present in nature, but not the most common variant of the gene or gene product, or "synthetic," produced by human or experimental intervention.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties. Naturally occurring residues may be divided into classes based on common side chain properties, for example: hydrophobic: norleucine, Met, Ala, Val, Leu, and Ile; neutral hydrophilic: Cys, Ser, Thr, Asn, and Gln; acidic: Asp and Glu; basic: His, Lys, and Arg; residues that influence chain orientation: Gly and Pro; and aromatic: Trp, Tyr, and Phe. Non-conservative substitutions may involve the exchange of a member of one of these classes for a member from another class; whereas conservative substitutions may involve the exchange of a member of one of these classes for another member of that same class.

As used herein, the term "percent sequence identity" refers to the degree (e.g., 50%, 60%, 70%, 80%, 90%, 95%, 98%, 99%, etc.) to which two polymer sequences (e.g., peptide, polypeptide, nucleic acid, etc.) have the same sequential composition of monomer subunits. If two polymers have identical sequences (e.g., 100% sequence identity) they may be referred to herein as having "sequence identity." The term "percent sequence similarity" refers to the degree (e.g., 50%, 60%, 70%, 80%, 90%, 95%, 98%, 99%, etc.) with which two polymer sequences (e.g., peptide, polypeptide, nucleic acid, etc.) have similar polymer sequences. For example, similar amino acids are those that share the same biophysical characteristics and can be grouped into the families (see above). If two polymers have sequences that have monomers at each position that share the same biophysical characteristics they may be referred to herein as having "sequence similarity." The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "pharmaceutically acceptable carrier" refers to non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

As used herein, the term "effective amount" refers to the amount of a composition (e.g., pharmaceutical composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., pharmaceutical compositions of the present invention) to a subject or in vivo, in vitro, or ex vivo cells, tissues, and organs. Exemplary routes of administration to the human body can be through the eyes (e.g., intraocularly, intravitrealy, periocularly, ophthalmic, etc.), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) (e.g., first and second SAC-activating dimerization constructs, SAC-activating dimerization constructs and dimerization inducer, system described herein and second cancer therapy, etc.) or therapies to a subject. In some embodiments, the co-administration of two or more agents or therapies is concurrent (e.g., in the same or separate formulations). In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "vector" refers to a polynucleotide that is used to express a polypeptide of interest in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, e.g., β-galactosidase). One skilled in the art can select suitable vector elements for the particular host cell and application at hand.

As used herein, the terms "treat," "treatment," and "treating" refer to reducing the amount or severity of a particular condition (e.g., angiogenesis), disease state (e.g., cancer), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process. Treatment may be achieved with surgery, radiation, and/or administration of one or more molecules, including, but not limited to, small molecules and polymers, such as polypeptides.

As used herein, the terms "prevent," "prevention," and "preventing" refer to reducing the likelihood of a particular condition or disease state (e.g., cancer) from occurring in a subject not presently experiencing or afflicted with the condition or disease state. The terms do not necessarily indicate complete or absolute prevention. For example "preventing cancer" refers to reducing the likelihood of cancer occurring in a subject not presently experiencing or diagnosed with cancer. In order to "prevent cancer" a composition or method need only reduce the likelihood of cancer, not completely block any possibility thereof. "Prevention," encompasses any administration or application of a therapeutic or technique to reduce the likelihood of a disease developing (e.g., in a mammal, including a human).

As used herein, the term "gene therapy" refers to the transfer of genetic material (e.g., DNA or RNA) of interest into a host to treat or prevent a genetic or acquired disease or condition. The genetic material of interest encodes a product, the production of which is desired in vivo. For a review see, in general, the text "Gene Therapy" (Advances in Pharmacology 40, Academic Press, 1997; herein incorporated by reference in its entirety).

DETAILED DESCRIPTION

Provided herein are compositions and methods for the treatment of cancer by activating the spindle assembly checkpoint (SAC) in cells. In particular, dimerized Mps1 and Spc105/KNL constructs are provided as tunable activators of SAC, allowing for control of chromosome segregation accuracy and prevention of aneuploidies that are common in cancer.

Experiments were conducted during development of embodiments herein that demonstrate that the microtubule-dependent proximity of two kinetochore proteins acts like a mechanical switch that controls SAC signaling. It also explains a functional significance of the stereotypical 'end-on' kinetochore-microtubule attachment and the nanoscale protein organization within this attachment.

The SAC is a surveillance mechanism that detects kinetochores that are not attached to the cell division apparatus. Even if one kinetochore is unattached, the SAC must arrest cell division to allow it to attach. However, the ability of the SAC to arrest the cell and its timely silencing depend on the expression levels of nine signaling proteins (refs.17, 18; herein incorporated by reference in their entireties) that participate in a cascade of five reactions (refs.17,19-23; herein incorporated by reference in their entireties). Aberrant expression of one or more proteins, which is common in tumor cells, and which occurs during aging, likely changes SAC signaling properties and leads to chromosome missegregation and genomic instability.

The proteins that form the mechanical switch for the SAC, Mps1, Hec1/Ndc80, and Spc105/KNL1, are all aberrantly expressed in cancer cells, and therefore, important potential targets of therapeutics. KNL1 (a.k.a. CASCS) is the human version and Spc105 is the yeast version of a protein encoded by this gene is a component of the multiprotein assembly that is required for creation of kinetochore-microtubule attachments and chromosome segregation. Analysis of the yeast kinetochore in both budding yeast and in HeLa cells during development of embodiments herein demonstrates that the SAC can be activated by inducing the dimerization of Mps1 and the phosphodomain of Spc105/KNL1 in the cytosol. This finding demonstrates that the 'wait-anaphase' signal can be generated to activate the SAC in a kinetochore-independent fashion.

In some embodiments, provided herein is a tunable SAC activator. In some embodiments, the SAC activator is genetically encoded. In some embodiments, the SAC activators herein provide control of the SAC signal in both cell lines and in whole animals (e.g., animal models, humans, patients, etc.). In some embodiments, the level of control is titratable. In some embodiments, compositions, methods, and systems are provided for the tunable activation of SAC and temporary cell cycle arrest (e.g., in metaphase) to allow for proper chromosome segregation, cell division, to prevent aneuploidy, and/or to treat or prevent cancer.

In some embodiments, the tunable SAC activators herein comprise an Mps1 component (e.g., a fragment of Mps-1, or a variant thereof, capable of phosphorylating Spc105/KNL1) and a Spc105/KNL1 component (e.g., a fragment of Spc105/KNL1, or a variant thereof, comprising one or more phosphodomains and capable of being phosphorylated by Mps1). In some embodiments, a tunable SAC activator comprises dimerizable Mps1 and Spc105/KNL1 components. In some embodiments, upon dimerization, the Mps1 component phosphorylates one or more phosphodomains on the Spc105/KNL1 component, thereby initiating/facilitating/enhancing the SAC cascade and temporary cell cycle arrest.

In some embodiments, a first component (e.g., Mps1 element) of a tunable SAC activator comprises an Mps1 domain (e.g. kinase domain). In some embodiments, the Mps1 domain is the functional domain of the first component of the tunable SAC activator. In some embodiments, the first component further comprises a dimerization domain (e.g., a peptide or polypeptide segment that facilitates dimerization with a second component of the tunable SAC activator) or a dimerization element (e.g., a non-peptide/non-polypeptide element that facilitates dimerization with a second component of the tunable SAC activator. In some embodiments, a second component (e.g., Spc105/KNL1 element) of a tunable SAC activator comprises an Spc105/KNL1 domain (e.g., phosphodomain). In some embodiments, the Spc105/KNL1 domain is the functional domain of the second component of the tunable SAC activator. In some embodiments, the second component further comprises a dimerization domain (e.g., a peptide or polypeptide segment that facilitates dimerization with a first component of the tunable SAC activator) or a dimerization element (e.g., a non-peptide/non-polypeptide element that facilitates dimerization with a first component of the tunable SAC activator. In some embodiments, the dimerization domain and/or dimerization element on the first component facilitates dimerization of the first and second components via noncovalent interaction with a dimerization domain and/or dimerization element on the second component.

In some embodiments, the Mps1 domain of the Mps1 element comprises the full-length sequence of Mps-1 (e.g., a naturally-occurring sequence). In some embodiments, the Mps1 domain of the Mps1 element comprises a synthetic variant of full-length Mps1 (e.g., comprising one or more non-naturally-occurring conservative or non-conservative substitutions relative to the wild-type Mps1). In some embodiments, the Mps1 domain of the Mps1 element comprises a fragment of Mps1. In some embodiments, the Mps1 domain of the Mps1 element comprises the Mps1 kinase domain. In some embodiments, the Mps1 domain of the Mps1 element comprises a fragment of Mps1 with one or more non-naturally-occurring substitutions (e.g., conservative or non-conservative substitutions). In embodiments in which the Mps1 domain of the Mps1 element comprises a synthetic variant and/or fragment of Mps1, the Mps1 domain is capable of phosphorylating one or more phosphodomains of Spc105/KNL1, or a variant or fragment (e.g., upon dimerization of the Mps1 element with a second element comprising a Spc105/KNL1 domain). In some embodiments, the Mps1 domain comprises at least 50% sequence identity (e.g., 50%, 55%, 60%, 65%, 70%, 75%, 80%, 85%, 90%, 95%, 96%, 97%, 98%, 99%, 100%, or any ranges there between) with full length Mps1 (SEQ ID NO:1) or a fragment thereof. In some embodiments, the Mps1 domain comprises at least 50% sequence similarity (e.g., 50%, 55%, 60%, 65%, 70%, 75%, 80%, 85%, 90%, 95%, 96%, 97%, 98%, 99%, 100%, or any ranges there between) with full length Mps1 (SEQ ID NO:1) or a fragment thereof. In some embodiments, the Mps1 domain comprises only conservative substitutions with respect to full length Mps1 (SEQ ID NO:1). In some embodiments, the Mps1 domain comprises at least 50% sequence identity (e.g., 50%, 55%, 60%, 65%, 70%, 75%, 80%, 85%, 90%, 95%, 96%, 97%, 98%, 99%, 100%, or any ranges there between) with the kinase domain of Mps1 (SEQ ID NO:2) or a fragment thereof. In some embodiments, the Mps1 domain comprises at least 50% sequence similarity (e.g., 50%, 55%, 60%, 65%, 70%, 75%, 80%, 85%, 90%, 95%, 96%, 97%, 98%, 99%, 100%, or any ranges there between) with the kinase domain of Mps1 (SEQ ID NO:2) or a fragment thereof. In some embodiments, the Mps1 domain comprises only conservative substitutions with respect to the kinase domain of Mps1 (SEQ ID NO:2) or a fragment thereof.

In some embodiments, the Spc105/KNL1 domain of the Spc105/KNL1 element comprises the full-length sequence of Spc105/KNL1 (e.g., a naturally-occurring Spc105 or KNL1 sequence). In some embodiments, the Spc105/KNL1 domain of the Spc105/KNL1 element comprises a synthetic variant of full-length Spc105/KNL1 (e.g., comprising one or more non-naturally-occurring conservative or non-conservative substitutions relative to a naturally-occurring Spc105 or KNL1 sequence). In some embodiments, the Spc105/KNL1 domain of the Spc105/KNL1 element comprises a fragment of a Spc105 or KNL1 sequence. In some embodiments, the Spc105/KNL1 domain of the Spc105/KNL1 element comprises a fragment of Spc105 or KNL1 with one or more non-naturally-occurring substitutions (e.g., conservative or non-conservative substitutions). In embodiments in which the Spc105/KNL1 domain of the Spc105/KNL1 element comprises a synthetic variant and/or fragment of Spc105 or KNL1, the Spc105/KNL1 domain is capable of being phosphorylated at one or more phosphodomains by Mps1 or an active fragment and/or variant thereof (e.g., upon dimerization of the Spc105/KNL1 element with a second element comprising a Mps1 domain). In some embodiments, the Spc105/KNL1 domain comprises at least 50% sequence identity (e.g., 50%, 55%, 60%, 65%, 70%, 75%, 80%, 85%, 90%, 95%, 96%, 97%, 98%, 99%, 100%, or any ranges there between) with a full-length naturally-occurring Spc105 (SEQ ID NO:7) or KNL1 (SEQ ID NO:4) or a fragment thereof. In some embodiments, the Spc105/KNL1 domain comprises at least 50% sequence similarity (e.g., 50%, 55%, 60%, 65%, 70%, 75%, 80%, 85%, 90%, 95%, 96%, 97%, 98%, 99%, 100%, or any ranges there between) with full length Spc105 (SEQ ID NO:7 or KNL1 (SEQ ID NO:4) or a fragment thereof. In some embodiments, the Spc105/KNL1 domain comprises only conservative substitutions with respect to full length Spc105 (SEQ ID NO:7 or KNL1 (SEQ ID NO:4) (SEQ ID NO:1). In some embodiments, the Spc105/KNL1 domain comprises at least 50% sequence identity (e.g., 50%, 55%, 60%, 65%, 70%, 75%, 80%, 85%, 90%, 95%, 96%, 97%, 98%, 99%, 100%, or any ranges there between) with the phosphodomain of Spc105 (SEQ ID NO:8) or KNL1 (SEQ ID NO:5) or a fragment thereof. In some embodiments, the Spc105/KNL1 domain comprises at least 50% sequence similarity (e.g., 50%, 55%, 60%, 65%, 70%, 75%, 80%, 85%, 90%, 95%, 96%, 97%, 98%, 99%, 100%, or any ranges there between) with the phosphodomain of Spc105 (SEQ ID NO:8) or KNL1 (SEQ ID NO:5) or a fragment thereof. In some embodiments, the Spc105/KNL1 domain comprises only conservative substitutions with respect to the phosphodomain of Spc105 (SEQ ID NO:8) or KNL1 (SEQ ID NO:5) or a fragment thereof.

In general, dimerization domains and elements (e.g., aka oligomerization domains and elements) that find use herein can be subdivided into two types: (1) domains/elements that are constitutive and (2) domains/elements that are regulated.

In some embodiments, constitutive domains/elements associate with their binding partner under suitable conditions (e.g., physiologically constitutive dimerization domains/elements will dimerize under physiologic conditions without the need for introduction of an initiator of dimerization). In some embodiments, a dimerization inducer is not required for dimerization of constitutive domains/elements. A skilled artisan will recognize that many heterologous domains whose associations are constitutive are well known in the art. Examples described in the art include, but are not limited to, heterodimerization of PDZ domains from the mammalian proteins neuronal nitric oxide synthase (nNOS) and syntrophin (Ung et al. (2001) EMBO J. 20: 3728-3737; herein incorporated by reference in its entirety), heterodimerization of the *Xenopus* XLIM1 and LDB1 proteins (Ung et al. (2001) EMBO J. 20: 3728-3737; herein incorporated by reference in its entirety), oligomerization of RFG (also named ELE1 or ARA70) through its coiled-coil domain (Monaco et al. (2001) Oncogene 20: 599-608; herein incorporated by reference in its entirety), oligomerization of the leucine zipper domain of yeast GCN4 (Harbury et al. (1993) Science 262: 1401-1407; herein incorporated by reference in its entirety), and oligomerization of the TEL helix-loop-helix (HLH) domain (Golub et al. (1996) Mol. Cell. Biol. 16, 4107-4116; herein incorporated by reference in its entirety) and their variants.

In some embodiments, regulated domains/elements associate with their binding partner in the presence of an inducer of dimerization. A skilled artisan will further recognize that many heterologous domains whose associations are regulated, rather than constitutive, are well known in the art. Examples include, but are not limited to, the Gyrase B-coumermycin system, the FKBP-rapamycin-FRAP system, and their variants. In some embodiments, these heterologous domains are domains from naturally occurring proteins or truncated active portions thereof. The binding domain can be small (e.g., <25 kDa), nonimmunogenic and accessible to cell permeable, nontoxic ligands.

Inducible/regulatable dimerization pairs include, for example, GyrB-GyrB (gyrase subunit B), FKBP-FRB (FK-binding protein-a domain (FRB) of the lipid kinase protein homologue FRAP (FKBP-rapamycin-associated protein)), $F_M$-$F_M$ (F36M mutation of FK-binding protein), ToxT-ToxT (ToxT Protein of V. cholerae), DHFR-DHFR (dihydrofolate reductase), FKBP-FKBP (FK-binding protein), FKBP-Cyp (FK-binding protein-cyclophilin) and Cyp-Cyp (Cyclophilin). In one embodiment, bacterial Gyrase B polypeptide or fragments or variants thereof (e.g. amino acids 1-220 of *E. coli* GyrB) are induced to dimerize in the presence of coumermycin or a coumermycin analog (Farrar et al. (1996) Nature 383, 178-181 and Farrar et al., U.S. Pat. No. 6,916, 846; herein incorporated by reference in their entireties). In another embodiment, a first functional domain is fused to the FRB (FRAP rapamycin binding) domain(s) or its variants of FRAP/mTOR or to an FKBP domain(s) or its variants of FKBP12 or its homologs, such that expression of the first functional domain fused to the FRB domain a dimer will form with a second functional domain fused to FKBP, or vice versa, in the presence of rapamycin or a rapamycin analog.

In some embodiments, both dimerization components are polypeptides or peptides (e.g., dimerization domains). Particular examples of such dimerizing polypeptides are GyrB, $F_M$, ToxT, FKBP, and DHFR. In other embodiments, one or both of the dimerization components is not a peptide or polypeptide.

In some embodiments, a first dimerization component is a polypeptide or peptide (e.g., dimerization domain) and a second dimerization component is a nucleic acid (e.g., dimerization element). Particular examples of such dimerizing pairs include, for example, E-ETR (MphR(A) protein and its operator ETR of *E. coli*), PIP-PIR (PIP protein of *Streptomyces pristinaespiralis* and its operator PIR), TetR-tetO (Tn10-derived tetracycline repressor TetR and its operator tetO), ArgR-argO (arginine-responsive repressor and its operator argO), ArsR-arsO (arsenic-responsive repressor and its operator arsO), HucR-hucO (uric acid-responsive repressor and its operator hucO), etc. Other such pairs are described by Ramos J. L. et al. (Microbiol Mol Biol Rev 69, 326-56, 2005) and Martinez-Bueno M. et al. (Bioinformatics 20, 2787-91, 2004); herein incorporated by reference in their entireties.

In some embodiments, a first dimerization component is a polypeptide or peptide (e.g., dimerization domain) and a second dimerization component is a small molecule (e.g., dimerization element). Particular examples of such dimerizing pairs include, for example, GyrB-coumarin antibiotics, FKBP-mTOR inhibitors, FRB-mTOR inhibitors, $F_M$-mTOR inhibitors, Cyp-cyclosporins, Cyp-ascomycins, DHFR-antifolate, streptavidin-biotin analog, avidin-biotin analog, neutravidin-biotin analog, steroid hormone receptors-steroid hormones and analogs thereof, and ToxT-virstatin.

In other embodiments, neither component of a dimerization pair is a peptide or polypeptide.

Dimerization domains may be attached to functional domains via the formation of a fusion polypeptide comprising the two domains. Non-peptide/non-polypeptide dimerization elements may be attached to functional domains via direct covalent attachment or through a linker element.

Dimerization approaches and components are further described, for example, in Intl. Pat. App. WO 2009/146929; herein incorporated by reference in its entirety. Any other commercially-available dimerization components, or systems/methods for formation of dimers that are known in the filed may find use in some embodiments herein.

In some embodiments, the systems described herein comprise the capacity to tune the level of SAC activation. Various methods are available for such tunable activation, including: varying dimerization inducer concentration, presence or absence of phosphorylation inhibitor/enhancer, varying concentration of one or both constructs of a system, etc. In some embodiments, methods herein comprise administering a Spc105/KNL1 construct and a Mps1 construct to a system, cell, tissue, tumor, organism, etc., followed by tunably activating SAC to a desired level via administration of a desired (e.g., known or determined empirically) concentration of dimerization inducing agent.

In some embodiments, constructs are provided in which a functional domain (e.g., Spc105/KNL1 or Mps1 domain) is linked to a dimerization domain or element. In some embodiments, the functional domain and dimerization domain/element are directly connected. In other embodiments, a linker moiety connects the functional domain and dimerization domain/element. Suitable linkers may be peptide or polypeptide linkers (e.g., connecting a polypeptide functional domain to a peptide/polypeptide dimerization domain), or may be chemical linkers (e.g., connecting a polypeptide functional domain to a non-peptide/non-polypeptide dimerization element), such as a straight-chain or branched carbon chain, optionally comprising one or more functional groups (e.g., heteroatom-containing functional groups).

In some embodiments, provided herein are fusion polypeptides comprising a functional domain (e.g., Spc105/ KNL1 or Mps1 domain) and a dimerization domain. In such embodiments, the two peptide/polypeptide domains may be directly connected (e.g., N-terminus to C-terminus) or may be connected via a peptide/polypeptide linker. An peptide/ polypeptide linker may be of and suitable sequence and may confer one or more desirable characteristics to the fusion polypeptide, such as: solubility, spacing between domains, flexibility, etc. Peptide/polypeptide linkers are not limited to fusion polypeptide constructs; rather, they may also find use in other constructs within the scope herein, such as constructs comprising a functional domain (e.g., Spc105/KNL1 or Mps1 domain) and a non-peptide/non-polypeptide dimerization element.

In some embodiments, provided herein are functional domains (e.g., Spc105/KNL1 or Mps1 domain) connected to a peptide/polypeptide dimerization domain or a non-peptide/non-polypeptide dimerization element via a chemical linker moiety. In some embodiments, a chemical linker moiety comprises a straight or branched chain of 1-30 carbon atoms, optionally comprising one or more heteroatoms and branched or main-chain substituents. In some embodiments, the linker moiety comprises a multiatom straight or branched chain of atoms selected from C, H, N, O, P, and S. Functional groups comprising the linker moiety include, but are not limited to —$CH_2$—, =CH—, =C=, CO, CONH, —$NH_2$, —OH, —SH, —O—, —S—, etc. In some embodiments, the linker moiety comprises one or more $(CH_2)_2O$ groups or CONH groups.

In some embodiments, provided herein are systems comprising a first construct comprising a Mps1 domain and a first dimerization domain/element and a second construct comprising a Spc105/KNL1 domain and a second dimerization domain/element, wherein the first dimerization domain/element and the second dimerization domain/element are complementary such that they constitutively, or upon induction (e.g., by contact with an inducing agent), dimerize to form a complex (e.g., stable complex). In some embodiments, formation of the dimerization complex facilitates phosphorylation of the Spc105/KNL1 domain of the second construct by the Mps1 domain of the first construct. In some embodiments, in the absence of formation of the dimerization complex, little or no (e.g., below background) phosphorylation of the Spc105/KNL1 domain of the second construct occurs.

In some embodiments, formation of the dimerization complex results in a significant increase in phosphorylation of the Spc105/KNL1 domain of the second construct (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 500-fold, $10^3$-fold, $10^4$-fold, $10^4$-fold, $10^5$-fold, $10^6$-fold, or more, or and suitable ranges there between). In some embodiments, the degree of increase in phosphorylation is proportional to the concentration of the first and/or second constructs. In some embodiments, the degree of activation of SAC is scalable/tunable based upon the concentration of the first and/or second constructs.

In some embodiments, induction of dimerization (e.g., by addition of a inducer of dimerization) results in a significant increase in phosphorylation of the Spc105/KNL1 domain of the second construct (e.g., 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 500-fold, $10^3$-fold, $10^4$-fold, $10^4$-fold, $10^5$-fold, $10^6$-fold, or more, or and suitable ranges there between). In some embodiments, the degree of increase in phosphorylation is proportional to the concentration of the first and/or second constructs. In some embodiments, the degree of activation of SAC is scalable/tunable based upon the concentration of the first and/or second constructs.

In some embodiments, methods are provided for activating the SAC in an in vitro or in vivo system (e.g., cell, tissue, tumor, organism, etc.) via the use of the Spc105/KNL1 and Mps1 dimerization constructs described herein. In some embodiments, tunable activation of the SAC is achieved by titrating (e.g., increasing/decreasing) the amount of Spc105/KNL1 dimerization construct, Mps1 dimerization construct, or dimerization inducer. In some embodiments, construct levels are controlled at the expression level. Systems and methods described herein are not limited by the routes of administering dimerization constructs and/or inducer or altering the concentrations thereof.

In many embodiments described herein, first and second constructs are provided for the activation (e.g., inducible activation, tunable activation, etc.) of SAC. In some embodiments, provided herein is a single construct comprising: (i) a Mps1 domain, (ii) a Spc105/KNL1 domain, and (iii) one or more domains, elements, or moieties configured to facilitate phosphorylation (e.g., tunable phosphorylation) of the Spc105/KNL1 domain by the Mps1 domain. For example, in some embodiments, Mps1 and Spc105/KNL1 domains are located at disparate locations in the primary sequence of a polypeptide fusion, such that phosphorylation of the Spc105/KNL1 domain by the Mps1 domain does not occur or occurs at a low rate. However, upon induction of dimerization or a pair of dimerization domains/elements located on the fusion polypepeitde, interaction of the Mps1 and Spc105/KNL1 domains is induced, phosphorylation of the Spc105/KNL1 domain by the Mps1 domain occurs, and SAC is activated. Any suitable orientation of Mps1 domain, Spc105/KNL1 domain, and dimerization domains/elements is within the scope herein (e.g., (Mps1 domain)-(dimerization domain 1)-(linker)-(dimerization domain 2)-(Spc105/KNL1 domain); (dimerization domain 1)-(Mps1 domain)-(linker)-(Spc105/KNL1 domain)-(dimerization domain 2); etc.).

Embodiments herein contemplate the delivery of exogenous nucleic acids encoding SAC-activating dimerization constructs, or the delivery of proteins themselves (e.g., recombinant SAC-activating dimerization constructs, etc.) to a system, cell, tissue, tumor, subject, etc. via any suitable method.

In some embodiments, nucleic acids are delivered within suitable vectors. The present invention is not limited to any particular vector. Indeed, a variety of vectors may be used to deliver the nucleic acids.

In certain embodiments, the nucleic acids are delivered via an adenovirus vector. (See e.g., Westfall et al., Meth. Cell Biol. 32:307-322 (1998); and U.S. Pat. No. 6,451,596, 6,083,750, 6,063,622, 6,057,158, or 5,994,132, all of which are herein incorporated by reference). In some embodiments, a nucleic acid encoding a construct(s) described herein are delivered via an adeno-associated vector (AAV). In some embodiments, the AAV vector integrates into the genome of the cells to which it is administered (e.g., a patient's cells (e.g., endothelial cells)). A number of AAV vectors which have been developed for gene therapy are useful in the present invention (See e.g., U.S. Pat. Nos. 5,173,414; 5,139,941; and 5,843,742; PCT publications WO92/01070 and WO93/03769; Lebkowski et al., Mol. Cell. Biol. 8:3988-3996 (1988); Carter, Curr. Opin. Biotech. 3:533-39, (1992); Muzyczka, Curr. Top, Microbiol. Immunol. 158:97-129, (1994); Kotin, Human Gene Ther. 5:793-801, (1994); Shelling and Smith, Gene Ther. 1:165-69, (1994); Zhou et al., J. Exp. Med. 179:1867-1875, (1994); U.S. Pat. Nos. 6,451,596, 6,083,750, 6,063,622, 6,057,158, or 5,994,132; Ferrari et al., Nature Med. 3(11):1295-97, (1997); and Gregorevic et al., Nature. Med. 10(8): 828 (2004), each of which is incorporated herein by reference in its entirety).

In some embodiments, recombinant adenovirus vectors are constructed by homologous recombination of a shuttle vector containing a nucleic acid encoding one or more SAC-activating dimerization constructs and the full-length adenovirus DNA following co-transfection into a cell line. In some embodiments, the full-length adenovirus DNA is provided from pJM17 which is a 0-100 map unit (m.u.) derivative of adenovirus serotype (Ad5) that contains a partial deletion in the E3 region and a 4.3-kb pBRX insert at 3.7 m.u. (See e.g., Graham and Prevec, Manipulation of Adenovirus Vectors, in Gene Transfer and Expression Protocols, E. J. Murray ed., Humana, Clifton, N.J. (1991); and Becker et al., Use of Recombinant Adenovirus for Metabolic Engineering of Mammalian Cells, in Methods in Cell Biology, Vol 43 M. G. Roth ed., Academic Press, N.Y. (1994); Grahm and Prevec, Methods Mol. Biol. 7, 109 (1991); herein incorporated by reference in their entireties). In some embodiments, a shuttle vector comprises 0-1 m.u. and 9-16 m.u. of the Ad5 genome flanking an expression cassette containing the nucleic acid encoding one or more SAC-activating dimerization constructs. Embodiments herein are not limited by the type of AAV or the methods of construction thereof.

In other embodiments, the nucleic acid encoding SAC-activating dimerization constructs are delivered via a liposome or naked DNA plasmid. In some embodiments, the liposome is a cationic liposome (See e.g., U.S. Pat. Nos. 5,908,777 and 5,676,954 each incorporated herein by reference in their entireties; Hug and Sleight, Biochim. Biophys. Acta. 1097:1-17, (1991); Straubinger et al., in Methods of Enzymology, Vol. 101 pp. 512-527 (1993); Felgner et al., Nature 337:387-388, (1989); and Felgner et al., PNAS (1987) 84:7413-7416) (1987); herein incorporated by reference in their entireties). An example of a commercially available cationic liposome carrier useful in the present invention is LIPOFECTIN (Bethesda Research Laboratories Life Technologies, Inc., Gaithersburg Md.).

In some embodiments, vector comprising nucleic acid encoding one or more SAC-activating dimerization constructs further includes a suitable promoter (e.g., cell specific promoter, etc.) and/or enhancer, and also any necessary ribosome binding sites, polyadenylation site, splice donor and acceptor sites, transcriptional termination sequences, and 5' flanking nontranscribed sequences. In other embodiments, DNA sequences derived from the SV40 splice, and polyadenylation sites may be used to provide the required non-transcribed genetic elements.

In some embodiments, nucleic acid constructs comprise elements for introduction of the Mps1 and Spc105/KNL1 constructs described herein via a CRISPR/Cas system (See, e.g., WO 2014093661, WO 2013176772, etc.; herein incorporated by reference in their entireties).

In some embodiments, the DNA sequence in an expression vector is operatively linked to an appropriate expression control sequence(s) (e.g., promoter) to direct mRNA synthesis. In some embodiments, the promoter is the cytomegalovirus (CMV) promoter. Other promoters useful in embodiments of the present invention include, but are not limited to, the LTR or SV40 promoter, the E. coli. lac or trp, the phage lambda $P_L$ and $P_R$, T3 and T7 promoters, HSV thymidine kinase, and mouse metallothionein-I promoters and other promoters known to control expression of genes in prokaryotic or eukaryotic cells (e.g., endothelial cells) or their viruses. In some embodiments, recombinant expression vectors include selectable markers permitting transformation of the host cell (e.g. dihydrofolate reductase or neomycin resistance for eukaryotic cell culture). In some embodiments, the promoter is a tissue specific and/or inducible promoter. In some embodiments, the promoter is regulated by an exogenous factor (e.g., diet, light, activator agent, etc.).

In some embodiments, transcription of the DNA encoding peptides and/or polypeptides described herein by higher eukaryotes is increased by inserting an enhancer sequence into the vector. Enhancers are cis-acting elements of DNA, usually about from 10 to 300 bp that act on a promoter to increase its transcription; Enhancers useful in the present invention include, but are not limited to, the SV40 enhancer (e.g., 100 to 270 base pairs on the late side of the replication origin), a cytomegalovirus early promoter enhancer, the polyoma enhancer (e.g., on the late side of the replication origin), and adenovirus enhancers.

In other embodiments, the expression vector also contains a ribosome binding site for translation initiation and a transcription terminator. In still other embodiments of the present invention, the vector includes appropriate sequences for amplifying expression.

In some embodiments, systems and methods are provided herein for the treatment of cancers or other diseases of conditions caused by of linked to aneuploidy or other chromosome separation abnormalities. In some embodiments, the Mps1 and Spc105/KNL1 polypeptide constructs described herein (or nucleic acids encoding such constructs) are used as therapeutics for the treatment or prevention of cancer, pre-cancer, metastasis, etc.

In some embodiments, systems and methods are provided for reducing or inhibiting the proliferation of cancer (e.g., tumor) cells in an individual. In some embodiments, an individual is identified on the basis that the individual is known to have, or be at risk of (e.g., based on prior occurance), an aneuploid cancer (e.g., tumor) and administering to said individual an effective amount of the compositions and/or systems herein to reduce or inhibit the proliferation of the cancer (e.g., tumor) cells in the aneuploid cancer (e.g., tumor). In some embodiments, compositions and/or systems herein are administered to an individual who has cancer. In some embodiments, the individual may not have been identified as having an aneuploid cancer (e.g., the cancer was not evaluated for aneuploidy or the cancer did not show present signs of aneuploidy).

In some embodiments, methods for determining if an individual should be administered an systems and/or compositions described herein are provided. In some embodiments, a cancer (e.g., tumor) sample is obtained from an individual and a karyotype analysis on the sample is performed to determine if the cancer (e.g., tumor) contains cells that are aneuploid. The presence of aneuploid cells in the cancer (e.g., tumor) sample indicates the cells should be treated as described herein. In some embodiments, Mps1 and/or Spc105/KNL1 constructs administered to the individual. The sample may be obtained from the individual by performing a biopsy. In some embodiments, the sample may be a DNA sample or a cellular sample. According to some aspects of the invention, methods of reducing or inhibiting cancer (e.g., tumor) cells lacking a functional endogenous tumor suppressor gene (e.g., with a mutation or deletion of one or both alleles) are provided. In some embodiments, cancer (e.g., tumor) cells lacking a functional endogenous tumor suppressor gene are contacted with an effective amount therapeutic compositions or systems herein. In some embodiments, the tumor suppressor gene is p53. In some embodiments, the individual is known to have one or more mutations in one or more oncogenes, such as ras, c-myc, erB-2, src, and bcl-2. In some embodiments, the individual is at risk of developing cancer or has been previously diagnosed with cancer. In some embodiments, the individual has one or more other indicia or risk factors for a disease or condition associated with aneuploidy.

Without being bound by theory, it should be appreciated that diseased tissues (e.g., tumor or cancer tissue) associated with aneuploid cells may entirely comprise aneuploid cells, may contain a subset of aneuploid cells (e.g., about 10%, about 20%, about 30%, about 40%, about 50%, about 60%, about 70%, about 80%, about 90%, or higher or lower percentages of aneuploid cells) as aspects of the invention are not limited in this respect. In some embodiments, the aneuploid cells may be homogeneous (all have the same genetic defects, for example the same genomic deletion, duplications, or combinations thereof). In some embodiments, the aneuploid cells may be heterogeneous (e.g., different cells or subsets of cells have different genetic defects, for example different extents of chromosomal deletions, duplications, or combinations thereof). It should be appreciated that certain diseases or conditions are associated with genomic instability leading to increasing levels of aneuploidy (e.g., larger amounts of genetic abnormalities within each aneuploid cells and/or more cells that are aneuploid) over time. Accordingly, aspects herein may be useful to treat subjects that have risk factors (e.g., one or more cancer-associated mutations) and/or indicia (e.g., low levels of genetic deletions and/or duplications) prior to the development of significant levels of aneuploidy (e.g., to prevent, reduce, or delay the development, growth or proliferation of aneuploid cells).

In some embodiments, aneuploidy is detected through karyotyping. Other techniques include Fluorescence In Situ Hybridization (FISH), Quantitative Polymerase Chain Reaction (PCR) of Short Tandem Repeats, Quantitative Fluorescence PCR (QF-PCR), Quantitative Real-time PCR (RT-PCR) dosage analysis, Quantitative Mass Spectrometry of Single Nucleotide Polymorphisms, Spectral karyotype analysis (SKY), and Comparative Genomic Hybridization (CGH). In some embodiments, karyotype analysis is performed on a cancer (e.g., tumor) sample that has been obtained from an individual. Tumor tissue removed from an individual by a biopsy can be used as a tumor sample. In some embodiments, the cancer (e.g., tumor) sample is a cellular sample or a DNA sample. Embodiments herein are not limited to the methods of detecting aneuploidy and that any method which allows the determination of aneuploidy can be used. As used herein, an individual includes a mammal, such as a human, non-human primate, cow, rabbit, horse, pig, sheep, goat, dog, cat, or rodent such a rat, mouse or a rabbit. In some embodiments, the individual is a human. In some embodiments, the methods are employed to reduce or inhibit the proliferation of the tumor or the unwanted mammalian cell proliferation in an individual, such as a mammal (e.g., human).

Systems, compositions, and methods of the invention are useful for treating diseased conditions in which subset of cells in an individual are aneuploid, such as certain tumors, cancers, neurological disorders such as Alzheimer's disease, and/or unwanted mammalian proliferation of aneuploid cells. Tumors treatable by the compounds of the invention include, for example, benign and malignant solid tumors, and benign and malignant non-solid tumors. Examples of solid tumors include but are not limited to: biliary tract cancer, brain cancer (including glioblastomas and medulloblastomas), breastcancer, cervical cancer, choriocarcinoma, colon cancer, endometrial cancer, esophageal cancer, gastric cancer, intraepithelial neoplasms, including Bowen's disease and Paget's disease, liver cancer, lung cancer, lymphomas, including Hodgkin's disease and lymphocytic lymphomas, neuroblastomas, oral cancer, including squamous cell carcinoma, ovarian cancer, including those arising from epithelial cells, stromal cells, germ cells and mesenchymal cells, pancreatic cancer, prostate cancer, rectal cancer, renal cancer including adenocarcinoma and Wilms tumor, sarcomas, including leiomyosarcoma, rhabdomyosarcoma, liposarcoma, fibrosarcoma and osteosarcoma, skin cancer, including melanoma, Kaposi's sarcoma, basocellular cancer and squamous cell cancer, testicular cancer, including germinal tumors (seminomas, and non-seminomas such as teratomas and choriocarcinomas), stromal tumors and germ cell tumors, and thyroid cancer, including thyroid adenocarcinoma and medullary carcinoma. In some embodiments, the tumor is non-pancreatic. Examples of non-solid tumors include but are not limited to hematological neoplasms. A hematologic neoplasm includes, for example, lymphoid disorders, myeloid disorders, and AIDS associated leukemias. Lymphoid disorders include but are not limited to acute lymphocytic leukemia and chronic lymphoproliferative disorders (e.g., lymphomas, myelomas, and chronic lymphoid leukemias). Lymphomas include Hodgkin's disease and non-Hodgkin's lymphoma. Chronic lymphoid leukemias include T cell chronic lymphoid leukemias and B cell chronic lymphoid leukemias. Myeloid disorders include chronic myeloid disorders such as for instance, chronic myeloproliferative disorders, myelodysplastic syndrome and acute myeloid leukemia. Chronic myeloproliferative disorders include but are not limited to angiogenic myeloid metaplasia, essential thrombocythemia, chronic myelogenous leukemia, polycythemia vera, and atypical myeloproliferative disorders. Atypical myeloproliferative disorders include, for example, atypical Chronic Myelogenous Leukemia (CML), chronic neutrophilic leukemia, mast cell disease, and chronic eosinophilic leukemia. Conditions of unwanted mammalian cell proliferation and treatable by this invention include familial adenomatous polyposis, dysplasia, hyperplasia (e.g., benign prostatic hyperplasia), fibrotic disorders, arteriosclerotic disorders, and dermatological disorders.

In some embodiments, provided herein are methods of reducing or inhibiting the proliferation of cancer (e.g., tumor) cells lacking one or more functional tumor suppressor gene(s). Tumor suppressor genes are genes which, in their wild type alleles, express proteins that suppress abnormal cell proliferation. Mutations of tumor suppressor genes can lead to loss of functional tumor suppressor protein expression and consequently, abnormal cell proliferation which may be accompanied by aneuploidy. In some embodiments, loss of tumor suppressor activity leads to aneuploidy. Examples of tumor suppressor genes include, but are not limited to, the retinoblastoma susceptibility gene or RB gene, the protein 53 (p53) gene (NM_000546.4; GI: 187830767; also known as antigen NY-CO-13, phosphoprotein p53, transformation-related protein 53 (TRP53), tumor suppressor p53), the deleted in colon carcinoma (DCC) gene (NM 005215.3; GI:260436868; also known as colorectal cancer suppressor) and the neurofibromatosis type 1(NF-1) tumor suppressor gene (NM OO1042492.2; GI:270132520). In some embodiments, methods comprise: identifying an individual with a tumor suppressor defect known to be associated with cancer and administering to the individual an effective amount of the therapeutic systems and compositions described herein. Methods to determine the suppressor or oncogene status of a tumor are known in the art and may involve mutational analysis by sequencing, DNA analysis, RNA analysis, and protein analysis The Spc105/KNL1 and/or Mps1 polypeptide dimerization constructs (or nucleic acids encoding such constructs) described herein may be administered to a subject per se or in the form of a pharmaceutical composition. Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiological acceptable carriers, diluents, excipients, or auxiliaries which facilitate processing of the therapeutic compositions into preparations which can be used pharmaceutically. Proper formulation is dependent upon the route of administration chosen.

For topical administration the compounds of the invention may be formulated as solutions, gels, ointments, creams, suspensions etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, therapeutic compositions may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, therapeutic compositions may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, therapeutic compositions may be readily formulated by combining with pharmaceutically acceptable carriers well known in the art. Such carriers enable the compounds of the invention to be formulated as tablets, pills, dragees, capsules, liquid gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium, carboxymethylcellulose, and/or polyvinylpyrrolidone (PVP); granulating agents; and binding agents. If desired, disintegrating agents may be added, such as the cross-linked polyvinylpyrrolidine, atgar, or alginic acid or a salt thereof such as sodium alginate. If desired, solid dosage forms may be sugar-coated or enteric-coated using standard techniques. For oral preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol the dosage unit may be determined by providing a valve to deliver a metered amount.

Therapeutic compositions may also be formulated in rectal or vaginal compositions such as suppositories or retention enemas, e.g., containing conventional suppository bases such as cocoa butter or other glycerides.

Alternatively, other pharmaceutical delivery system may be employed. Liposomes and emulsions are well known examples of delivery vehicles. Certain organic solvents such as dimethylsulfoxide also may be employed, although usually at the cost of greater toxicity. Additionally, therapeutic compositions may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The Spc105/KNL1 and/or Mps1 polypeptide dimerization constructs (or nucleic acids encoding such constructs) described herein will generally be used in an amount effective to achieve the intended purpose. For use to treat or prevent cancer, therapeutic compositions are administered or applied in a therapeutically effective amount. By therapeutically effective amount is meant an amount which is effective to ameliorate, or prevent the symptoms of the disease or disorder, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the IC50 as determined in cell culture (i.e. the concentration of test compound that inhibits 50% of Survivin dimerization). Such information can be used to more accurately determine useful doses in humans.

In some embodiments, one or more chemotherapeutics or other cancer therapies are provided as co-therapies with Spc105/KNL1 and/or Mps1 polypeptide dimerization constructs (or nucleic acids encoding such constructs) described herein, with or without (known) synergism between the co-administered therapies.

In some embodiments, exemplary anticancer agents suitable for co-administeration include, but are not limited to: 1) alkaloids, including microtubule inhibitors (e.g., vincristine, vinblastine, and vindesine, etc.), microtubule stabilizers (e.g., paclitaxel (Taxol), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies (e.g., conjugated with anticancer drugs, toxins, and/or radionuclides, etc.; neutralizing antibodies; etc.); 9) biological response modifiers (e.g., interferons (e.g., IFN-.alpha., etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); and 22) modulators of p53 protein function.

In some embodiments, the co-administered agents are formulated into a single dose and/or composition. In some embodiments, the co-administered agents are in separate doses and/or compositions. In some embodiments in which separate doses and/or compositions are administered, the doses and/or compositions are administered simultaneously, consecutively, or spaced over a time span (e.g., <30 minutes, 1 hour, 2 hours, 4 hours, 6 hours, 12 hours, 1 day, 2 days, 3 days, 4 days, 5 days, 6 days, 1 week, or more, or any suitable ranges therebetween).

In some embodiments, systems, compositions and methods herein find use in the prevention of aneuploidy in cells in vitro. In some embodiments, the Mps1 and Spc105/KNL1 constructs (and optionally dimerization inducer) are administered or introduced into cultured cells (e.g., for research or clinical uses). In some embodiments, cells comprise induced pluripotent stem cells (iPSs) or embryonic stem cells (ESCs). In some embodiments, methods herein reduce the occurrence of aneuploidy in ECSs and iPSs in culture. In some embodiments, following treatment or introduction of the Mps1 and Spc105/KNL1 constructs and systems herein into ECSs and/or iPSs, the cells are administered or introduced (e.g., therapeutically) into a subject for treatment of a disease of condition. In some embodiments, the methods and systems described herein reduce aneuploidy and cancers resulting the transplantation of iPSs and/or ECSs into a subject.

EXPERIMENTAL

Example 1

Figure 1A:
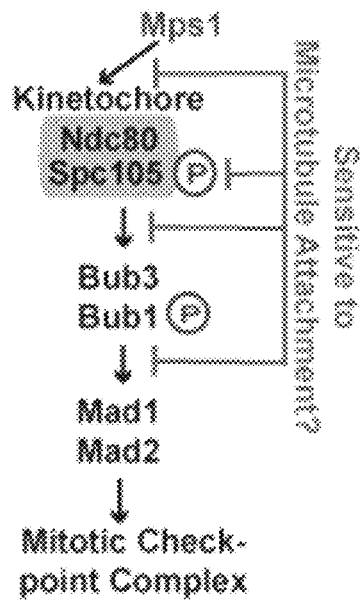
FIG. 1A-E. (a) The steps in the kinetochore-based signaling cascade of the SAC (P's indicate Mps1-mediated phosphorylation) that may be disrupted by microtubule attachment. (b) Top: Protein architecture of the metaphase kinetochore-microtubule attachment. Bottom: Schematic of the rapamycin-induced dimerization technique used to anchor Mps1 to the C terminus of Mtw1 (Mtw1-C). (c) Top: Micrographs show the anchoring of Mps1-Frb-GFP at Mtw1-C (time after rapamycin addition indicated; scale bars, ~3 μm). The stereotypical distribution of kinetochores in between the spindle pole bodies in metaphase visualized with Mtw1-GFP and Spc97-mCherry is shown on the right. Schematic underneath depicts the metaphase spindle morphology. Bottom: Kinetics of rapamycin-induced anchoring of Mps1-Frb-GFP to Mtw1-C. (d) Left: Representative transmitted-light images of yeast cells before and 1 h after the addition of rapamycin to anchor Mps1 at Mtw1-C. Right: Localization of Bub1-GFP and Mad1-GFP, and kinetochores (visualized by Spc24-mCherry) in untreated cells (control) and in cells that have Mps1 anchored at Mtw1-C (+ RAP). Scale bar, ~3 μm. (e) Top: Domain organization of Spc105. The end-to-end length of the unstructured domain of Spc105 (amino acids 1-455) is predicted to be 11.7±5 nm (mean±s.d. using the worm-like chain model). The maximum length of its α-helical region (amino acids 455-709) is 38 nm (3.6 amino acids per turn with a 0.54 nm pitch). The predicted kinetochore-binding domain is ~6 nm long. The depiction is not drawn to scale. The six Mps1 phosphorylation sites are depicted as bars. Bottom: Cell-cycle progression of asynchronous cells with the indicated genotypes observed on anchoring Mps1 at Mtw1-C. Accumulation of large-budded cells indicates mitotic arrest.
Figure 1B:
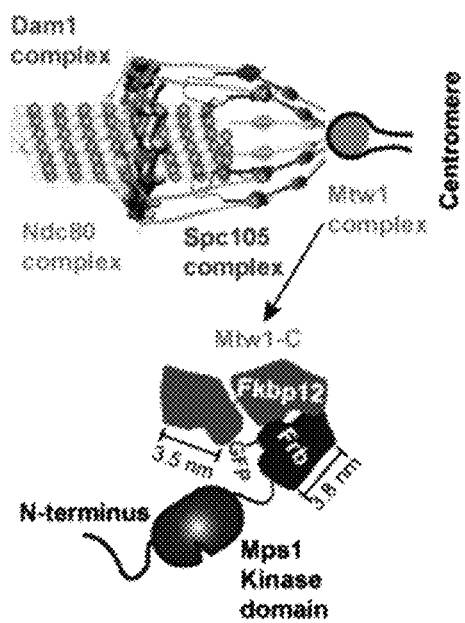
Figure 1C:
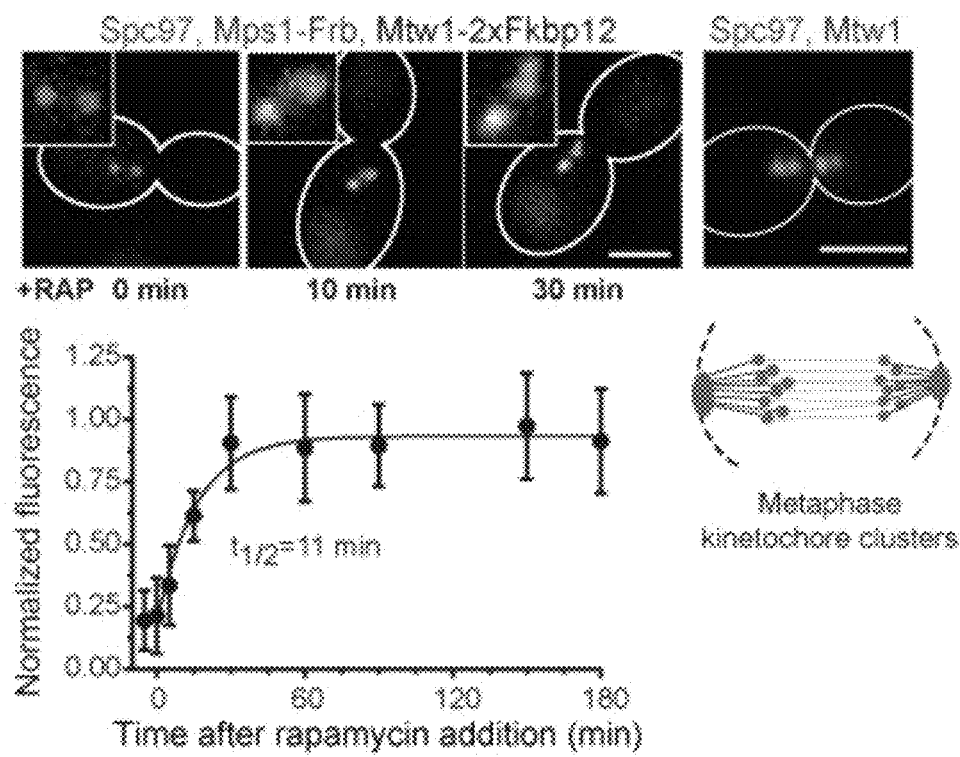
Figure 2A:
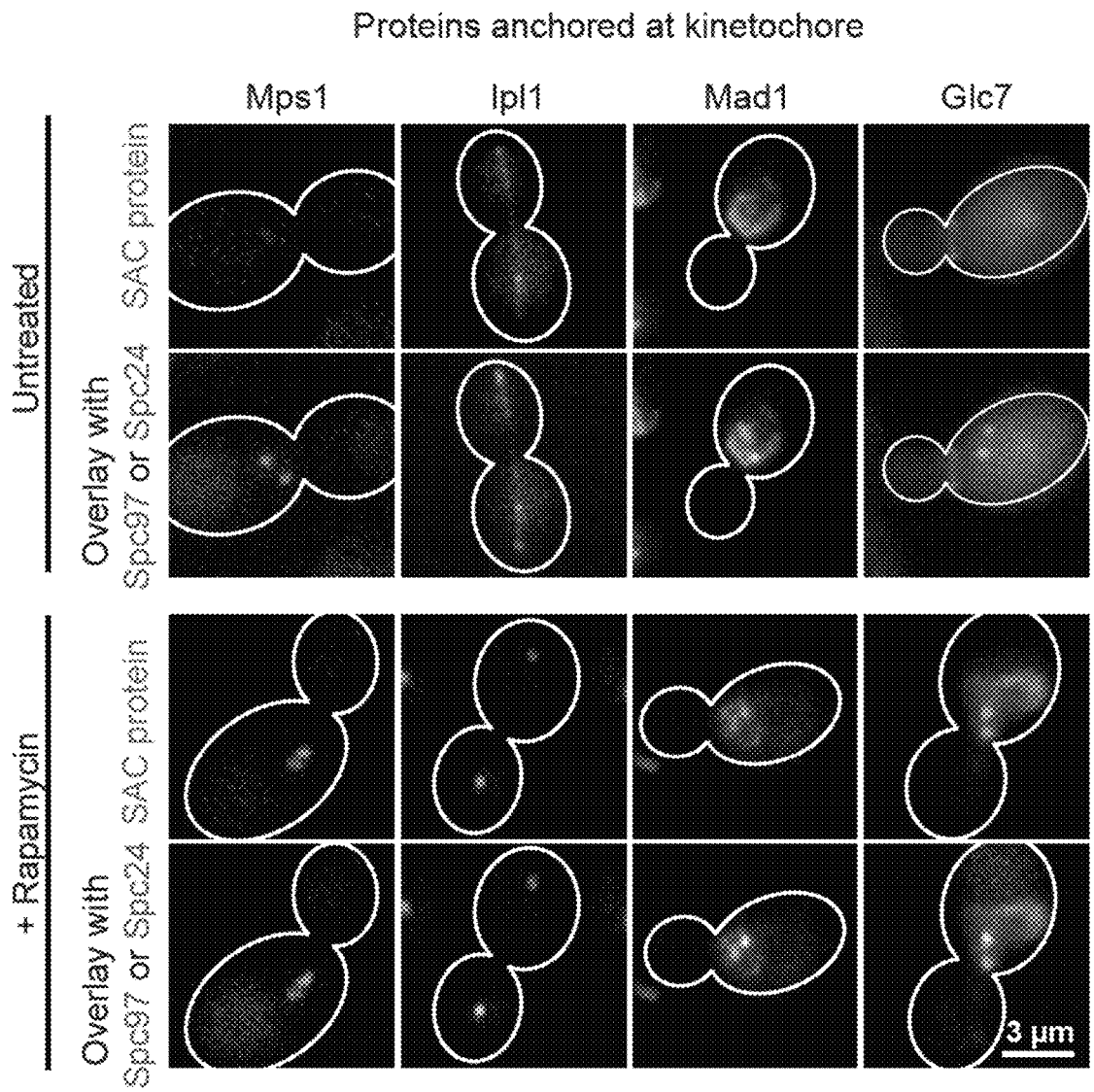
FIG. 2A-F. Effects of anchoring key SAC regulators to Mtw1-C on the cell cycle. (a) Top: Representative images display the expected localization of SAC proteins tagged with Frb-GFP in untreated cells and one hour after the addition of rapamycin. Bottom: Benomyl sensitivity of indicated strains. (b) Representative transmitted light micrographs of four strains treated with rapamycin for 135 minutes to anchor Mps1, Ipl1, Mad1, or Glc7, at Mtw1-C. The bar graph displays the percentage of large-budded in each case averaged from two independent experiments. (c) Effect of the ATP analog 1-NAPP1 on the localization of the Ipl1 substrate Sli15-GFP in cells expressing ipl1-as6, an analog-sensitive allele of the Ipl1 kinase. Representative pre-anaphase cells expressing Sli15-GFP are shown on the right. Quantification of Sli15-GFP fluorescence on the shown on the left. Spindle localization of Sli15-GFP significantly increased following 1-NAPP1 treatment indicating that the analog inhibits ipl1-as6. (d) Cell cycle kinetics following the release of S-phase synchronized cells into media containing 1-NAPP1 and rapamycin. Blocking ipl1-as6 activity did not have any effect on SAC activation induced by Mps1 anchored at Mtw1-C. (e) Bar graph: Frequency of prometaphase and metaphase cells with kinetochore-localized Mps1. Spindle length was used to classify cells as prometaphase or metaphase cells. Scatter plot (mean±95% confidence interval; n=21, 46 and 66 kinetochore clusters from left to right) displays the abundance of kinetochore-localized Mps1-Frb-GFP in prometaphase, metaphase-arrested cells (by repressing CDC20), and when it is anchored to Mtw1-C in heterozygous diploid strains. (f) Quantification of Mps1 localization to kinetochores soon after release from metaphase compared to that in. Micrographs on the right show localization of Mps1 relative to spindle pole bodies over a period of 6 minutes during the metaphase to anaphase transition.
Figure 2A:
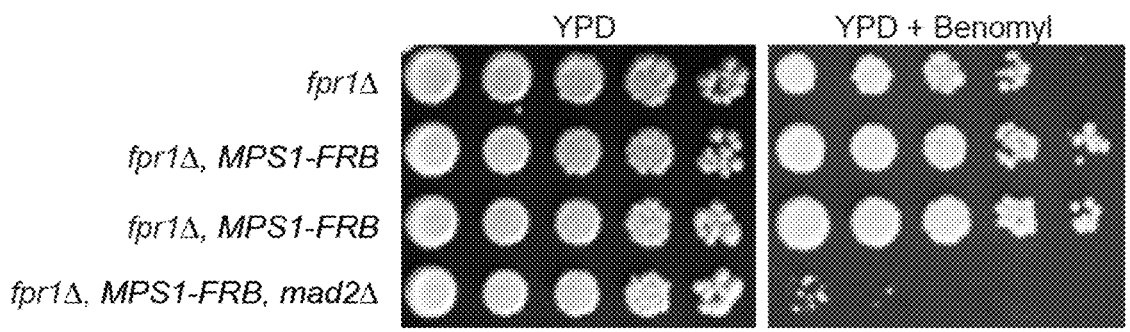

Mps1, Artificially Localized to the Kinetochore, Phosphorylates Spc105 and Activates the SAC Experiments were conducted during development of embodiments of the present invention to determine whether microtubule attachment to the kinetochore silences the SAC by promoting the dissociation of SAC proteins from the kinetochore (FIG. 1a), and whether engineering persistent localization of key SAC proteins at the kinetochore constitutively activates the SAC. Rapamycin-induced dimerization of 2xFkbp12 and Frb was used to artificially localize or 'anchor' key phosphoregulators and SAC proteins: Mps1, Ipl1 (Aurora B), Glc7 (PP1) or Mad1 within the kinetochore (FIG. 1b). In the absence of rapamycin, each Frb-tagged protein retained its normal cellular distribution. Addition of rapamycin to the culture media rapidly anchored it to the kinetochore subunit tagged with 2xFkbp12 (FIG. 1c and FIG. 2a).

Figure 1D:
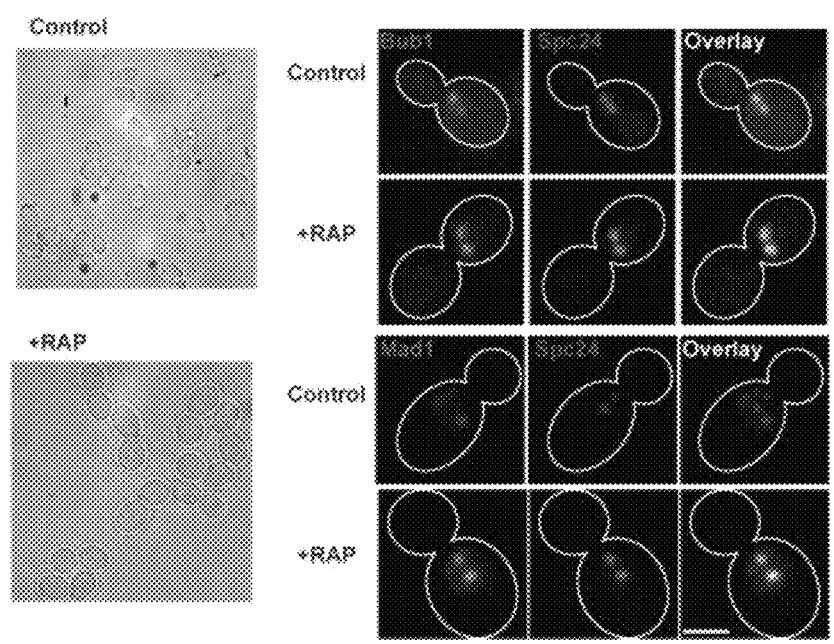
Figure 1E:
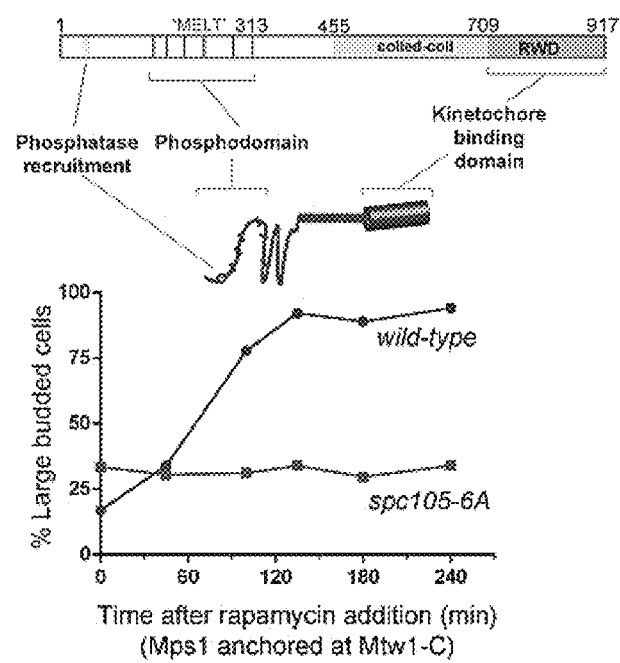
Figure 2B:
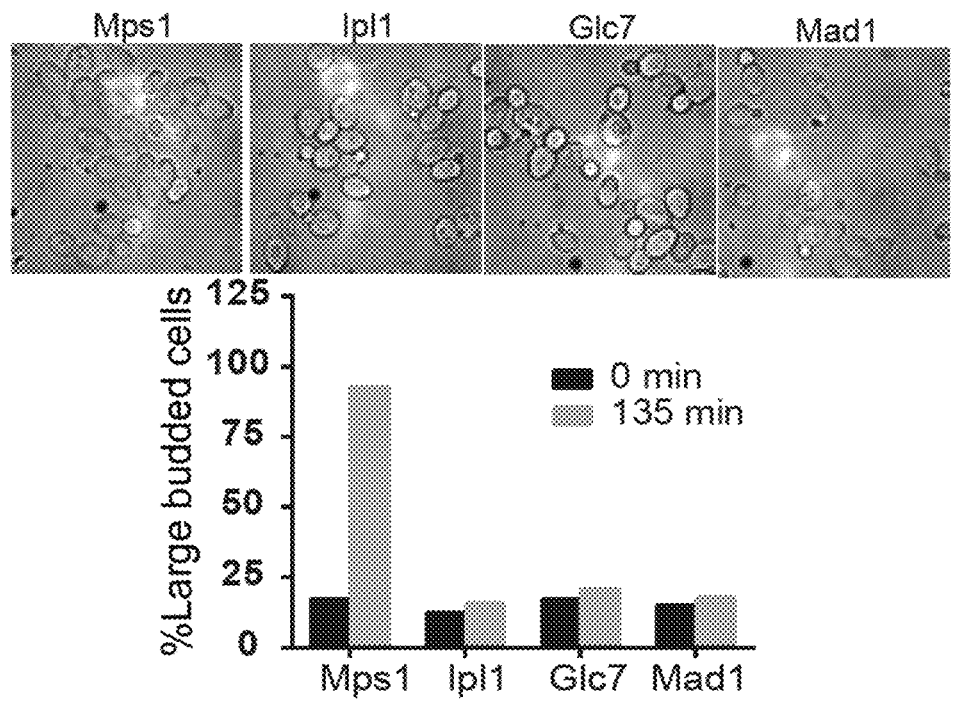
Figure 2C:
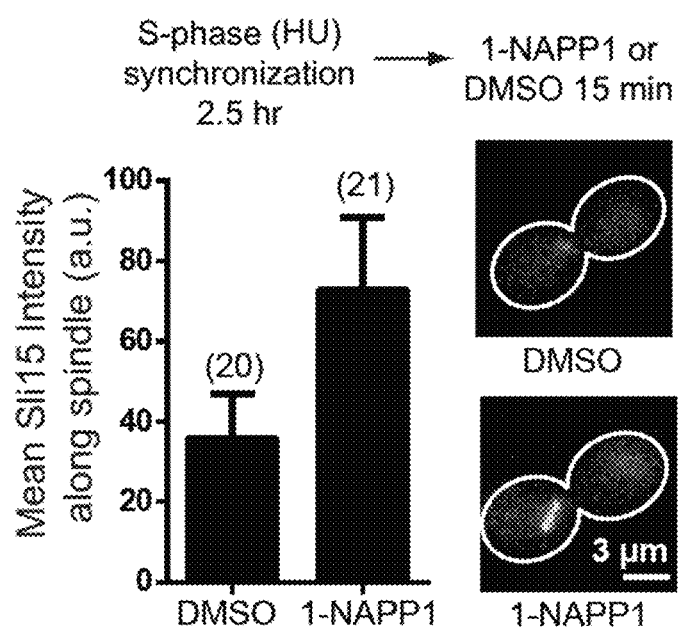
Figure 2D:
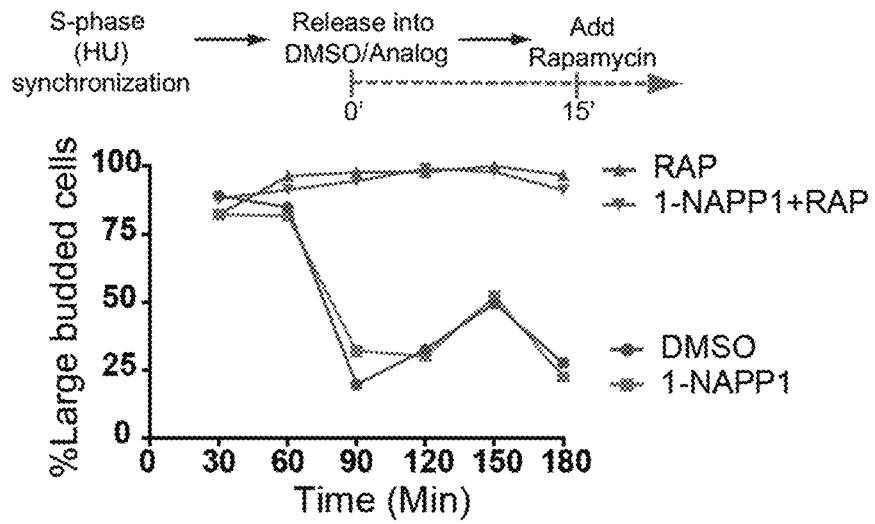

Mps1 anchored at Mtw1-C in this manner led to the accumulation of large-budded cells that were arrested in metaphase (FIG. 1d, e). The kinetochores in these cells recruited both Bub1 and Mad1, indicating that the arrest was mediated by the SAC (FIG. 1d). These observations are consistent with findings that Mps1 fused to kinetochore proteins activates the SAC (refs 10, 11; herein incorporated by reference in their entireties). Other SAC proteins tested: Ipl1, Mad1 and Glc7, did not delay the cell cycle when anchored to Mtw1-C (FIG. 2b). The phosphorylation of the kinetochore protein Spc105 at one or more of its conserved 'MELT' motifs was necessary for the anchored Mps1 to activate the SAC (ref. 12; herein incorporated by reference in its entirety; FIG. 1e). These effects did not require the kinase activity of Ipl1, indicating that the anchored Mps1 did not activate the SAC indirectly by disrupting either microtubule attachment or force generation (ref. 13; herein incorporated by reference in its entirety; FIG. 2c, d). This is consistent with data from other organisms and with the dispensability of Ipl1 for SAC signalling in budding yeast (refs. 14, 15; herein incorporated by reference in their entireties). Thus, anchoring Mps1 to the kinetochore is sufficient for inducing constitutive SAC signaling.

SAC Proteins that Act Downstream from Mps1 can Function Within Attached Kinetochores The above experiments were performed in asynchronous yeast cultures. Consequently, it could not ascertained whether the anchored Mps1 activated the SAC mostly in prometaphase, before all kinetochores attach to microtubules, or if Mps1 can reactivate the SAC when anchored within stably attached kinetochores. To test this, CDC20, the gene that encodes the activating subunit of the anaphase-promoting complex (APC), was repressed to prevent yeast cells from entering anaphase even after all of the kinetochores were attached and the SAC was satisfied. Mps1 was anchored at Mtw1-C in such cells, released them from the arrest by inducing CDC20 expression, and then monitored cell-cycle progression (FIG. 3a). It was found that cells that had Mps1 anchored at Mtw1-C underwent a persistent cell-cycle arrest, whereas control cells completed anaphase within 20 min (FIG. 3a). Thus, Mps1 reactivates the SAC, when it is anchored to kinetochores with stable microtubule attachments.

These results demonstrate that SAC proteins downstream from Mps1 bind to and function from attached kinetochores. No significant changes were detected when the nanoscale separation between key kinetochore domains in metaphase and rapamycin-treated cells were compared using high-resolution co-localization (FIG. 3b). This indicates that if architectural changes that facilitate SAC protein binding do occur, they do so when the kinetochore is attached. these data demonstrates that microtubule attachment to the kinetochore hampers either Mps1 localization to the kinetochore or its kinase activity to silence the SAC.

Endogenous Mps1 Binds to Attached Kinetochores

Figure 2E:
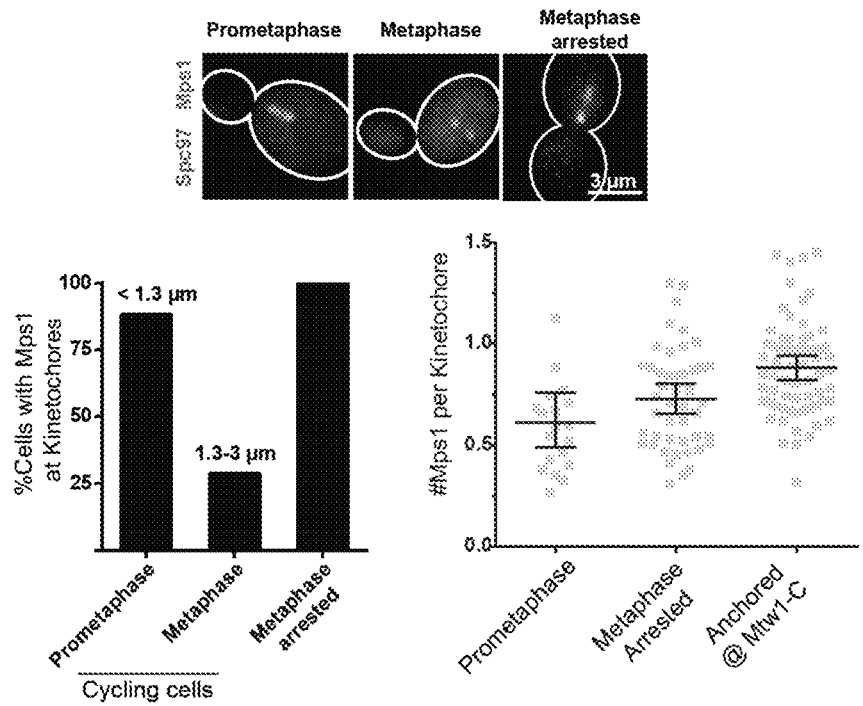
Figure 2F:
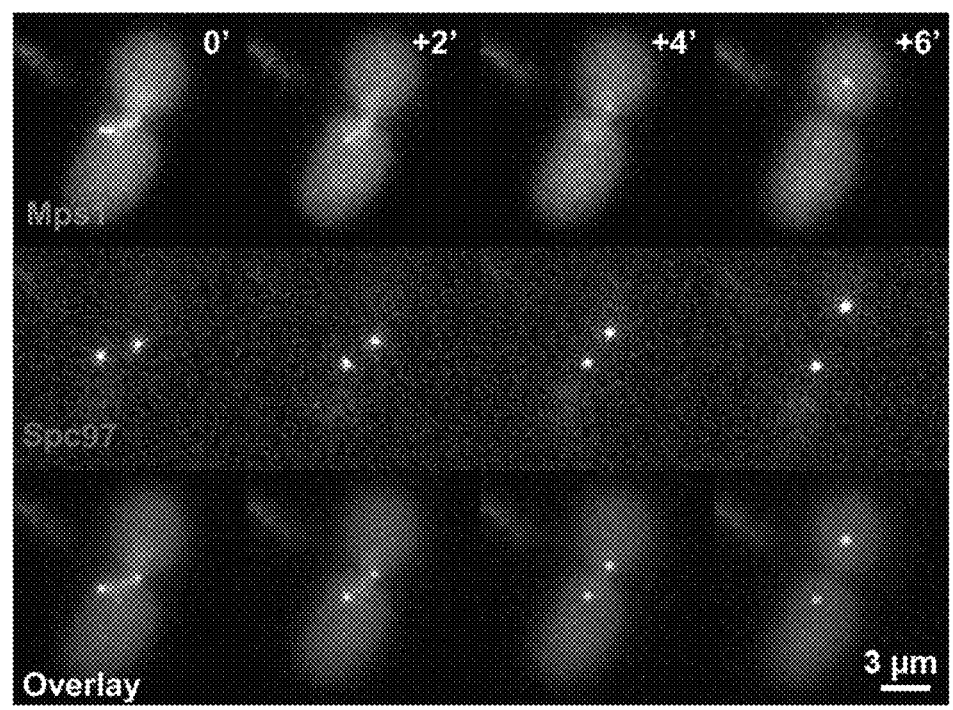
Figure 2F:
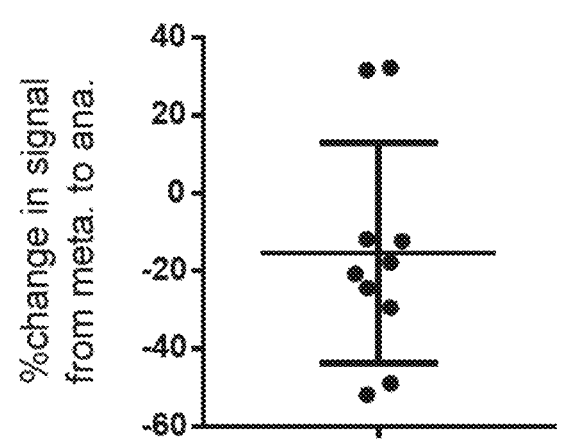

Mps1 gradually disappears from the kinetochore clusters as yeast cells progress from prometaphase to metaphase (FIG. 2e). However, Mps1 is targeted for degradation by the APC (ref. 17; herein incorporated by reference in its entirety). Upon inactivation of the APC using CDC20 repression, Mps1-Frb-GFP autonomously localized to attached kinetochores (FIG. 3c, left). The autonomously localized Mps1 did not activate the SAC, because both Bub3 and Mad1 were absent from the kinetochores (FIG. 3c, right). Furthermore, these cells entered anaphase without any detectable delay following release from the metaphase block (FIG. 3a, dotted line). Mps1 was present at the kinetochore even as these cells entered anaphase (FIG. 2f). Thus, the removal of Mps1 from the kinetochore is not necessary for either SAC silencing or anaphase onset.

Mps1 molecules that autonomously localize to attached kinetochores do not activate the SAC, but a similar number of Mps1 molecules anchored at Mtw1-C activate it constitutively (FIG. 2e). It is contemplated that the inability of the autonomously localized Mps1 to activate the SAC is due to: inability to reach and phosphorylate Spc105 from its endogenous binding position in the kinetochore; the inhibition of the kinetochore-bound Mps1 kinase; or the upregulation of Glc7 phosphatase activity in attached kinetochores (refs. 18, 19; herein incorporated by reference in their entireties). Upregulation of Glc7 activity is unlikely to be the main mechanism that silences the SAC, because Glc7 is not necessary for anaphase onset19. Therefore, experiments were conducted during development of embodiments herein to investigate how microtubule attachment affects Mps1 kinase activity within the kinetochore.

The Ability of Mps1 to Activate the SAC Depends on its Position Within the Kinetochore It was tested whether the binding position of Mps1 within the kinetochore can affect its ability to phosphorylate Spc105 and initiate SAC signaling. In metaphase, the budding yeast kinetochore spans ~80 nm along its longitudinal axis, from the amino terminus of Ndc80 to the centromeric nucleosome (ref 20; herein incorporated by reference in its entirety). It contains ~8 copies of the Ndc80 complex and Spc105 molecules distributed with an average inter-molecular spacing of ~8 nm around the microtubule circumference (refs. 21, 22; herein incorporated by reference in their entireties), and with little inter-molecular staggering along the length of the microtubule (ref 23; herein incorporated by reference in its entirety) (FIG. 1b). This architecture indicates that the proximity of Mps1 to Spc105 along the longitudinal axis of the kinetochore affects its ability to phosphorylate Spc105.

Figure 4A:
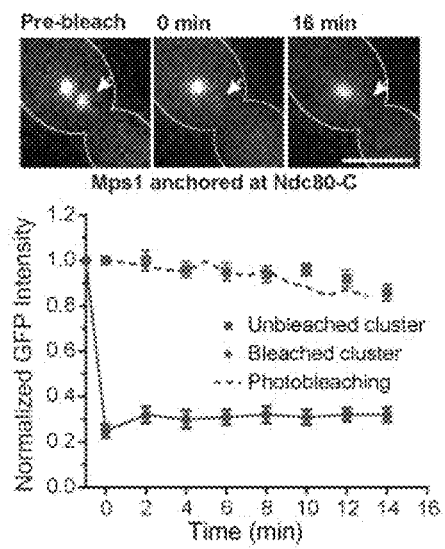
FIG. 4A-D. The ability of Mps1 to activate the SAC depends on its position in the kinetochore. (a) Fluorescence recovery after photobleaching of Mps1-frb-GFP anchored at Ndc80-C (circles), and loss of anchored protein from the unbleached cluster (squares). Dashed line shows the expected rate of photobleaching as a result of imaging determined in cells expressing Ndc80-GFP. Scale bar, ~3 μm. (b) Top: Structure of the Ndc80 complex and the positions of fluorescent tags used for FRET. Scatter plot: Proximity ratio, which is directly proportional to the FRET efficiency35, for FRET between Spc25-mCherry or Nuf2-mCherry and Mad1-Frb-GFP anchored to Spc24-C. The proximity ratio is defined as the acceptor fluorescence resulting from FRET normalized by the sum of mCherry cross-excitation and GFP emission bleed-through into the mCherry imaging channel. FRET between the anchored donor, Mad1-Frb-GFP, and the acceptor, Spc25-mCherry, was readily detected, but it was absent when the mCherry was fused to Nuf2-C. Spc25-C is <3 nm away from Spc24-C, where the donor is anchored, whereas Nuf2-C is >10 nm away. Mad1 was used, rather than Mps1, in this experiment to ensure that the number of donors is equal to the number of acceptor molecules (either Spc25-mCherry or Nuf2-mCherry) for accurate FRET quantification. (c) Number of protein molecules anchored at Ndc80-C, measured 30 min after rapamycin addition. (d) Top: The organization of yeast kinetochore proteins along the microtubule axis. The N-terminal half of Spc105 is not drawn to scale. Bottom: Bar graph shows the number of colonies formed on rapamycin-containing plates relative to control plates. Right: Representative photographs of plates for three strains.
Figure 4B:
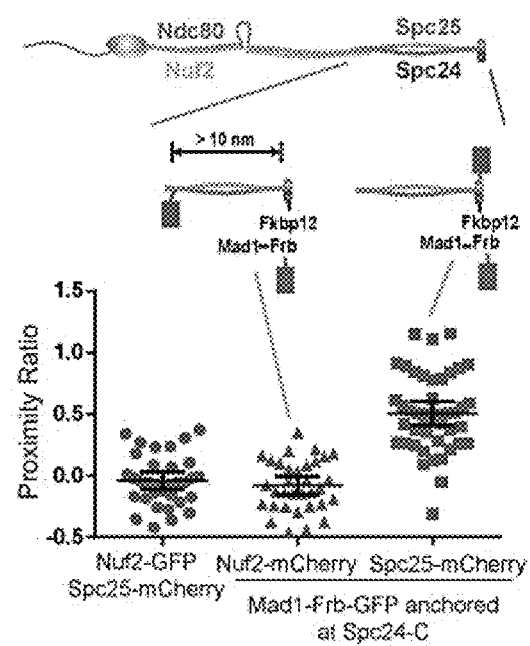
Figure 4C:
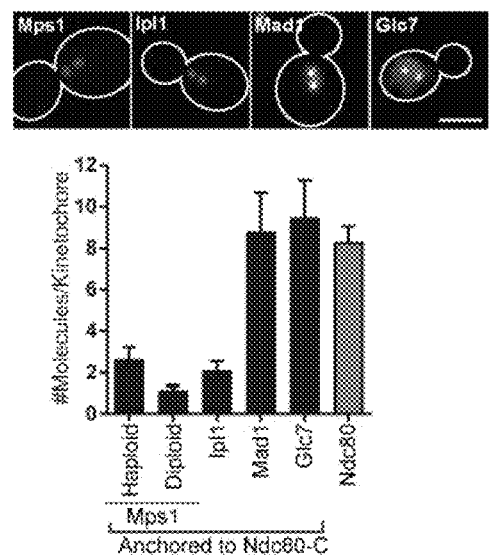

To reveal the position-specific activity of Mps1, rapamycin-induced dimerization stably anchors and confines it at specific kinetochore positions. This was determined using three measurements (FIG. 4a-c). First, it was found that the anchoring was stable, as indicated by negligible turn-over of Mps1-Frb-GFP anchored at Ndc80-C (FIG. 4a). Although this high stability is ideal for studying positions specific activity, it may be non-physiological 24. Second, Förster resonance energy transfer (FRET) measurements indicated that the anchored protein is confined within a 10 nm region around the anchoring point (FIG. 4b). Finally, the total number of molecules anchored within the kinetochore was determined by the abundance of the anchored protein (ref 25; herein incorporated by reference in its entirety) and also its kinetochore anchor (ref. 21; herein incorporated by reference in its entirety) (FIG. 4c). As a result, the entire nuclear pool of low-abundance proteins such as Mps1 and Ipl1 was anchored at the selected kinetochore position.

Figure 4D:
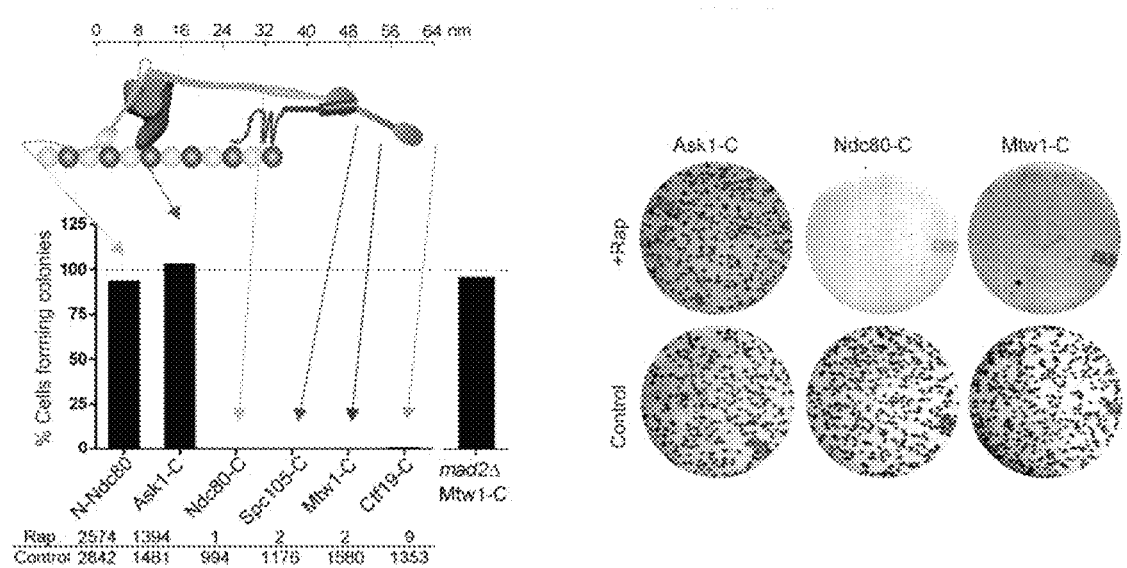
Figure 5A:
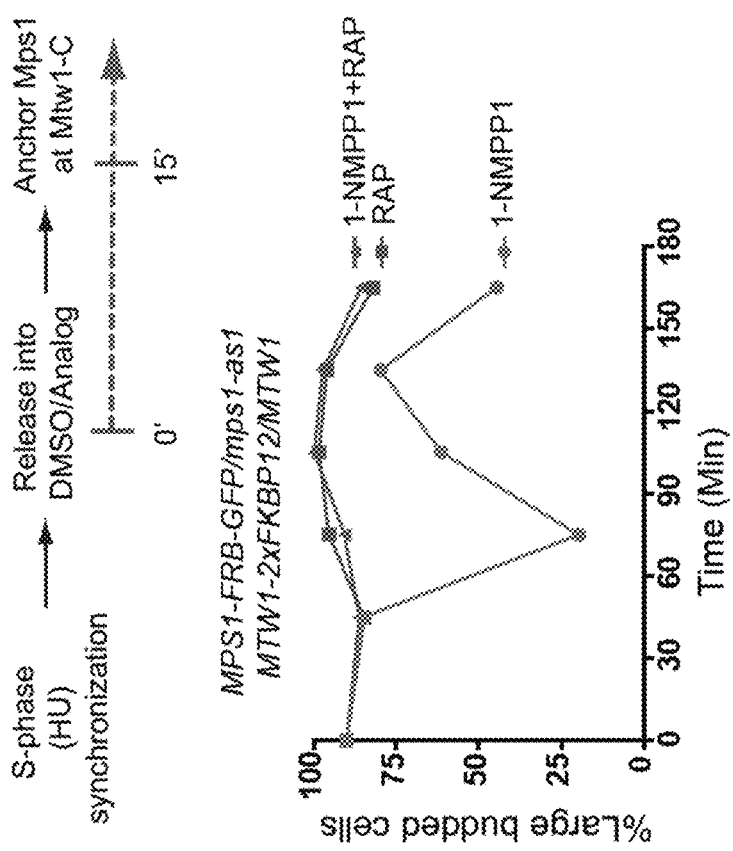
FIG. 5A-C. Kinase activity of the kinetochore-anchored Mps1 is sufficient for SAC activation. (a) Cells expressing the analog-sensitive Mps1 allele, mps1-as1 or wild type Mps1 were treated as indicated at the top. Bar graph displays the percentage of two-budded cells (which form when a mitotic cell fails to sustain the SAC in the presence of a damaged spindle and produce a new bud by re-entering the cell cycle). (b) Inhibition of the diffusible mps1-as1 does not affect SAC activation by Mps1-Frb anchored at the kinetochore. Heterozygous diploid strains expressing mps1-as1 and Mps1-Frb were synchronized in S-phase and released into 1-NMPP1 for 15 minutes. Rapamycin was then added to anchor Mps1-Frb at Mtw1-C. The anchored Mps1 arrested the cell cycle robustly, and the cells retained the large-budded morphology for a prolonged period of time. (c) Micrographs: Mad1 localization relative to the spindle pole body in haploid cells that have Mps1 anchored to the indicated subunit. Bar graph displays the percentage of cells with visible Mad1 localization in between the spindle poles in each case. The corresponding metaphase spindle length in each case is presented in the scatter plot.
Figure 5B:
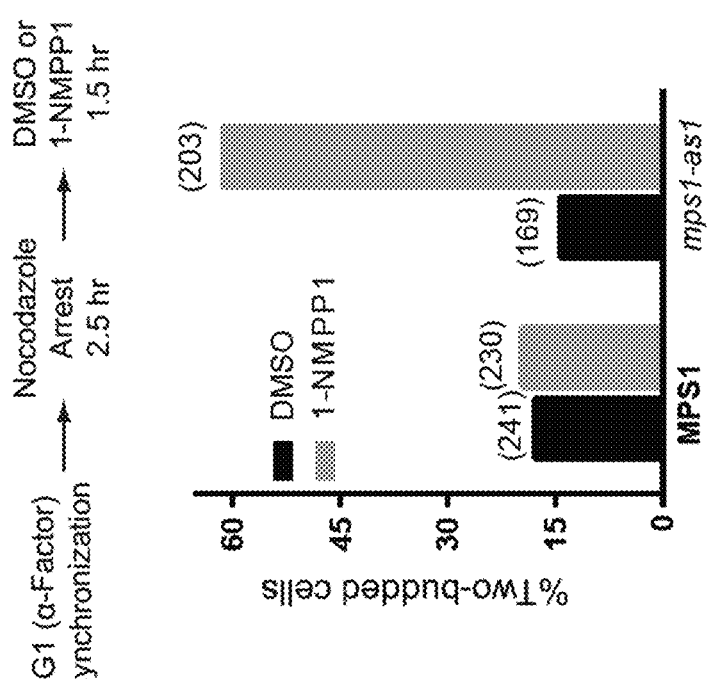
Figure 5C:
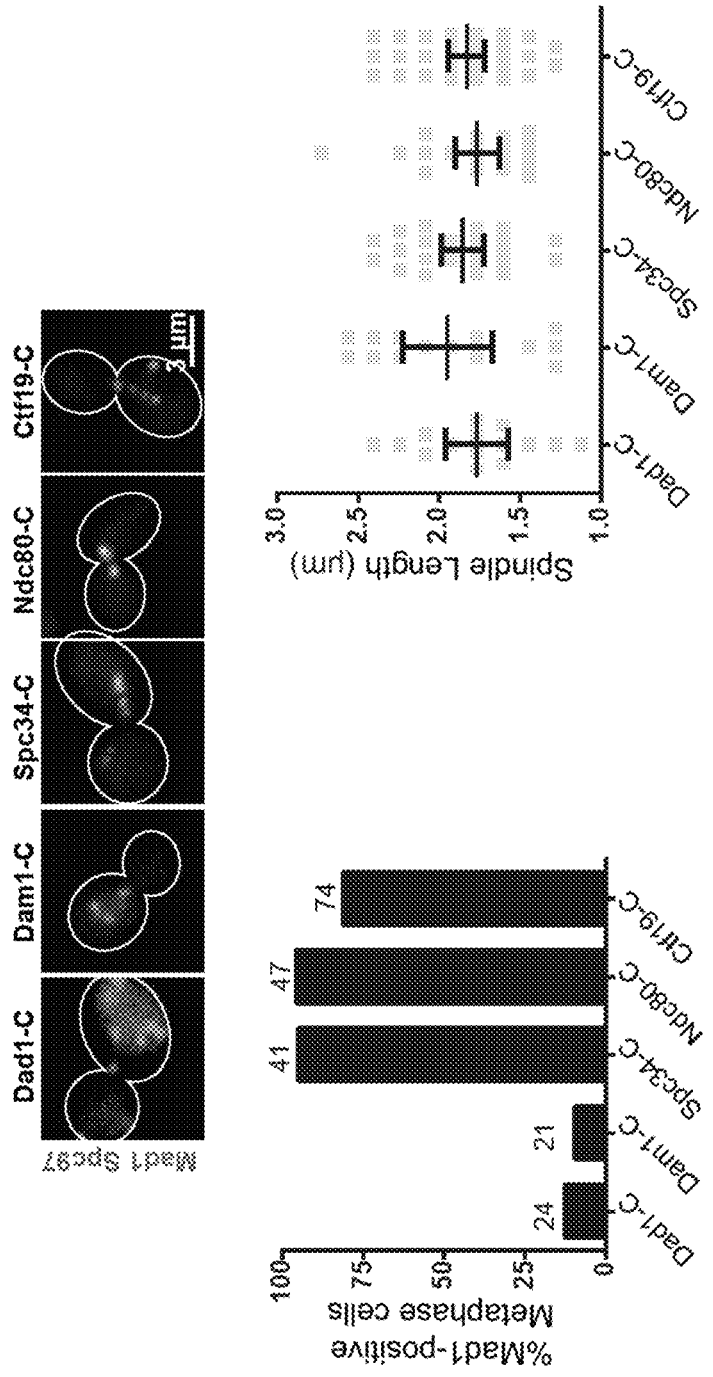

Mps1 was constitutively anchored at six distinct positions selected to sample the 80 nm length of the kinetochore-microtubule attachment (FIG. 4d, top). To assess the effects of anchoring Mps1 on the cell cycle, an equal number of cells were plated on control plates and on plates containing rapamycin, and compared the number of colonies formed in each case (FIG. 4d, right). These experiments were performed in heterozygous diploids that also expressed wild-type Mps1, because Mps1 activity is also essential for other cellular functions (ref. 26; herein incorporated by reference in its entirety). Even though the wild-type, diffusible Mps1 provides these essential functions, it is not required for SAC activation (FIG. 5a, b). Furthermore, haploids expressing only Mps1-Frb also exhibited identical SAC activation phenotypes (FIG. 5c).

Figure 6A:
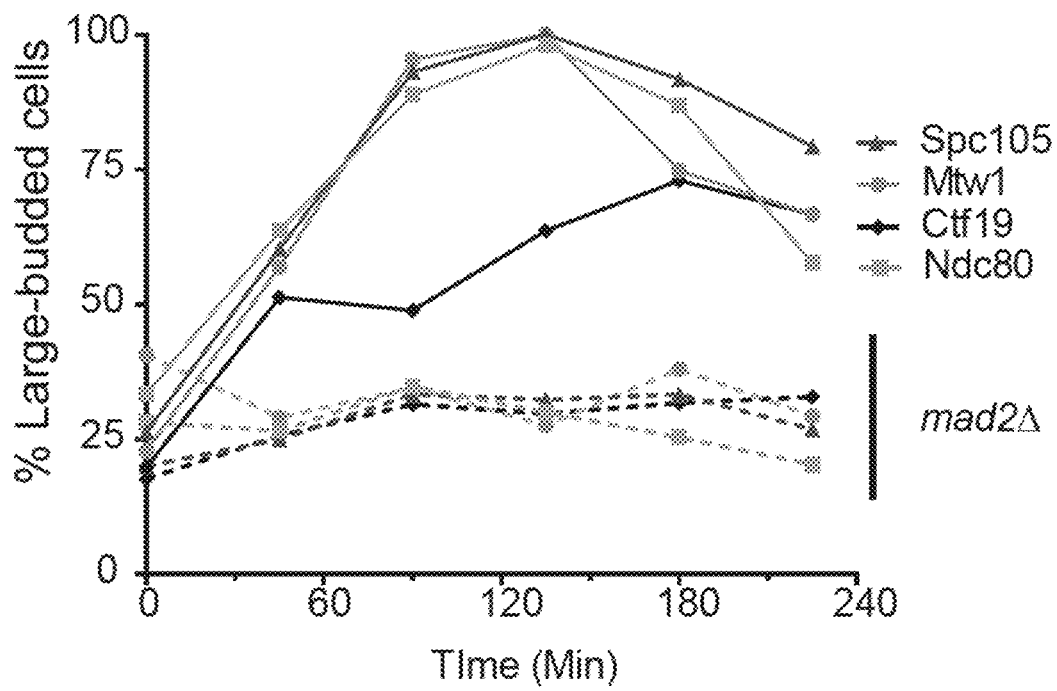
FIG. 6A-G. Cell cycle effects of anchoring Mps1, Ipl1 or Mad1 constitutively within the kinetochore. (a) Cell cycle kinetics of asynchronous cultures where Mps1 is anchored at the C-termini of indicated kinetochore subunits in wild-type or SAC null strains (mad2Δ). (b) Quantification of Mps1-Frb-GFP anchored at indicated kinetochore subunits measured 45 minutes after rapamycin treatment and normalized relative to endogenous Mps1 in metaphase-arrested cells. The recruitment of Mps1 at Dad4-C and Ctf19-C that activates the SAC is comparable to that at Ask1-C which does not activate the SAC. (c) Reducing the length of the flexible linker connecting Mps1 and Frb (from 24 to 7 amino acids) did not change the effect of anchoring Mps1 on colony growth. (d-e) The number of colonies formed on rapamycin-containing plates relative to control plates, when Ipl1 (in d) or Mad1 (in e) is constitutively anchored at the indicated positions. (f) Mad1 anchored at N-Ndc80 generates unattached kinetochores (arrowheads) in a large fraction of cells. (g) Graph presents the fraction of cells expressing Spc105-6A or Spc105 that arrested with large-buds when Mad1 was anchored at N-Ndc80 (rapamycin treatment for 4 hours).
Figure 6B:
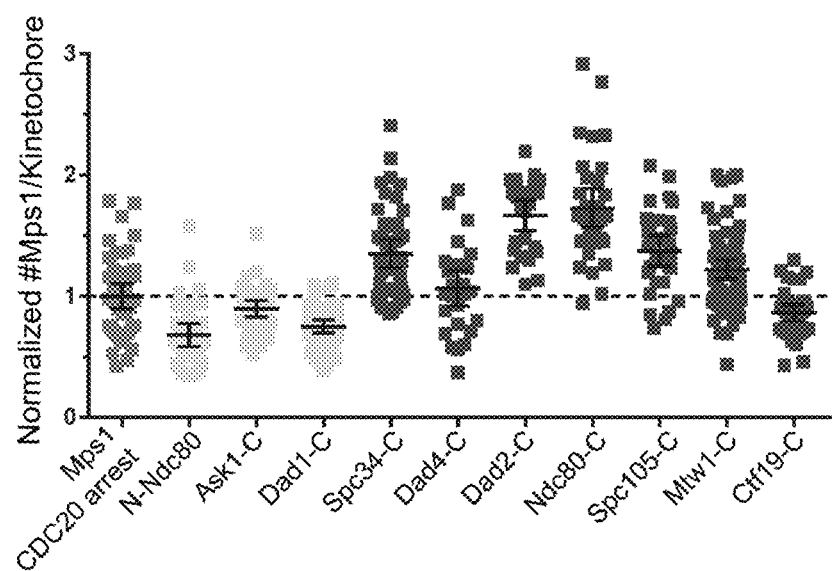
Figure 6C:
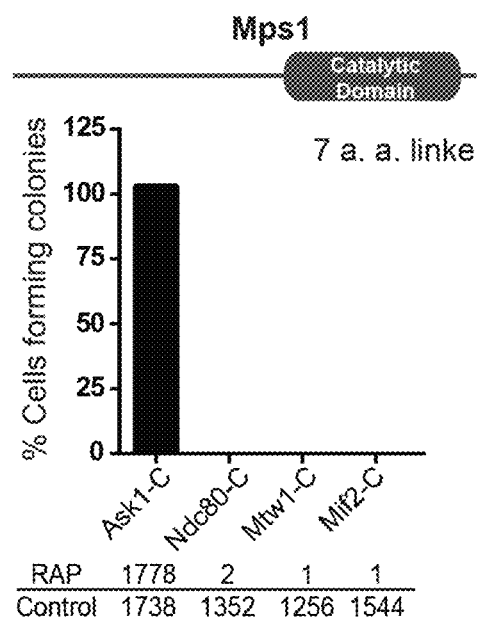
Figure 6D:
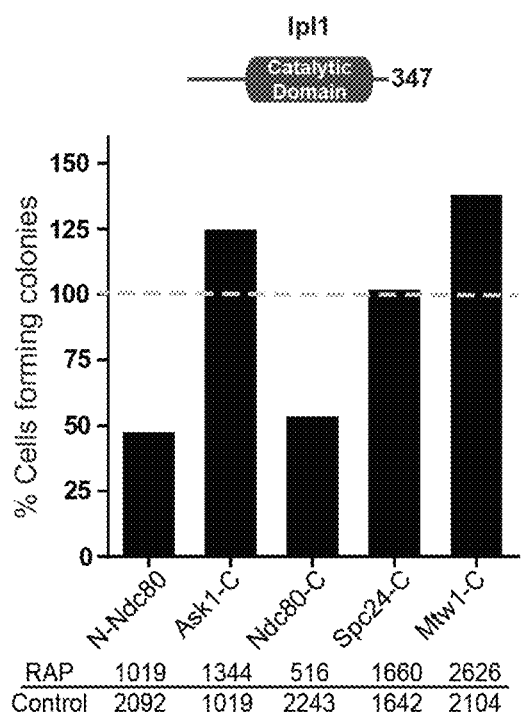
Figure 6E:
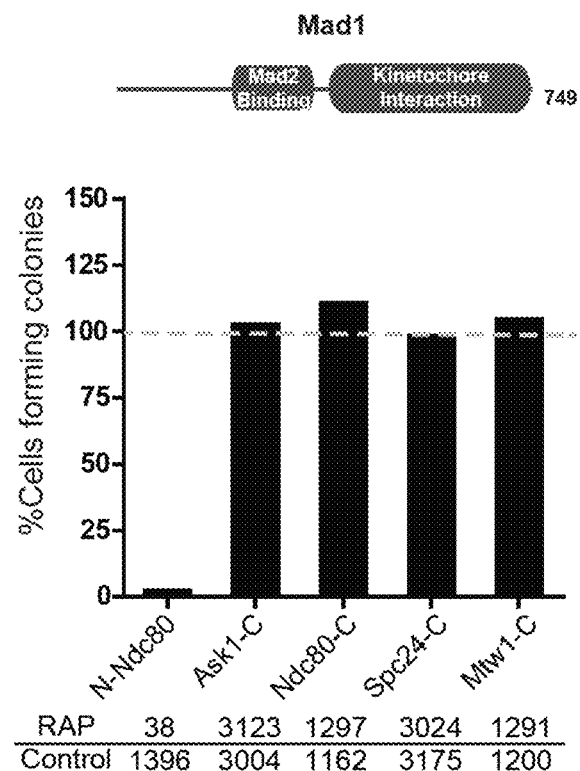
Figure 6F:
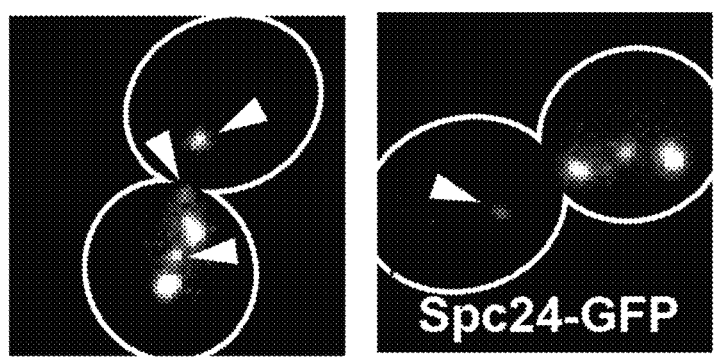
Figure 6G:
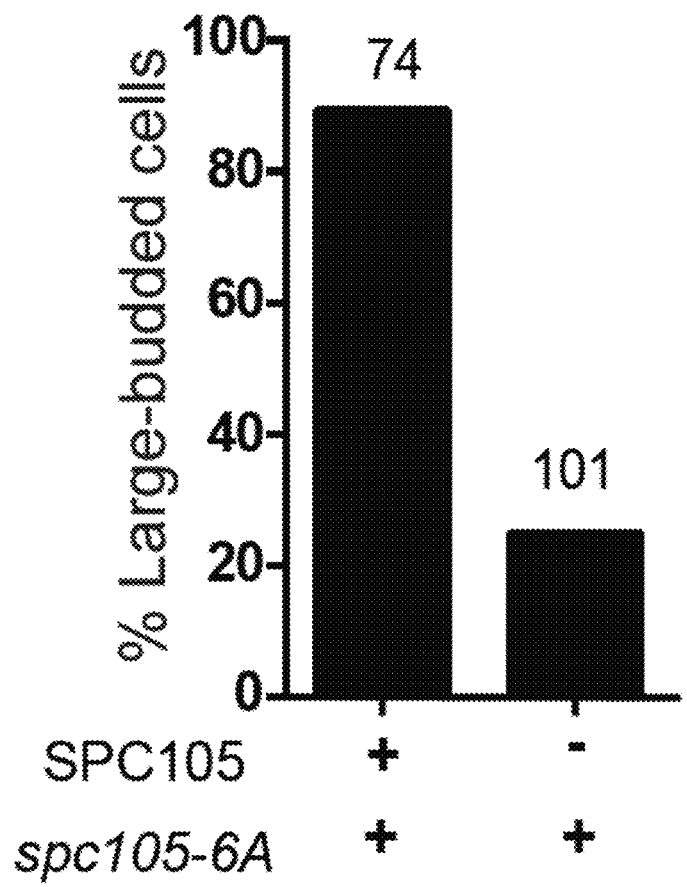

When Mps1 was constitutively anchored at four different locations within the inner kinetochore, ranging from Ndc80-C to Ctf19-C, it completely inhibited colony growth (FIG. 4d). MAD2 deletion restored colony growth, indicating that the lack of growth was due to constitutive SAC activation (FIGS. 4d and 6a). Mps1 anchored at two positions located in the outer kinetochore, N-Ndc80 and Ask1-C (a Dam1 complex subunit), had no effect on colony growth (FIG. 4d). Although the number of Mps1 molecules anchored in the inner kinetochore positions was 30-50% higher than the number of Mps1 molecules anchored in the outer kinetochore, these differences did not strictly correlate with SAC activation phenotypes (FIG. 6b). Reducing the length of the linker between Mps1 and Frb-GFP did not affect the observed phenotypes (FIG. 6c). Finally, the observed effects were specific to Mps1: constitutive anchoring of Ipl1 or Mad1 at the same positions did not result in the same phenotypes (FIG. 6d-g).

These data demonstrate that the position of Mps1 within the kinetochore affects its ability to activate the SAC. As Mps1 phosphorylates Spc105 to activate the SAC, the observed phenotypes likely reflect whether or not the anchored Mps1 can access the phosphodomain of Spc105. It is also notable that Mps1 activates the SAC from different locations over a 30 nm span20 (the metaphase separation between Ndc80-C and Ctf19-C), even though its kinase activity is spatially confined to individual anchoring locations. It is contemplated that to encounter the confined kinase activity over this wide span, the long and unstructured phosphodomain of Spc105 assumes variable conformations.

Mps1 Anchored in the Outer Kinetochore does not Activate the SAC

Figure 7A:
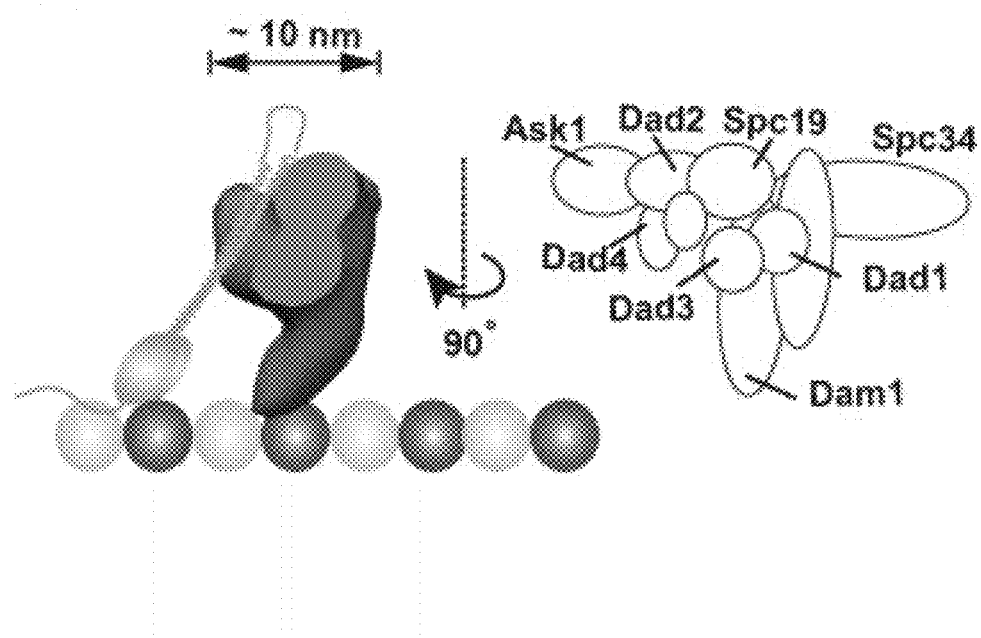
FIG. 7A-F. The Dam1 complex defines a boundary for SAC signaling by anchored Mps1. (a) Schematic: Position of the Dam1 complex relative to the Ndc80 complex23 and subunit organization within the Dam1 complex. EMD1372 was used to infer the dimensions of the Dam1 complex. (b) Colony growth (also see Supplementary FIG. 4a) on control (Ctrl) and rapamycin (+ Rap) plates. The number of days after plating is indicated at the top; the anchoring subunit is indicated on the left. (c) Cell-cycle progression when Mps1 is anchored to a Dam1 subunit (indicated on the left) in cells released from an experimentally imposed S-phase arrest. S-phase synchronization was used to ensure that the kinetochores formed end-on attachments and loaded the Dam1 complex before Mps1 was anchored. (d) Normalized distribution of Dad4-mCherry on the spindle when Mps1 was anchored to the indicated positions for 1 h. Control data are from untreated metaphase cells. Micrographs on the right show the localization of Dad4-mCherry relative to that of Mps1-frb-gfp anchored to the indicated subunits (scale bars, ~3 μm). (e) The separation between kinetochore clusters in the cells in d, measured as the separation between maximum-intensity pixels in the two Dad4-mCherry puncta in each cell. Although there is a small decrease in kinetochore cluster separation when Mps1 is anchored at Dad3-C, cell-cycle progression is unaffected as seen in c. (f) Left: Classification of Dam1 complex subunits inferred from the Mps1 anchoring experiments. Right: Activity map of the anchored Mps1 along the length of the kinetochore-microtubule attachment. Arrows from the Dam1 complex depict the proposed orientation of the C termini of subunits used as anchors.
Figure 7B:
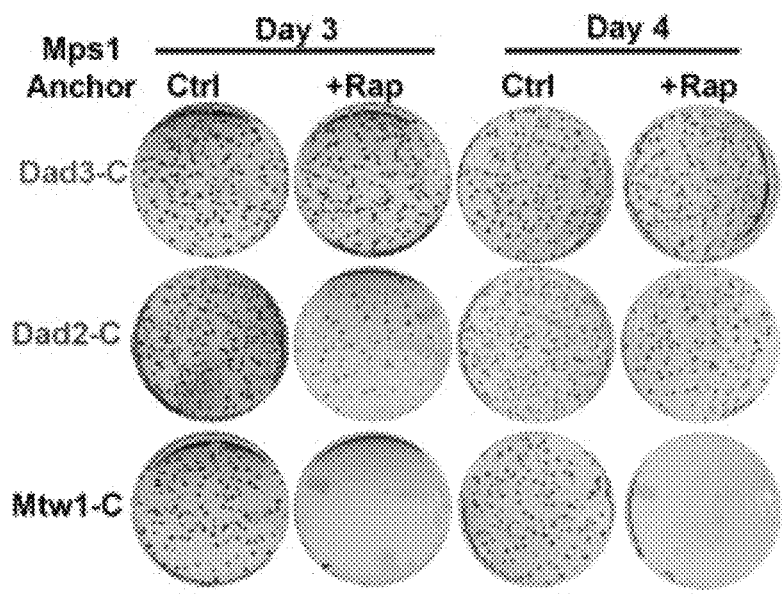
Figure 7E:
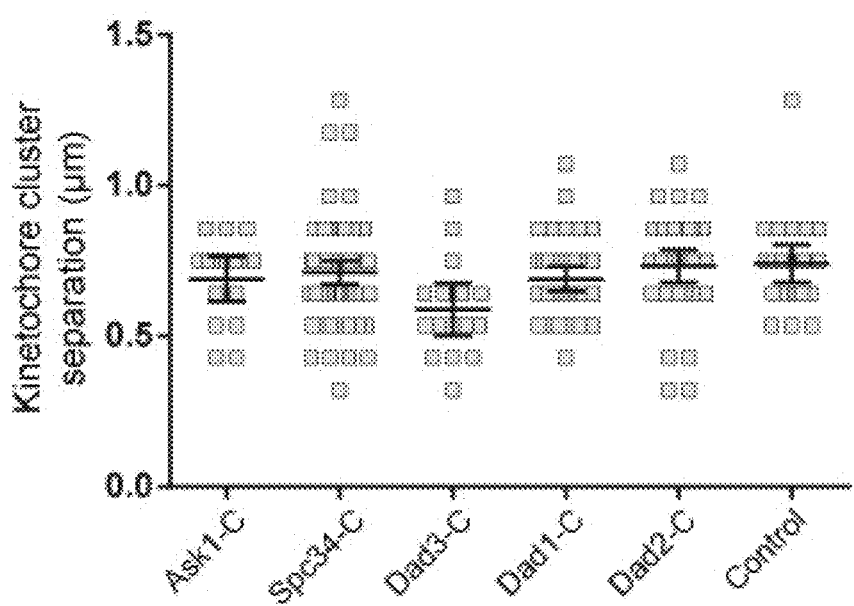
Figure 7C:
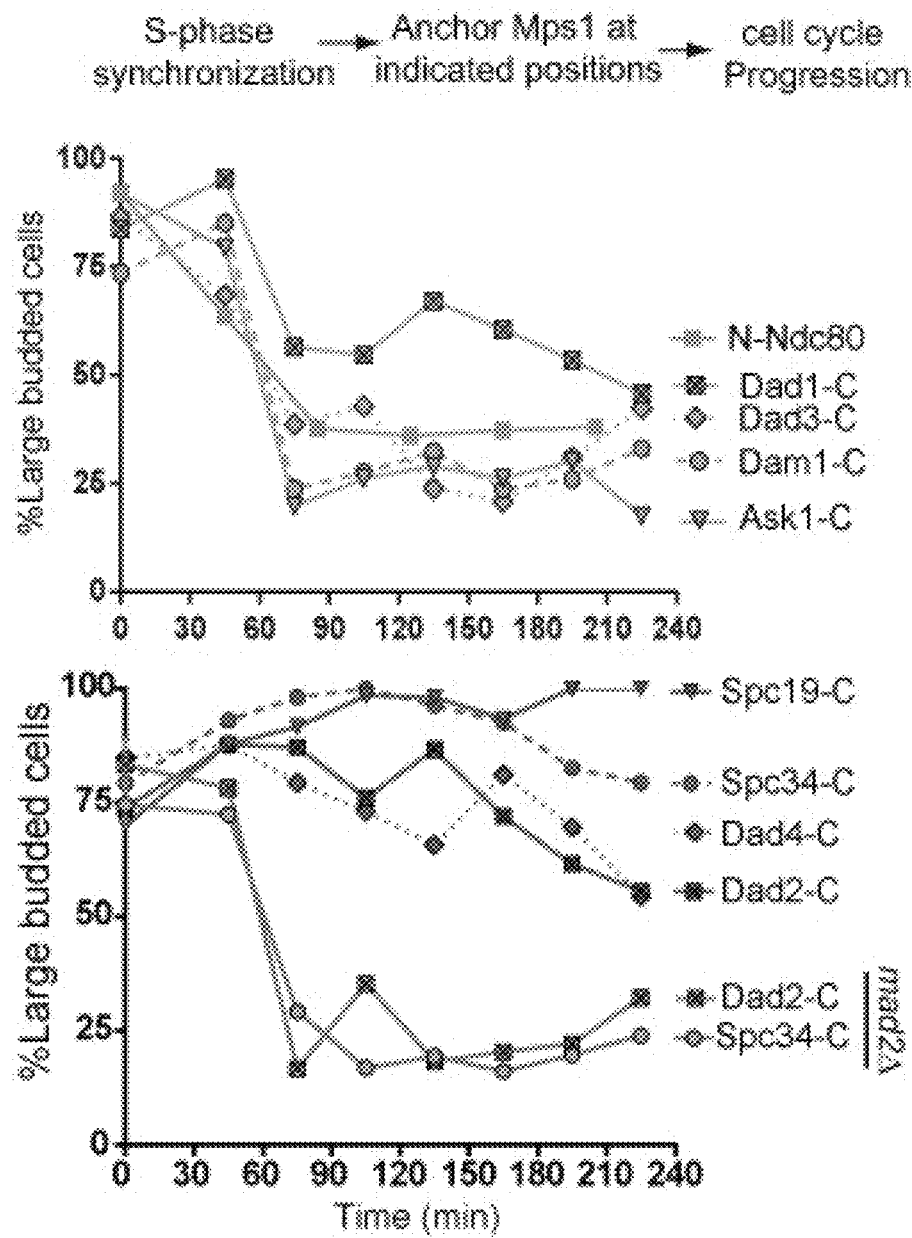
Figure 8A:
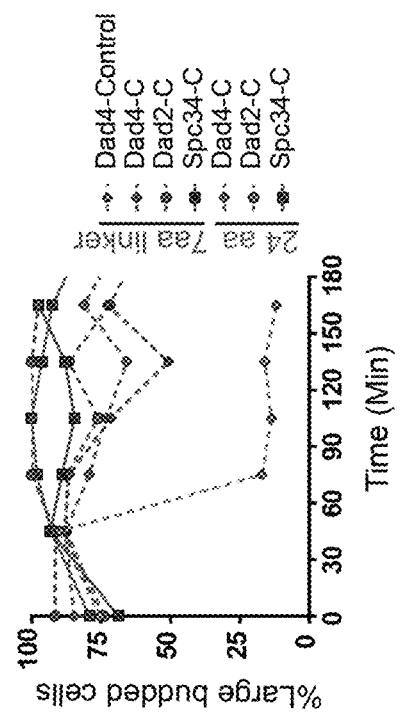
FIG. 8A-B. Anchoring Mps1 to Dam1 subunits leads to different phenotypes. (a) Subunit organization of the Dam1 complex, and bar graph displaying the number of colonies formed on rapamycin relative to the control plates. The total numbers of colonies scored are displayed at the bottom. (b) Cell cycle kinetics of rapamycin treated (to anchor Mps1 at indicated subunits) or untreated (control) cells.
Figure 8B:
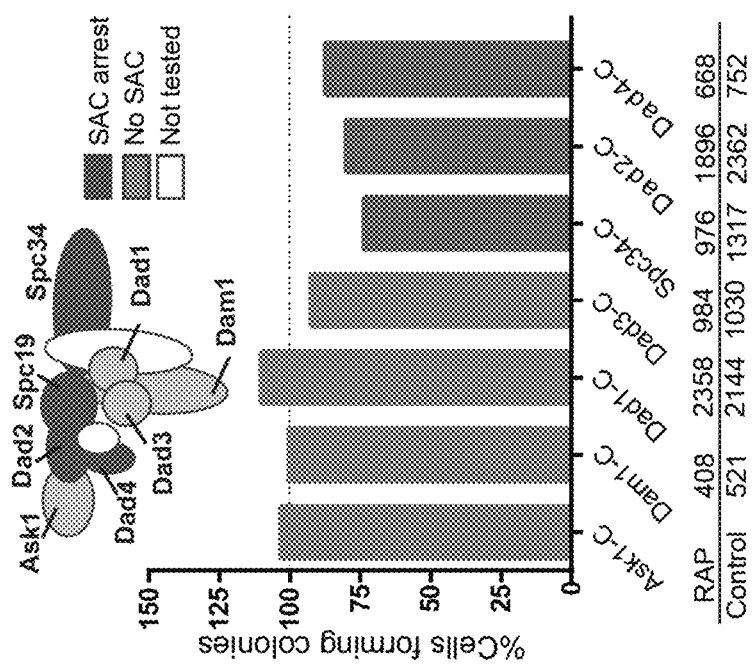

To confirm that the inability of Mps1 to activate the SAC from the outer kinetochore is due to inability to phosphorylate Spc105, the effects were characterized of anchoring Mps1 to the carboxy termini of seven other subunits of the heterodecameric Dam1 complex (ref 27; herein incorporated by reference in its entirety) (FIG. 7a). In addition to Ask1, Mps1 anchored to three other Dam1 subunits did not affect the colony growth (FIGS. 7b and 8a). Mps1 anchored to four other subunits delayed colony formation, but did not seem to affect the number of colonies formed (FIGS. 7b and 8a). It is contemplated that low colony growth was due to a transient SAC-mediated delay in the cell cycle (FIGS. 7c and 5c). As before, reduced length of the flexible linker fusing the Mps1 kinase domain to Frb did not affect the observed cell-cycle delay (FIG. 8b).

Figure 7D:
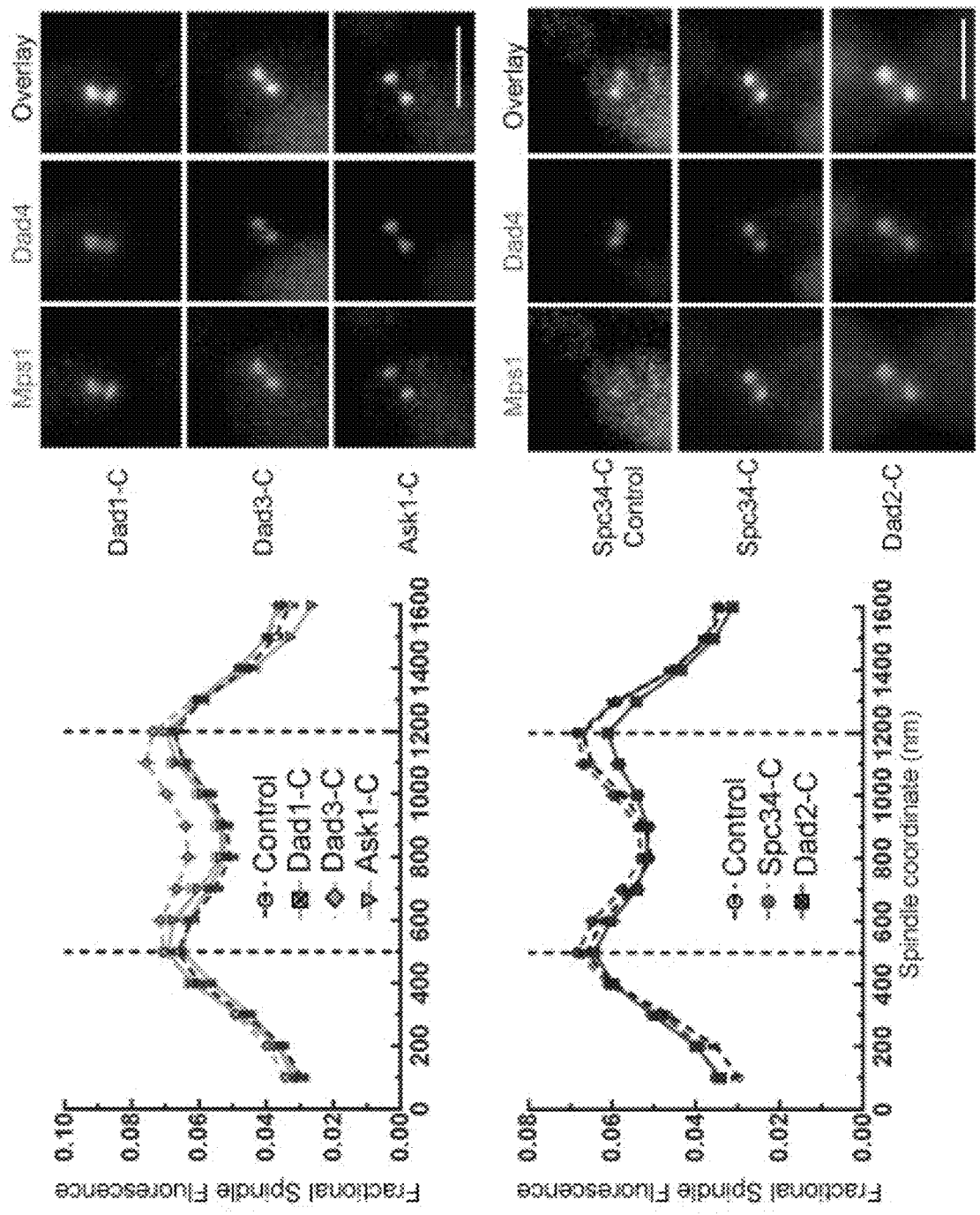

Experiments were conducted during development of embodiments herein to determine whether the anchored Mps1 perturbed Dam1 complex localization and function, because Dam1 subunits are known Mps1 substrates (refs. 27, 28; herein incorporated by reference in their entireties). Distribution of Dad4 was quantified over the mitotic spindle after anchoring Mps1 to other Dam1 subunits (FIG. 7d). Dad4-mCherry co-localized with the anchored Mps1-Frb-GFP in every case, and its distribution was indistinguishable from Dad4 distribution in untreated cells. Thus, the association of the Dam1 complex with the kinetochore remained unaffected. The separation between kinetochore clusters in rapamycin-treated cells was also indistinguishable from the corresponding length in untreated cells (FIG. 7e). This indicates that force generation at the kinetochore, a process in which the Dam1 complex is the dominant contributor, was not affected (ref 29; herein incorporated by reference in its entirety). Thus, the anchored Mps1 does not perturb Dam1 complex function, and the observed phenotypes reflect whether or not the anchored Mps1 can phosphorylate Spc105.

Figure 7F:
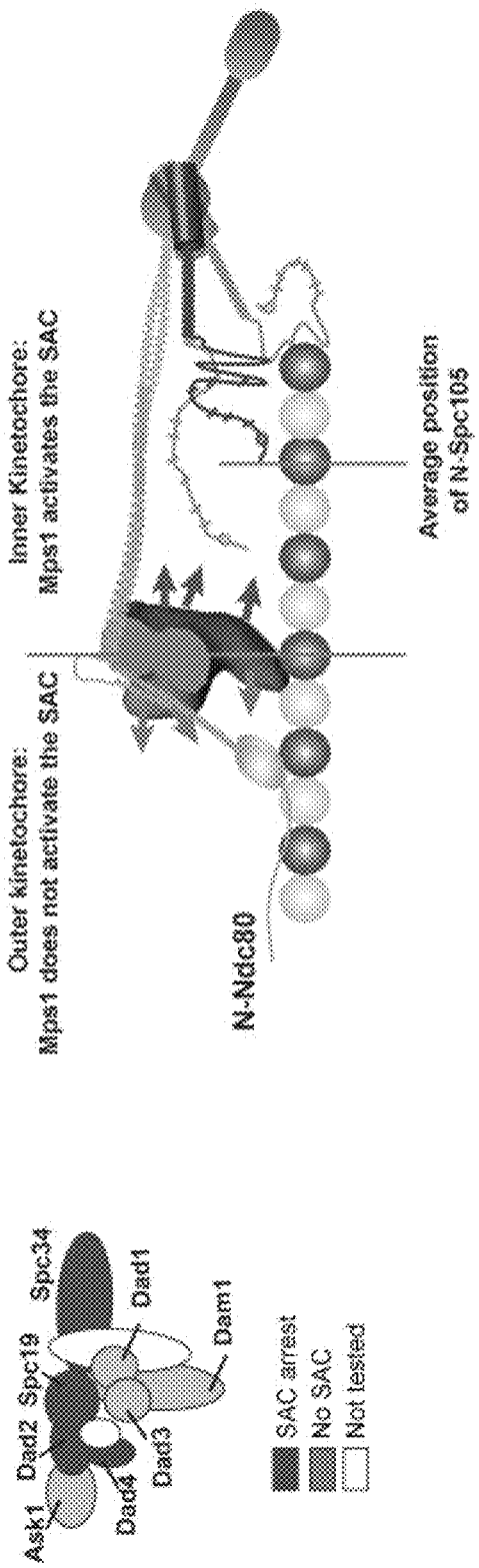

This is because dimensions of the Dam1 complex (ref. 27; herein incorporated by reference in its entirety) and its narrow distribution along the length of the kinetochore-microtubule attachment (ref 23; herein incorporated by reference in its entirety) indicate that all of the anchoring points are confined within a ~10-nm-wide zone. Although the structure of the Dam1 complex is unknown, data are consistent with the C termini of Dam1 subunits facing towards or away from the centromere (FIG. 7f, arrows). It is contemplated that this orientation constrains the orientation of the anchored Mps1, and determines whether or not Mps1 phosphorylates Spc105 to activate the SAC.

Phosphorylation of Spc105 by Mps1 is Sufficient to Initiate SAC Signaling

Figure 9A:
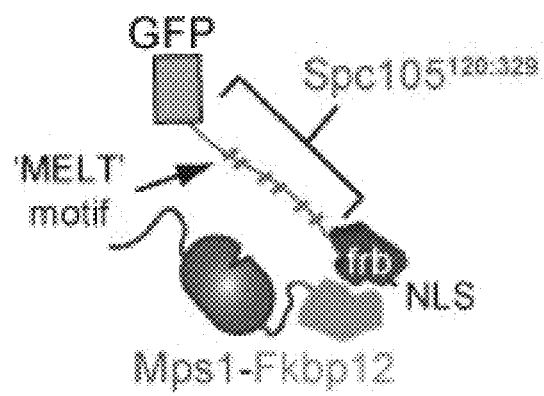
FIG. 9A-E. Phosphorylation of the Spc105 phosphodomain by Mps1 is sufficient to activate the SAC. (a) Schematic of $Spc105^{120:329}$, the minimal Spc105 phosphodomain. NLS: nuclear localization signal used to send $Spc105^{120:329}$ to the nucleus. (b) Cell-cycle kinetics following rapamycin addition to anchor the phosphorylatable (solid black line) or non-phosphorylatable $Spc105^{120:329}$ (solid grey line) to Mps1-C. The dashed black line shows the cell-cycle progression of the mad2Δ strain after anchoring $Spc105^{120:329}$ to Mps1. (c) Localization of $Spc105^{120:329}$ or $Spc105^{120:329:6A}$ when anchored to Mps1. Scale bars, ~3 μm. (d) Strategy to anchor $Spc105^{120:329}$ at N-Ndc80, and the localization of $Spc105^{120:329}$ at the indicated times after rapamycin addition. Scale bar, ~3 μm. (e) Recruitment of Mad1 to the kinetochore clusters when $Spc105^{120:329}$ (top) or $Spc105^{120:329:6A}$ (bottom) is anchored at NNdc80. Asterisk: known Mad1 localization at the nuclear envelope. Scale bar, ~3 μm.
Figure 9B:
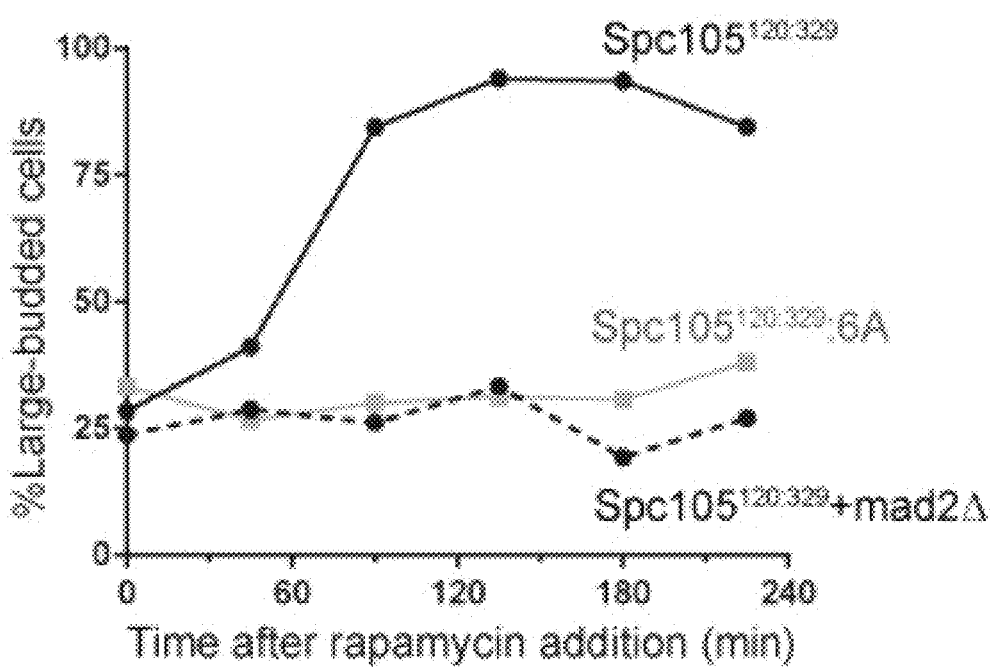
Figure 9C:
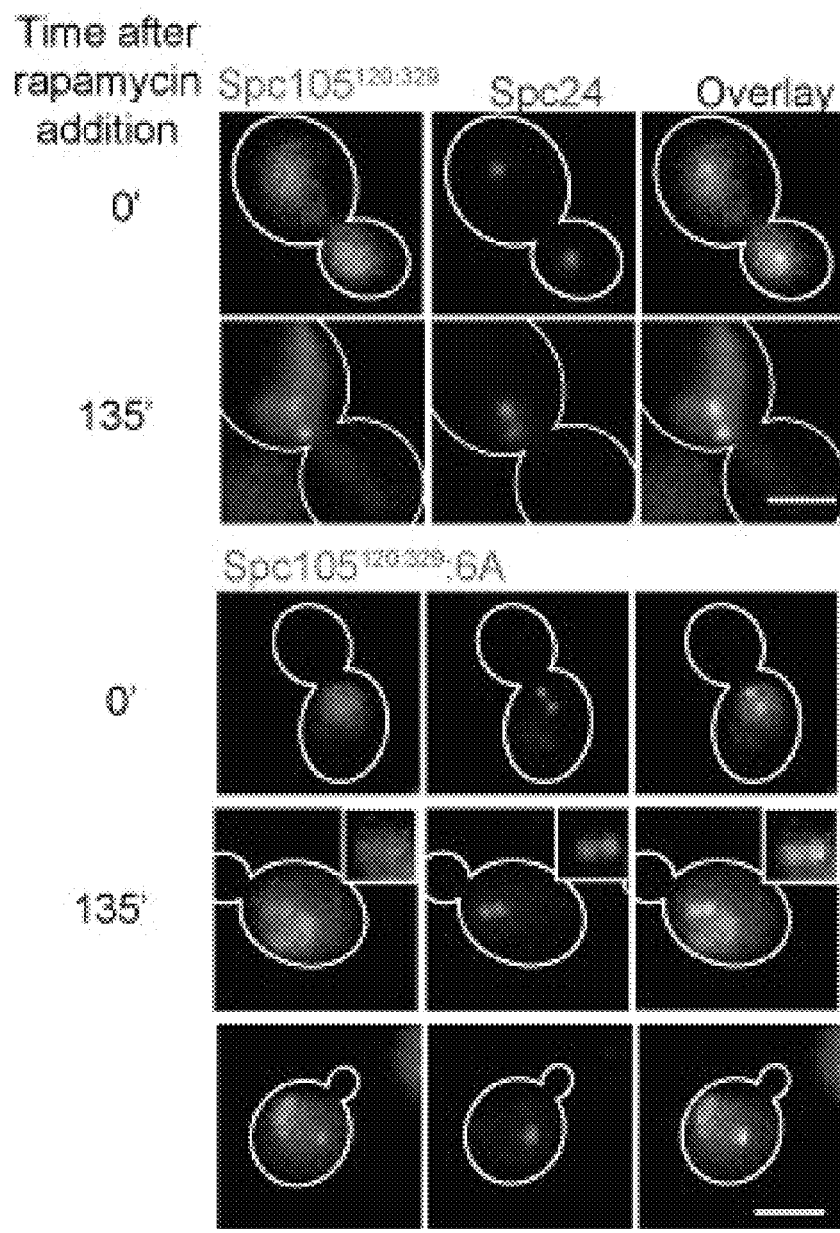
Figure 10A:
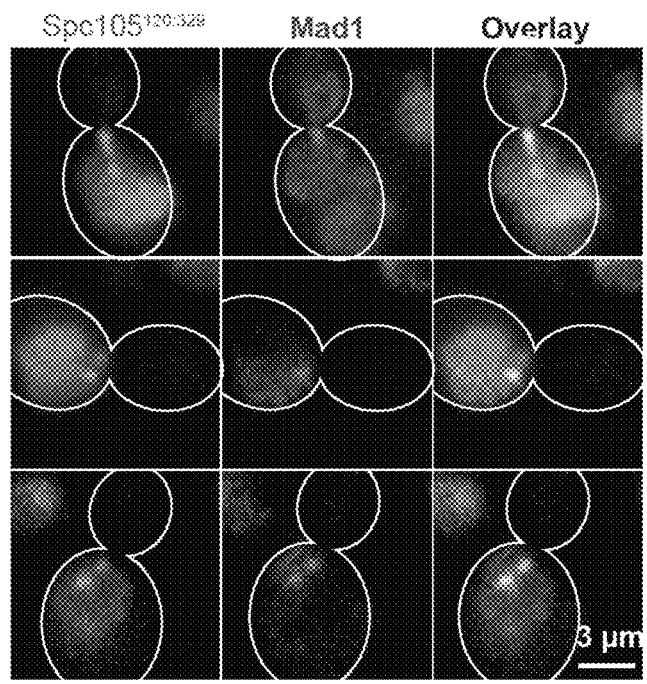
FIG. 10A-B. SAC signaling induced by rapamycin-induced dimerization of $Spc105^{120:329}$ and Mps1 does not require functional kinetochores. (a) Representative images show $Spc105^{120:329}$ anchored to Mps1 (rapamycin treatment for 45 minutes) localizing to the kinetochores. Mad1 also co-localizes with these kinetochore clusters. (b) Cells carrying the temperature-sensitive ndc10-1 allele and expressing $Spc105^{120:329}$ and Mps1-Fkbp12 were treated as indicated at the top. When released at the restrictive temperature from G1 arrest, these cells go through the cell cycle without assembling functional kinetochores and fail in cytokinesis, and give rise to cells with two buds (black bars; also see transmitted light micrograph top-right). However, when the same experiment was conducted in rapamycin containing media, the emergence of two budded cells was delayed by an hour (light gray bars).

The physical proximity between the Mps1 kinase and the phosphodomain of Spc105 controls the state of the SAC. Therefore, experiments were conducted to determine whether a forced interaction between the two outside the kinetochore is sufficient to activate the SAC. We engineered a minimal, anchorable phosphodomain comprising residues 120-329 of Spc105 (referred to as Spc105120:329, FIG. 9a). It contains all 6 MELT motifs, but no known kinetochore-binding activity. When Spc105120:329 was anchored to Mps1-Fkbp12 in asynchronously dividing cells, the cells arrested in metaphase (FIG. 9b). Spc105120:329 also localized to kinetochore clusters under these conditions and recruited Mad1 (FIGS. 9c and 10a). The kinetochore localization of Mad1 and Spc105120:329, when the latter anchored to Mps1, is mediated by Mps1 binding to the kinetochores. MAD2 deletion abolished the cell-cycle arrest indicating that the arrest resulted from SAC activation (FIG. 9b, dashed line). When Spc105120:329:6A, the non-phosphorylatable version of Spc105120:329, was anchored to Mps1, it did not activate the SAC (FIG. 9b, c). Thus, the phosphorylation of MELT motifs in Spc105120:329 by Mps1 is necessary for the observed cell-cycle arrest.

Figure 10B:
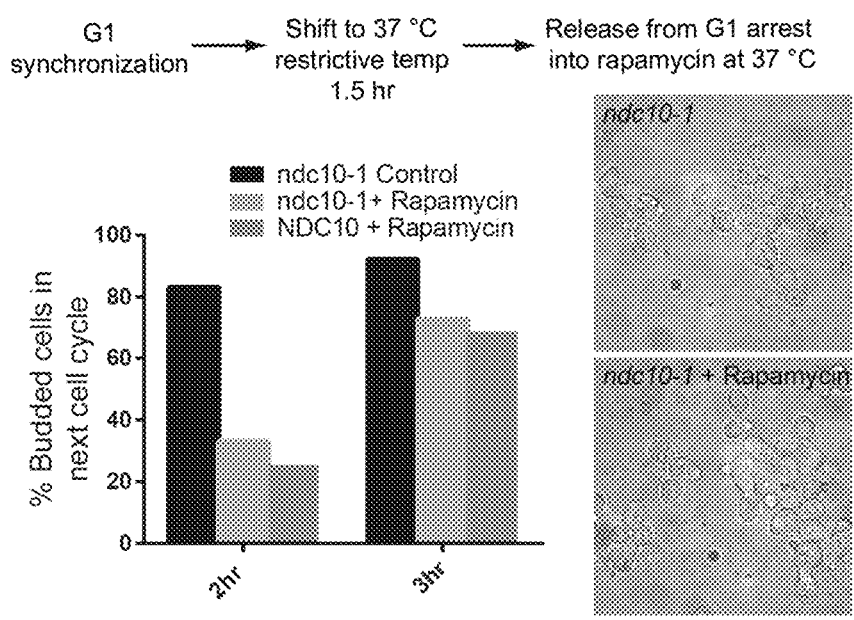

To examine whether kinetochores contributed to the SAC signaling, cells carrying ndc10-1, a temperature-sensitive allele of the gene encoding the centromeric protein Ndc10 (ref. 30; herein incorporated by reference in its entirety), were used. At the restrictive temperature, these cells do not assemble functional kinetochores, and are thus unable to activate the SAC. However, when Spc105120:329 was anchored to Mps1 at the restrictive temperature, ndc10-1 cells experienced a cell-cycle delay similar to the delay seen in NDC10 cells under the same conditions (FIG. 10b). Thus, the SAC signaling induced by the forced interaction between Spc105120:329 and Mps1 does not require functional kinetochores (ref31; herein incorporated by reference in its entirety). These data demonstrate that the interaction between Mps1 and the phosphodomain of Spc105 is both necessary and sufficient to activate the SAC. IT is contemplated that the kinetochore serve as the scaffold that makes this interaction sensitive to microtubule attachment; although, the present invention is not limited to any particular mechanism of action and an understanding of the mechanism of action is not necessary to practice the present invention.

Figure 11:
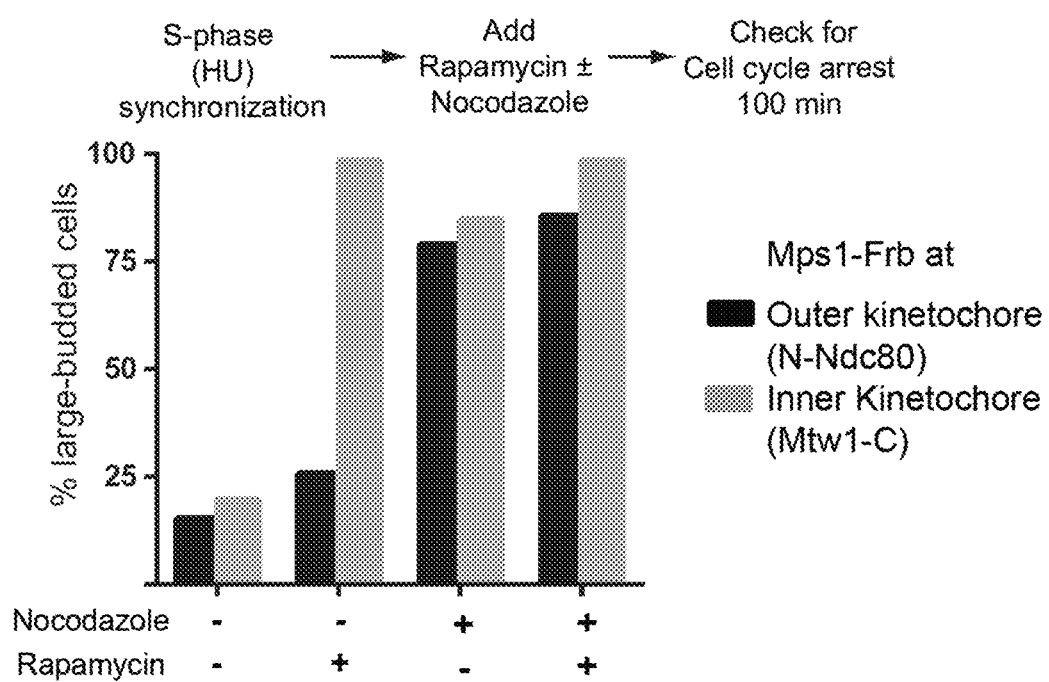
FIG. 11. SAC signaling induced by Mps1 anchored at N-Ndc80 depends on the attachment-state of the kinetochore. S-phase synchronized cells were treated as indicated in the schematic at the top and the percentage of large-budded cells formed after 100 minutes was measured as an indicator of cell cycle arrest Mps1 anchored at Mtw1-C constitutively activated the SAC in the presence of attachments and in nocodazole. However, Mps1 anchored at N-Ndc80 allowed normal cell cycle progression and caused cell cycle arrest only in the presence of unattached kinetochores in nocodazole.

Spc105120:329 Activates the SAC when Anchored in the Outer Kinetochore, but not the Inner Kinetochore Data herein indicate an organization of Mps1 and Spc105 relative to one another that makes their interaction sensitive to the attachment state of the kinetochore. When Mps1 is anchored in the inner kinetochore, proximal to the phosphodomain of Spc105, it activates the SAC constitutively even from attached kinetochores. In contrast, if it is anchored in the outer kinetochore, distal from the phosphodomain of Spc105, it activates the SAC conditionally, only from unattached kinetochores (FIG. 11). Therefore, to implement attachment-sensitive SAC signaling, endogenous Mps1 bind to a site within the outer kinetochore. Consistent with this, Mps1 physically interacts with the CH domain of Ndc80, which is located in the outer kinetochore (ref. 32, 33; herein incorporated by reference in their entireties).

Figure 9D:
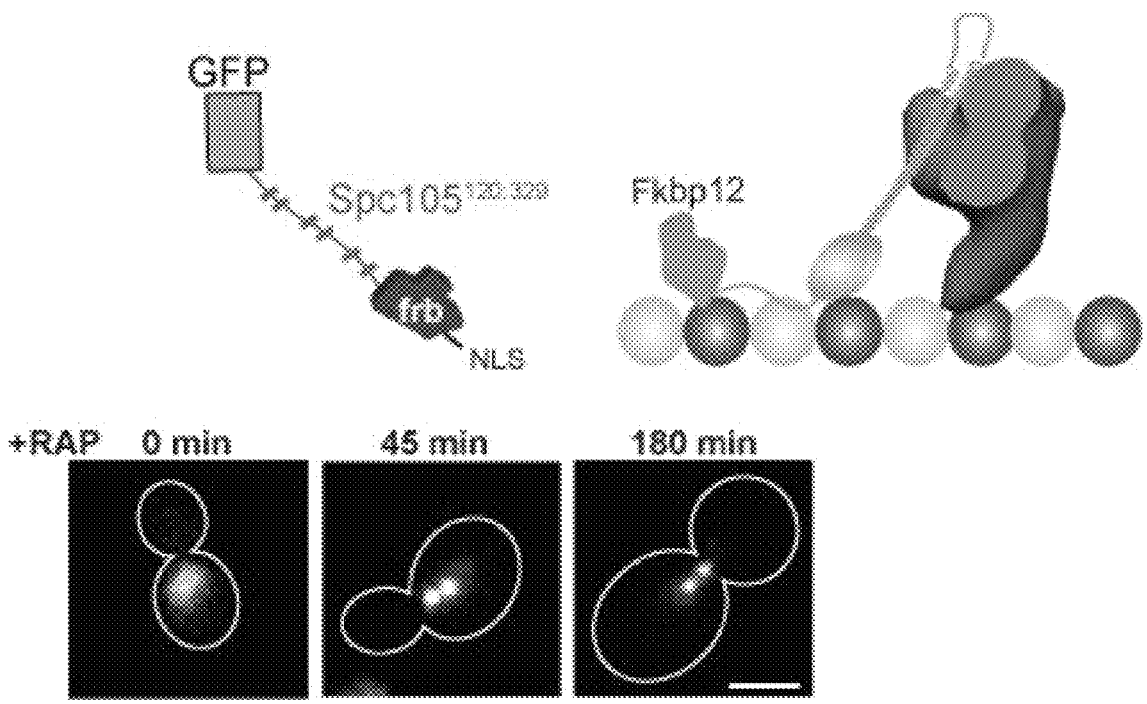
Figure 9E:
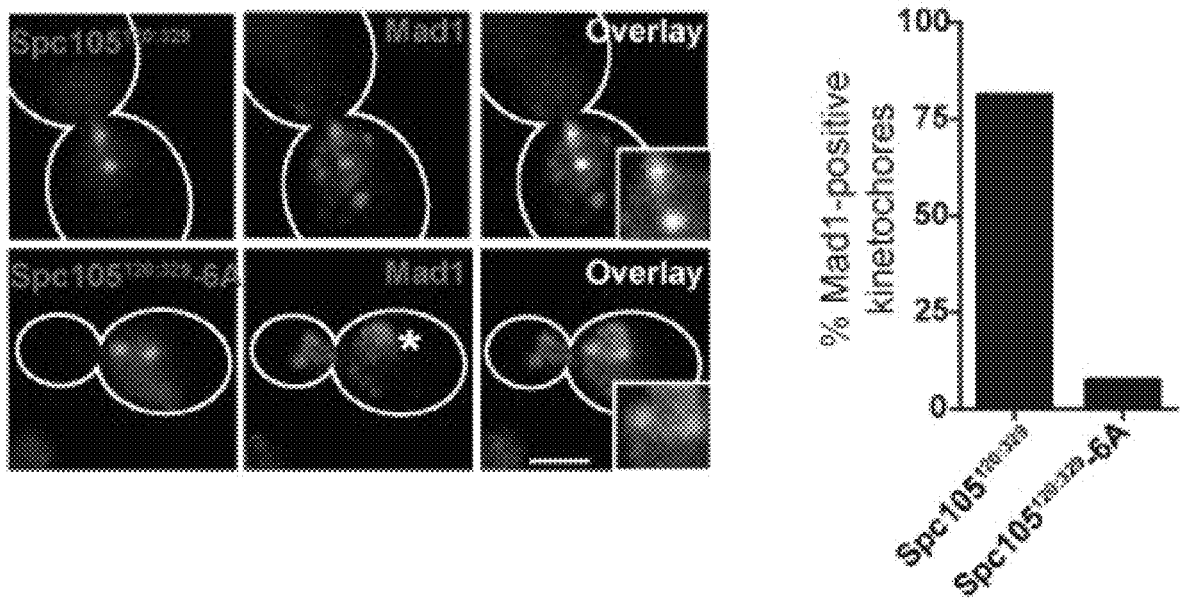

To investigate whether endogenous Mps1 binds within the outer kinetochore, Spc105120:329 at N-Ndc80 was anchored proximal to the CH domain (FIG. 9d, top). In metaphase cells, the anchored Spc105120:329 exhibited the stereotypical, metaphase kinetochore distribution: two distinct puncta separated by <1 μm. It also recruited Mad1, and the cells remained arrested for a prolonged period (FIG. 9d, e). The cell cycle arrest was absent when Spc105120:329:6A was anchored to N-Ndc80, revealing that the phosphorylation of the MELT motifs in Spc105120:329 by kinetochore-localized Mps1 is required for SAC activation. These results demonstrate that catalytically active Mps1 binds to the outer kinetochore even after stable microtubule attachments form.

Figure 12A:
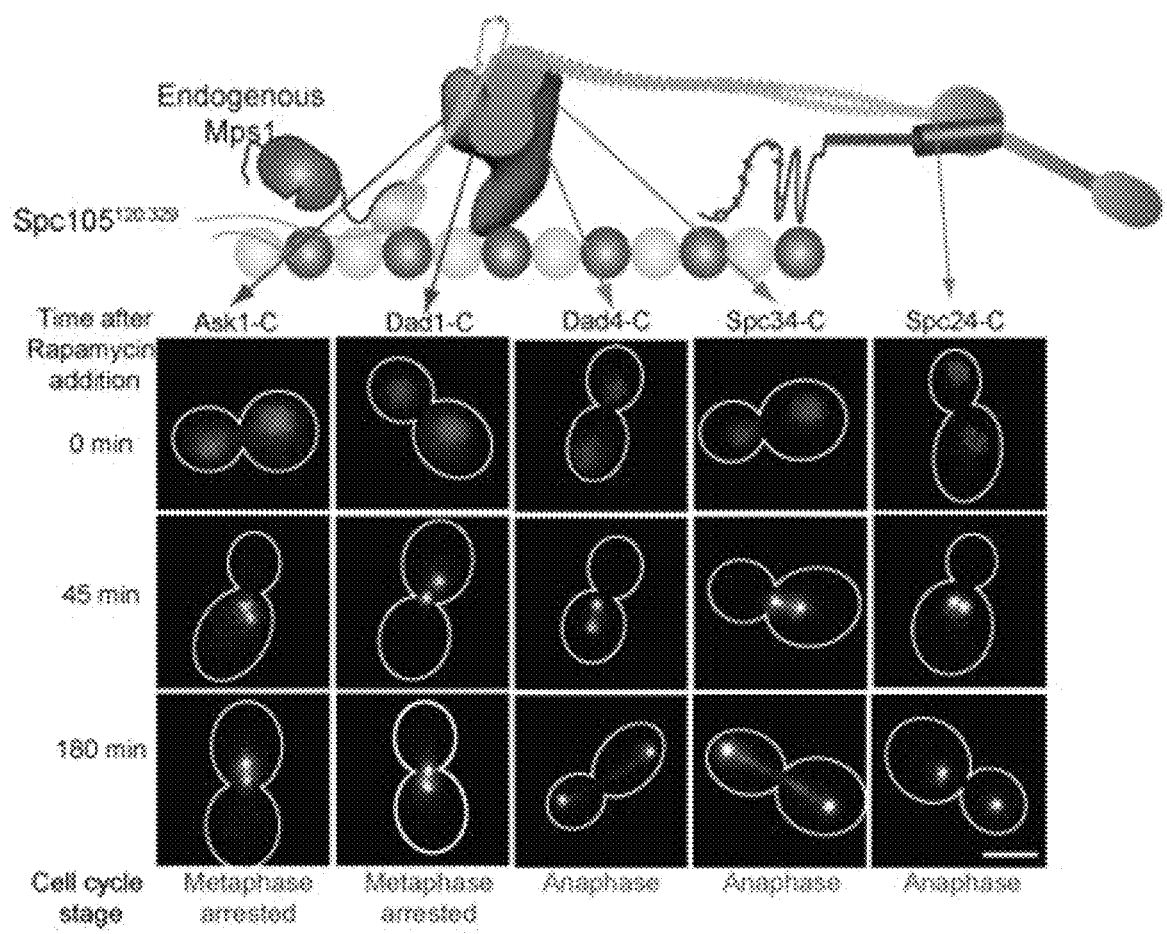
FIG. 12A-E. Spc105$^{120:329}$ activates the SAC only when it is anchored in the outer kinetochore. (a) Representative micrographs of asynchronously dividing cells showing the localization of Spc105$^{120:329}$ and cell-cycle progression as a function of the anchoring position (indicated at the top; scale bar, ~3 µm). Large-budded cells with <2 µm separation between kinetochore clusters were characterized as metaphase-arrested cells. (b) Accumulation of metaphase-arrested cells after rapamycin addition, when either Spc105$^{120:329}$ (solid lines) or its non-phosphorylatable version, Spc105$^{120:329:6A}$ (dashed lines), was anchored at the indicated positions. (c) Mad1-mCherry localization after anchoring Spc105$^{120:329}$ at the indicated positions for 1 h (scale bar, ~3 µm). The bar graph shows the fraction of metaphase cells that recruit Mad1 to the kinetochores in each case. Total number of cells analysed in each case is indicated on top of the bars. (d) Top: Cell-cycle progression as in a when a modified version of the Spc105 phosphodomain that includes the Glc7-recruitment motif (Spc-105$^{120:329}$, solid lines) or its non-phosphorylatable version (Spc105$^{120:329:6A}$ dashed line) was anchored at the indicated kinetochore positions. Bottom: Micrographs (scale bar, ~3 µm) and quantification of kinetochore-localized Bub3-mCherry 45 min after either Spc105$^{120:329}$ or Spc105$^{120:329:6A}$ was anchored at Ask1-C in cells arrested in metaphase using CDC20 repression. (e) Map of the SAC activity of the anchored Spc105$^{120:329}$.
Figure 12B:
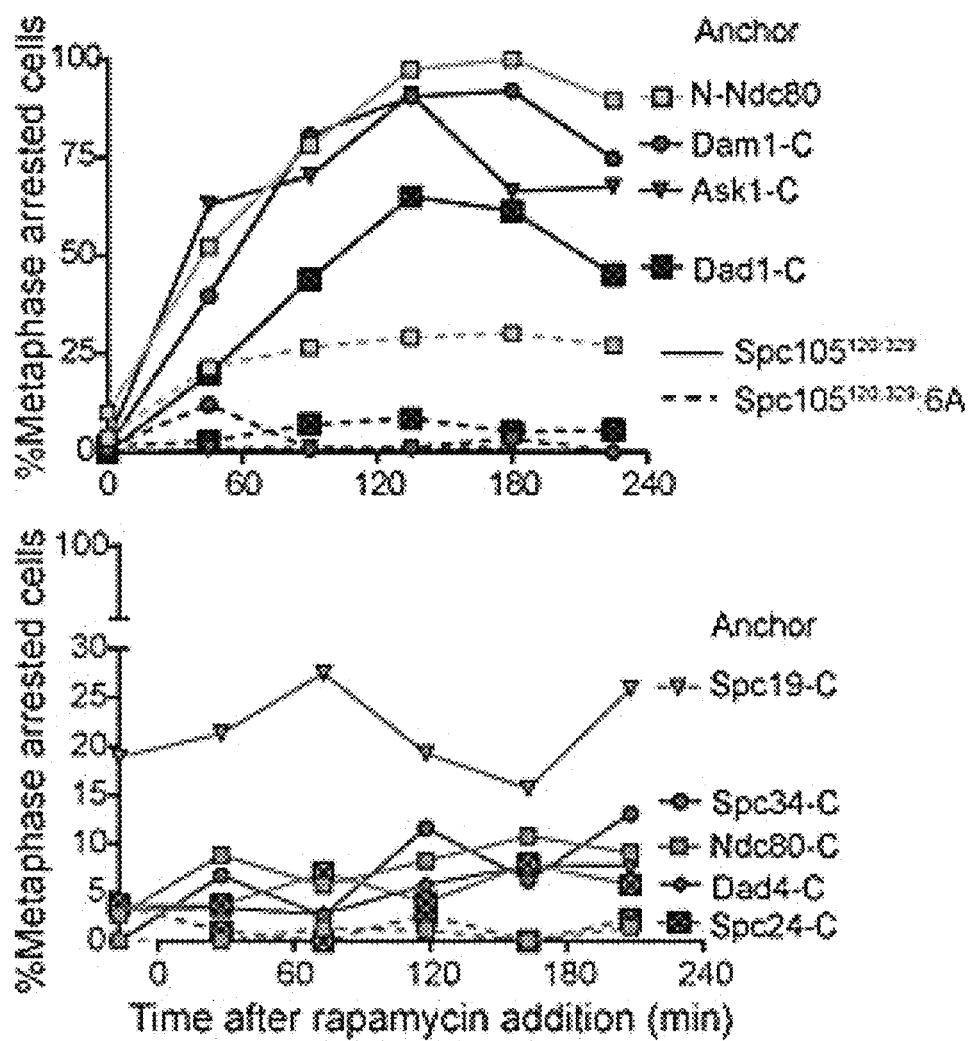
Figure 12C:
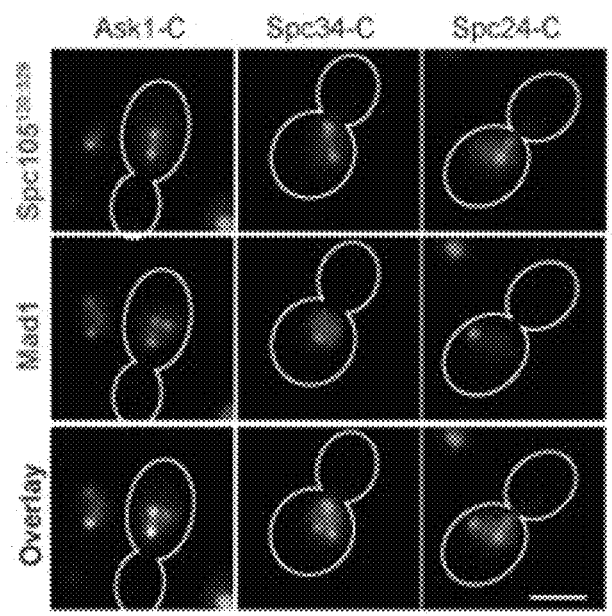
Figure 12C:
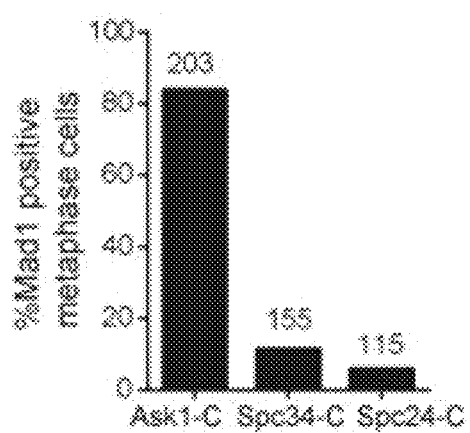

The entire kinetochore was then probed for additional Mps1-binding sites (FIG. 12a). When Spc105120:329 was anchored to Dam1 subunits expected to face towards the outer kinetochore (Ask1-C, Dam1-C, or Dad1-C, see FIG. 7f), the kinetochores recruited Mad1, and the cells arrested in mitosis (FIG. 12b top 12c). Strikingly, when Spc105120: 329 was anchored to positions in the inner kinetochore, including the Dam1 subunit termini predicted to face towards the centromere (Dad4-C, Spc34-C and Spc19-C), it had no effect on the cell cycle (FIG. 12b bottom and 12c). Spc105120:329:6A did not affect the cell cycle when anchored at any of the positions (FIG. 12b, dashed lines). These results demonstrate that catalytically active Mps1 is absent from the inner kinetochore.

Figure 12D:
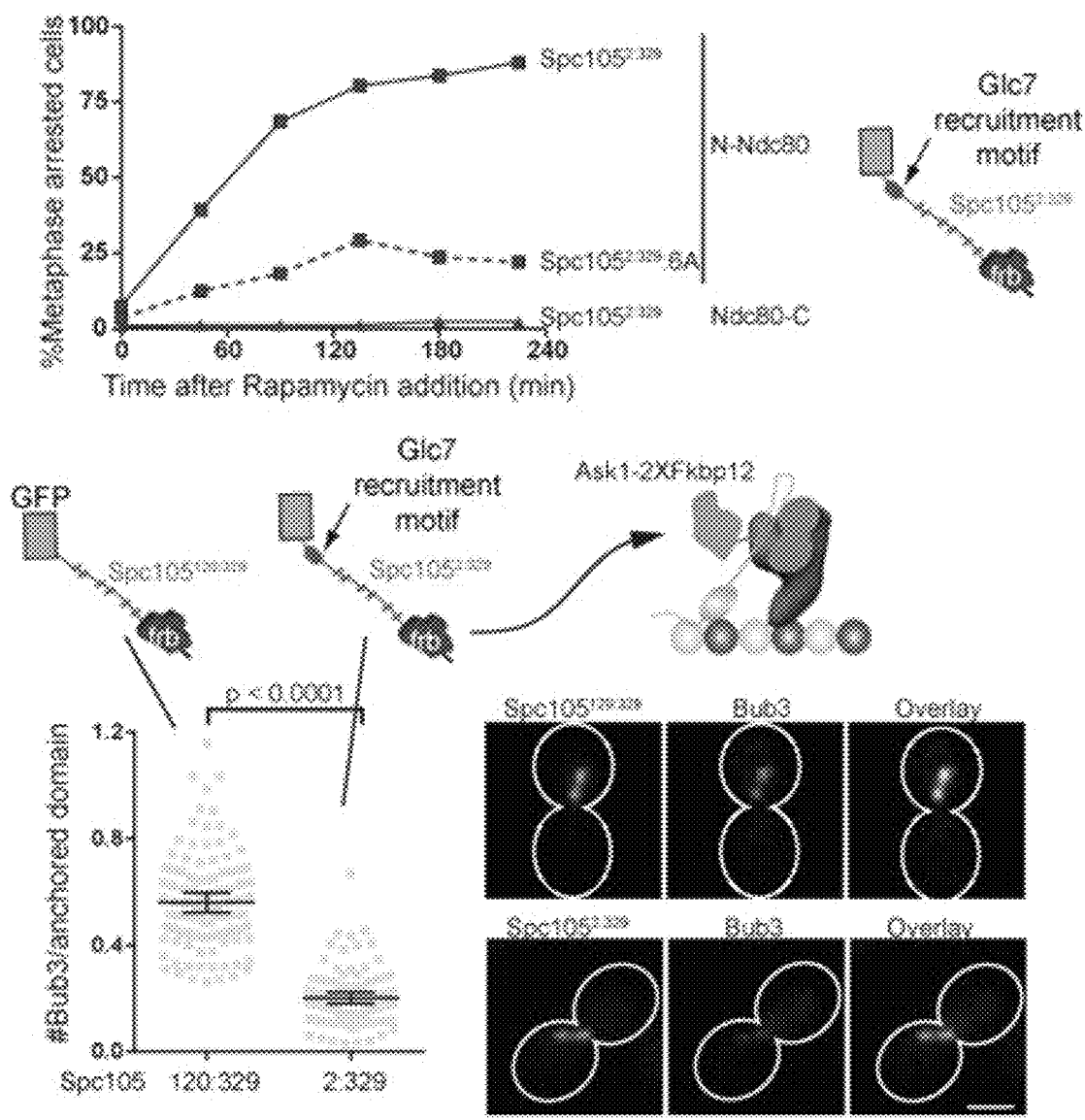
Figure 12E:
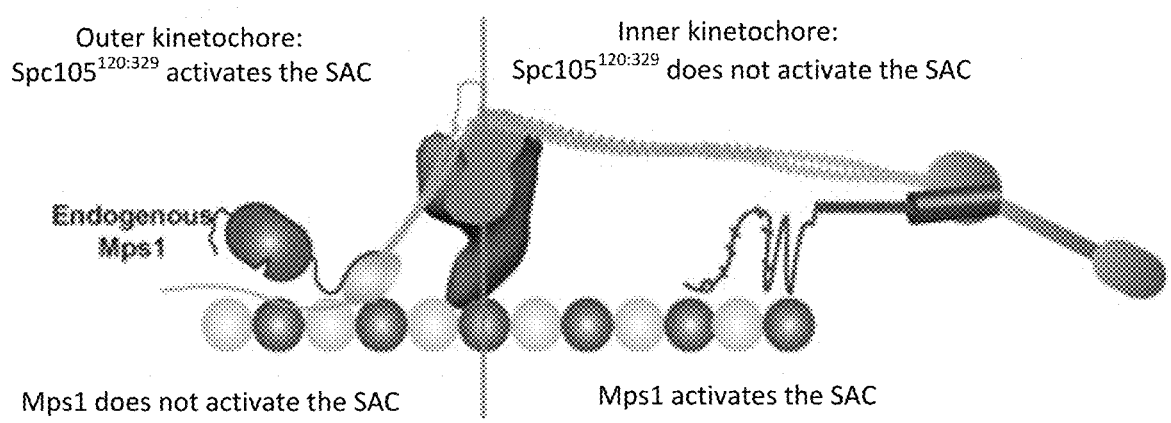
Figure 14A:
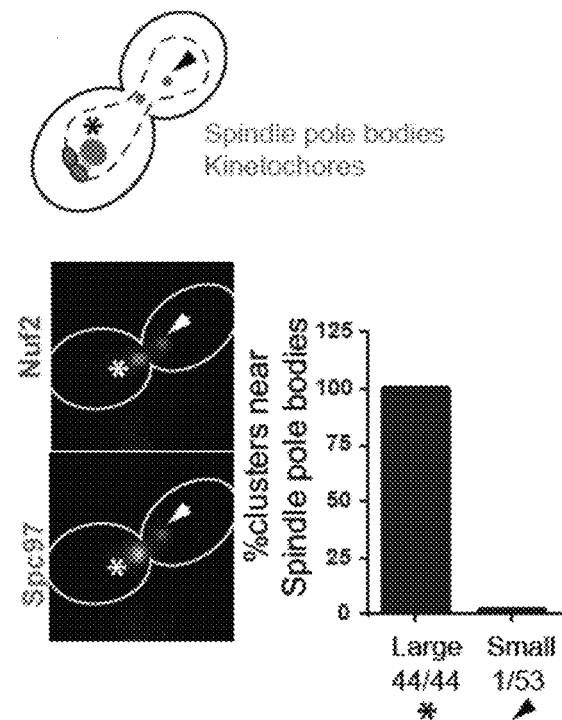
FIG. 14A-D. Effect of spindle disruption on SAC protein recruitment and kinetochore architecture. (a) Spindle disruption with nocodazole generates two or three kinetochore clusters within the nuclei of most budding yeast cells as reported previously. The cluster that contained majority of the kinetochores (large, asterisks) localized proximal to the collapsed spindle pole bodies (visualized by Spc97-GFP). One or two smaller kinetochore clusters (small, arrowheads) were found distal to the spindle pole bodies. Bar graph displays the percentage of large or small clusters that are proximal to the spindle pole body. (b) The smaller kinetochore clusters (arrowheads) in nocodazole recruit significantly higher levels of Mps1 and Bub1 than the large cluster.
Figure 14B:
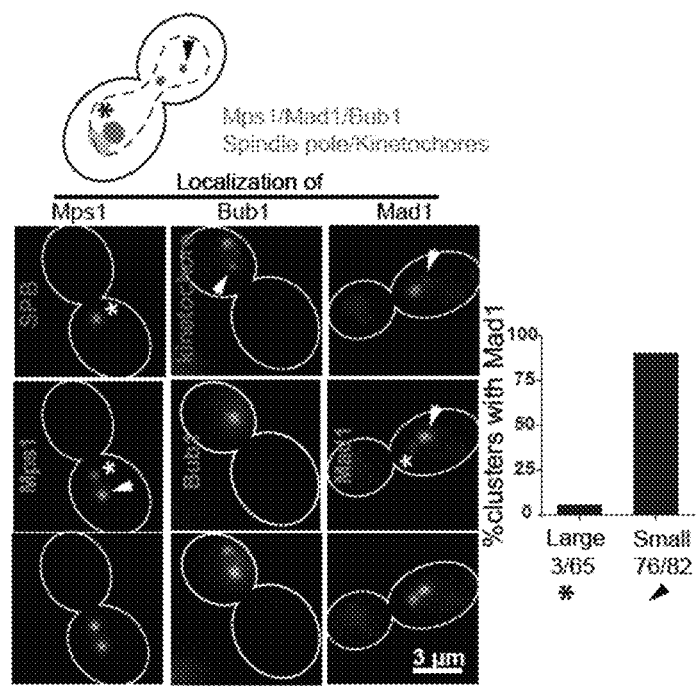
Figure 14C:
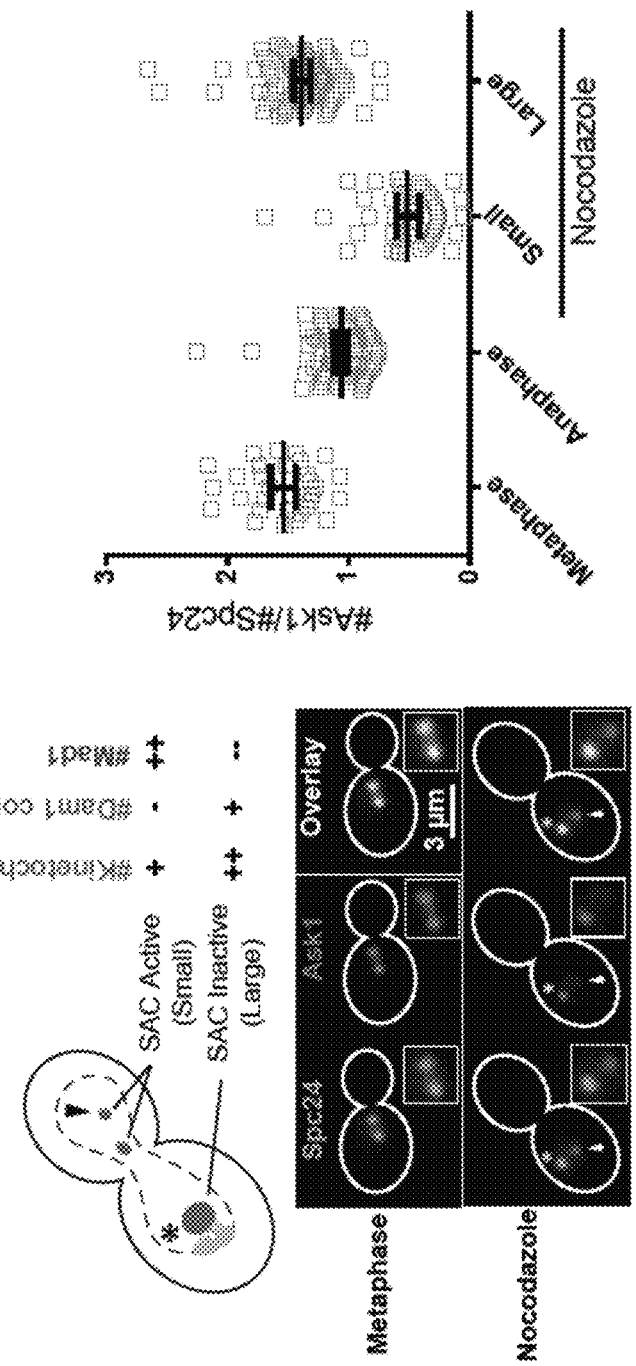
Figure 14D:
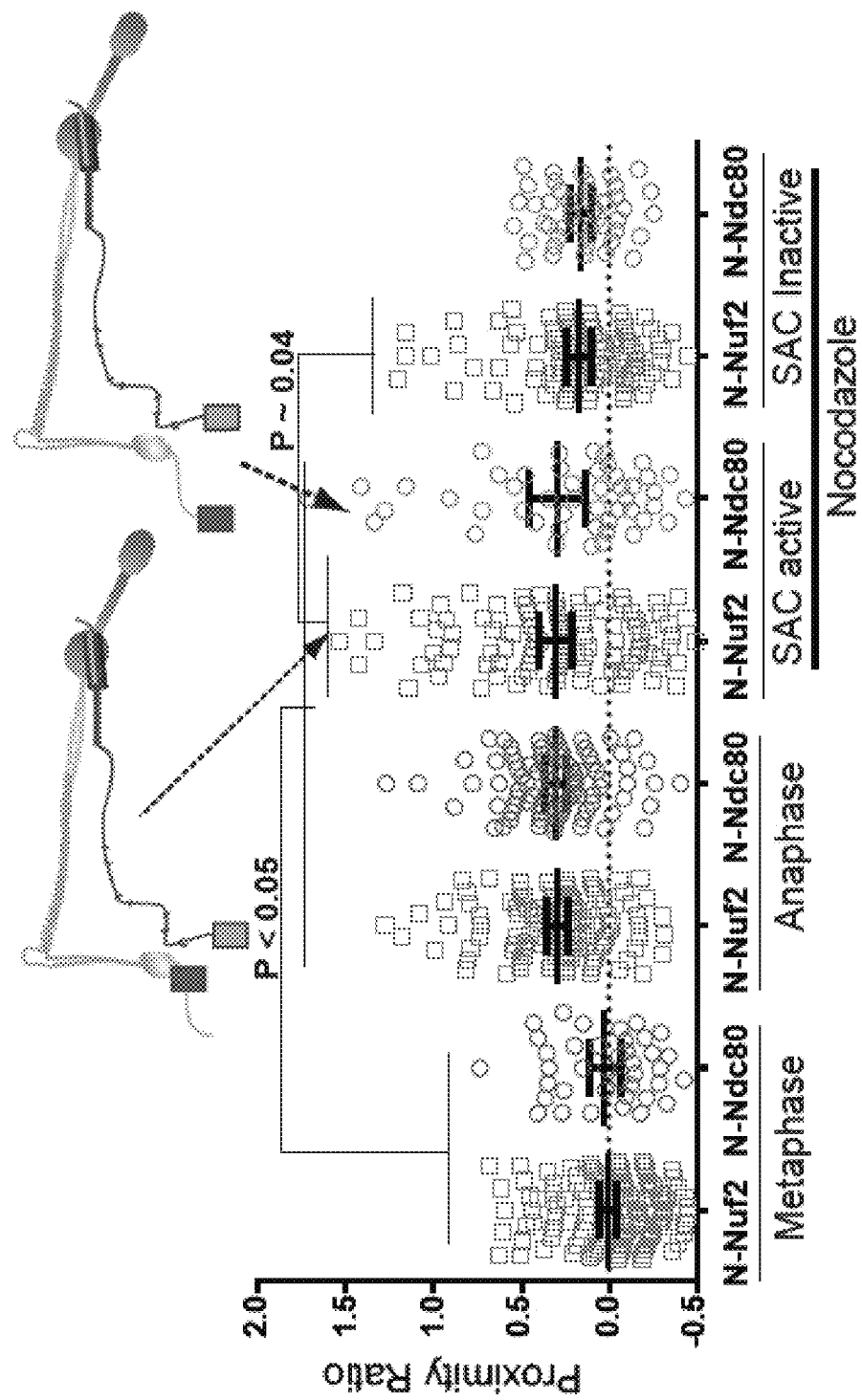

The N terminus of Spc105 localizes to the inner kinetochore and contains a Glc7-binding motif (ref. 18; herein incorporated by reference in its entirety), which is not present in Spc105120:329. Therefore, the lack of Glc7 activity in the outer kinetochore, rather than localized Mps1 activity, could also produce the observed SAC activation phenotypes. To determine whether this is the case, a phosphodomain was constructed that contains the Glc7-binding motif (Spc1052:329, FIG. 12d). Spc1052:329 anchored at N-Ndc80 or at Ndc80-C produced the same phenotypes as Spc105120:329 (FIG. 12d, top). To determine whether Spc105²:329 recruits Glc7 activity, either Spc105²:329 or Spc105120:329 was anchored to Ask1-C, and the kinetochore-recruitment of Bub3 was quantified (FIG. 12d). As Bub3 specifically binds to phosphorylated MELT motifs (ref. 34; herein incorporated by reference in its entirety), significantly reduced Bub3 recruitment in the former case confirmed that Spc105²:329 recruits Glc7 activity (FIG. 12d, bottom). These data build an activity map for Spc105120:329 and demonstrate that catalytically active Mps1 kinase binds exclusively in the outer kinetochore even after the kinetochore establishes stable microtubule attachment. Strikingly, this map is the mirror image of the activity map for the anchored Mps1 kinase, with the Dam1 complex demarcating the boundary in both maps (FIGS. 7f and 12e). These data indicate that the Dam1 complex contributes to SAC silencing by acting as a physical barrier that separates the phosphodomain of Spc105 from Mps1.

Separation Between CH Domains of Ndc80 and N-Spc105 Changes with the Attachment State of the Kinetochore Data indicates that microtubule attachment to kinetochores physically separates the CH domains of Ndc80 and the phosphodomain of Spc105 to silence the SAC. By corollary, unattached kinetochores bring them in close proximity to activate the SAC. To determine whether the separation between these two domains and the attachment state of the kinetochore are correlated, FRET was measured between N-Spc105 and either N-Nuf2 or N-Ndc80, which are proximal to the CH domains (FIGS. 13a and 14). In both cases, FRET was undetectable in metaphase as predicted by the >30 nm separation between N-Spc105 and both N-Ndc80 and N-Nuf2 (ref 20; herein incorporated by reference in its entirety)). In contrast, moderate FRET was detected in unattached kinetochores created by treating the cells with nocodazole, indicating that mCherry and GFP fused to the respective N termini were, on average, ~8 nm apart35.

Proximity Between the CH Domains and Spc105120:329 Controls SAC Signalling in Attached Linetochores Independently of the Endogenous Spc105

Experiments were conducted during development of embodiments herein to investigate whether Spc105120:329 restores the SAC in attached and unattached kinetochores in a position-dependent manner in spc105-6A strains that are SAC-deficient. The kinetochore provides only the architectural scaffold in this experiment. Spc105120:329 arrested the cell cycle when anchored proximal to the CH domains (at N-Ndc80), but not when anchored distal to the CH domains (at Spc24-C, FIG. 13b). Even within unattached kinetochores, Spc105120:329 restored the SAC when it was anchored at N-Ndc80, as expected (FIG. 15). However, Spc105120:329 anchored at Spc24-C also activated the SAC in unattached kinetochores, indicating that Mps1 accesses Spc105120:329, even though its anchoring position is expected to be distal to the CH domains. It is contemplated that the inherent flexibility of Ndc80 and Spc105 and the presence of multiple molecules of these proteins in the kinetochore are responsible for this unexpected phenotype.

Example 2

Strain and Plasmid Construction

Strains used in the anchoring experiments were constructed by deleting FPR1 in wild-type strains to eliminate the rapamycin-binding protein product of this gene. These strains also express tor1-1, which encodes the dominant-negative, rapamycinresistant form of the Tor1 kinase. At least one copy of TOR1 in diploid strains was mutated to tor1-1.

Frb-GFP(S65T) (or Frb alone) was fused to the C terminus of selected SAC proteins with a 24- or 7-amino-acid linker (with the amino acid sequence 'RIPGLIN-SGGGGGSGGGSGGGGAS' (SEQ ID NO:10) or 'SGGG-GAS' (SEQ ID NO:11), respectively). Two tandem copies of Fkbp12 (2xFkbp12) were fused to the C terminus of kinetochore proteins with the linker coding 'RIPGLIK' (SEQ ID NO:12). 2xFkbp12 was fused to the N terminus of Ndc80 through the linker sequence 'GAAAAG' (SEQ ID NO:13). A 7-amino-acid linker (sequence: 'RIPGLIN' (SEQ ID NO:14)) was used to fuse fluorescent proteins (either GFP (S65T) or mCherry) to the amino or carboxy terminus of selected proteins.

spc105-6A strains were constructed using plasmid shuffling. The genomic copy of SPC105 was deleted in a parent strain containing a centromeric plasmid containing SPC105 and the URA3 gene as the auxotrophic marker (pAJ274). Next, pSB1878 linearized with NsiI was integrated at the his3 locus (ref. 12; herein incorporated by reference in its entirety). Finally, the centromeric plasmid carrying the wild-type SPC105 was kicked out by counter-selecting for URA3 on the drug 5-FOA.

Plasmids containing the minimal phosphodomain of Spc105, pAJ349 and pAJ350 were constructed by subcloning the PCR amplification product of the phosphodomain of Spc105 (amino acids: 120-329 from pSB1332 for wild-type, or from pSB1878 for the phosphonull version12) into pAFS144 carrying the frb domain using AatII and KasI sites. These plasmids, after linearization with NsiI, were integrated at the his3 locus. For integration at the LEU2 locus, the HIS3 gene in pAJ349 and pAJ350 was replaced with LEU2 to construct pAJ351 and pAJ352, respectively. The plasmids were linearized with BstEII for integration at the leu2 locus.

Cell Culture

Cells were grown in yeast extract, peptone and dextrose (YPD) media at 32° C. and imaged at room temperature in synthetic media supplemented with essential amino acids and an appropriate carbon source. To express N-terminally labelled kinetochore proteins from the galactose promoter (pGAL1), strains were grown in YP Raffinose media supplemented with 0.1-0.4% galactose. The galactose concentration was adjusted empirically (ref. 35; herein incorporated by reference in its entirety).

Stock solution (1 mg ml$^{-1}$) of rapamycin in DMSO was diluted ×1,000 to achieve 1 µg ml$^{-1}$ final concentration in all experiments involving rapamycin-induced dimerization.

To depolymerize metaphase spindles with nocodazole64, mid-log-phase cells were synchronized in G1 with α-factor (2 µg ml$^{-1}$) for 2 h and then released into nocodazole-containing media (15 µg ml$^{-1}$) for 1.5-2 h.

Benomyl Sensitivity Assay

Tenfold serial dilutions of log-phase cultures were frogged on YPD or plates containing (30 µg ml-1) benomyl. Colonies were allowed to develop for 2-3 days at 30° C. before pictures of the plates were taken.

Metaphase Arrest by CDC20 Repression

Cells expressing Cdc20 from a methionine-repressible promoter (pMET3) were synchronized in G1 by treatment with a-factor (2 µg ml$^{-1}$) for 2 h in synthetic media lacking methionine. They were then released into YPD supplemented with 2 mM methionine for two hours to repress CDC20 and then treated with rapamycin for 10 min. Cells were washed into synthetic media lacking methionine to initiate CDC20 expression.

Inhibiting Ipl1 or Mps1 Kinase Activity Using ATP Analogues

The ATP analogues 1-NMPP1 and 1-NAPP1 (final concentration 50 μM) were used to block the activity of mps1-as1 and ipl1-as6, respectively. Cells were first synchronized in S-phase using 100 mM hydroxyl urea (HU) for 2.5 h, washed with YPD, and then released into media containing the appropriate inhibitor for 15 min. This was followed by the addition of rapamycin to the media to anchor Mps1-Frb at Mtw1-C. The bud size was used to monitor cell-cycle progress.

To examine the ability of 1-NMPP1 to block the kinase activity of mps1-as1, the cells were treated with nocodazole to depolymerize the spindle and activate the SAC (ref. 65; herein incorporated by reference in its entirety). Next, the cells were treated with either 1-NMPP1 or DMSO, and cell morphology was monitored. Mps1 kinase activity is necessary to maintain an active SAC and arrest the cells in mitosis. If the SAC remains active, then the cells remain arrested in mitosis as large-budded cells. However, SAC-deficient cells escape the mitotic arrest and also fail in cytokinesis. They enter the next cell cycle and produce another bud thus giving rise to two-budded cells (ref. 66; herein incorporated by reference in its entirety).

To study the effect of 1-NAPP1 on ipl1-as6 activity, the spindle localization of Sli15-GFP was measured in pre-anaphase cells67. The bud size was used to find pre-anaphase cells. If the bud was smaller than 50% in size as compared with the mother cell, and contained a short bar of Sli15-GFP located within the mother cell and at the bud neck, then the cell was deemed to be in pre-anaphase.

Scoring Mitotically Arrested Cells

The cells were scored as 'large-budded' (for example, FIGS. 1e and 5b), if the size of the bud was more than ⅔ the size of the mother as seen from bright-field images. Anaphase cells in cycling cultures will also be scored as large-budded cells by this criterion. In strains carrying fluorescent markers, the separation of the kinetochore clusters or spindle pole bodies was used to determine whether or not the cells arrested in mitosis. Large-budded cells with kinetochore-cluster separation smaller than 1 μm or spindle length smaller than 2 μm were scored as metaphase-arrested cells (ref. 68; herein incorporated by reference in its entirety).

Colony-Counting Assays

Approximately 300 cells (estimated from the attenuance of liquid cultures measured at 660 nm) were plated on control and rapamycin-containing plates. After allowing the colonies to grow for 3 days at 30° C., colony number was determined. It was ensured that the strains used in this experiment were rapamycin-resistant, by verifying that the parental haploid strains expressing either the Frb-fused SAC protein or the Fkbp12-fused kinetochore protein produced the same number of colonies on both control and rapamycin-containing plates.

Microscopy and Image Acquisition

A Nikon Ti-E inverted microscope with a 1.4 NA, 100×, oil-immersion objective was used in imaging (ref. 35; herein incorporated by reference in its entirety). A ten-plane Z-stack was acquired (200 nm separation between adjacent planes). The total fluorescence from each kinetochore cluster with GFP- or mCherry-tagged protein was measured using ImageJ, or a semi-automated MATLAB program. The copy numbers of kinetochore proteins and anchored proteins were calculated from the known copy number of the Ndc80 complex per kinetochore-8 molecules per kinetochore.

For photobleaching, an argon-ion laser (Photonics Instruments) beam filtered with the ET-GFP filter cube was focused on the sample by the objective. The target was manually aligned with the pre-determined location of the laser focus, and then exposed to 488 nm light for 50 ms. Five-plane Z-stacks were acquired starting immediately after bleaching for 14 min, at 2 min intervals. Fluorescence was quantified from the images as above.

FRET, high-resolution co-localization and fluorescence distribution analyses were conducted as previously described in ref. 20, 35, and 69; herein incorporated by reference in their entireties.

Time-lapse imaging was used to follow the Mps1-Frb-GFP that autonomously bound to the kinetochore clusters in metaphase-arrested cells. Cells were released from the metaphase arrest by activating CDC20 expression, and a 6-plane Z-stack was acquired at 1 min intervals for 20 min. Anaphase entry was inferred from spindle elongation tracked from the spindle pole body protein (Spc97-mCherry). The change in Mps1-Frb-GFP intensity during this period was quantified, after correcting for two factors: GFP photobleaching expected from imaging and; fluorescence emission from Spc97-mCherry due to cross-excitation while imaging GFP. The representative images in FIG. 2f have not been corrected for these factors.

Example 3

Experiments conducted during development of embodiments herein demonstrate control of the yeast SAC independently of the kinetochore by 'short-circuiting' the kinetochore-based mechanical switch (See, e.g., Example 1). Further experiments have demonstrated that this short-circuiting approach also works in human cells. Recombinant-mediated cassette exchange (RMCE) was used to stably integrate a cassette that constitutively expresses M3-M3-neonGFP-2xFkbp12, wherein M3-M3 corresponds to a fragment of the phosphodomain of human KNL1 containing 6 MELT motifs (a kind gift from the Kops lab. This protein construct did not localize to the kinetochore. Frb-mCherry-Mps1 is conditionally expressed by a TetON promoter (FIG. 16). Cells expressing both fragments underwent a prolonged arrest in metaphase when rapamycin was added to the culture media (FIG. 16). This arrest was absent in the absence of rapamycin, or even in the presence of rapamycin if the cell did not express a detectable level of Frb-Mps1.

To verify that the metaphase arrest is due to the activation of SAC, HeLa cells are synchronized using double thymidine block, released into the cell cycle, and cell-cycle progress is monitored in the presence and absence of rapamycin using biochemical markers (Pds1/Securin levels) and microscopic examination (fixed cells stained for phospho-histone H3). Analog-sensitive Mps1 and non-phosphorylatable M3-M3 allele are used to ensure that the arrest results from the phosphorylation of M3-M3 by Mps1. It is tested whether dimerization activates the SAC even when Ndc80/Hec1, which is essential for SAC signaling from the kinetochore, is knocked-down. SAC activation in the absence of Ndc80 confirms that the kinetochores do not participate in the signaling induced by the cytosolic dimerization of Mps1 and M3-M3. Together, these experiments demonstrate that the interaction between Mps1 and KNL1 is both necessary and sufficient for activating the SAC in human cells. These experiments indicate that the function of the kinetochore is to control this interaction, and make it sensitive to microtubule attachment.

Example 4

Figure 17B:
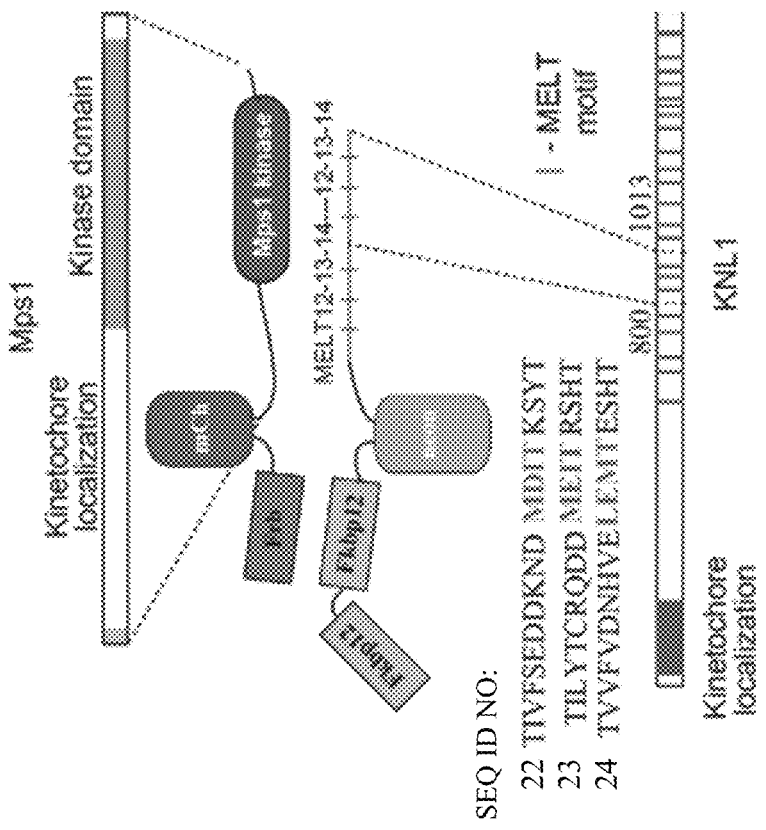
Figure 17A:
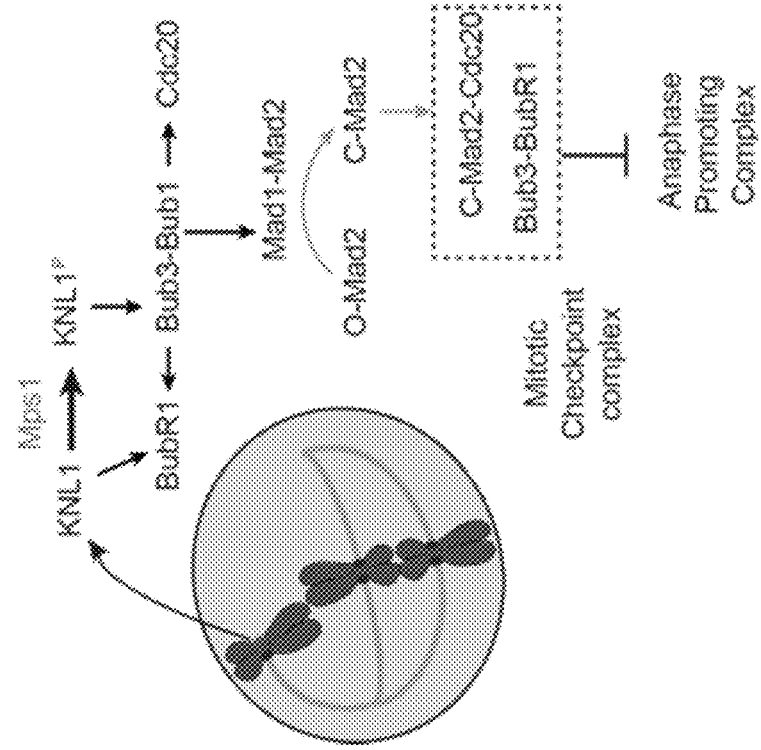
Figure 17C:
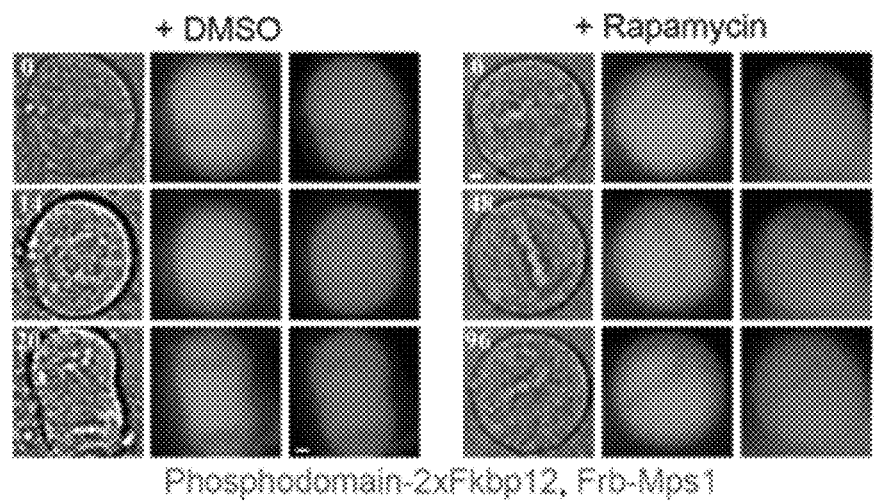
Figure 17C:
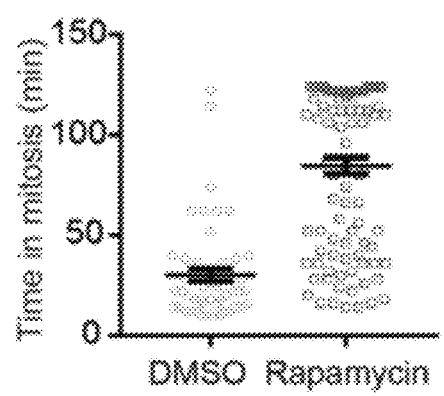
Figure 17D:
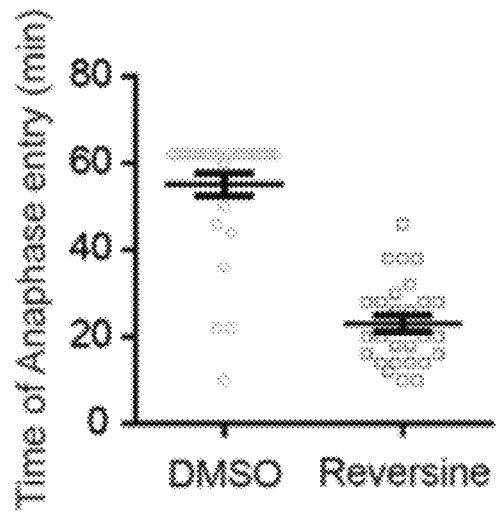
Figure 17E:
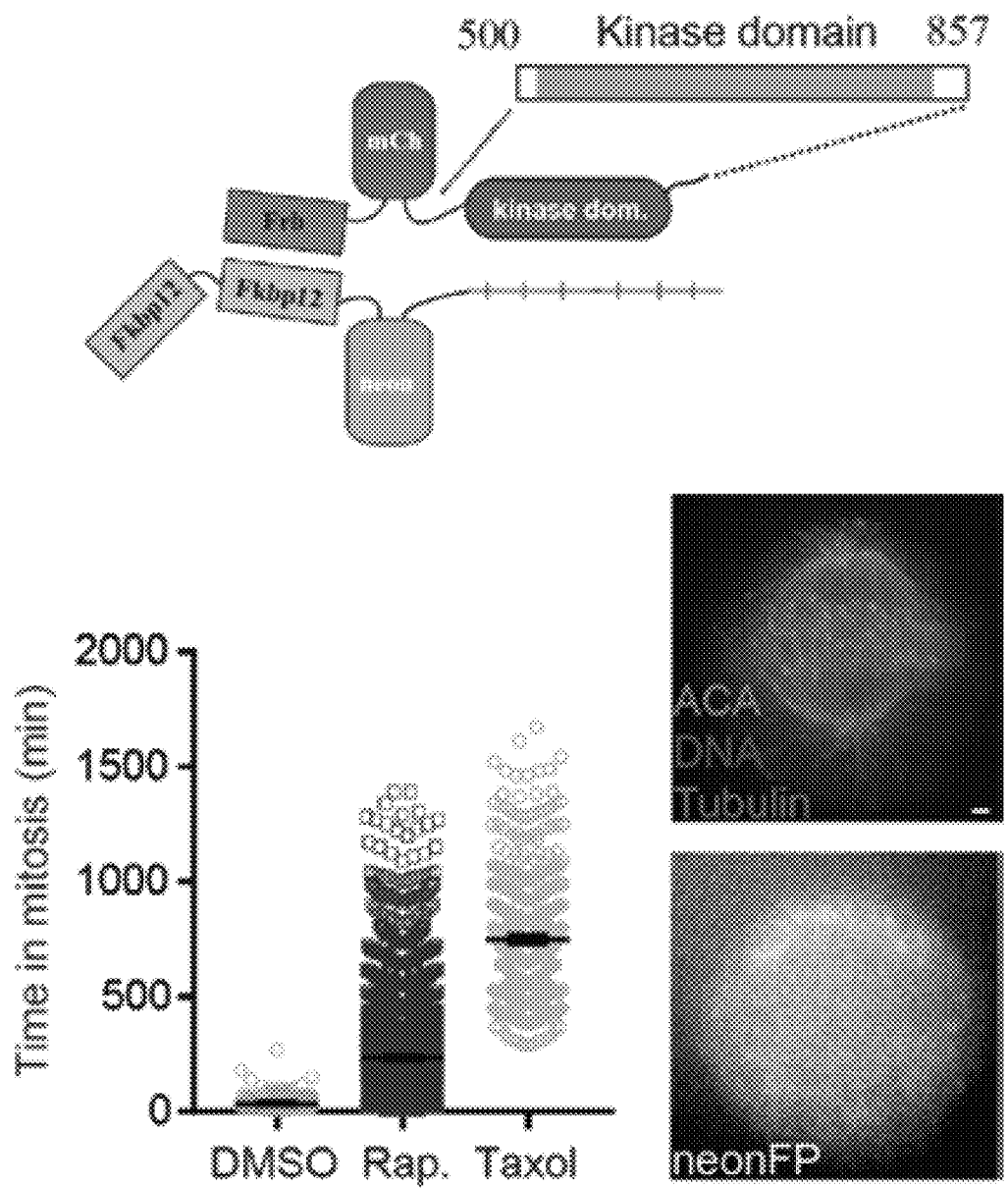

As described elsewhere herein, a kinetochore-independent SAC activator was engineered which comprises a region of KNL1 that contains a series of Mps1 phosphorylation sites, known as "MELT repeats", which are necessary for SAC activation, but lacks the kinetochore-localization domain at the C-terminus or the newly identified transient localization domain at its N-terminus (FIG. 21). FKBP12 was fused to this minimal KNL1 phosphodomain and FRB to Mps1, and rapamycin was used to induce dimerization of the fusion proteins in HeLa cells (FIGS. 17B, 22). Upon induction of KNL1 phosphodomain-Mps1 dimerization by adding rapamycin, cells displayed a prolonged mitotic arrest indicative of SAC activation (FIG. 17C). These cells maintained an aligned metaphase plate indicating an inability to initiate anaphase and that the observed mitotic arrest was not due to the disruption of kinetochore-microtubule interactions. The arrest was reversed rapidly upon inhibition of Mps1 kinase activity by the small molecule inhibitor Reversine, indicating that it required Mps1 kinase activity (FIG. 17D). To further ensure kinetochore-independent operation of the dimerized proteins, the kinetochore-localization domain of Mps1 was removed (FIG. 17E). Rapamycin-induced dimerization of this minimal Mps1 kinase domain with the minimal KNL1 phosphodomain also produced a sustained mitotic arrest without any detectable kinetochore localization (FIG. 17E). Furthermore, individually inhibiting the kinase activity of exogenous Mps1 using an analog-sensitive version of the kinase domain or preventing the phosphorylation of the minimal KNL1 phosphodomain by using a non-phosphorylatable version of the phosphodomain each prevented the rapamycin-induced mitotic arrest (FIG. 23). Thus, the catalytic activity of the Mps1 kinase domain and the Mps1 phosphorylation sites within the minimal phosphodomain are both essential for the rapamycin-induced metaphase arrest. These data demonstrate that phosphorylation of the MELT repeats in KNL1 by Mps1 in the cytosol is sufficient to institute a metaphase arrest in human cells. The above described system of FKBP12/FRB-dimerizable Mps1 kinase domain and KNL1 phosophodomains is referred to in this example as an ectopic SAC activation system (eSAC).

Figure 18A:
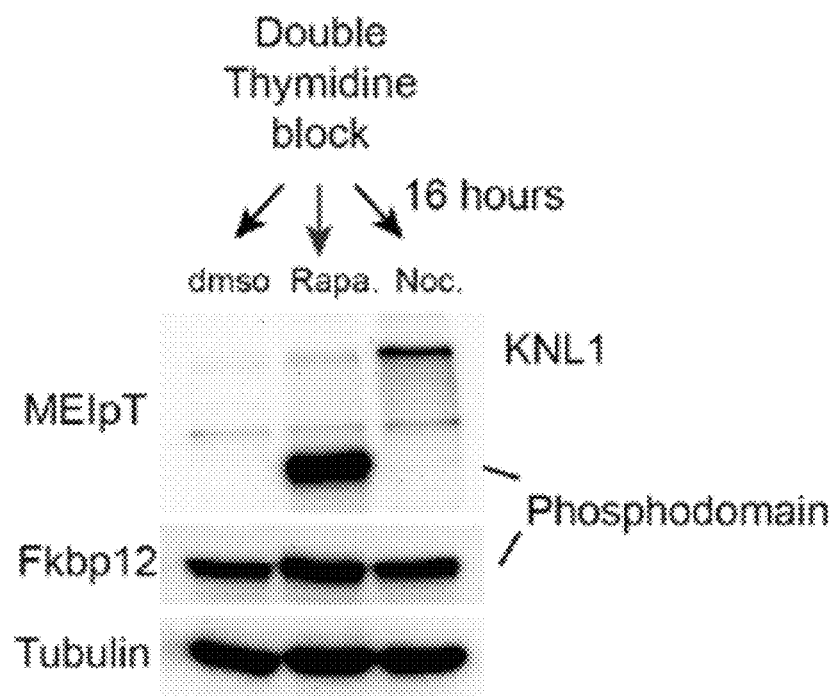
Figure 18B:
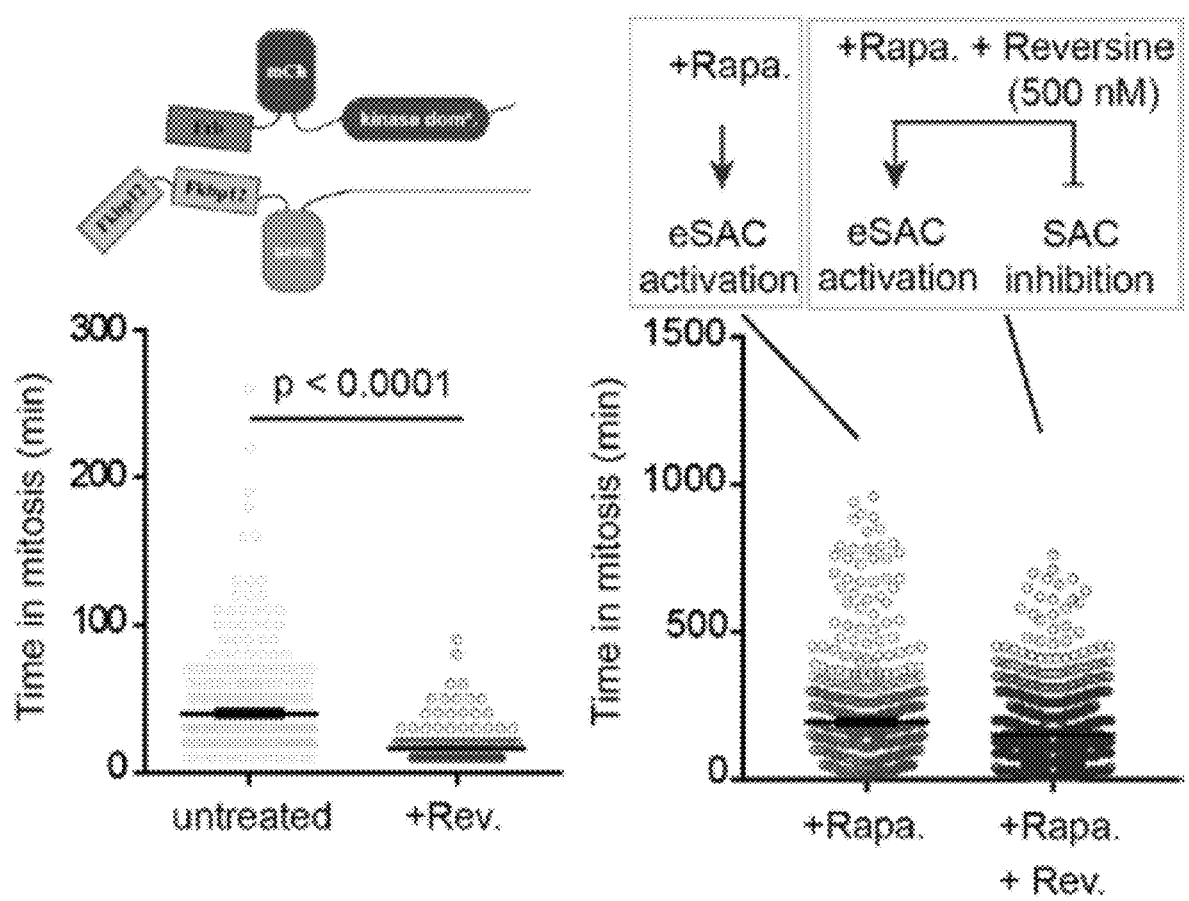
Figure 18C:
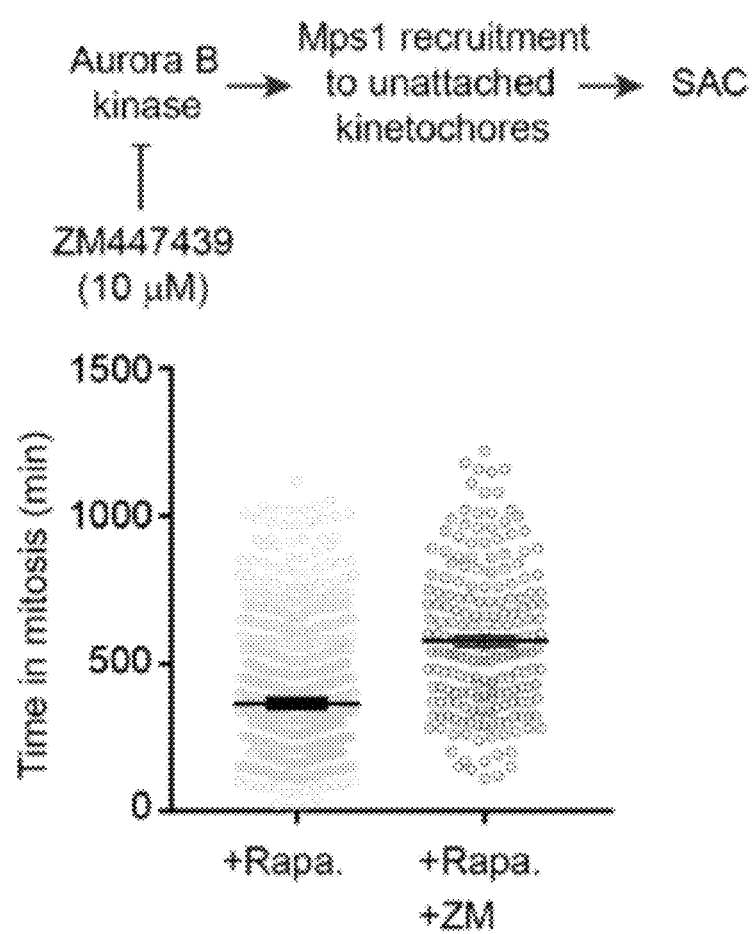
Figure 18D:
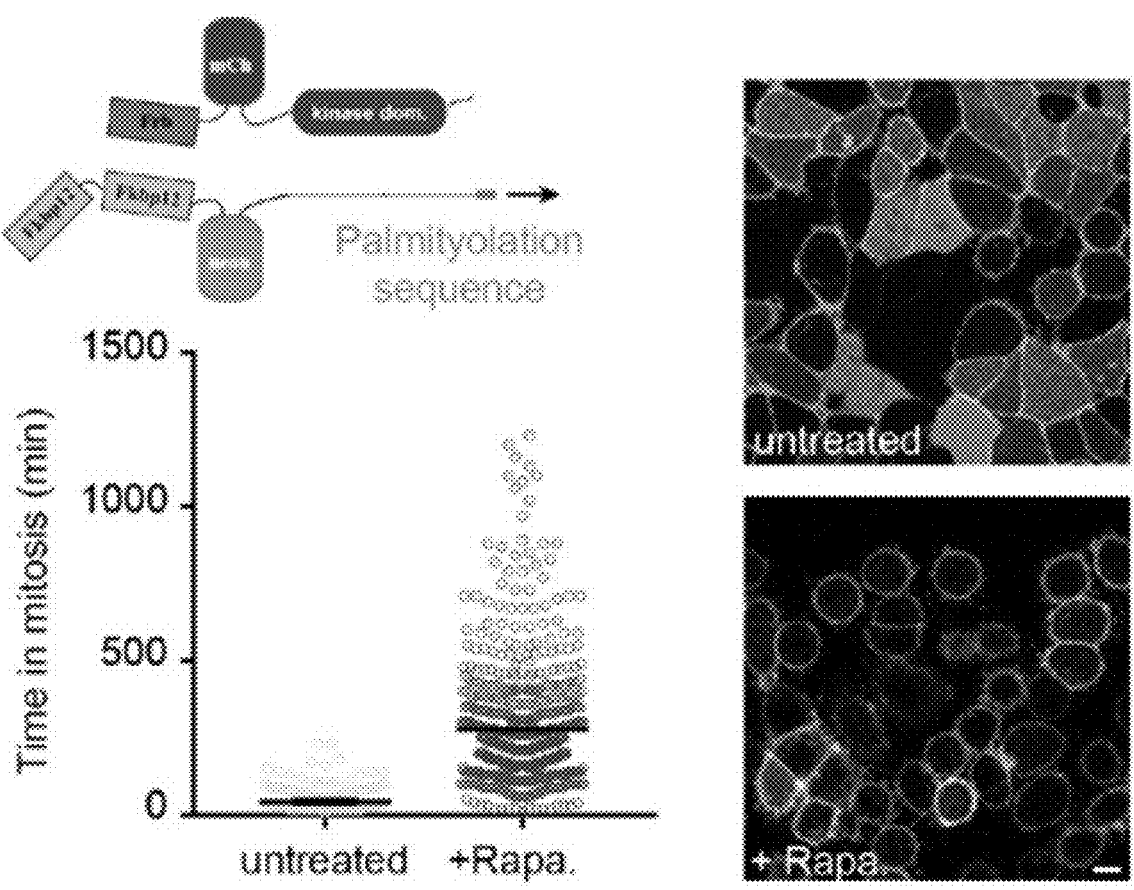

Experiments were conducted during development of embodiments herein to demonstrate that the eSAC is completely independent of the kinetochore-based SAC activation machinery. MELT repeats in the eSAC phosphodomain were phosphorylated only in the presence of rapamycin, and were not phosphorylated if the SAC was activated by creating unattached kinetochores by treatment with the microtubule depolymerizing drug nocodazole (FIG. 18A). Reciprocally, the MELT repeats in endogenous KNL1 were not appreciably phosphorylated in rapamycin-treated cells, but were strongly phosphorylated in nocodazole-treated cells. Thus, there is negligible cross-talk in the phospho-regulation of the eSAC phosphodomain and endogenous KNL1. The kinetochore-based SAC signaling was selectively inactivated by Reversine treatment (FIG. 18B, left) to determine whether an eSAC, which uses a partially Reversine-resistant allele of the Mps1 kinase domain, still arrests mitosis (FIG. 18B). Activation of this eSAC significantly delayed mitosis even in the presence of Reversine, demonstrating that kinetochore-based SAC signaling is dispensable for eSAC activity (FIG. 18B, right). The observed reduction in the average mitotic time was expected because the Mps1 allele is only partially resistant to Reversine (IC50~130 nM compared to ~30 nM for the wild-type Mps1). Kinetochore-independent operation of the eSAC was further confirmed by the observation that inhibiting Aurora B kinase activity, which contributes to the recruitment of Mps1 and SAC proteins to kinetochores, did not reduce the eSAC-induced mitotic delay (FIG. 18C). Next, the eSAC phosphodomain was targeted to the plasma membrane by incorporating a palmitoylation sequence at its N-terminus; when complexed with the Mps1 kinase domain, this membrane-tethered phosphodomain induced a potent mitotic arrest similar to that induced by its cytosolic version (FIG. 18D). The experiments conducted during development of embodiments herein demonstrate that the eSAC operates independently of the kinetochore to inhibit anaphase.

Figures 18E, 18F:
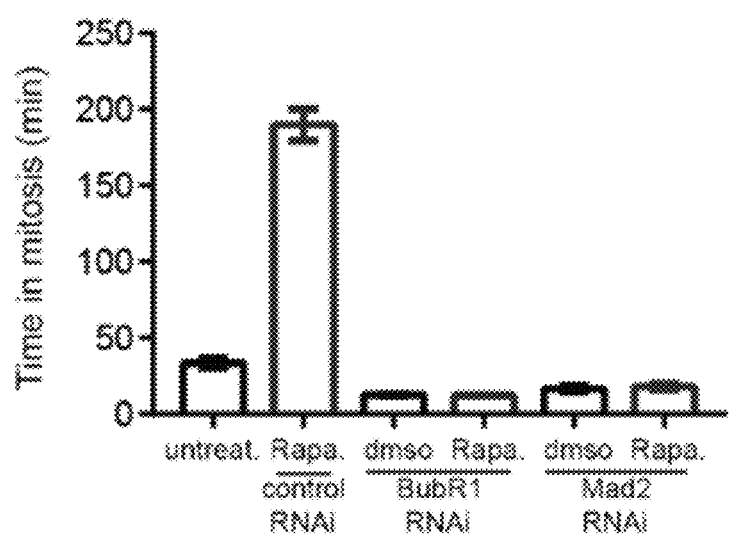

Experiments were conducted during development of embodiments herein to define the events that occur downstream of eSAC activation. Mass spectrometry analysis was performed on immunoprecipitated eSAC phosphodomain (FIG. 18E). When the eSAC phosphodomain was isolated from cells arrested in mitosis by nocodazole, this analysis identified peptides from KNL1 and FKBP12, but not from Mps1 or any of the SAC proteins. In contrast, affinity purification of the eSAC phosphodomain following rapamycin treatment isolated the SAC proteins Bub3 and Bub1, in addition to the Mps1 kinase domain. To identify dynamic interacting partners for the eSAC phosphodomain, cells were treated with the crosslinking agent formaldehyde prior to the affinity purification to trap weakly associated proteins. These purifications additionally isolated BubR1, a key component of the Mitotic Checkpoint Complex (MCC). Thus, the eSAC phosphodomain recruits components of the SAC signaling cascade and the mitotic checkpoint complex only when it is phosphorylated by Mps1. Next, the eSAC was activate in cells depleted for BubR1 or Mad2, the essential components of the MCC, using RNAi, to determine whether the eSAC-induced metaphase arrest requires the formation of the MCC. In both cases, rapamycin-treatment was unable to cause a mitotic arrest (FIG. 18F). The data indicate that eSAC activation generates phosphorylated MELT repeats in the cytosol, which then recruit SAC proteins and catalyze the formation of the MCC. The MCC inhibits Anaphase Promoting Complex, and delays anaphase onset. Thus, the eSAC is a minimal, but potent, system that institutes a controllable biochemical block to anaphase without interfering with the mechanics of cell division.

Figure 19A:
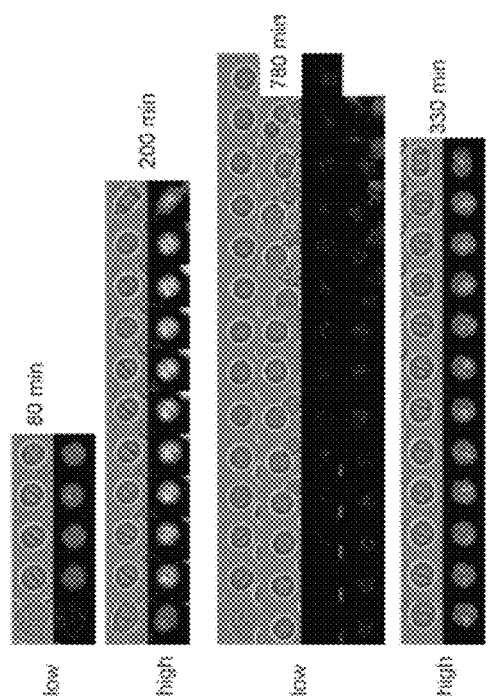
Figure 19B:
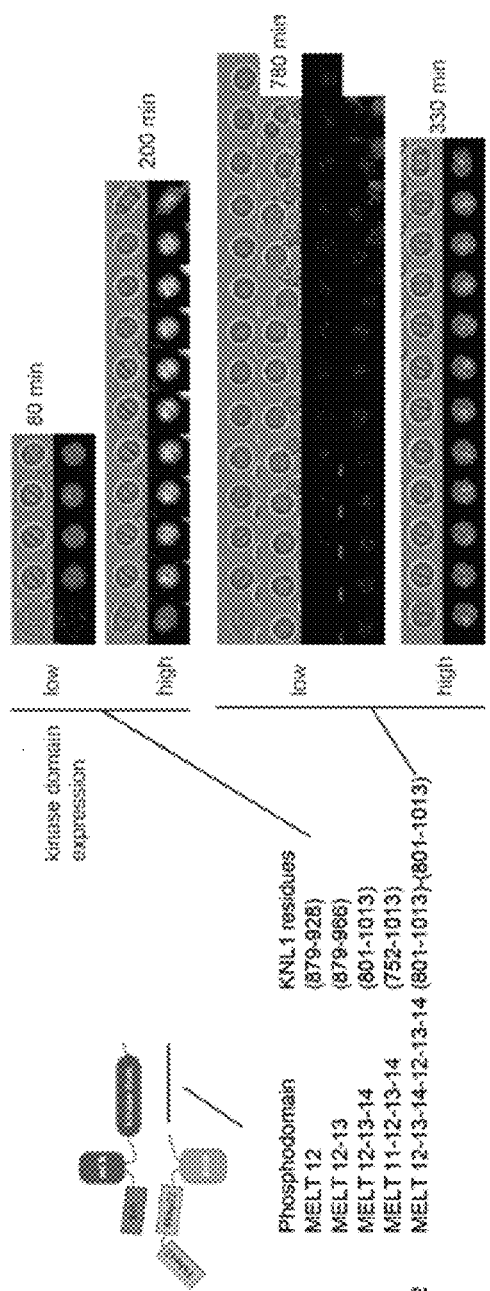
Figure 19C:
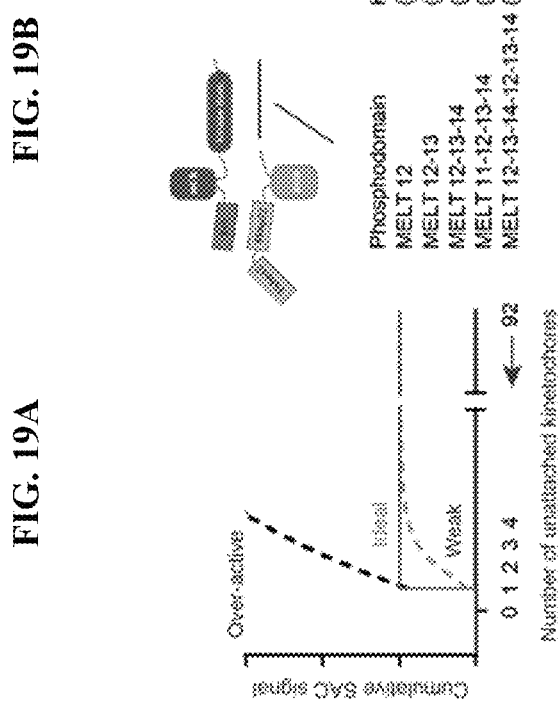

Experiments conducted during development of embodiments herein to analyze the dose-response characteristics of the eSAC: the relationship between the abundance of the dimeric eSAC activator and the corresponding duration of mitotic arrest (FIG. 19B-C). In these assays, it was found that the duration of mitosis was strongly affected only by the limiting abundance of the mCherry-tagged Mps1 kinase domain, and not by the abundance of the highly-expressed phosphodomain (FIG. 24). Therefore, mCherry fluorescence intensity was used as the measure of the eSAC activator complex (FIG. 24). Frb-mCherry-Mps1 abundance was in a range comparable to that of endogenous Mps1 (FIG. 25). Therefore, the dose-response curves probed SAC function in a physiologically relevant concentration range.

Figures 19D, 19E, 19F:
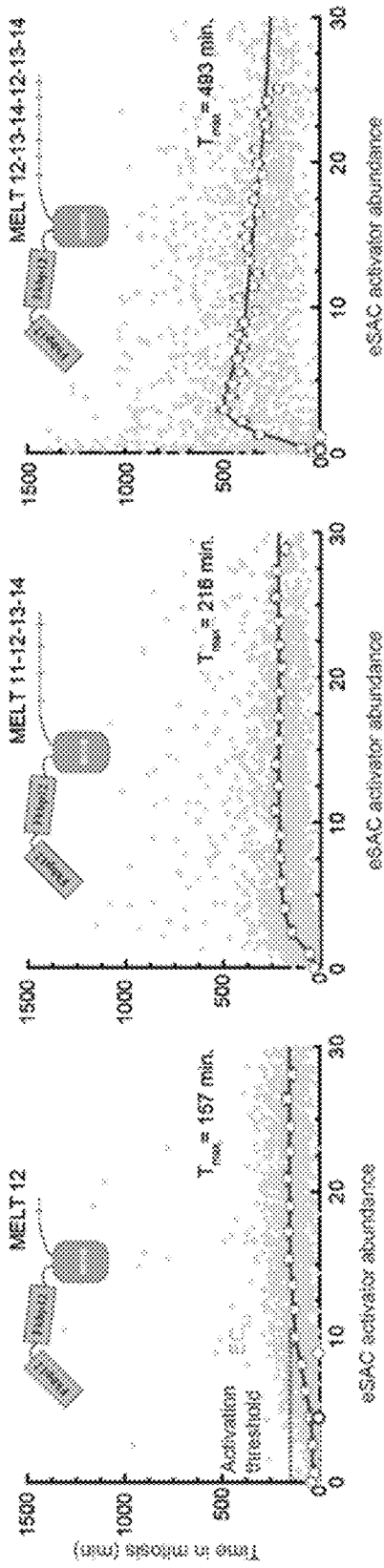

It was found that the cellular abundance of the eSAC activator and the number of MELT repeats per eSAC phosphodomain had striking, systematic effects on the duration of mitosis. With phosphodomains containing up to four MELT repeats, each eSAC dose-response relationship was sigmoidal (FIGS. 19-E, 26). Each curve possessed a characteristic 'activation threshold', defined as the eSAC activator abundance necessary to increase mitotic duration by 10% over its baseline value (FIG. 19D-E). Beyond this threshold, mitotic duration increased proportionally with eSAC activator abundance before reaching a plateau. As the number of MELT repeats in the eSAC phosphodomains increased, the activation threshold decreased, the slope of the linear regime increased. The final, asymptotic delay in anaphase onset also increased, but in a complex, non-intuitive manner.

Figure 19I:
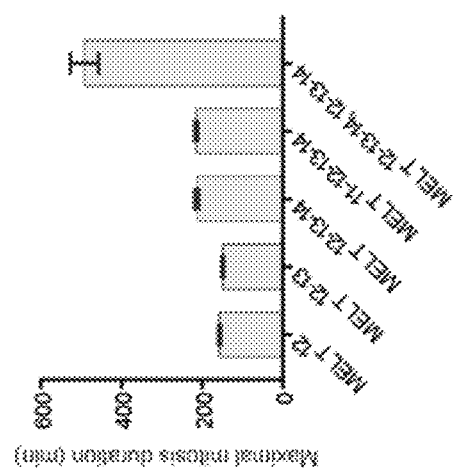
Figure 19H:
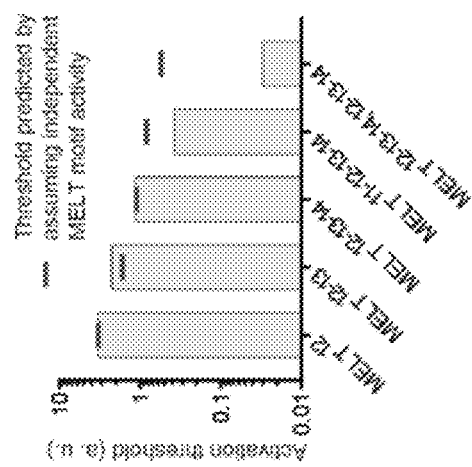
Figure 19G:
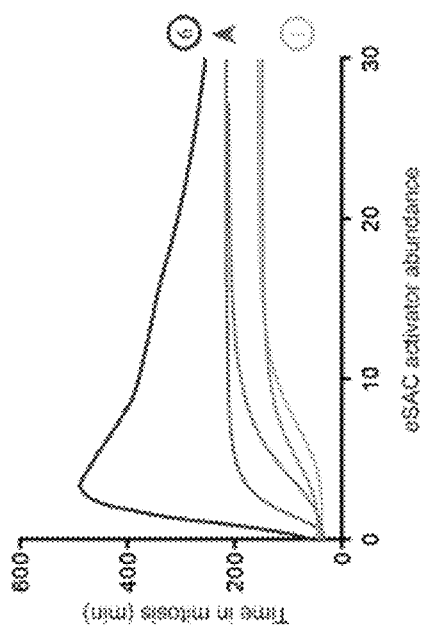

Because the eSAC delays mitosis by stimulating the SAC signaling cascade, its dose-response characteristics reflect the relationship between the steady-state concentration of MCC and the duration of mitosis. Thus, beyond their respective activation thresholds, eSAC phosphodomains containing up to 4 MELT repeats generate gradually increasing concentrations of MCC. Consequently, over this limited range of eSAC activator abundance, the operation of the SAC signaling cascade resembles that of a rheostat resisting anaphase onset. Saturation of the maximal time in mitosis at high eSAC concentrations indicates that MCC generation does not increase any further, for example, because of the limited concentration or activity of downstream SAC proteins. The activation threshold and the steepness of the dose-response curve are both critical characteristics of each phosphodomain, because they indicate the smallest concentration of the respective phosphodomain that delays anaphase onset and the signaling strength per molecule respectively. Increasing the number of MELT repeats per eSAC phosphodomain reduced the activation threshold and increased the signaling strength approximately proportionally (FIG. 19G-I). This trend partially explains why multiple MELT repeats per KNL1 are evolutionarily favored.

The data imply that endogenous KNL1 will possess a much smaller activation threshold and higher signaling strength, because it contains 19 MELT repeats. However, KNL1 alleles with only 6 MELT repeats are capable of recruiting the same number of Bub3-Bub1 molecules and activating the SAC as wild-type KNL1. This counter-intuitive finding is explained by the complex dose-response relationship for the eSAC phosphodomain with 6 MELT repeats (FIG. 19F). This phosphodomain displayed a surprisingly low activation threshold and high signaling strength. It also achieved a disproportionately large increase in the maximal duration of mitosis (FIG. 19G-I). In effect, the phosphodomain containing 6 MELT repeats stimulated the SAC signaling cascade like a switch (FIGS. 19F, 27). The disproportionately large increase in signaling strength suggests that the concurrent recruitment of SAC proteins by MELT repeats within the same phosphodomain molecule produces a synergistic output. This conclusion is further bolstered by the gradual decline in the response with increasing concentrations of the eSAC activator. As the eSAC activator concentration increases, the phosphodomains compete with one-another to recruit the limited pool of downstream signaling proteins. Consequently, individual eSAC phosphodomains no longer recruit multiple SAC proteins, which diminishes synergistic activity. Therefore, at high eSAC concentration the dose-response curve for the phosphodomain with 6 MELT repeats approaches the asymptotic plateau for eSAC phosphodomains containing 3-4 repeats (FIG. 19G).

A mathematical model of the eSAC (FIG. 20) was constructed which assumes that each MELT motif recruits SAC proteins with a characteristic affinity (Table 1). The model represents all the SAC proteins are represented by a single factor named 'Bub', because quantitative measurements for these recruitment reactions are not available (FIG. 20A-B). For eSAC phosphodomains containing more than one MELT motif, the model calculates the steady state concentration of all possible species of the phosphodomain characterized by MELT motifs bound by the SAC proteins (concentrations for eSAC phosphodomains with one and 4 MELT repeats displayed in the middle graphs in FIGS. 20A and B, respectively). The model further assumes that the abundance of one or more SAC proteins is lower than the abundance of the eSAC activator. Consequently, the abundance of eSAC phosphodomains bound with different numbers of SAC proteins strongly depends on the eSAC activator abundance (FIGS. 20A-B, 28). The steady-state MCC generated by kinetochores depends on the amount of SAC proteins that they recruit. Therefore, it was assume that the rate of conversion of the SAC-active form of Mad2 (FIG. 20A-B, right panels), and hence the steady-state MCC concentration generated by the eSAC, is proportional to the number of SAC proteins recruited by the eSAC phosphodomains. To simulate the time in mitosis as a function of eSAC abundance, the cumulative MCC generated by all the phosphodomains was relayed to a mathematical representation of a bi-stable switch that controls the onset of anaphase (FIGS. 29-30). This model captured the average dose-response characteristics of eSAC phosphodomains containing up to 4 MELT repeats (FIG. 20C). However, this simple scheme did not reproduce the complex dose-response relationship for the phosphodomain with 6 MELT repeats (FIG. 20C, dashed black curve). In this case, it was assumed that eSAC phosphodomains that had more than one MELT repeat bound by SAC proteins produced MCC at a modestly higher rate (≤20% increase due to synergistic output, FIG. 31). With this modification, the model accurately captured the dose-response characteristics for the eSAC phosphodomain containing 6 MELT repeats (FIG. 20C).

TABLE 1

Rate constants for Bub binding.

| Parameter | Value | Parameter | Value | Vleugel et al. classification |
|---|---|---|---|---|
| $k_{f11}$ | 1 nM$^{-1}$ min$^{-1}$ | $k_{r11}$ | 0.1 min$^{-1}$ | High |
| $k_{f12}$ | 1 nM$^{-1}$ min$^{-1}$ | $k_{r12}$ | 0.1 min$^{-1}$ | High |
| $k_{f13}$ | 1 nM$^{-1}$ min$^{-1}$ | $k_{r13}$ | 5 min$^{-1}$ | Low |
| $k_{f14}$ | 1 nM$^{-1}$ min$^{-1}$ | $k_{r14}$ | 0.1 min$^{-1}$ | Intermediate |

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

REFERENCES

The following references, some of which are cited above by number, are herein incorporated by reference in their entireties.
1. Sacristan, C. & Kops, G. J. Joined at the hip: kinetochores, microtubules, and spindle assembly checkpoint signaling. *Trends Cell Biol.* 25, 21-28 (2014).

2. Foley, E. A. & Kapoor, T. M. Microtubule attachment and spindle assembly checkpoint signalling at the kinetochore. *Nat. Rev. Mol. Cell Biol.* 14, 25-37 (2013).
3. Funabiki, H. & Wynne, D. J. Making an effective switch at the kinetochore by phosphorylation and dephosphorylation. *Chromosoma* 122, 135-158 (2013).
4. McIntosh, J. R. Structural and mechanical control of mitotic progression. *Cold Spring Harb. Symp. Quant. Biol.* 56, 613-619 (1991).
5. Maresca, T. J. & Salmon, E. D. Intrakinetochore stretch is associated with changes in kinetochore phosphorylation and spindle assembly checkpoint activity. *J. Cell Biol.* 184, 373-381 (2009).
6. Wan, X. et al. Protein architecture of the human kinetochore microtubule attachment site. *Cell* 137, 672-684 (2009).
7. Uchida, K. S. et al. Kinetochore stretching inactivates the spindle assembly checkpoint. *J. Cell Biol.* 184, 383-390 (2009).
8. Santaguida, S. & Musacchio, A. The life and miracles of kinetochores. *EMBO J.* 28, 2511-2531 (2009).
9. Haruki, H., Nishikawa, J. & Laemmli, U. K. The anchor-away technique: rapid, conditional establishment of yeast mutant phenotypes. *Mol. Cell* 31, 925-932 (2008).
10. Jelluma, N., Dansen, T. B., Sliedrecht, T., Kwiatkowski, N. P. & Kops, G. J. Release of Mps1 from kinetochores is crucial for timely anaphase onset. *J. Cell Biol.* 191, 281-290 (2010).
11. Ito, D., Saito, Y. & Matsumoto, T. Centromere-tethered Mps1 pombe homolog (Mph1) kinase is a sufficient marker for recruitment of the spindle checkpoint protein Bub1, but not Mad1. *Proc. Natl Acad. Sci. USA* 109, 209-214 (2012).
12. London, N., Ceto, S., Ranish, J. A. & Biggins, S. Phosphoregulation of Spc105 by Mps1 and PP1 regulates Bub1 localization to kinetochores. *Curr. Biol.* 22, 900-906 (2012).
13. Pinsky, B. A., Kung, C., Shokat, K. M. & Biggins, S. The Ipl1-Aurora protein kinase activates the spindle checkpoint by creating unattached kinetochores. *Nat. Cell Biol.* 8, 78-83 (2006).
14. Biggins, S. et al. The conserved protein kinase Ipl1 regulates microtubule binding to kinetochores in budding yeast. *Genes Dev.* 13, 532-544 (1999).
15. Heinrich, S., Windecker, H., Hustedt, N. & Hauf, S. Mph1 kinetochore localization is crucial and upstream in the hierarchy of spindle assembly checkpoint protein recruitment to kinetochores. *J. Cell Sci.* 125, 4720-4727 (2012).
16. Yeong, F. M., Lim, H. H., Padmashree, C. G. & Surana, U. Exit from mitosis in budding yeast: biphasic inactivation of the Cdc28-Clb2 mitotic kinase and the role of Cdc20. *Mol. Cell* 5, 501-511 (2000).
17. Palframan, W. J., Meehl, J. B., Jaspersen, S. L., Winey, M. & Murray, A. W. Anaphase inactivation of the spindle checkpoint. *Science* 313, 680-684 (2006).
18. Rosenberg, J. S., Cross, F. R. & Funabiki, H. KNL1/Spc105 recruits PP1 to silence the spindle assembly checkpoint. *Curr. Biol.* 21, 942-947 (2011).
19. Pinsky, B. A., Nelson, C. R. & Biggins, S. Protein phosphatase 1 regulates exit from the spindle checkpoint in budding yeast. *Curr. Biol.* 19, 1182-1187 (2009).
20. Joglekar, A. P., Bloom, K. & Salmon, E. D. In vivo protein architecture of the eukaryotic kinetochore with nanometer scale accuracy. *Curr. Biol.* 19, 694-699 (2009).
21. Aravamudhan, P., Felzer-Kim, I. & Joglekar, A. P. The budding yeast point centromere associates with two Cse4 molecules during mitosis. *Curr. Biol.* 23, 770-774 (2013).
22. Joglekar, A. P., Bouck, D. C., Molk, J. N., Bloom, K. S. & Salmon, E. D. Molecular architecture of a kinetochore-microtubule attachment site. *Nat. Cell Biol.* 8, 581-585 (2006).
23. Aravamudhan, P., Felzer-Kim, I., Gurunathan, K. & Joglekar, A. P. Assembling the protein architecture of the budding yeast kinetochore-microtubule attachment using FRET. *Curr. Biol.* 24, 1437-1446 (2014).
24. Howell, B. J. et al. Spindle checkpoint protein dynamics at kinetochores in living cells. *Curr. Biol.* 14, 953-964 (2004).
25. Ghaemmaghami, S. et al. Global analysis of protein expression in yeast. *Nature* 425, 737-741 (2003).
26. Liu, X. & Winey, M. The MPS1 family of protein kinases. *Annu. Rev. Biochem.* 81, 561-585 (2012).
27. Ramey, V. H. et al. Subunit organization in the Dam1 kinetochore complex and its ring around microtubules. *Mol. Biol. Cell* 22, 4335-4342 (2011).
28. Shimogawa, M. M. et al. Mps1 phosphorylation of Dam1 couples kinetochores to microtubule plus ends at metaphase. *Curr. Biol.* 16, 1489-1501 (2006).
29. Cheeseman, I. M., Enquist-Newman, M., Muller-Reichert, T., Drubin, D. G. & Barnes, G. Mitotic spindle integrity and kinetochore function linked by the Duo1p/Dam1p complex. *J. Cell Biol.* 152, 197-212 (2001).
30. Goh, P. Y. & Kilmartin, J. V. NDC10: a gene involved in chromosome segregation in *Saccharomyces cerevisiae*. *J. Cell Biol.* 121, 503-512 (1993).
31. Fraschini, R., Beretta, A., Lucchini, G. & Piatti, S. Role of the kinetochore protein Ndc10 in mitotic checkpoint activation in *Saccharomyces cerevisiae*. *Mol. Genet. Genomics* 266, 115-125 (2001).
32. Kemmler, S. et al. Mimicking Ndc80 phosphorylation triggers spindle assembly checkpoint signalling. *EMBO J.* 28, 1099-1110 (2009).
33. Nijenhuis, W. et al. A TPR domain-containing N-terminal module of MPS1 is required for its kinetochore localization by Aurora B. *J. Cell Biol.* 201, 217-231 (2013).
34. Primorac, I. et al. Bub3 reads phosphorylated MELT repeats to promote spindle assembly checkpoint signaling. *eLife* 2, e01030 (2013).
35. Joglekar, A. P., Chen, R. & Lawrimore, J. G. A sensitized emission based calibration of FRET efficiency for probing the architecture of macromolecular machines. *Cell Mol. Bioeng.* 6, 369-382 (2013).
36. Guimaraes, G. J., Dong, Y., McEwen, B. F. & Deluca, J. G. Kinetochore-microtubule attachment relies on the disordered N-terminal tail domain of Hec1. *Curr. Biol.* 18, 1778-1784 (2008).
37. Maldonado, M. & Kapoor, T. M. Constitutive Mad1 targeting to kinetochores uncouples checkpoint signalling from chromosome biorientation. *Nat. Cell Biol.* 13, 475-482 (2011).
38. Hewitt, L. et al. Sustained Mps1 activity is required in mitosis to recruit O-Mad2 to the Mad1-C-Mad2 core complex. *J. Cell Biol.* 190, 25-34 (2010).
39. Tipton, A. R. et al. Monopolar spindle 1 (MPS1) kinase promotes production of closed MAD2 (C-MAD2) conformer and assembly of the mitotic checkpoint complex. *J. Biol. Chem.* 288, 35149-35158 (2013).
40. Kim, S. et al. Phosphorylation of the spindle checkpoint protein Mad2 regulates its conformational transition. *Proc. Natl Acad. Sci. USA* 107, 19772-19777 (2010).

41. London, N. & Biggins, S. Mad1 kinetochore recruitment by Mps1-mediated phosphorylation of Bub1 signals the spindle checkpoint. *Genes Dev.* 28, 140-152 (2014).
42. Li, Y. et al. The mitotic spindle is required for loading of the DASH complex onto the kinetochore. *Genes Dev.* 16, 183-197 (2002).
43. Ciferri, C. et al. Implications for kinetochore-microtubule attachment from the structure of an engineered Ndc80 complex. *Cell* 133, 427-439 (2008).
44. Wang, H. W. et al. Architecture and flexibility of the yeast Ndc80 kinetochore complex. *J. Mol. Biol.* 383, 894-903 (2008).
45. Tien, J. F. et al. Kinetochore biorientation in *Saccharomyces cerevisiae* requires a tightly folded conformation of the Ndc80 complex. *Genetics* 198, 1483-1493 (2014).
46. Wei, R. R. et al. Structure of a central component of the yeast kinetochore: the Spc24p/Spc25p globular domain. *Structure* 14, 1003-1009 (2006).
47. Pagliuca, C., Draviam, V. M., Marco, E., Sorger, P. K. & De Wulf, P. Roles for the conserved Spc105p/Kre28p complex in kinetochoremicrotubule binding and the spindle assembly checkpoint. *PLoS ONE* 4, e7640 (2009).
48. Espeut, J Cheerambathur, D. K., Krenning, L., Oegema, K. & Desai, A. Microtubule binding by KNL1 contributes to spindle checkpoint silencing at the kinetochore. *J. Cell Biol.* 196, 469-482 (2012).
49. Hardwick, K. G., Weiss, E., Luca, F. C., Winey, M. & Murray, A. W. Activation of the budding yeast spindle assembly checkpoint without mitotic spindle disruption. *Science* 273, 953-956 (1996).
50. McCleland, M. L. et al. The highly conserved Ndc80 complex is required for kinetochore assembly, chromosome congression, and spindle checkpoint activity. *Genes Dev.* 17, 101-114 (2003).
51. DeLuca, J. G. et al. Nuf2 and Hec1 are required for retention of the checkpoint proteins Mad1 and Mad2 to kinetochores. *Curr. Biol.* 13, 2103-2109 (2003).
52. Howell, B. J. et al. Cytoplasmic dynein/dynactin drives kinetochore protein transport to the spindle poles and has a role in mitotic spindle checkpoint inactivation. *J. Cell Biol.* 155, 1159-1172 (2001).
53. Ballister, E. R., Riegman, M. & Lampson, M. A. Recruitment of Mad1 to metaphase kinetochores is sufficient to reactivate the mitotic checkpoint. *J. Cell Biol.* 204, 901-908 (2014).
54. Kuijt, T. E., Omerzu, M., Saurin, A. T. & Kops, G. J. Conditional targeting of MAD1 to kinetochores is sufficient to reactivate the spindle assembly checkpoint in metaphase. *Chromosoma* 123, 471-480 (2014).
55. McEwen, B. F., Heagle, A. B., Cassels, G. O., Buttle, K. F. & Rieder, C. L. Kinetochore fiber maturation in PtK1 cells and its implications for the mechanisms of chromosome congression and anaphase onset. *J. Cell Biol.* 137, 1567-1580 (1997).
56. Zhang, G. et al. The Ndc80 internal loop is required for recruitment of the Ska complex to establish end-on microtubule attachment to kinetochores. *J. Cell Sci.* 125, 3243-3253 (2012).
57. Daum, J. R. et al. Ska3 is required for spindle checkpoint silencing and the maintenance of chromosome cohesion in mitosis. *Curr. Biol.* 19, 1467-1472 (2009).
58. Varma, D. et al. Recruitment of the human Cdt1 replication licensing protein by the loop domain of Hec1 is required for stable kinetochore-microtubule attachment. *Nat. Cell Biol.* 14, 593-603 (2012).
59. Hsu, K-S. & Toda, T. Ndc80 internal loop interacts with Dis1/TOG to ensure proper kinetochore-spindle attachment in fission yeast. *Curr. Biol.* 21, 214-220 (2011).
60. Zhou, H. X. Polymer models of protein stability, folding, and interactions. *Biochemistry* 43, 2141-2154 (2004).
61. Petrovic, A. et al. Modular assembly of RWD domains on the Mis12 complex underlies outer kinetochore organization. *Mol. Cell* 53, 591-605 (2014).
62. Scott, R. J., Lusk, C. P., Dilworth, D. J., Aitchison, J. D. & Wozniak, R. W. Interactions between Mad1p and the nuclear transport machinery in the yeast *Saccharomyces cerevisiae*. *Mol. Biol. Cell* 16, 4362-4374 (2005).
63. Wei, R. R., Sorger, P. K. & Harrison, S. C. Molecular organization of the Ndc80 complex, an essential kinetochore component. *Proc. Natl Acad. Sci. USA* 102, 5363-5367 (2005).
64. Gillett, E. S., Espelin, C. W. & Sorger, P. K. Spindle checkpoint proteins and chromosome-microtubule attachment in budding yeast. *J. Cell Biol.* 164, 535-546 (2004).
65. Jones, M. H. et al. Chemical genetics reveals a role for Mps1 kinase in kinetochore attachment during mitosis. *Curr. Biol.* 15, 160-165 (2005).
66. Norden, C. et al. The NoCut pathway links completion of cytokinesis to spindle midzone function to prevent chromosome breakage. *Cell* 125, 85-98 (2006).
67. Nakajima, Y. et al. Ipl1/Aurora-dependent phosphorylation of Sli15/INCENP regulates CPC-spindle interaction to ensure proper microtubule dynamics. *J. Cell Biol.* 194, 137-153 (2011).
68. Marco, E. et al. *S. cerevisiae* chromosomes biorient via gradual resolution of syntely between S phase and anaphase. *Cell* 154, 1127-1139 (2013).
69. Sprague, B. L. et al. Mechanisms of microtubule-based kinetochore positioning in the yeast metaphase spindle. *Biophys. J.* 84, 3529-3546 (2003).

The invention claimed is:

1. A cellular or in vitro biochemical system comprising:
   (a) a kinase domain of the wild-type Mps1 (SEQ ID NO:2) linked to a first dimerization element; and
   (b) a phosphodomain of the wild-type KNL1 (SEQ ID NO:5) linked to a second dimerization element,
   wherein the kinase domain is capable of phosphorylating the phosphodomain, and
   wherein dimerization of the first dimerization element and second dimerization element facilitates phosphorylation of the KNL1 polypeptide by the Mps1 polypeptide.

2. The system of claim 1, wherein the phosphorylation of the phosphodomain by the kinase domain is sufficient to activate a spindle assembly checkpoint (SAC) in a cell within which the phosphorylation occurs.

3. The system of claim 1, wherein the first or second dimerization element is Frb and the other dimerization element is Fkbp12.

4. The system of claim 1, further comprising a dimerization inducer, wherein the dimerization inducer alters the degree of dimerization in a concentration dependent manner.

* * * * *